US008058243B2

(12) United States Patent
Tyers et al.

(10) Patent No.: US 8,058,243 B2
(45) Date of Patent: Nov. 15, 2011

(54) METHOD FOR TREATING A BRAIN CANCER WITH IFENPRODIL

(75) Inventors: Mike Tyers, Toronto (CA); Phedias Diamandis, Toronto (CA); Peter B. Dirks, Toronto (CA)

(73) Assignees: HSC Research and Development Limited Partnership (CA); Mount Sinai Hospital (CA)

( * ) Notice: Subject to any disclaimer, the term of this patent is extended or adjusted under 35 U.S.C. 154(b) by 604 days.

(21) Appl. No.: 11/871,562

(22) Filed: Oct. 12, 2007

(65) Prior Publication Data

US 2009/0076019 A1 Mar. 19, 2009

Related U.S. Application Data

(60) Provisional application No. 60/851,615, filed on Oct. 13, 2006.

(51) Int. Cl.
*A61P 35/00* (2006.01)
*C12N 5/095* (2010.01)
(52) U.S. Cl. ........ 514/19.3; 435/377; 514/18.1; 558/483
(58) Field of Classification Search .................. None
See application file for complete search history.

(56) References Cited

U.S. PATENT DOCUMENTS

2005/0054650 A1* 3/2005 Ikonomidou ................ 514/249

OTHER PUBLICATIONS

Ohgaki et al., Cancer Science, 100(12): 2235-2241, Dec. 2009.*
Ahn et al., "In vivo analysis of quiescent adult neural stem cells responding to Sonic hedgehog" Nature, 437(3994):894-897 (Oct. 2005).
Baker et al., "Dopaminergic nigrostriatal projections regulate neural precursor proliferation in the adult mouse subventricular zone" Eur J Neurosci., 20(2):575-579 (Jul. 2004).
Bao et al., "Glioma stem cells promote radioresistance by preferential activation of the DNA damage response" Nature, 444(7120):756-760 (Dec. 7, 2006; e-pub: Oct. 18, 2006).
Barak et al., "Reduced cancer incidence among patients with schizophrenia" Cancer, 104(12):2817-2821 (Dec. 15, 2005).
Burger et al., "Glioblastoma multiforme and anaplastic astrocytoma. Pathologic criteria and prognostic implications" Cancer, 56(5):1106-1111 (Sep. 1, 1985).
Berman et al., "Medulloblastoma growth inhibition by hedgehog pathway blockade" Science, 297(5586):1559-1561 (Aug. 30, 2002).
Carney et al., "Occurrence of cancer among people with mental health claims in an insured population" Psychosom Med., 66(5):735-743 (Sep.-Oct. 2004).
Chen et al., "Self-renewal of embryonic stem cells by a small molecule" Proc. Natl. Acad. Sci. USA., 103(46):17266-17271 (Nov. 14, 2006; e-pub Nov. 6, 2006).
Cohen et al., "Food and Drug Administration Drug approval summary: temozolomide plus radiation therapy for the treatment of newly diagnosed glioblastoma multiforme" Clin. Cancer Res., 11(19 pt 1):6767-6771 (Oct. 1, 2005).
Corcoran et al., "A mouse model for medulloblastoma and basal cell nevus syndrome" J. Neuro-oncol., 53(3):307-318 (Jul. 2001).
Dalton et al., "Depression and cancer risk: a register-based study of patients hospitalized with affective disorders, Denmark, 1969-1993" Am. J. Epidemiol., 155(12):1088-1095 (Jun. 15, 2002).
Dalton et al., "Risk for cancer in a cohort of patients hospitalized for schizophrenia in Denmark, 1969-1993" Schizophr. Res., 75(2-3):315-324 (Jun. 15, 2005; e-pub: Dec. 13, 2004).
Ding et al., "A role for chemistry in stem cell biology" Nat. Biotechnol., 22(7):833-840 (Jul. 2004; e-pub: Jun. 30, 2004).
Diamandis et al., "Chemical genetics reveals a complex functional ground state of neural stem cells" Nat. Chem. Biol., 3(5):268-273 (May 2007; e-pub: Apr. 8, 2007).
Encinas et al., "Fluoxetine targets early progenitor cells in the adult brain" Proc. Natl. Acad. Sci. USA, 103(21):8233-8238 (May 23, 2006; e-pub: May 15, 2006).
Enver et al., "Loops, lineage, and leukemia" Cell, 94(1):9-12 (Jul. 10, 1998).
Galanis et al., "Chemotherapy for high-grade gliomas" Br. J. Cancer, 82(8):1371-1380 (Apr. 2000).
Galli et al., "Isolation and characterization of tumorigenic, stem-like neural precursors from human glioblastoma" Cancer Res., 64(19):7011-7021 (Oct. 1, 2004).
Ge et al., "GABA sets the tempo for activity-dependent adult neurogenesis" Trends Neurosci., 30(1):1-8 (Jan. 2007; e-pub: Nov. 20, 2006).
Goldacre et al., "Schizophrenia and cancer: an epidemiological study" Br. J. Psychiatry, 187:334-338 (Oct. 2005).
Gritti et al., "Epidermal and fibroblast growth factors behave as mitogenic regulators for a single multipotent stem cell-like population from the subventricular region of the adult mouse forebrain" J. Neurosci., 19(9):3287-3297 (May 1, 1999).
Groszer et al., "PTEN negatively regulates neural stem cell self-renewal by modulating $G_0$-$G_1$ cell cycle entry" Proc. Natl. Acad. Sci. USA, 103(1):111-116 (Jan. 3, 2006; e-pub: Dec. 22, 2005).
Hagell et al., "Apomorphine in the treatment of Parkinson's disease" J. Neurosci. Nurs., 33(1): 21-34, 37-38 (Feb. 2001).
Hagg T., "Molecular regulation of adult CNS neurogenesis: an integrated view" Trends Neurosci., 28(11): 589-95 (Nov. 2005; e-pub: Sep. 8, 2005).
Harrist et al., "Alteration of hippocampal cell proliferation in mice lacking the β2 subunit of the neuronal nicotinic acetylcholine receptor" Synapse, 54(4):200-206 (Dec. 15, 2004).
Hemmati et al., "Cancerous stem cells can arise from pediatric brain tumors" Proc. Natl. Acad. Sci. USA, 100(25):15178-15183 (Dec. 9, 2003; e-pub: Nov. 26, 2003).
Hertz et al., "Receptor expression in primary cultures of neurons or astrocytes" Prog. Neuropsychopharmacol. Biol. Psychiatry, 8(4-6):521-527 (1984).
Hitoshi et al., "Notch pathway molecules are essential for the maintenance, but not the generation, of mammalian neural stem cells" Genes Dev., 16(7):846-58 (Apr. 1, 2002).

(Continued)

*Primary Examiner* — Lorraine Spector
*Assistant Examiner* — Stacey MacFarlane
(74) *Attorney, Agent, or Firm* — Howson & Howson LLP

(57) ABSTRACT

A clonogenic neurosphere assay is described that carries out high throughput screens (HTS) to identify potent and/or selective modulators of proliferation, differentiation and/or renewal of neural precursor cells, neural progenitor cells and/or self-renewing and multipotent neural stem cells (NSCs). Compositions comprising the identified modulators and methods of using the modulators and compositions, in particular to treat neurological disorders (e.g. brain or CNS cancer) or damage are also disclosed.

4 Claims, 26 Drawing Sheets

OTHER PUBLICATIONS

Höglinger et al., "Dopamine depletion impairs precursor cell proliferation in Parkinson disease" Nat. Neurosci., 7(7):726-735 (Jul. 2004; e-pub Jun. 13, 2004).

Iacovelli et al., "Pharmacological activation of mGlu4 metabotropic glutamate receptors inhibits the growth of medulloblastomas" J. Neurosci., 26(32): 8388-8397 (Aug. 9, 2006).

Kevorkov et al., "Statistical analysis of systematic errors in high-throughput screening" J. Biomol. Screen., 10(6):557-567 (Sep. 2005; e-pub Aug. 15, 2005).

Kippin et al., "Dopamine specifically inhibits forebrain neural stem cell proliferation, suggesting a novel effect of antipsychotic drugs" J. Neurosci., 25(24):5815-5823 (Jun. 15, 2005).

Lalonde et al., "Are dopamine antagonists a risk factor for breast cancer? An answer from Parkinson's disease" Breast, 12(4):280-282 (Aug. 2003).

Lee et al., "Tumor stem cells derived from glioblastomas cultured in bFGF and EGF more closely mirror the phenotype and genotype of primary tumors than do serum-cultured cell lines" Cancer Cell, 9(5):391-403 (May 2006).

Lie et al., "Wnt signalling regulates adult hippocampal neurogenesis" Nature, 437:1370-1375 (Oct. 27, 2005).

Lledo et al., "Adult neurogenesis and functional plasticity in neuronal circuits" Nat. Rev. Neurosci., 7(3):179-193 (Mar. 2006).

MacDonald et al., "Identifying off-target effects and hidden phenotypes of drugs in human cells" Nat. Chem. Biol., 2(6):329-337 (Jun. 2006; e-pub: May 7, 2006).

Molofsky et al., "Bmi-1 dependence distinguishes neural stem cell self-renewal from progenitor proliferation" Nature, 425(6961): 962-967 (Oct. 30, 2003; e-pub: Oct. 22, 2003).

Nacher et al., "NMDA receptor antagonist treatment increases the production of new neurons in the aged rat hippocampus" Neurobiol. Aging, 24(2):273-284 (Mar.-Apr. 2003).

Newlands et al., "Temozolomide: a review of its discovery, chemical properties, pre-clinical development and clinical trials" Cancer Treat Rev., 23(1):35-61 (Jan. 1997).

Lichtermann et al., "Incidence of cancer among persons with schizophrenia and their relatives" Arch. Gen. Psychiatry, 58(6):573-578 (Jun. 2001).

Phillips et al., "Molecular subclasses of high-grade glioma predict prognosis, delineate a pattern of disease progression, and resemble stages in neurogenesis" Cancer Cell, 9(3):157-173 (Mar. 13, 2006).

Pomeroy et al., "Prediction of central nervous system embryonal tumour outcome based on gene expression" Nature, 415(6870):436-442 (Jan. 24, 2002).

Reynolds et al., "Clonal and population analyses demonstrate that an EGF-responsive mammalian embryonic CNS precursor is a stem cell" Dev. Biol., 175(90):1-13 (Apr. 10, 1996).

Reynolds et al., "Neural stem cells and neurospheres—re-evaluating the relationship" Nat. Methods, 2(5):333-336 (May 2005; e-pub: Apr. 21, 2005).

Santos et al., "'Stemness':Transcriptional profiling of embryonic and adult stem cells" Science, 298(5593):597-600 (Oct. 18, 2002; e-pub: Sep. 12, 2002).

Santarelli et al., "Requirement of hippocampal neurogenesis for the behavioral effects of antidepressants" Science, 301(5634):805-809 (Aug. 8, 2003).

Seifert et al., "Astrocyte dysfunction in neurological disorders: a molecular perspective" Nat. Rev. Neurosci., 7(3):194-206 (Mar. 2006).

Sharom et al., "From large networks to small molecules" Curr. Opin. Chem. Biol., 8(1):81-90 (Feb. 2004).

Singh et al., "Identification of human brain tumour initiating cells" Nature, 432: 396-401 (Nov. 18, 2004).

Singh et al., "Identification of a cancer stem cell in human brain tumors" Cancer Res., 63(18):5821-5828 (Sep. 15, 2003).

Taylor et al., "Radial glia cells are candidate stem cells of ependymoma" Cancer Cell, 8:323-335 (Oct. 17, 2005).

Tropepe et al., "Distinct neural stem cells proliferate in response to EGF and FGF in the developing mouse telencephalon" Dev. Biol., 208(1):166-188 (Apr. 1, 1999).

Uchida et al., "Direct isolation of human central nervous system stem cells" Proc. Natl. Acad. Sci. USA, 97(26):14720-14725 (Dec. 19, 2000).

Vescovi et al., "Brain tumour stem cells" Nat. Rev. Cancer, 6(6):425-436 (Jun. 2006).

Wishart et al., "DrugBank: a comprehensive resource for in silico drug discovery and exploration" Nucleic Acids Res., 34(Database Issue):D668-672 (Jan. 1, 2006).

Zhang et al., "A simple statistical parameter for use in evaluation and validation of high throughput screening assays" J. Bio. Screen., 4(2):67-73 (1999).

Stratton et al, Characterization of the human cell line TE671, Carcinogenesis, 10(5):899-905 (Marh 1989) (abstract only).

Rzeski et al, Glutamate antagonists limit tumor growth, PNAS, 98(11):6372-6377 (May 2001).

* cited by examiner

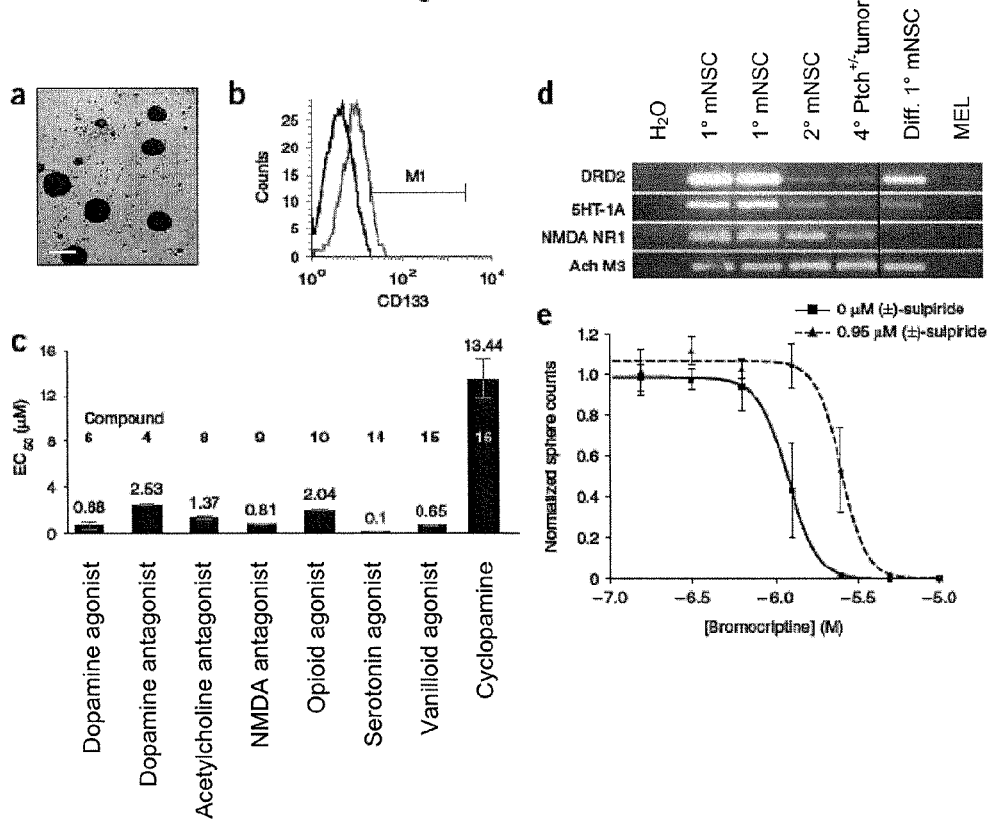
Figure 12 a to e

US 8,058,243 B2

METHOD FOR TREATING A BRAIN CANCER WITH IFENPRODIL

BACKGROUND OF INVENTION

The invention relates to compositions and methods to treat neurological disorders or damage, in particular brain or CNS cancer.

The identification of self-renewing and multipotent neural stem cells (NSC) in the mammalian brain holds promise for the treatment of many neurological diseases and has yielded new insight into brain cancer (5-7). However, the NSC "ground state"—defined by the complete repertoire of pathways that govern NSC proliferation, self-renewal and differentiation—remains largely uncharacterized. The in vitro culture of embryonic or postnatal brain cells isolated from anatomic precursor compartments in serum-free conditions containing FGF and EGF results in the expansion of a rare subpopulation of precursor cells and the formation of floating clonogenic clusters termed neurospheres (8-10) (FIG. 1a,b). Analysis of these neurosphere cultures has made it possible to elucidate the individual roles of developmental signaling pathways including the PTEN, Bmi 1, Notch, Wnt and Sonic Hedgehog (Shh) pathways in neural precursor proliferation, in concert with the known functions of these pathways in vivo (11-15). Although the candidate gene approach has been successful at uncovering vital pathways in NSC biology, to date only a small set of highly-studied networks has been sampled.

SUMMARY OF INVENTION

Applicants have developed a clonogenic neurosphere assay to carry out high throughput screens (HTS) to identify potent and/or selective modulators of proliferation, differentiation and/or renewal of neural precursor cells, neural progenitor cells and/or NSCs. The modulators disclosed herein and/or identified by a method described herein are also referred to herein as "NSC Modulating Agents".

In one aspect, a method is provided for identifying putative NSC Modulating Agents comprising incubating a neurosphere culture in the presence of a test agent and determining the effect of the test agent on proliferation, differentiation and/or renewal of neural precursor cells, neural progenitor cells and/or NSCs in the culture, wherein a difference in proliferation and/or renewal of neural precursor cells, neural progenitor cells and/or NSCs compared with a control neurosphere culture indicates that the test agent is a putative NSC Modulating Agent.

A method further comprises assessing the selectivity and/or potency of a putative NSC Modulating Agent by determining the effect of a putative NSC Modulating Agent on a normal astrocyte cell line. In an aspect, selectivity and/or potency are assessed by constructing dose-response curves and $EC_{50}$s for the normal astrocyte cell line and calculating a neurosphere selectivity ratio. A neurosphere selectivity ratio can be defined as $EC_{50}$ astrocytes/$EC_{50}$ precursor cells. A neurosphere selectivity ratio greater than that observed in controls indicates that the putative NSC Modulating Agent is potent and/or selective. Therefore a method may further comprise assessing the selectivity and/or potency of a putative modulator by comparing a neurosphere selectivity ratio of the modulator in a normal astrocyte cell line to that of a control. In certain embodiments, the controls comprise cycloheximide, etoposide and carboplatin. In other embodiments, the neurosphere selectivity ratio is greater than 3, 4, 5, 6, 7, 8, 9 or 10.

Using the methods described herein, modulators have been identified that modulate proliferation, differentiation and/or renewal of normal and diseased (e.g. cancerous) neural precursor cells, neural progenitor cells and/or NSCs.

In another aspect, a composition comprising one or more NSC Modulating Agents, and a pharmaceutically acceptable carrier, excipient or diluent is provided.

In a further aspect, a composition is also provided and comprises one or more NSC Modulating Agent in a therapeutically effective amount for inhibiting proliferation, differentiation and/or renewal of neural precursor cells, neural progenitor cells and/or NSCs, in particular diseased (e.g., cancerous) neural precursor cells, neural progenitor cells and/or NSCs.

In one embodiment, a composition comprising one or more NSC Modulating Agent in a therapeutically effective amount for treatment of a brain or CNS cancer, more particularly a primary CNS tumor is further provided.

In another embodiment, a composition comprising one or more NSC Modulating Agent in a therapeutically effective amount for treatment of a brain tumor having a genetic profile resembling that of normal and embryonic neural precursor cells is also provided.

In another embodiment, a composition comprises one or more NSC Modulating Agent in a therapeutically effective amount for treatment of a brain tumor enriched for cancer stem cells.

In other embodiments of compositions for treating a condition requiring inhibition of proliferation, differentiation and/or renewal of neural precursor cells, neural progenitor cells and/or NSCs, the NSC Modulating Agents in the composition are one or more agents that modulate neurotransmission in the dopamine, serotonin, opioid, glutamate, and/or vanilloid pathways. More particularly, the NSC Modulating Agents in the composition are one or more of a dopamine receptor antagonist, a dopamine receptor agonist, an acetylcholine receptor antagonist, an NMDA receptor antagonist, an opioid receptor agonist, a retinoic acid receptor agonist, a JAK3 antagonist, a p38 MAPK antagonist, a serotonin receptor agonist, or a vanilloid receptor agonist. Most particularly the NSC Modulating Agents are one or more of (±)butaclamol, R(−) propylnorapomorphine, apomorphine, cis-(Z) flupenthixol, hexahydro-sila-difenidol, ifenprodil tartrate, carbetapentane citrate, fenretinide, WHI-P131, SB 202190, p-aminophenethyl-m-trifluoromethylphenyl piperazine (PAPP), and dihydrocapsaicin. In certain aspects, the NSC Modulating Agent in the composition is one or both of apomorphine and ifenprodil.

In another aspect, a composition comprises one or more NSC Modulating Agent in a therapeutically effective amount for inducing proliferation of normal neural precursor cells and/or neural progenitor cells.

In still another aspect, a composition comprising one or more NSC Modulating Agent in a therapeutically effective amount for inducing differentiation and/or renewal of normal neural precursor cells, neural progenitor cells and/or NSCs is further provided.

In yet a further aspect, a composition comprises an NSC Modulating Agent in a dosage effective for inducing proliferation of neural stem cells into an increased amount of neural progenitor cells, or for inducing proliferation of neural stem cells or neural progenitor cells into an increased amount of neural cells, e.g., glia, neurons, astrocytes and/or oligodendrocytes.

In another aspect, a composition for treatment of a neural disorder, in particular a neurological disease, neurodegenerative disease, or central nervous system (CNS) trauma is provided and comprises an NSC Modulating Agent in a dosage effective for inducing proliferation of neural stem cells into an increased amount of neural progenitor cells.

In yet another aspect, a composition is provided for treatment of a neural disorder, in particular a neurological disease, a neurodegenerative disease, or central nervous system (CNS) trauma comprising an NSC Modulating Agent in a dosage effective for inducing proliferation and/or differentiation of neural stem cells or neural progenitor cells into an increased amount of neural precursor cells or neural cells, e.g., glia, neurons, astrocytes and/or oligodendrocytes.

Proliferation, differential and/or renewal of neural precursor cells, neural progenitor cells and/or NSCs neural precursor cells may be induced ex vivo or in vivo. The composition can be in a pharmaceutically acceptable carrier, excipient, or vehicle.

Additionally provided is a method of preparing a stable pharmaceutical composition comprising one or more NSC Modulating Agent. A method can comprise mixing one or more NSC Modulating Agent and a pharmaceutically acceptable carrier, excipient, or vehicle, in particular, a pharmaceutically acceptable carrier, excipient, or vehicle which may be effective to physically stabilize the compound(s). After compositions have been prepared, they can be placed in an appropriate container and labeled for treatment of an indicated condition. For administration of a composition described herein, such labeling would include amount, frequency, and method of administration.

NSC Modulating Agents may be used in the treatment of conditions that require modulation of proliferation, differentiation and/or renewal of normal or diseased neural precursor cells, neural progenitor cells and/or NSCs.

Therefore, in an aspect, a method is provided for treating or preventing a condition requiring modulation (e.g., inhibition) of proliferation, differentiation and/or renewal of diseased neural precursor cells, neural progenitor cells and/or NSCs comprising administering to a subject in need thereof a therapeutically effective amount of an NSC Modulating Agent or a composition of the invention. In embodiments of this aspect, the NSC Modulating Agent is one or more of a dopamine receptor antagonist, a dopamine receptor agonist, an acetylcholine receptor antagonist, an NMDA receptor antagonist, an opioid receptor agonist, a retinoic acid receptor agonist, a JAK3 antagonist, a p38 MAPK antagonist, a serotonin receptor agonist, or a vanilloid receptor agonist. More particularly, the NSC Modulating Agents are one or more of (±)butaclamol, R(−) propylnorapomorphine, apomorphine, cis-(Z) flupenthixol, hexahydro-sila-difenidol, ifenprodil tartrate, carbetapentane citrate, fenretinide, WHI-P131, SB 202190, p-aminophenethyl-m-trifluoromethylphenyl piperazine (PAPP), and dihydrocapsaicin.

In another aspect, a method for treating or preventing a condition requiring modulation of proliferation, differentiation and/or renewal of normal neural precursor cells, neural progenitor cells and/or NSCs is provided and comprises administering to a subject in need thereof a therapeutically effective amount of an NSC Modulating Agent or a composition described herein.

Also contemplated is the use of an NSC Modulating Agent or a composition described for the preparation of medicaments for treating or preventing a condition requiring modulation of proliferation, differentiation and/or renewal of normal or diseased neural precursor cells, neural progenitor cells and/or NSCs. Additionally provided are uses of a pharmaceutical composition described herein in the preparation of medicaments for the prevention and/or treatment of conditions and/or diseases disclosed herein.

The invention has particular application in preventing and/or treating brain or CNS cancer. Thus, a method of treatment is provided and comprises administering a therapeutically effective amount of one or more NSC Modulating Agent or a composition described herein which upon administration to a subject with symptoms of a brain or CNS cancer produces beneficial effects, preferably sustained beneficial effects (e.g., inhibition of proliferation, differentiation and/or renewal of normal or diseased neural precursor cells, neural progenitor cells and/or NSCs), in particular cancerous neural precursor cells.

In an embodiment, a method is provided for preventing and/or treating a primary CNS tumor comprising administering a therapeutically effective amount of one or more NSC Modulating Agent or a composition discussed herein.

In a further embodiment, a method for ameliorating progression of a condition and/or disease or obtaining a less severe stage of a condition and/or disease in a person suffering from a brain or CNS cancer, in particular a primary CNS tumor, is provided and comprises administering a therapeutically effective amount of one or more NSC Modulating Agent or a composition discussed herein.

A method of delaying the progression of a brain or CNS cancer, in particular a primary CNS tumor, is further provided and comprises administering a therapeutically effective amount of one or more NSC Modulating Agent or a composition provided herein.

A kit is also provided and comprises one or more one or more NSC Modulating Agent or a composition described herein. In an aspect, a kit is provided for preventing and/or treating brain or CNS cancer, containing a composition comprising one or more NSC Modulating Agent or a composition described herein, a container, and instructions for use. The composition of the kit can further comprise a pharmaceutically acceptable carrier, excipient, or vehicle.

These and other aspects, features, and advantages of the present invention should be apparent to those skilled in the art from the following drawings and detailed description.

DETAILED DESCRIPTION OF THE INVENTION

Glossary

Figure 1:
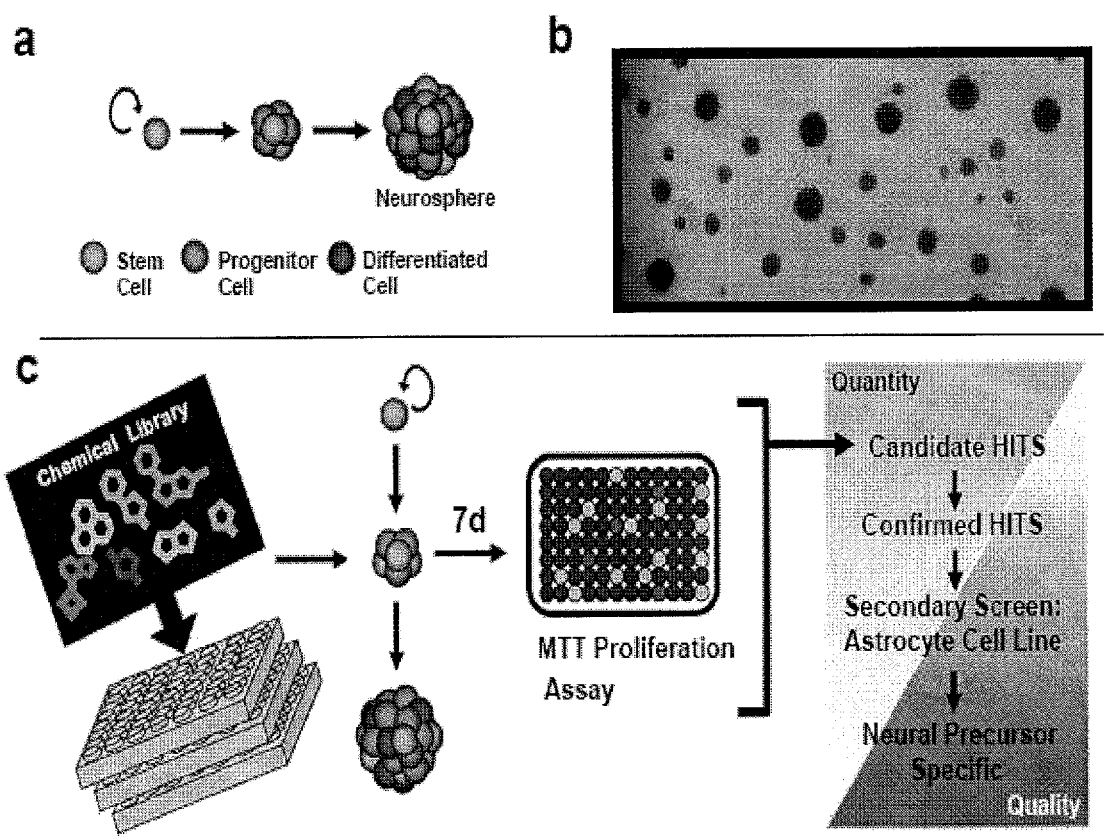
FIG. 1 shows a Schematic of HTS of neural precursor cells (a) Neurospheres are derived from self-renewing multi-potent NSCs and contain a heterogeneous mixture of stem, progenitor, and a very small number of differentiated cells. (b) Light microscope image of neurospheres grown for seven days at clonal density. Scale bar, 100 µM (c) Schematic of the small molecule screen. Primary neurospheres were dissociated and screened against small molecules in 96-well plates. Compounds that affect neural precursor proliferation (including NSC self renewal) were identified with an MTT proliferation assay and verified hits interrogated in other assays.

For convenience, certain terms employed in the specification, examples, and appended claims are collected here.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. Thus, for example, reference to a composition containing "a NSC Modulating Agent" includes a mixture of two or more compounds. The term "about" means plus or minus 0.1 to 50%, 5-50%, or 10-40%, preferably 10-20%, more preferably 10% or 15%, of the number to which reference is being made.

The terms "subject" and "patient" are used interchangeably herein and refer to an animal including a warm-blooded animal such as a mammal, which is afflicted with or suspected of having or being pre-disposed to a condition disclosed herein. Preferably, the terms refer to a human. The terms also include domestic animals bred for food, sport, or as pets, including horses, cows, sheep, poultry, fish, pigs, cats, dogs, and zoo animals. The methods herein for use on subjects and patients contemplate prophylactic as well as curative use. Typical subjects for treatment include persons susceptible to, suffering from or that have suffered a condition disclosed herein.

The terms "administering" or "administration" refers to the process by which a therapeutically effective amount of an NSC Modulating Agent or composition contemplated herein is delivered to a patient for prevention and/or treatment purposes. Compositions are administered in accordance with good medical practices taking into account the patient's clinical condition, the site and method of administration, dosage, patient age, sex, body weight, and other factors known to physicians.

The term "pharmaceutically acceptable carrier, excipient, or vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbants that may be needed in order to prepare a particular composition. The use of such media and agents for an active substance is well known in the art.

By "pharmaceutically acceptable salts" is meant those salts which are suitable for use in contact with the tissues of a subject or patient without undue toxicity, irritation, allergic response and the like, and are commensurate with a reasonable benefit/risk ratio. Pharmaceutically acceptable salts are well known in the art and are described for example, in S. M. Berge, et al., J. Pharmaceutical Sciences, 1977, 66:1

The term "pharmaceutically acceptable salt(s)" includes salts of acidic or basic groups which may be present in the compounds which can be employed. In particular, pharmaceutically acceptable acid addition salts of an NSC Modulating Agent are provided. Acids which can be used to prepare the pharmaceutically acceptable acid addition salts are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, para-toluenesulfonate and pamoate [i.e., 1,1'-methylene-bis-(2-hydroxy-3-naphthoate)] salts. In other aspects, pharmaceutically acceptable base addition salts of an NSC Modulating Agent are also provided. Chemical bases that may be used as reagents to prepare pharmaceutically acceptable base salts are those that form nontoxic base salts with such compounds. Suitable nontoxic base salts include, without limitation, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

The term "treating" refers to reversing, alleviating, or inhibiting the progress of a disease, or one or more symptoms of such disease, to which such term applies. Depending on the condition of the subject, the term also refers to preventing a disease, and includes preventing the onset, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition described herein to a subject that is not at the time of administration afflicted with the disease. "Preventing" also refers to preventing the recurrence of a disease, or of one or more symptoms associated with such disease. The terms "treatment" and "therapeutically," refer to the act of treating, as "treating" is defined above. The purpose of prevention and intervention is to combat the disease, condition, or disorder and includes the administration of the active compounds to prevent or delay the onset of the symptoms or complications, or alleviating the symptoms or complications, or eliminating the disease, condition, or disorder.

The terms "treating" and "treatment" utilized herein in respect to a CNS tumor or primary CNS tumor refer to a situation where the severity of a symptom of a CNS tumor, including the volume of the tumor or the frequency with which any symptom or sign of the tumor is experienced by a patient, or both, is reduced, or where time to tumor progression or survival time is increased.

A "beneficial effect" refers to an effect of an NSC Modulating Agent or composition described herein that is greater than the effect without the agent or composition. The beneficial effect includes favorable pharmacological and/or therapeutic effects, and improved pharmacokinetic properties and biological activity. In another aspect, the beneficial effect is a "sustained beneficial effect" where the beneficial effect is sustained for a prolonged period of time after termination of treatment. A beneficial effect may be sustained for at least about 1 to 5 days, 2 to 7 days, 1 to 2 weeks, 1 to 4 weeks, and 1 to 6 weeks, 2 to 16 weeks, 2 weeks to 6 months or periodically following treatment. The period of time a beneficial effect is sustained may correlate with the duration and timing of the treatment. A subject may be treated continuously for about 1 to 3 days, 1 to 5 days, 2 to 7 days, 1 to 2 weeks, 1 to 4 weeks, and 1 to 6 weeks, 2 to 16 weeks, 2 weeks to 6 months or periodically.

The beneficial effect may be a statistically significant effect in terms of statistical analysis of an effect of an agent when compared to no agent. "Statistically significant" or "significantly different" effects or levels with an agent may represent levels that are higher or lower than a standard. In one embodiment, the difference may be 1.5, 2, 3, 4, or 5 times higher or lower compared with the effect obtained without the agent.

A "medicament" refers to a pharmaceutical composition suitable for administration of a pharmaceutically active compound(s) (i.e., NSC Modulating Agent) to a patient.

"Therapeutically effective amount" relates to the amount or dose of an active compound or composition described herein that will lead to one or more therapeutic effect, in particular desired beneficial effects. A therapeutically effective amount of a substance can vary according to factors such as the disease state, age, sex, and weight of the subject, and the ability of the substance to elicit a desired response in the subject. Dosage regime may be adjusted to provide the optimum therapeutic response. For example, several divided doses may be administered daily or the dose may be proportionally reduced as indicated by the exigencies of the therapeutic situation.

A "neural stem cell" refers to an undifferentiated neural cell capable of proliferation, self-maintenance, and production of differentiated functional progeny.

A "neural progenitor cell" refers to an undifferentiated cell derived from a neural stem cell, which is not itself a stem cell. Some progenitor cells can produce progeny that are capable of differentiating into more than one cell type. A progenitor cell, unlike a stem cell, has limited proliferative ability and thus does not exhibit self-maintenance. It is committed to a particular path of differentiation and will, under appropriate conditions, eventually differentiate into neurons, glia, astrocytes or oligodendrocytes. In one embodiment, the neural progenitor cells are early neural progenitor cells.

The term "neural precursor cells" refers to the progeny of neural stem cells, and thus includes both progenitor cells and daughter neural stem cells.

A "modulator" includes an "inhibitor", "antagonist", "stimulator", "activator", "enhancer" or "agonist". An "inhibitor" or "antagonist" is defined by any molecule/compound/agent that is capable of eliciting a decrease in an activity or response (e.g., a NSC Modulating Agent that elicits a decrease in proliferation, differentiation and/or renewal of neural precursor cells, neural progenitor cells and/or NSCs). A "stimulator", "activator", "enhancer" or "agonist" is defined by any molecule/compound/agent that is capable of eliciting an increase in an activity or response (e.g., a NSC Modulating Agent that elicits an increase in proliferation, differentiation and/or renewal of neural precursor cells, neural progenitor cells and/or NSCs).

"NSC Modulating Agent" refers to a modulator that modulates proliferation, differentiation and/or renewal of neural precursor cells, neural progenitor cells and/or NSCs. Examples of NSC Modulating Agents that modulate proliferation, differentiation and/or renewal of diseased neural precursor cells, neural progenitor cells and/or NSCs include without limitation, dopamine receptor antagonists, dopamine receptor agonists, acetylcholine receptor antagonists, NMDA receptor antagonists, opioid receptor agonists, retinoic acid receptor agonists, JAK3 antagonists, p38 MAPK antagonists, serotonin receptor agonists, or vanilloid receptor agonists. An NSC Modulating Agent may be a commercially available drug or a new formulation of a commercially available drug adapted for treating a condition disclosed herein.

A "dopamine receptor" refers to a receptor that mediates dopaminergic neurotransmission in the central nervous system and in particular members of the G protein-coupled receptor family, more particularly striatal dopamine receptors. Dopamine receptors include without limitation D1, D2, D3, D4, and D5 dopaminergic receptors.

"Dopamine receptor agonists" include natural and synthetic agents that function as specific agonists acting on dopamine receptors, in particular striatal dopamine receptors. Suitable agonists are well known in the art and readily available for use within the methods and compositions described herein. A principal class of dopamine receptor agonists for use herein includes natural and synthetic or semisynthetic ergolines derived or modeled after ergot alkyloids, for example, apomorphines and ergotamines.

Particular examples of dopamine receptor agonists include, without limitation, levodopa/carbidopa, amantadine, bromocriptine, pergolide, R(−) propylnorapomorphine, apomorphine, benserazide, lysuride, mesulergine, lisuride, lergotrile, memantine, metergoline, piribedil, tyramine, tyrosine, phenylalanine, bromocriptine mesylate, pergolide mesylate, and the like, preferably R(−) propylnorapomorphine or apomorphine.

The dopamine receptor agonist may be selected from among adrogolide, A-86929, rotigotine, NeurVex, Nolomirole, pramipexole, talipexole, CHF 1512, (−)-stepholidine, DAR-201, Diacrin/Genzyme, bromocriptine, Bupropion, LEK-8829, BAM-1110, AIT-203, NS-2330, Terguride, Aripiprazole, OPC-4392, GMC-1111, PD-148903, apomorphine HCl, PD-89211, PD-158771, cabergoline, sumanirole, PNU-14277E, POL-255, dihydrexidine, GBR-12783, quinagolide HCl, (R)-bupropion, S-32504, S-33592, SKF-80723, SKF-83959, fenoldopam, ropinirole, SKF-82958, SKF-77434, DU 127090, SLV-308, SLV 318, NeuroCRIB, SP-1037C, spheramine, Gallotrank, Preclamol, DAB-452, YM-435, BP-897, ProSavin, Etilevodopa, P63, A 68930, A 77636, Alaptide, Alentemol, CI 1007; PD 143188, BLSI, JA 116a; JA 116, Melevodopa; Levodopa methyl; CHF 1301; NSC 295453; Levomet, MR 708, PD 128483, RD 211, SKF 38393, SKF 81297, U 86170F, U 91356A, WAY 124486 and Z 15040.

A dopamine receptor agonist that acts on one or more specific dopamine receptors may be selected. For example, certain tetralins and related ergoline derivatives have been reported as centrally acting D2 dopamine receptor agonists (Wickstrom, *Prog Med. Chem.* 29:185-216, 1992); and 5-hydroxy-2-N,N-n-dipropylaminotetralin (5-OH-DPAT), 7-OH-DPAT and 8-OH-DPAT, have been reported as specific and selective ligands for the D3 receptors (Levesque, *Proc. Natl. Acad. Sci. USA* 89:8155-8159, 1992; Mulder, et al., *Arch. Pharmacol* 336: 494-501, 1987; and Beart, et al, *Arch. Pharmacol.* 336: 487-493, 1987)

Additional dopamine receptor agonists that may be useful include for example, SKF-38393 HCl (SKF), a D1 dopaminergic receptor agonist (Muralikrishnan, *Brain Res.* 892:241-7, 2001); ropinirole (SKF-101468) (Reaville et al., *J. Pharm. Pharmacol* 52:1129-35, 2000); and, ABT-431, a D1 agonist (Self et al., *Ann. N Y Acad. Sci.* 909:133-44, 2000). See also DeWald et al., *J. Med. Chem.* 33:445-450, 1990; Grol et al., *J. Pharm. Pharmacol.* 43:481-485, 1991; Hall et al., *J. Med. Chem.* 30:1879-1887, 1987; Horn et al., *J. Med. Chem.* 27: 1340-1343, 1984; Johansson et al., *J. Med. Chem.* 30: 1827-1837, 1987; Jobansson et al., *Mol. Pharmacol.* 30:258-269, 1986; Johansson et al., *J. Med. Chem.* 28:1049-1053, 1985; Johansson et al., *J. Med. Chem.* 30:602-611, 1987; Johansson et al., *J. Org. Chem.* 51: 5252-5258, 1986; Johansson et al., *J. Med. Chem.* 33:2925-2929, 1990; Jones et al., *J. Med. Chem.* 27:1607-1613; 1984; Langlois et al., *Synthetic Comm.* 22:1723-1734, 1992; Martin et al., *J. Pharmacol. Exp. Ther.* 230:569-576, 1989; Neumeyer et al., *J. Med. Chem.* 34:24-28, 1991; Seiler et al., *Mol. Pharmacol.* 22:281-289, 1982; and Sibley et al., *TIPS* 13: 61-68, 1992 for additional teachings regarding identification, selection, pharmacology, and production of dopamine receptor agonists and their derivatives and analogs for use within the methods and compositions described herein.

"Dopamine receptor antagonists" include natural and synthetic agents that function as specific antagonists acting on dopamine receptors, in particular striatal dopamine receptors. A dopamine receptor antagonist is generally capable of blocking, either completely or partially, the action and/or function of the receptor. Suitable antagonists are well known in the art and readily available for use within the methods and compositions described herein. Particular examples of dopamine receptor antagonists are cis-(Z) flupenthixol, perphenazine, (±) butaclamol, and alkylphosphocholines, in particular miltefosine, domperidone and pimozide, preferably butaclamol.

"NMDA receptor antagonist" refers to compounds which are capable of blocking, either completely or partially, the action and/or function of the NMDA receptor or the NMDA receptor complex. NMDA receptor antagonists block the ion channel, others act at the glycine(B) site, and still others are selective for NR2B NMDA receptor subtypes (see, inter alia, Danysz and Parsons (2002) Neurotox Res 4, 119-126 or Danysz et al (2002) Curr Pharm Des 8, 835-843). "NMDA receptor antagonists" include natural and synthetic agents that function as specific antagonists acting directly on an NMDA receptor. NMDA receptor antagonists are well known and can be selected for use herein.

An NMDA receptor antagonist to be employed preferably inhibits/blocks a human NMDA receptor(s). Human NMDA receptors have been described in the art and are also described by their protein structure and/or their encoding nucleotide sequences. Sequences for NMDA receptors may easily be obtained in current databases, like the EMBL-EBI™ database under www.ebi.ac.uk or the NCBI database under www.ncbi.nlm.nih.gy. Exemplified, non limiting NMDA receptors comprise the receptors encoded by nucleotide sequences as shown under NM 00835 and NM 00833 in the NCBI database (gene accession number).

Examples of NMDA receptor antagonists include 1-amino-alkylcyclohexanes like memantine or neramexane (MRz 2/579 or 1-amino-1,3,3,5,5-pentamethyl-cyclohexane) (see International Patent Publication No. WO 2005/009421, US Patent Publication No. 2004/0087658, U.S. Pat. No. 4,122,193; U.S. Pat. No. 4,273,774 or U.S. Pat. No. 5,061, 703), 6,7-dichloro-5-nitro-1,4-dihydro-2,3-quinoxalinedione (licostinel) (ACEA 1021), gavestinel, CP-101606, Ro-25-6981, Co101244 (see Kohl (2001) Curr Med. Chem. 8, 1275-1289), eliprodi (see U.S. Pat. No. 5,547,963, International Patent Publication No. WO 97/33582, International Patent Publication No. WO 97/02823, U.S. Pat. No. 5,023, 266), dizocilpine, conantokins, ifenprodil, ifenprodil tartrate, arcaine, pentamidine isethionate, L-701, 324, CGP4O1 16, LY235959, LY233053, MRZ2/576, LU73068, 4-Cl-KYN or pharmaceutically acceptable salts or prodrugs of these substances, including the hydrochloride salt of neramexane, namely 1-amino-1,3,3,5,5-pentamethyl-cyclohexane hydrochloride, and the mesylate salt of neramexane, namely 1-amino-1,3,3,5,5-pentamethyl-cyclohexane mesylate. In one embodiment, the NMDA receptor antagonist is ifenprodil, ifenprodil tartrate, memantine or neramexane.

"Acetylcholine receptor antagonists" include natural and synthetic agents that function as specific antagonists acting on acetylcholine receptor. An acetylcholine receptor antagonist is generally capable of blocking, either completely or partially, the action and/or function of the receptor. Suitable antagonists are well known in the art and readily available for use within the methods and compositions described herein. Particular examples of acetylcholine receptor antagonists are the M1 antagonists R-trihexyphenidyl, telenzepine and pirenzepine, the M3 antagonists hexahydro-sila-difenidol and p-fluorohexahydro-siladifenidol, and the M2 and M4 antagonists himbacine methoctramine, AF-DX 116 and AQ-RA 741, preferably hexahydro-sila-difenidol.

"Opioid receptor agonists" include natural and synthetic agents that function as specific agonists acting on an opioid receptor. An opioid dopamine receptor agonist is generally capable of stimulating or enhancing, either completely or partially, the action and/or function of the receptor. Suitable antagonists are well known in the art and readily available for use within the methods and compositions discussed herein. Particular examples of opioid receptor agonists are carbetapentane citrate, dextromethorphan, dextromethorphan hydrobromide, noscapine, metaphit methanesulfonate, and chlophedianol hydrochloride, preferably carbetapentane citrate.

"Retinoic acid receptor agonists" include natural and synthetic agents that function as specific agonists acting on a retinoic acid receptor. A retinoic acid receptor agonist is generally capable of stimulating or enhancing, either completely or partially, the action and/or function of the receptor. Suitable agonists are well known in the art and readily available for use within the methods and compositions provided herein. An "RAR agonist" can be either naturally occurring or a synthetic retinoid, preferably having selective activity as an agonist for RARs and high potency in antagonism of AP-1-dependent gene expression. Examples of naturally occurring retinoids with activity as RAR agonists are all-trans retinoic acid (all-trans RA) and 9-cis retinoic acid (9-cis RA), which are stereoisomers, all-trans RA being naturally converted into 9-cis RA during metabolism (J. G. Allen, et al., Pharmac. Ther. 40:1-27, 1989). Synthetically retinoids are well known in the art. For example, U.S. Pat. No. 5,234,926, discloses methods of synthesizing disubstituted acetylenes bearing heteroaromatic and heterobicyclic groups with selective activity as RAR agonists. U.S. Pat. No. 4,326,055 discloses methods for synthesizing 5,6,7,8-tetrahydro naphthyl and indanyl stilbene derivatives with retinoid-like activity. Examples of synthetic RAR agonists that may be used are ethyl 6-[2-(4,4-dimethylthiochroman-6-yl)ethynyl]nicotinate and 6-[2-(4,4-dimethylchroman-6-yl)ethynyl]nicotinic acid (see U.S. Pat. No. 5,234,926); and p-[(E)-2-(5,6,7,8-tetrahydro-5,5,8,8-tetramethyl-2-naphthyl)propenyl]-benzoic acid (see U.S. Pat. No. 4,326,055). In one aspect, the retinoic acid receptor agonist is fenretinide.

"JAK3 antagonists" include natural and synthetic agents that function as specific antagonists acting on JAK3. A JAK3 antagonist is generally capable of blocking, either completely or partially, the action and/or function of JAK3. Suitable antagonists are well known in the art and readily available for use within the methods and compositions described herein. Particular examples of JAK3 antagonists are WHI-P131 and the JAK3 inhibitors disclosed in U.S. Pat. No. 6,933,300 including without limitation 4-(4'-hydroxylphenyl)-amino-6,7-dimethoxyquinazoline (P131), 4-(3'-bromo-4'-hydroxylphenyl)-amino-6,7-dimethoxyquinazoline (P154), 4-(3'-hydroxyphenyl)-amino-6,7-dimethoxyquinazoline, (P180) and 4-(3',5'-dibromo-4'-hydroxyphenyl)-6,7-dimethoxyquinazoline (P97).

"p38 MAPK antagonists" include natural and synthetic agents that function as specific antagonists acting on the p38 subfamily of MAP kinases, including p38α, p38β, p38γ, and p38δ. A p38 MAPK antagonist is generally capable of blocking, either completely or partially, the action and/or function of a MAP kinase. Suitable antagonists are well known in the art and readily available for use within the methods and compositions described herein. Particular examples of p38 MAPK antagonists are SB 202190 (Sigma Aldrich), SB203580 and PD169316 (Fu Y et al, Biochem Biophys Res Commun. 2003 Oct. 17; 310(2):391-7), and FR167653 (Nishikawa et al, Arthritis Rheum. 2003 September; 48(9): 2670-81).

"Serotonin receptor agonists" include natural and synthetic agents that function as specific agonists acting on a serotonin receptor. A serotonin receptor agonist is generally capable of stimulating or enhancing, either completely or partially, the action and/or function of the receptor. Suitable agonists are well known in the art and readily available for use within the methods and compositions provided herein. Particular examples of serotonin receptor agonists are aminophenethyl-m-trifluoromethylphenyl piperazine (PAPP), 8-OH-DPAT, sumatriptan, L694247 (2-[5-[3-(4-methylsulphonylamino) benzyl-1,2,4-oxadiazol-5-yl]-1H-indol-3yl]ethanamine), buspirone, alnitidan, zalospirone, ipsapirone, gepirone, zolmitriptan, risatriptan, 311C90, α-Me-5-HT, BW723C86 (1-[5(2-thienylmethoxy)-1H-3-indolyl[propan-2-amine hydrochloride), and MCPP (m-chlorophenylpiperazine).

"Vanilloid receptor agonists" include natural and synthetic agents that function as specific agonists acting on a vanilloid receptor. A vanilloid receptor agonist is generally capable of stimulating or enhancing, either completely or partially, the action and/or function of the receptor. Suitable agonists are well known in the art and readily available for use within the methods and compositions herein. Particular examples of opioid receptor agonists are dihydrocapsaicin, resiniferatoxin and other resiniferatoxin-like complex polycyclic compounds such as tinyatoxin, capsaicin and other capsaicin analogs such as dihydrocapsaicin, ovanil, anandamid, eicosinoids prostacyclin, $PGE_2$, 20-homovanillyl esters of diterpenes such as 12-deoxyphorbol 13-phenylacetate 20-homovanillate and mezerein 20-homovanillate (see U.S. Pat. Nos. 4,939,194; 5,021,450; and 5,232,684), analogs of capsaicins including vanillylacylamides, homovanillyl acylamides, carbamate derivatives, sulfonamide derivatives, urea derivatives, aralkylamides and thioamides, aralkyl aralkanamides, phenylacetamides and phenylacetic acid esters, olvanil (N-vanillyl-9-octadecenamide). See, e.g., U.S. Pat. No. 5,962,532; U.S. Pat. No. 5,762,963; U.S. Pat. No. 5,221,692; U.S. Pat. No. 4,313,958; U.S. Pat. No. 4,532,139; U.S. Pat. No. 4,544,668; U.S. Pat. No. 4,564,633; U.S. Pat. No. 4,544,669; and U.S. Pat. Nos. 4,493,848; 4,532,139; 4,564,633; and 4,544,668; and the agonists described in International Patent Publication No. WO 00/50387, and agonists disclosed by Hwang et al., *PNAS* 97 (11): 6155-6160 (2000).

The terms "dopainine receptor agonists", "dopamine receptor antagonists", "acetylcholine receptor antagonist", "NMDA receptor antagonist", "opioid receptor agonist", "retinoic acid receptor agonist", "JAK3 antagonist", "p38 MAPK antagonist", "serotonin receptor agonist", and "vanilloid receptor agonist" as used herein also embrace chemically modified analogs, derivatives, salts and esters of the agonists/antagonists which are "pharmaceutically acceptable," for example salts and esters that are suitable for use in contact with mucosal tissues of humans and other mammals, without undue toxicity, irritation, allergic response, and the like, and which retain activity for their intended use. Pharmaceutically acceptable salts can be prepared in situ during isolation and purification of the agonists or antagonists, or separately by reacting the free base or acid functions of the agonists or antagonists with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, lauryl sulphate salts and the like. Representative alkali or alkaline earth metal salts include the sodium, calcium, potassium and magnesium salts, and the like.

As used herein, the terms "condition" and "disease" are used interchangeably to refer to a condition or disease in a subject. "Condition" and "disease" include but are not limited to diseases or disorders where there is neurological damage or a neurological disorder.

In one aspect, the disease is a disease of the brain or central nervous system. In particular aspects utilizing NSC Modulating Agents that are antagonists or inhibitors of proliferation, differentiation and/or renewal of diseased (e.g. cancerous) neural precursor cells, neural progenitor cells and/or NSCs, the condition or disease is an abnormal growth in the brain or central nervous system, more particularly a primary CNS tumor. In an embodiment, the condition is brain or CNS cancer, more particularly a primary CNS tumor. In embodiments, the condition is a brain tumor having a genetic profile resembling that of normal and embryonic neural precursor cells. In other embodiments, the condition is a brain tumor enriched for cancer stem cells.

"Primary CNS tumor" includes a neoplasia with origins in the brain, in that the cancerous cells did not originate in another part of the body and metastasize to the brain. Examples of primary CNS tumors include, but are not limited to, gliomas, well-differentiated astrocytomas, anaplastic astrocytomas, glioblastoma multiforme, ependymomas, oligodendrogliomas, ganglioneuromas, mixed gliomas, brain stem gliomas, optic nerve gliomas, meningiomas, pineal tumors, pituitary tumors, pituitary adenomas, reactive gliosis, primitive neuroectodermal tumors, medulloblastomas, schwannomas, lymphomas, vascular tumors, and lymphomas.

In aspects utilizing NSC Modulating Agents that are agonists or stimulators of proliferation, differentiation and/or renewal of normal neural precursor cells, neural progenitor cells and/or NSCs the condition or disease is a neurological disorder including Down Syndrome, Parkinson's disease, Huntington's Chorea, pathogenic psychotic conditions, schizophrenia, neurodegenerative disorders including cognitive dysfunction and dementia (e.g., Alzheimer's disease) or central nervous system (CNS) trauma (e.g., stroke and epilepsy).

In particular aspects utilizing NSC Modulating Agents that are agonists or stimulators of proliferation, differentiation and/or renewal of normal neural precursor cells, neural progenitor cells and/or NSCs, the condition or disease is a neurological disorder including without limitation a presenile dementia (early onset Alzheimer's disease), senile dementia (dementia of the Alzheimer's type), Parkinsonism including Parkinson's disease, Huntington's chorea, tardive dyskinesia, hyperkinesias, mania, attention deficit disorder, attention deficit hyperactivity disorder, sleep-wake disorder, chronic-fatigue syndrome, tremor, epilepsy, neuropathic pain, addiction (e.g., nicotine addiction), anxiety, dyslexia, schizophrenia, obsessive-compulsive disorder, and Tourette's syndrome.

DETAILED DESCRIPTION OF EMBODIMENTS OF THE INVENTION

A pharmaceutical composition which has been adapted for administration to a subject to treat a condition or disease disclosed herein (e.g., brain or CNS tumors) is provided. In an aspect the composition is in a form such that administration to a subject results in modulation of proliferation, differentiation and/or renewal of normal or diseased (e.g. cancerous) neural precursor cells, neural progenitor cells and/or NSCs. In an embodiment, the composition is in a form such that administration to a subject results in inhibition of proliferation, differentiation and/or renewal of diseased (e.g. cancerous) neural precursor cells, neural progenitor cells and/or NSCs. In another embodiment, the composition is in a form such that administration to a subject results in stimulation of proliferation, differentiation and/or renewal of normal neural precursor cells, neural progenitor cells and/or NSCs.

Methods are provided for the prevention, treatment or intervention of a condition in a subject comprising administering an NSC Modulating Agent or a pharmaceutical composition described herein to provide a beneficial effect, more particularly a sustained beneficial effect.

In an aspect, a method is also provided for the prevention or intervention of a condition discussed herein in a subject comprising administering a therapeutically effective amount of an NSC Modulating Agent. In one aspect, a treatment or intervention is provided which provides beneficial effects, including sustained beneficial effects following treatment.

In methods providing beneficial effects, in particular statistically significant beneficial effects or sustained beneficial effects, an NSC Modulating Agent inhibits proliferation, differentiation and/or renewal of diseased neural precursor cells, neural progenitor cells and/or NSCs.

The invention relates to a method of treatment comprising administering a therapeutically effective amount of at least one NSC Modulating Agent which upon administration to a subject with symptoms of, or diagnosed brain or CNS cancer, produces beneficial effects, preferably sustained beneficial effects, manifested as decreased proliferation, differentiation and/or renewal of diseased neural precursor cells, early neural progenitor cells and/or NSCs.

In another aspect, methods are provided for treating a primary CNS tumor in a patient in need thereof by administering a composition comprising an NSC Modulating Agent in a therapeutically effective amount to decrease proliferation differentiation and/or renewal of diseased neural precursor cells, early neural progenitor cells and/or NSCs.

Also contemplated is the use of a composition comprising an NSC Modulating Agent for the preparation of a medicament. In one aspect, a therapeutically effective amount of at least one NSC Modulating Agent is used to r provide beneficial effects, preferably sustained beneficial effects, in treating a disease disclosed herein. In another aspect, the use of an NSC Modulating Agent for the preparation of a medicament for inhibiting proliferation, differentiation and/or renewal of diseased (e.g. cancerous) neural precursor cells, neural progenitor cells and/or NSCs is provided. In a further aspect, the use of an NSC Modulating Agent for the preparation of a medicament for stimulating proliferation, differentiation and/ or renewal of normal neural precursor cells, neural progenitor cells and/or NSCs is provided.

The compounds, compositions, and medicaments discussed herein can be administered by any means that produce contact of the active agent(s) with the agent's sites of action in the body of a subject or patient. The compounds, compositions, and medicaments in the described dosages are administered by conventional methods including without limitation orally, intranasally, by inhalation, intraperitoneally, subcutaneously, intramuscularly, transdermally, sublingually or intravenously.

The active ingredients can be administered simultaneously or sequentially, and in any order at different points in time, to provide the desired beneficial effects. The compounds and compositions can be formulated for sustained release, for delivery locally or systemically. It lies within the capability of a skilled physician or veterinarian to select a form and route of administration that optimizes the effects of the compositions and treatments.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen.

A dosage regimen will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of a condition can be readily determined by an ordinarily skilled physician or veterinarian.

A composition, medicament, or treatment may comprise a unit dosage of at least one NSC Modulating Agent. A "unit dosage" refers to a unitary i.e. a single dose which is capable of being administered to a patient, and which may be readily handled and packed, remaining as a physically and chemically stable unit dose comprising either the active agents as such or a mixture with one or more solid or liquid pharmaceutical excipients, carriers, or vehicles.

In another aspect, an improved pharmaceutical composition is provided comprising therapeutically effective suboptimal amounts of a NSC Modulating Agent in a form for chronic or acute therapy of a condition disclosed herein, in particular a brain or CNS cancer.

A composition or formulation may be administered to a subject continuously or periodically.

The compositions or fractions thereof typically comprise suitable pharmaceutical diluents, excipients, vehicles, or carriers selected based on the intended form of administration, and consistent with conventional pharmaceutical practices. The carriers, vehicles etc. may be adapted to provide an additive, synergistically effective or therapeutically effective amount of the active compounds. Suitable pharmaceutical diluents, excipients, vehicles, and carriers are described in the standard text, Remington: The Science and Practice of Pharmacy (21$^{st}$ Edition. 2005, University of the Sciences in Philadelphia (Editor), Mack Publishing Company), and in The United States Pharmacopeia: The National Formulary (USP 24 NF 19) published in 1999. By way of example, for oral administration in the form of a capsule or tablet, the active components can be combined with an oral, non-toxic pharmaceutically acceptable inert carrier such as lactose, starch, sucrose, methyl cellulose, magnesium stearate, glucose, calcium, sulfate, dicalcium phosphate, mannitol, sorbital, and the like. For oral administration in a liquid form, the agents may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof.

In one aspect, a pharmaceutical composition has a pH from about 7 to 10.

Formulations for parenteral administration of a composition may include aqueous solutions, syrups, aqueous or oil suspensions and emulsions with edible oil such as cottonseed oil, coconut oil or peanut oil. Dispersing or suspending agents that can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives, e.g. methylhydroxybenzoate or similar additives.

In an embodiment, a solid form pharmaceutical composition is provided (e.g. tablets, capsules, powdered, or pulverized form) comprising a crystalline or amorphous NSC Modulating Agent.

In another embodiment, a liquid drug formulation is provided and comprises pharmaceutically acceptable salts of an NSC Modulating Agent, and to lyophilized drug formulations that can be reconstituted to provide suspensions that are stable and suitable for parenteral administration.

A composition described herein may be sterilized by, for example, filtration through a bacteria retaining filter, addition of sterilizing agents to the composition, irradiation of the composition, or heating the composition. Alternatively, the compounds and compositions may be provided as sterile solid preparations e.g. lyophilized powder, which are readily dissolved in sterile solvent immediately prior to use.

After pharmaceutical compositions have been prepared, they can be placed in an appropriate container and labeled for treatment of an indicated condition. For administration of a composition, such labeling would include amount, frequency, and method of administration.

Kits are also provided. In an aspect, a kit comprises or consists essentially of agents or compositions described herein. The kit is a package that houses a container which contains agents, a NSC Modulating Agent or composition disclosed herein, and also houses instructions for administering the agent or composition to a subject. In one aspect, a pharmaceutical pack or kit is provided comprising one or more containers filled with one or more NSC Modulating Agent or one or more ingredients of a composition described herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration.

As there may be advantages to mixing a component of a composition described herein and a pharmaceutically acceptable carrier, excipient or vehicle near the time of use, the invention encompasses kits in which components of the compositions are packaged separately. For example, the kit can contain an active ingredient in a powdered or other dry form in, for example, a sterile vial or ampule and, in a separate container within the kit, a carrier, excipient, or vehicle, or a component of a carrier, excipient, or vehicle (in liquid or dry form). In an aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that is diluted prior to administration. Any of the components described herein, any of the carriers, excipients or vehicles described herein, and any combination of components and carriers, excipients or vehicles can be included in a kit.

A kit can include two or more therapeutic agents. The components can be combined with a carrier, excipient, or vehicle or packaged separately. For example, a kit can contain an NSC Modulating Agent, and, in a separate container, another therapeutic agent.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing (e.g., tubing to facilitate intravenous administration) alcohol swabs and/or the Band-Aid® applicator). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other embodiments, the kits can include pre-mixed compositions and instructions for solubilizing any precipitate that may have formed during shipping or storage. Kits containing solutions of one or more NSC Modulating Agent and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Small molecule high throughput screens in complex cell-based assays hold great promise for drug discovery but have not yet been widely applied to primary precursor cells (1). A library of 1,267 pharmacologically active compounds was screened against clonogenic colonies derived from murine neural stem cells (NSCs). From 160 initial hits, 12 potent and selective inhibitors of both normal and cancerous neural precursor cell proliferation and self renewal were characterized. These inhibitory compounds spanned a broad range of neurotransmission modulators, suggesting that the NSC may be anchored in a complex "ground state" in which proliferation and cell fate determination are regulated by myriad neural signaling pathways (2,3). These findings suggest that the mechanism of action of neuroactive drugs must be re-evaluated in the context of the NSC and that redeployment of clinically approved agents may afford a potent means to treat intractable CNS tumors. (4,5).

Although the candidate gene approach has been successful at uncovering vital pathways in NSC biology, to date only a small set of highly-studied networks has been sampled. Comprehensive identification of the signaling signature that regulates the neural precursor compartment is essential to define the NSC ground state. Because previous studies have demonstrated an intimate relationship between NSC self-renewal and neurosphere proliferation (13), a chemical genetic screen for inhibitors of neurosphere proliferation was undertaken in order to systematically profile the operational circuitry of the NSC (FIG. 1c).

The following methods were employed in the study described in the Examples:

Primary Embryonic Murine Neural Stem Cell (mNSC) Isolation and Culture. Isolation and culture of primary embryonic (e14.5) mouse NSCs was performed as previously described (36). Briefly, pregnant FVB mice were sacrificed by cervical dislocation at gestational age 14.5 (E14.5) and embryonic telencephalons were dissected in artificial cerebral spinal fluid (ACSF). After mechanical dissociation with a flame-narrowed Pasteur pipette, the telencephalic tissue was then passed through a 40 μm cell strainer (Falcon) and quantified for viable cells using trypan blue exclusion. Living cells were plated at a density of $10^6$ cells/mL at 37° C. in chemically-defined neural stem cell media (37) containing 20 $ng/mL^{-1}$ human recombinant epidermal growth factor (EGF) (Sigma), 20 $ng/mL^{-1}$ basic fibroblast growth factor (bFGF) (Upstate) and 2 $\mu g/mL^{-1}$ heparin (Sigma) and fed every 2-3 days.

Secondary mNSC Neurosphere Culture and Chemical Screens. Prior to chemical screens and other manipulations, the NSC fraction in culture was expanded by growing freshly dissected cells as primary neurospheres (8,38) in bulk culture ($10^6$ cells/mL). After 7 days, primary neurospheres were collected and enzymatically digested for 3 minutes at 37° C. using the ACCUTASE™ reagent (Sigma) and then briefly mechanically dissociated with a 1 mL pipette. Cells were then strained and counted as above. Viable cells were plated at clonal density (20 cells/μL) in 96-well plates (Falcon) in a final volume of 100 μL and screened in singlets against the LOPAC™ library (Sigma) at a concentration of 3 μM (0.03% DMSO). On day 4, each well in the screen was supplemented with an additional 50 μL of fresh mNSC media and another aliquot of the LOPAC™ library (maintaining the final concentration of each compound at 3 μM). Secondary neurosphere cultures were then incubated for an additional 3 days (day 7) at which point the effect of each compound was assessed by quantifying the total proliferation of each well using the MTT proliferation assay. Z-score and p-values for the entire screen are listed in Table 3.

Figure 7:
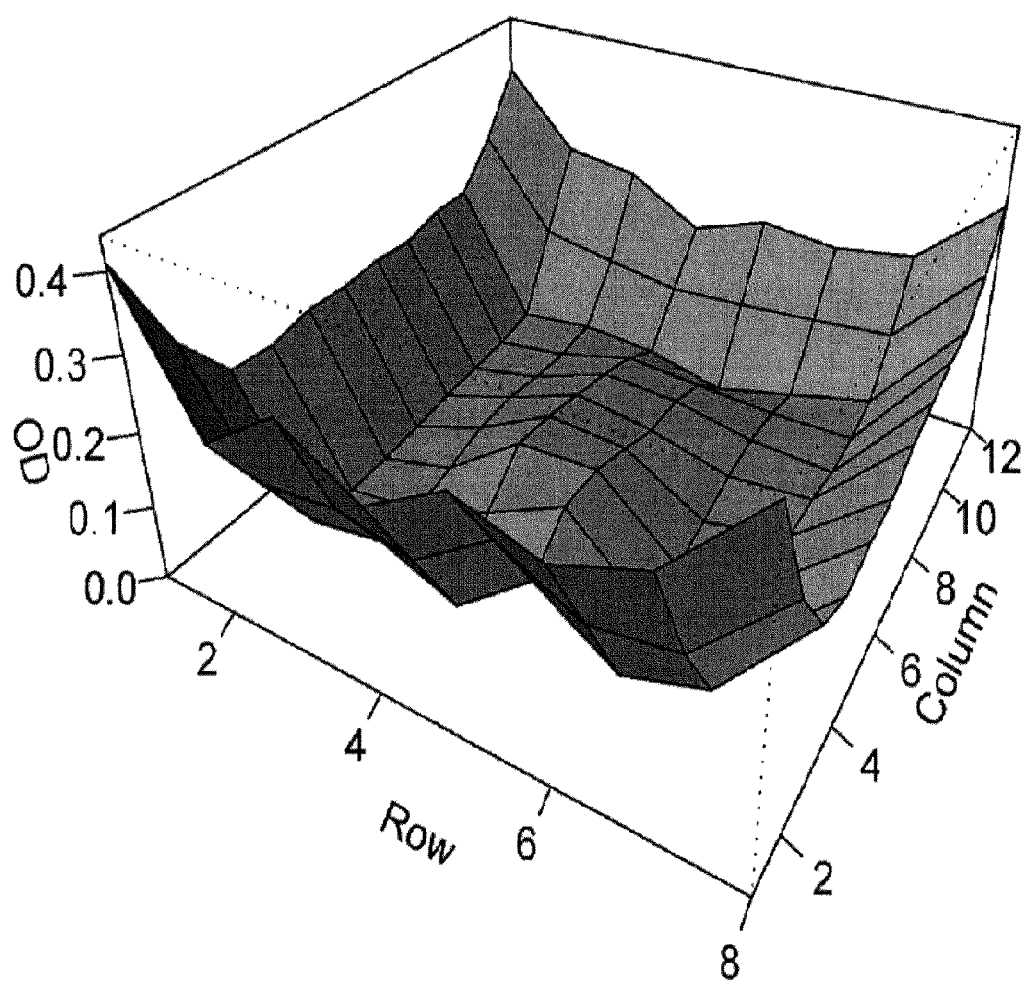
FIG. 7 shows the assessment of plate edge effects. Optical density scatter and mesh plot of MTT values as a function of well row and column are shown. Due to the long incubation time of plates at 37° C., a row and column-dependant edge effect emerged due to differential evaporation over the course of the screen. Systematic noise was removed as described in FIG. 8.
Figure 8:
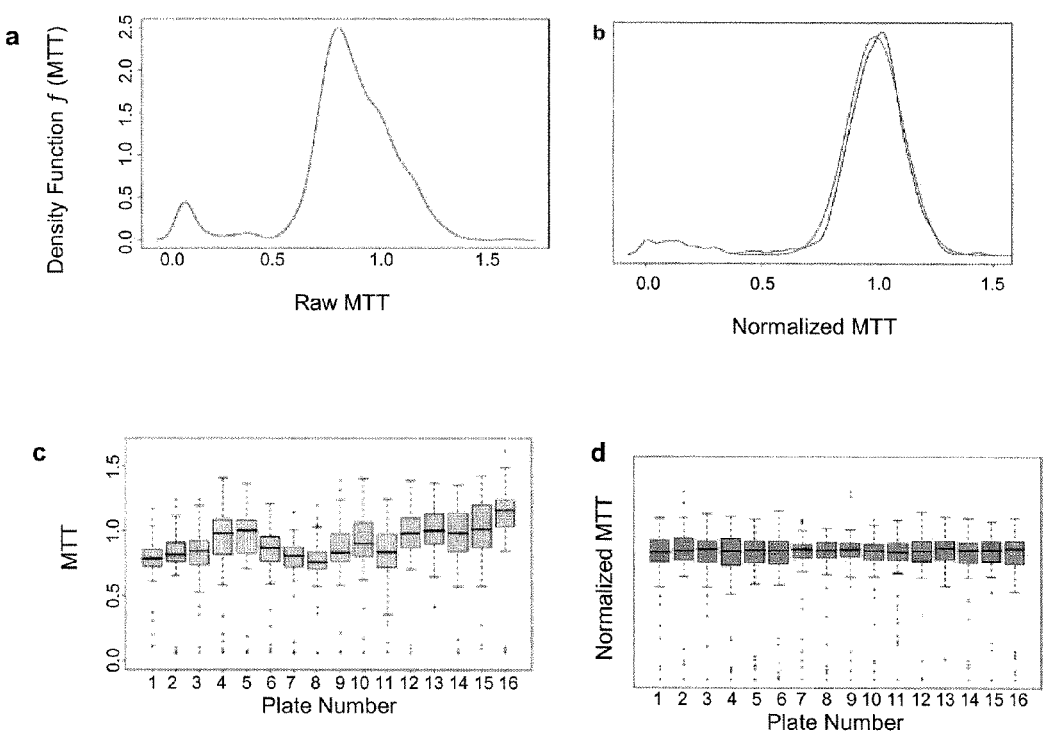
FIG. 8 shows the correction for plate edge effects in the screen. (a) Density function of the raw data obtained from the HTS of neurospheres prior to the correction for edge-effects. (b) Density function of the normalized (curve with the right-most peak on the graph) and the fitted theoretical distribution (curve with the left-most peak on the graph) used to calculate significance. (c) Box plot representation of the raw data of each plate in the screen. (d) Re-plot of data after the removal of the evaporation induced systematic error helped to reduce the number of both false positives and negatives. Box length for each plot represents the interquartile range (IQR) (Q3-Q1). The solid black line represents the median value for each plate and cutoffs represent values 1.5*(IQR) from Q3 and Q1.

Assessment of Total Neurosphere Culture Proliferation. Total neurosphere proliferation for all experiments was assessed after seven days using the Thiazolyl Blue Tetrazolium Bromide (MTT) (Sigma) calorimetric proliferation assay (5 mg/mL). Briefly, 15 μL of MTT were added to the 150 μL of media in each well and incubated at 37° C. for 4 hours. After this time, the reaction was quenched by solubilizing the cells with 100 μL of 10% SDS/0.01 M HCl. Each well was then quantified using a microplate reader (Versamax) at an optical density of 575 nm. Background plate effects (FIG. 7) occurring from the evaporation of media over the course of the experiment was estimated by:

$$b_i = \frac{1}{N - N_i^h} \sum_{j=1}^{N} x'_{i,j}$$

where $x'_{i,j}$ is the value at well i of plate j, h is the number of excluded hits that were 2 standard deviations below the mean and $b_i$ represents the estimated background at each well position (39). The respective background was then subtracted from the raw MTT value measured for each point (FIG. 8). To calculate significance, the theoretical probability density function [N(1.0,0.11)] was fitted to the empirical normalized distribution obtained from the screen (FIG. 8b). Compounds that caused optical density readings to significantly deviated from this function (P<0.01) were designated as bioactive (40).

Dose-Response Curves and $EC_{50}$ Calculations. Potency of confirmed bioactive compounds was quantified by generating dose-response curves for mNSC under the same cell density and culture conditions described for the initial screen. Starting from initial concentrations between 300-30 μM, each compound was titrated across a series of 10 half-log dilutions. Each agent was tested in triplicate in at least three independent experiments. The average effective concentration that decreased the MTT reading by 50% ($EC_{50}$) after seven days was calculated by fitting the data points to the four-parameter logistic sigmoidal dose-response curve:

$$Y = EC_{100} + \frac{EC_0 - EC_{100}}{1 + 10^{\log(EC_{50} - X)(Hill\ Slope)}}$$

where X is the logarithm of concentration and Y is the predicted response. Curve fitting was performed with the Graph-Pad PRISM® Software.

Assessment of the Neural Stem Cell Specific Effects of Selected Inhibitory Agents. To directly address if the identified agents and their respective pathways were specifically affecting the NSC fraction of the precursor cultures, the number of neurospheres generated from a single cell suspension of 2000, 1000, and 500 cells following chemical pretreatment were counted. Specifically, primary neurospheres were dissociated into a single cell suspension and subjected to the estimated $EC_{75}$ of selected agents from different neurotransmission classes for 7 days. These cultures were then taken, dissociated once again and plated in fresh media. Neurospheres (>50 μm in diameter) generated from these cultures after seven days were then used as an index of the number of NSC present in culture following treatment. Data shown represents the average of two independent experiments each containing 6 replicates.

Astrocyte Screen and Neurosphere Selectivity Assessment. Selectivity of each compound for mNSC was assessed by constructing dose-response curves and $EC_{50}$ calculations for the normal astrocytic GFAP expressing cell line C8-D1A (ATCC), which was derived from cells from the cerebellum of an 8 day old mouse. For consistency, cell densities and feeding schedules for these cells were identical to those described in the in NSC cultures. For all experiments, astrocytes were grown in DMEM media (GIBCO) supplemented with 10% fetal bovine serum and cultured as described in the ATCC product information guide.

Murine Medulloblastoma Generation and Culture. Tumor cells were isolated from the cerebellum of 16 week old patched heterozygous ($ptc1^{+/-}$) mice displaying ataxia. Mice were sacrificed using cervical dislocation and the cerebellum immediately removed and washed with artificial cerebrospinal fluid (ACSF). Tumors were macroscopically separated from normal tissue/blood and resuspended in 2 mL of the ACCUTASE™ reagent. The tissue was gently triturated with a flamed polished Pasture pipette and incubated at 37° C. for 5 minutes. Cells were then washed with DMEM/F12 and resuspended in the serum-free chemically defined media described above. Subsequent culture and HTS of these cells was preformed as described above for normal E14.5 NSC; data shown represents the average and standard deviation of a single experiment preformed in triplicate.

Flow Cytometry. To confirm that precursor markers found in human brain tumors are also expressed in $ptc1^{+/-}$ tumors, primary spheres were dissociated to single cell suspension using the ACCUTASE™ reagent, resuspended in 1×PBS with 0.5% BSA and 2 mM EDTA and passed through a 40 μM cell strainer. Four μL CD133-PE (eBioscience) was added to 100 μL of cell suspension and incubated for 30 min in the dark at 4° C. 4 μg/mL Propidium Iodide was added to exclude dead cells. Prominin-1 expression was assessed by the proportion of cells that were positive for expression above the levels see in the unstained control.

Results

Figure 5:
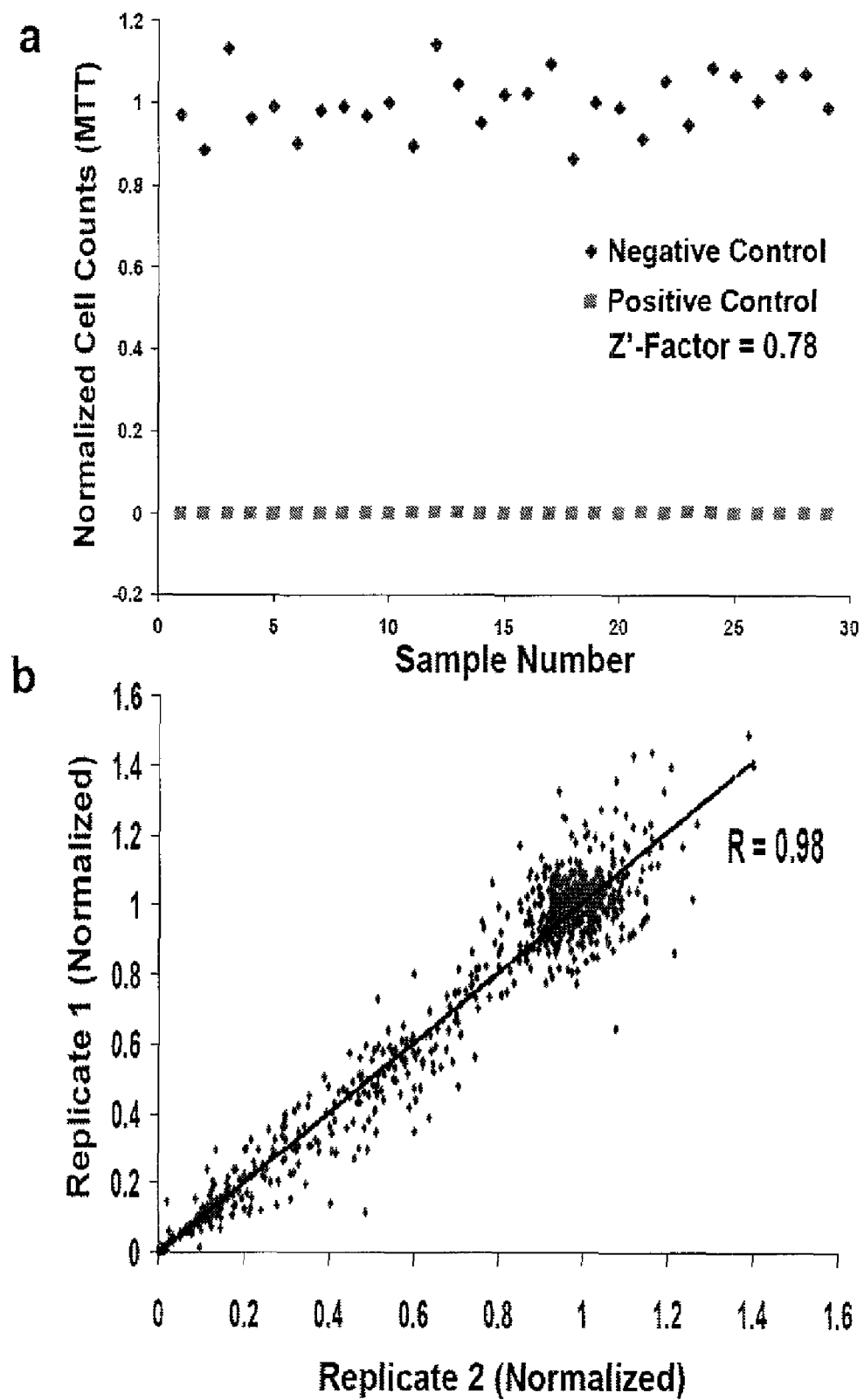
FIG. 5 shows the validation of a HTS assay for neurosphere cultures. (a) Scatter plot of positive (3 μM cycloheximide) and negative controls (vehicle: 0.03% DMSO) demonstrate the dynamic range of the HTS neurosphere assay. Z'-factor analysis confirmed the suitability of the assay for screening. (b) Pearson R correlation of pilot experiments performed in replicate demonstrated reproducibility and accuracy of values over the dynamic range of the screen.

To assess if the clonogenic neurosphere assay was suitable for high throughput screening (HTS), the Z'-factor (a measurement of HTS assay quality)(16) of neural precursor cells grown at clonal density for seven days was determined. Incorporation of the vital dye Thiazolyl Blue Tetrazolium Bromide (MTT) was used to compare proliferation of cultures grown in the presence of negative (0.03% DMSO) and positive (3 M cycloheximide) controls; the Z'-factor of this assay was 0.78, well within a suitable range for HTS (FIG. 5a). Correlation of over 1,000 MTT values for replicate experiments scattered throughout the dynamic range of the assay revealed a Pearson correlation co-efficient of 0.981, again confirming the reliability of the assay (FIG. 5b).

Figure 2:
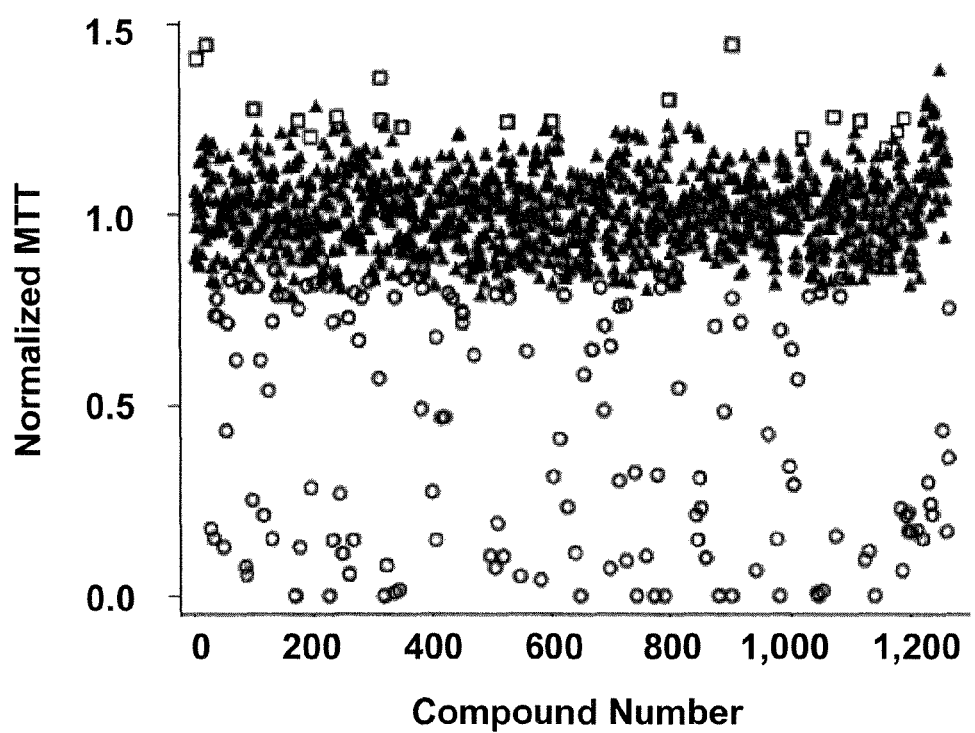
FIG. 2 shows the HTS of neurosphere cultures. (a) Scatter plot of all 1,267 compounds of the LOPAC™ library screened against neural precursor cells. One hundred sixty compounds (○) were identified as inhibitors of neurosphere proliferation (P<0.01), 19 compounds (□) were identified as activators (P<0.01) and the rest of the agents (▲) screened did not have any significant effects on proliferation (P>0.01). (b) Examples of phenotypic variation observed in response to particular agents. Scale bars, 250 µM.
Figure 2:
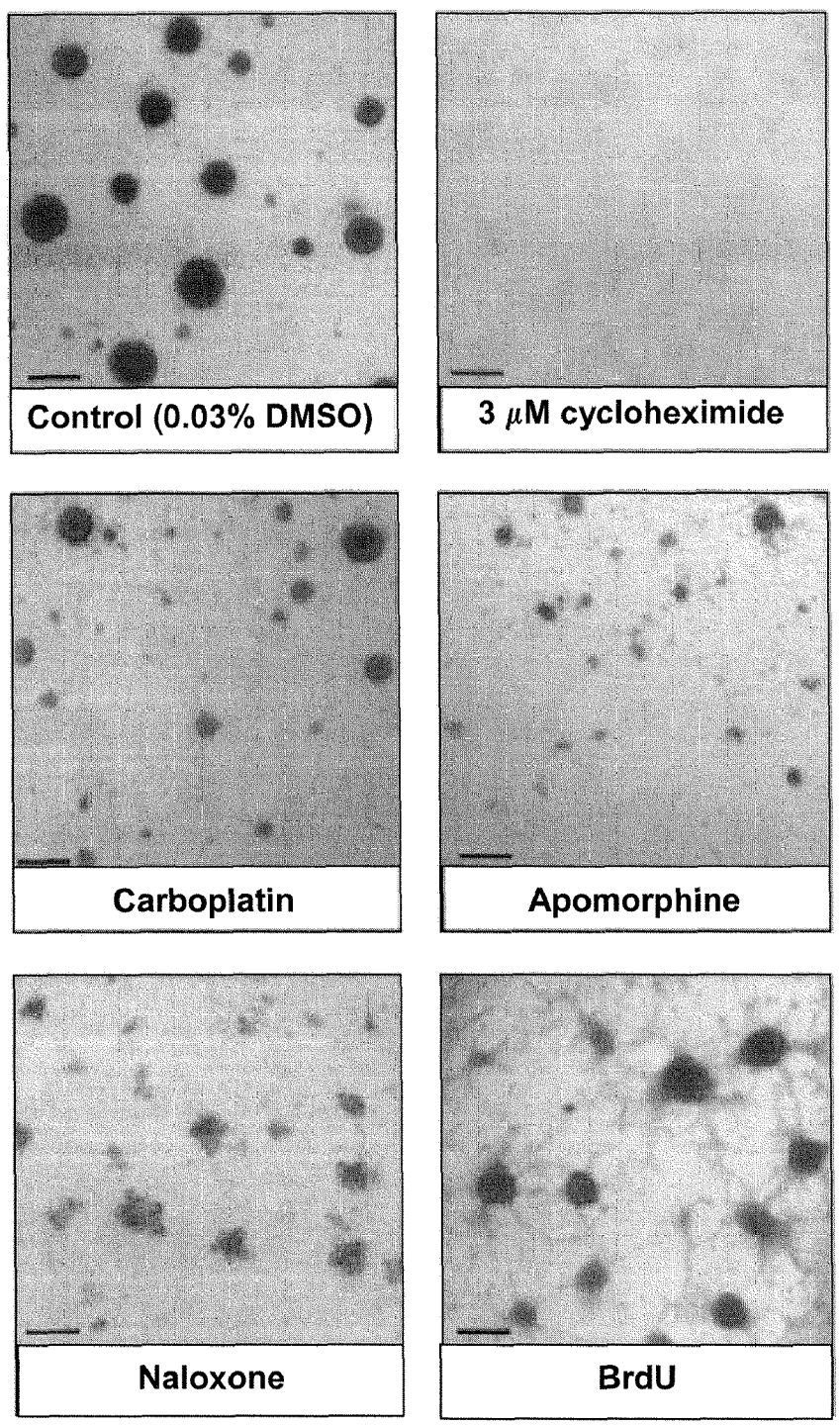
Figure 6:
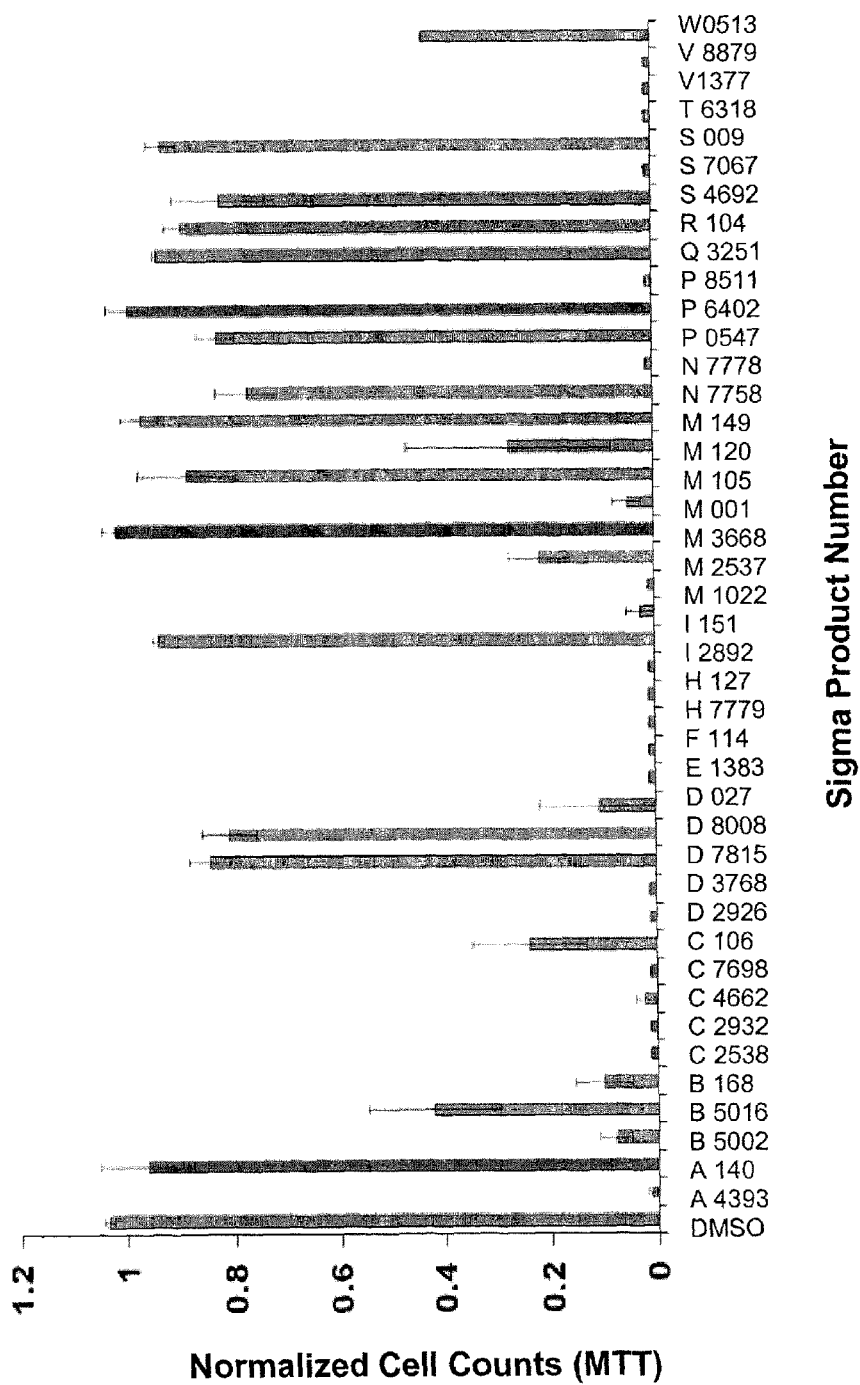
FIG. 6 shows the confirmation of HTS hits. Normalized MTT values of a representative sample of hits taken from different pharmacological classes in the LOPAC™ library collection. Compounds are annotated by Sigma-Aldrich catalog number. All values represent the mean of triplicate values of three independent experiments and error bars represent s.e.m. Of the 43 compounds retested, 40 (93%) (light gray bars) were confirmed as significant (P<0.05) when compared to control wells (DMSO) using Student's t-test.

1,267 compounds in the Library of Pharmacologically Active Compounds (the LOPAC™ library, Sigma MO) were screened for inhibitors of neurosphere proliferation. 160 compounds significantly decreased MTT values from the predicted underlying distribution of the screen (P<0.01) (FIG. 6a, Table 3). To assess if multiple agents in specific drug classes had a propensity for inhibiting neurosphere proliferation, compounds were clustered into groups of known pharmacologic action (Table 1, Table 4). Drug classes that non-specifically target essential cellular processes scored as hits in the screen, including alkylating agents, apoptosis inducers, cytoskeleton inhibitors and antibiotics. Unexpectedly, however, many agents that modulate neurotransmission in the dopamine, serotonin, opioid, glutamate, vanilloid, and other pathways potently inhibited growth of the undifferentiated population of precursor cells. Many of these agents are used in the clinical treatment of neurological disorders and are traditionally thought to act on mature CNS cell populations. Different compounds induced a variety of neurosphere phenotypes, including changes in sphere number, sphere size, and cell-cell or cell-surface adhesion properties (FIG. 2b). This variety of differentiated states suggests that an elaborate balance of signaling pathways dictates neural precursor cell fate.

Figure 3A:
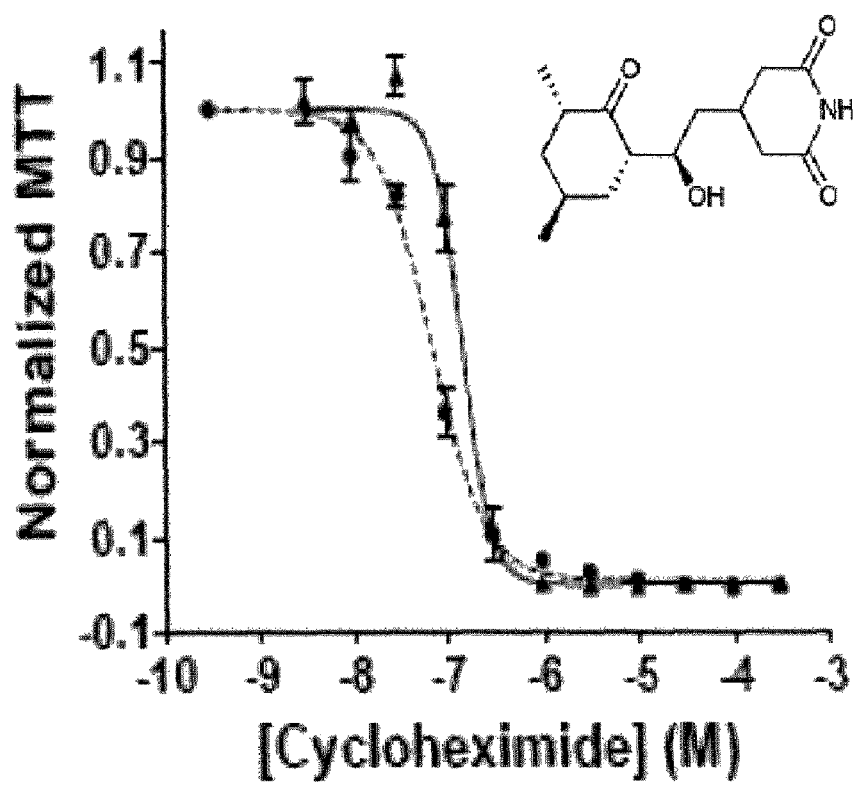
FIG. 3 shows the identification of potent neural precursor cell-specific compounds. Dose-response curves and chemical structures of controls: (a) cycloheximide, (b) etoposide, and (c) carboplatin, and selected newly identified compounds: (d) dihydrocapsaicin, (e) apomorphine, and (f) PAPP. Each plot displays the fitted sigmoidal logistic curve to MTT proliferation assay readings of both astrocytes (- -•- -) and neurosphere cultures (-▲-). All points represent the mean of triplicates from three independent experiments; standard error of the mean (s.e.m.) is shown. (g) Replating colony forming efficiency of pretreated neurosphere cultures. Values represent the number of secondary neurospheres arising from an inoculum of 2000 or 1000 cells following a seven day pretreatment with the indicated inhibitor at the estimated $EC_{75}$ value. As the $EC_{75}$ of apomorphine did not allow the recovery of sufficient cells, an $EC_{50}$ pretreatment was used for this agent. All values represent the mean of 6 replicates from two independent experiments; s.e.m. is shown. Asterisks indicate that the replating efficiency of the treated precursor population was significantly reduced (P<0.05) compared to corresponding control at both cell densities.
Figure 3B:
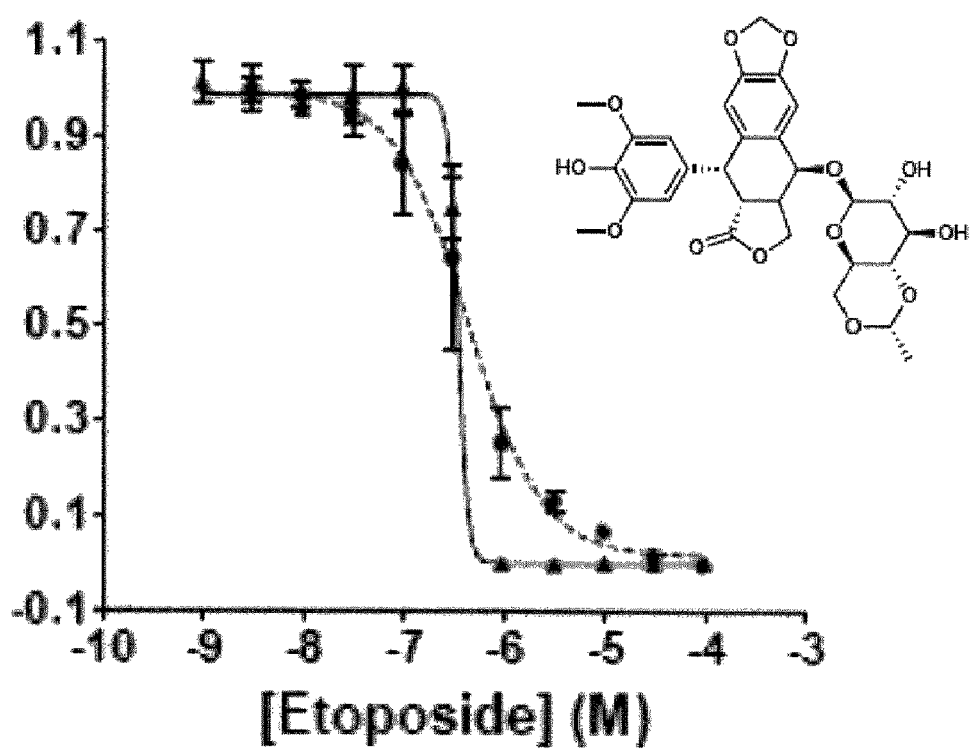
Figure 3C:
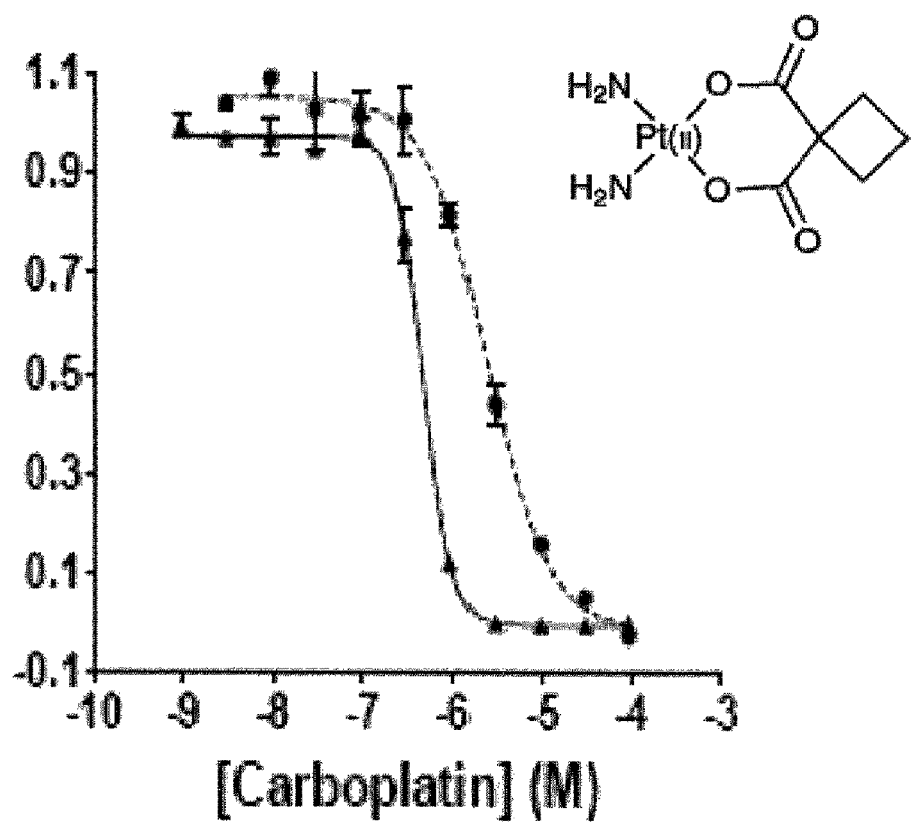
Figure 3D:
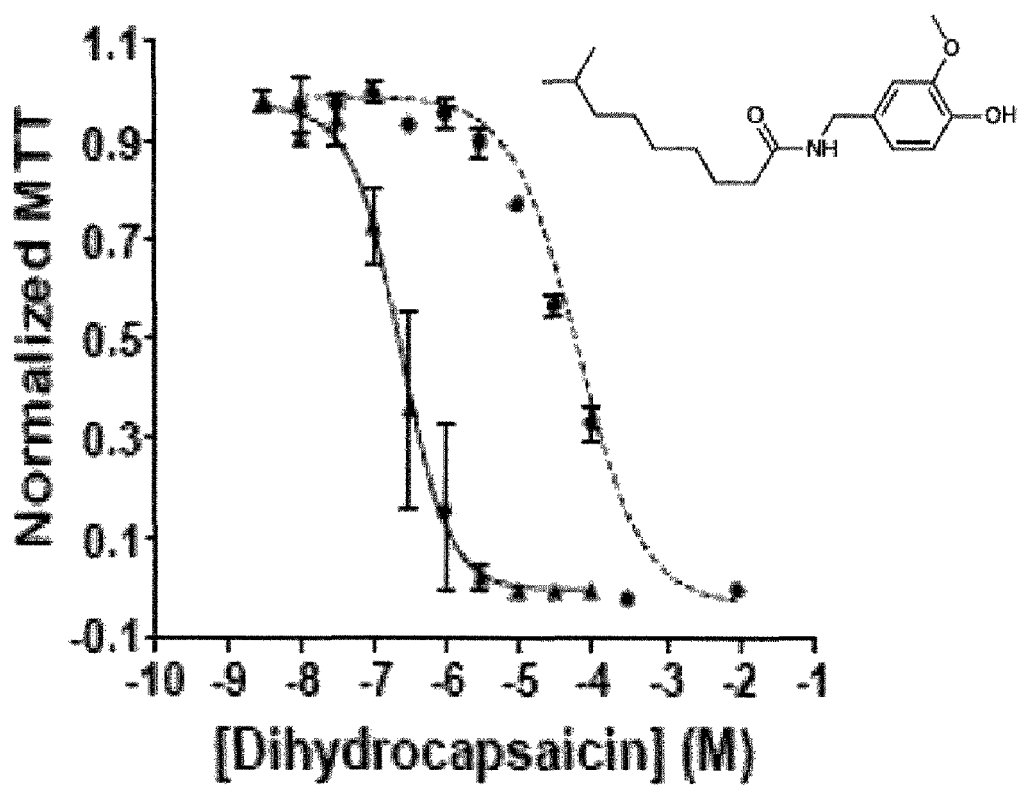
Figure 3E:
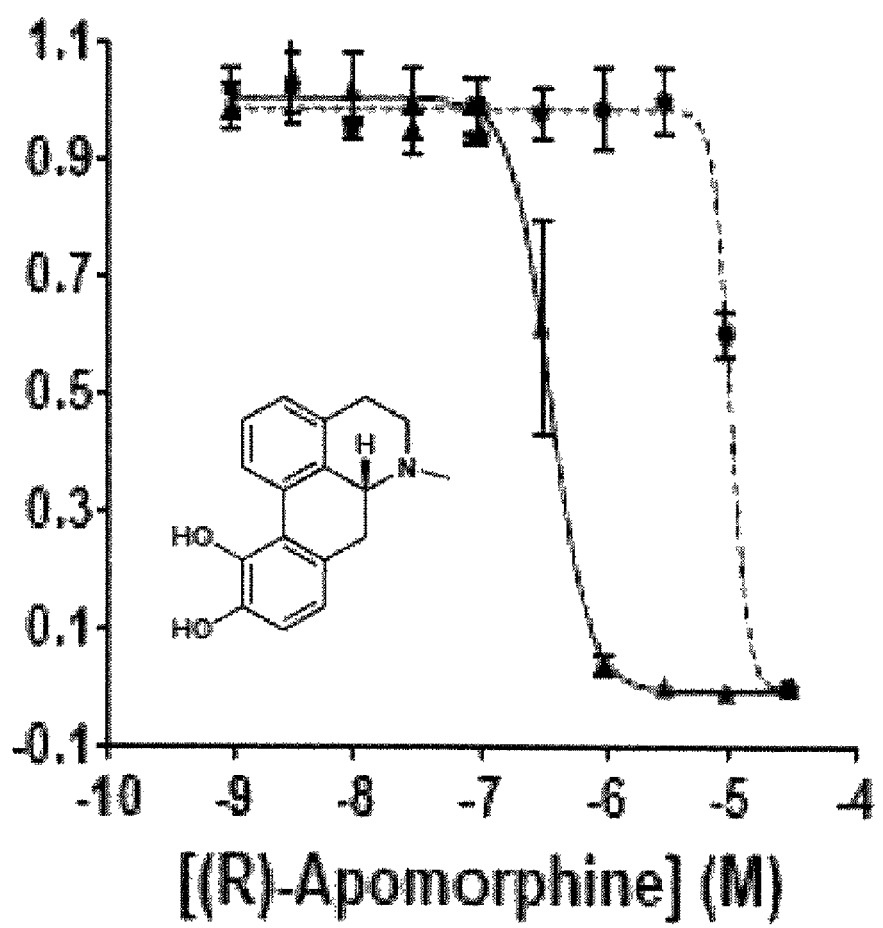
Figure 3F:
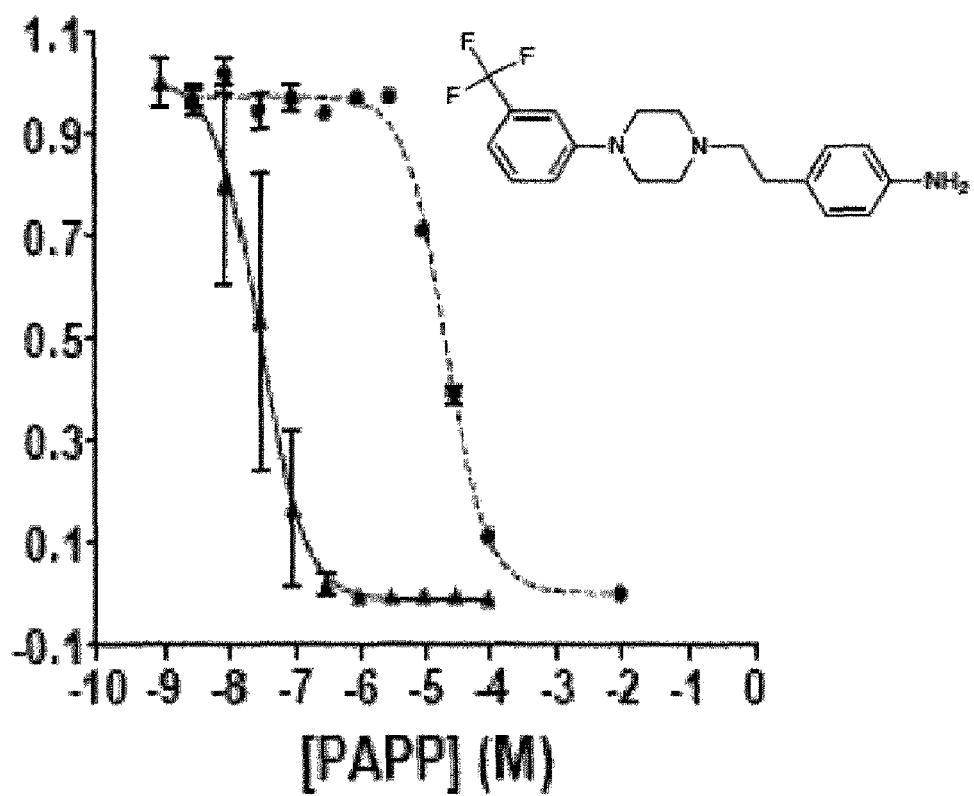

To verify hits from the primary screen, a representative sample of candidate agents from each pharmacological class were retested at the original screen concentration of 3 μM. Of the 43 candidates retested, 93% exhibited significant activity (P<0.05) when compared to vehicle control in triplicate for three independent experiments (see FIG. 6). Because other neural cell types such as astrocytes are known to express and signal through neurotransmitter receptors (17), a counter-screen was performed in a proliferating normal mouse astrocyte cell line to assess the selectivity and potency of each agent for neurosphere cultures. It was reasoned that this counter-screen would allow not only the identification of small molecules that were specific for signaling pathways present in neural precursors, but it would also help rule out non-specific cytotoxic agents. Dose response curves were performed for the 43 compounds in both neurosphere and astrocyte cultures and used to determine the effective concentration needed to decrease proliferation by 50% ($EC_{50}$) (FIG. 3a-f, Table 5). A neurosphere selectivity ratio, defined as $EC_{50\ astrocytes}/EC_{50\ precursor\ cells}$, for each compound was determined and compared to that of three known non-specific inhibitors of proliferation (cycloheximide, etoposide and carboplatin; FIG. 3a-c). Compounds that exhibited a neurosphere selectivity ratio (n.s.r.) greater than that observed in the control agents (n.s.r.>5.08) were defined as neural precursor cell-specific agents (FIG. 3d-f, Table 2). From the focused set of 43 candidates, 12 highly potent and highly selective compounds were identified that attenuate neurosphere proliferation through a variety of different signaling pathways. Notably, the serotonin agonist PAPP (p-aminophenethyl-m-trifluoromethylphenyl piperazine) and the vanilloid receptor ligand dihydrocapsaicin were respectively 702 and 192 fold more selective for normal neural precursors than astrocyte cultures.

Figure 3G:
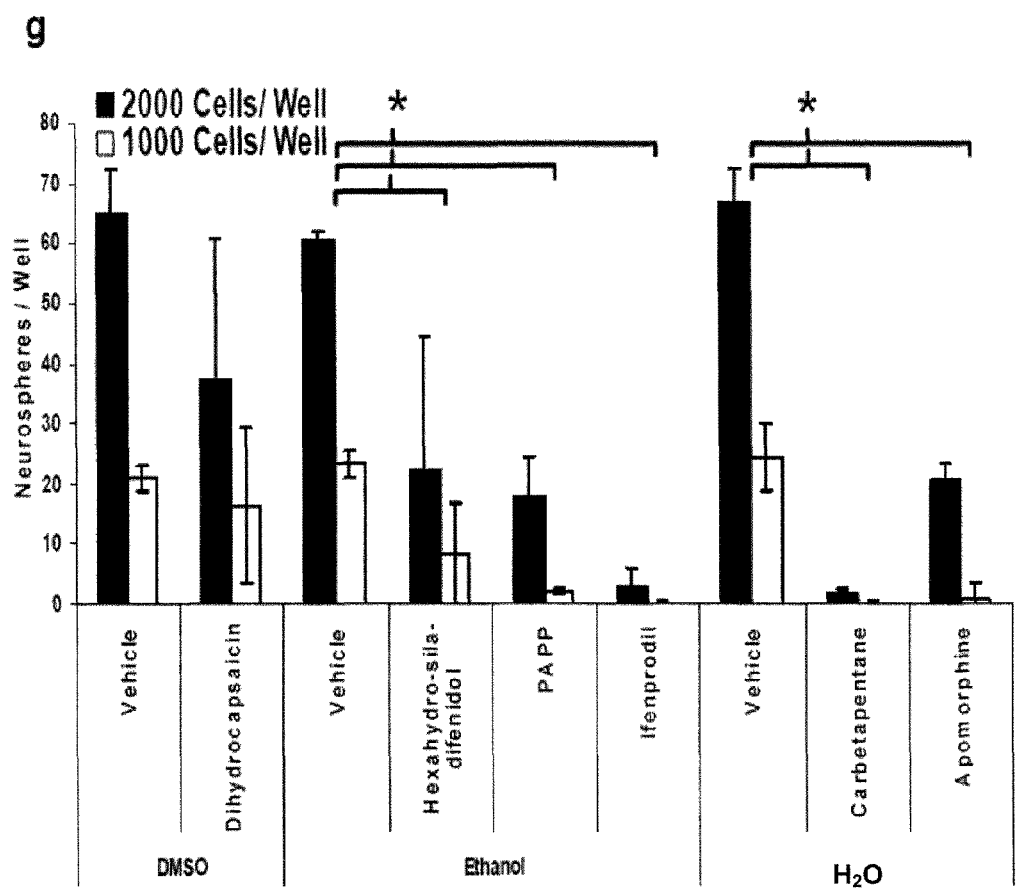

Neurospheres are comprised of a heterogeneous population of neural stem cells and lineage restricted progenitor cells (10). To determine if the inhibitors affected NSC self renewal, as opposed to proliferation of more committed precursor populations, the colony forming efficiency of treated neurosphere cultures was analyzed. With the exception of dihydrocapsaicin from the vanilloid class, representative compounds from each major class reduced secondary neurosphere formation upon re-culture in the absence of drug (FIG. 3g). This result demonstrates that the inhibitors selectively targeted the NSC pool that is predominantly responsible for sphere formation.

Figure 4:
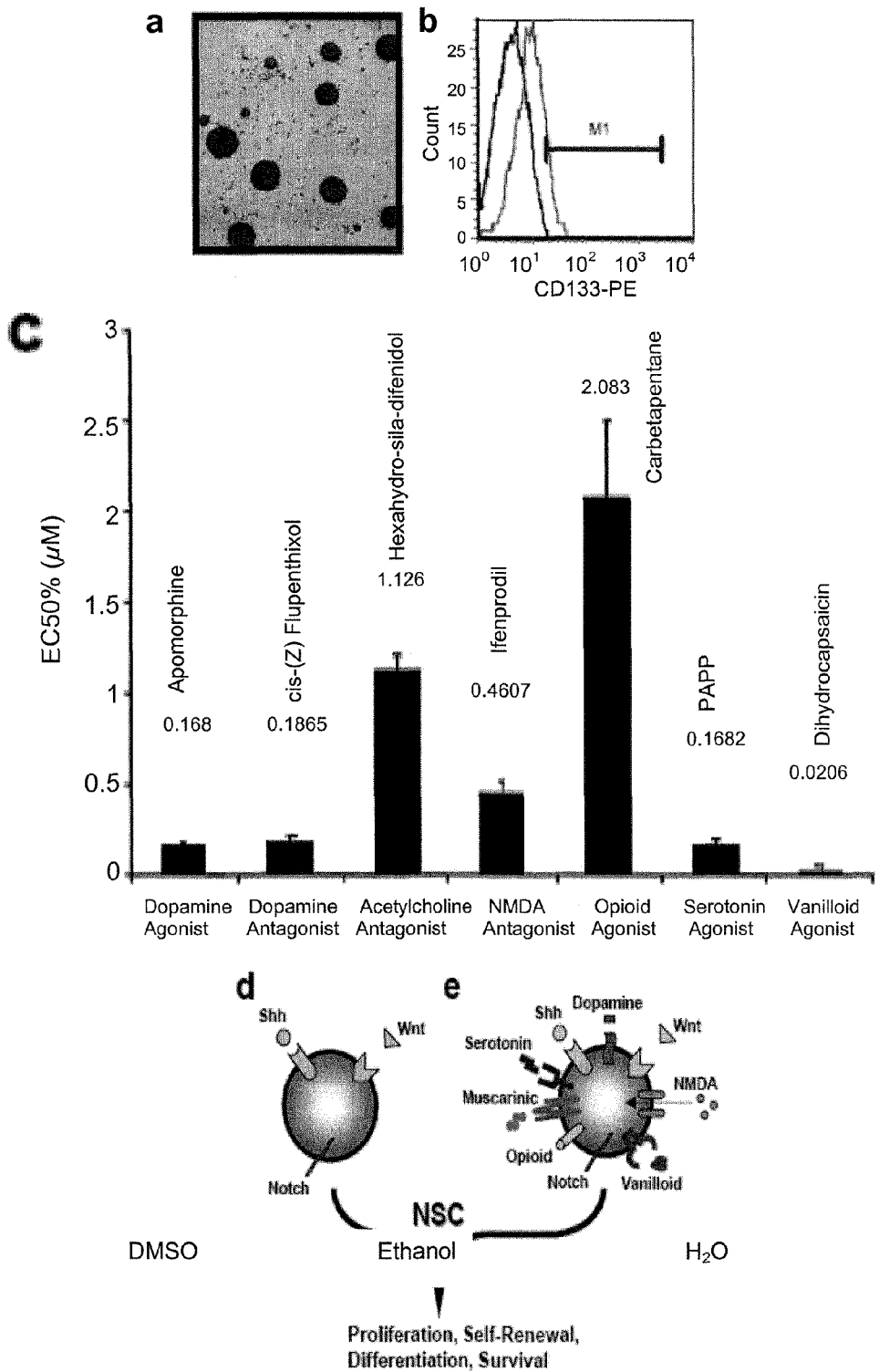
FIG. 4 shows the promiscuous neurotransmitter drug sensitivity in medulloblastoma precursor cells. (a) Cells isolated from $ptc1^{+/-}$ tumors contain self-renewing neurosphere-forming cells in vitro. (b) $Ptc1^{+/-}$ tumors contain cells that stain positive (M1) for the early precursor marker Prominin1 (CD133 homolog) at comparable levels to primary human medulloblastomas (11.6%). Unstained (black) and stained (gray) specimens are shown. (c) $EC_{50}$ values for inhibition of tumor sphere MTT proliferation by various neurotransmission agents. Values represent the average and standard deviation of triplicate cultures. (d, e) Functional ground state of NSCs: (d) Current models of the NSC hierarchy focus on developmental signaling pathways such as Wnt, Notch, and Sonic Hedgehog. (e) Compounds identified in the HTS approach reveal that the NSC ground state and cell fate decision-making depends on a complex circuitry that includes many neurotransmission signaling pathways.

As gene expression profiles of a variety of brain tumor subtypes resembles that of normal and embryonic neural precursor cells (118-21), agents that inhibit normal neural precursor growth might inhibit cultures of brain tumors that are enriched for cancer stem cells. Therefore the activity of the 12 most selective inhibitors of neural precursor growth were assessed against low passage (<4) neurosphere cultures of a spontaneous medulloblastoma from a heterozygous patched (ptc1$^{+/-}$) mouse (22). Like their normal counterparts, cancerous precursor cells isolated from the tumors of these mice grow as spheres in the absence of serum and in the presence of EGF and FGF and express the neural precursor marker prominin1 (CD133) (FIG. 4a,b). The 12 neural precursor-specific agents also potently suppressed the proliferation of the ptc1$^{+/-}$ medulloblastoma precursor cells (FIG. 4c, Table 6). Notably, some of these agents were an order of magnitude more effective in inhibition of ptc1$^{+/-}$ tumor cell growth in vitro than reported concentrations of the sonic hedgehog signaling inhibitor cyclopamine (0.5 µM versus 5 µM) (23). Pharmacologically active small molecules that inhibit normal neural precursor proliferation are thus also candidate chemotherapeutics against brain tumor stem cells.

The ex vivo and in situ manipulation of NSC for treating neurological disorders, including brain cancer, will require a global understanding of the pathways that regulate the behavior of these cells. Through a chemical genetic approach the existence of a complex functional "ground state" has been uncovered in neural stem cells, as defined operationally by the plethora of pathways that suppress neural precursor proliferation (FIG. 4d, e). The observed sensitivity of neural precursor cells to agents from different neurotransmitter classes reveals that neural precursor cells are modulated by signaling pathways previously thought to function only in mature CNS cells. The release of NSC proliferation from the ground state may require an appropriate local environment of neurotransmitter activities (24). Recent studies on individual pathways support the notion that proliferation of different neural stem and progenitor subpopulations in vivo may be regulated by dopamine, serotonin, acetylcholine and glutamate (25-31). Moreover, neurosphere cultures have been reported to express receptors for various neurotransmitters (32). The systematic chemical genetic analysis substantially elaborates the cohort of pathways that control NSC proliferation (Table 1, Table 4) and, importantly, demonstrates the simultaneous operation of these pathways in precursor cells cultured under uniform experimental conditions. This promiscuous functional sensitivity of precursor cultures to a spectrum of neuroactive compounds supports the notion of lineage-priming in the NSC compartment, similar to that seen in hematopoietic stem cells (2).

The strong selectivity of many agents for precursor cultures and primary medulloblastoma cells suggests that the affected pathways lie high in the hierarchical organization of the NSC lineage. Furthermore, the often complete inhibition of neurosphere proliferation and the effects on secondary replating suggests that stem cells and/or very early progenitor components of the population are affected by these agents. The finding that both inhibitors and activators of specific pathways inhibit neurosphere proliferation (e.g. dopamine receptor agonists and antagonists) suggests that a complex signaling landscape dictates NSC fate (33). It is also possible that off-target effects account for these observations in neural precursors (34).

The results of this small molecule screen have important implications for current clinical practice in the treatment of neurological diseases. The unanticipated actions of well-characterized clinical agents on the neural precursor compartment may be partly or even solely responsible for the observed clinical benefits of these agents and/or the adverse side-effects that arise after prolonged therapy. Investigation of these possibilities for various neurological disorders may enable the development of novel NSC-specific or NSC-sparing approaches in the clinic.

In light of evidence that CNS tumors are maintained by cancer stem cells (5,6), which have similarities to normal neural stem cells (18), the potent and selective anti-proliferative agents identified in this study may presage a next generation of therapeutic agents in brain cancer. That the same agents can also potently suppress primary medulloblastoma sphere cultures supports this prospect. Intriguingly, a retrospective analysis of cancer incidence in Parkinson's patients revealed a significant reduction in the prevalence of brain tumors (35); it is suggested that this correlation may derive from the effect of anti-Parkinsonian drugs on the precursor cells from which brain tumors are thought to arise. If the complex neuronal precursor ground state as proposed also defines the identity of brain tumor stem cells, redeployment of pharmacologically-approved agents may well afford a potent and non-toxic means to treat often intractable CNS tumors.

Example 2

The cancer stem cell hypothesis posits that important functional analogies exist between normal neural stem cells (NSCs) and brain tumor stem cells (BTSCs). New insights into human brain tumour biology and treatment will thus likely emerge from further study of normal neural stem cells. These parallels have recently been exploited in a chemical genetic screen that identified a surprising repertoire of neurotransmission modulators that inhibit the growth of both NSC and BTSC cultures in vitro (see Example 1). Prompted by these findings, an investigation was conducted to determine whether epidemiological evidence supports a hypothesis that brain tumors might be regulated by neurotransmission pathways in vivo. Analysis of previously published retrospective studies suggests that patients with a wide variety of neuropsychiatric disorders exhibit a decrease in brain tumor incidence. This reduction may derive from the use of drugs that collaterally affect the neural stem cell compartment, and thereby limit the precursor populations that give rise to brain tumors. Standard chronic neuropharmacological interventions that have been used for decades in neuropsychiatric care are thus candidates for redeployment as low toxicity brain cancer therapeutics. This is the first application of concepts in stem cell biology to identify previously unappreciated sub-populations with reduced cancer incidence.

In adults, high grade gliomas represent at least one third of all primary brain tumors diagnosed. Even with intensive radio- and chemotherapy following surgical resection, the median survival of these patients is 9-12 months, with only 8-12% of patients surviving past 2 years [Burger, P. C., V et al Cancer 56, 1106-1111 (1985); Galanis, E. & Buckner, J. Br. J. Cancer 82, 1371-1380 (2000)]. The recent introduction of the DNA alkylating agent temozolomide, which prolongs the median survival time from 12.1 to 14.6 months [Cohen, M. H., et al., Clin. Cancer Res. 11, 6767-6771 (2005)], represents the most significant chemotherapeutic advancement in the management of gliomas in the last 30 years [Newlands, E. S., et al., Cancer Treat Rev. 23, 35-61 (1997)]. With such a grim prognosis and so few, if any, documented examples of complete remission [Stupp, R. et al. N. Engl. J. Med. 352, 987-996 (2005)], brain tumor treatment strategies must apparently shift away from traditional anti-neoplastic drug classes.

Recent evidence suggests that brain tumors are maintained by rare cancer cells with stem cell-like properties [Singh, S. K. et al. Nature 432, 396-401 (2004) and Vescovi, A. L., et al., Nat. Rev. Cancer 6, 425-436 (2006)]. Moreover, the discovery of stem cells in the postnatal brain suggests not only that normal neural stem cells (NCSs) may direct neuronal regeneration but that such cells may be the root cause of brain cancers. The inability of traditional therapeutics to eliminate rare brain tumour stem cells (BTSCs) may account for frequent therapeutic failure and uniform clinical relapse [Bao, S. et al. Nature 444, 756-760 (2006)]. The development of agents that act on BTSCs offers the prospect of more effective means to treat brain cancer. Although a number of studies suggest a role for neurotransmission pathways in NSC proliferation and/or differentiation, it is unknown if similar regulatory networks influence cancer of the brain. To substantiate this, evidence was sought that suggests that patients initially diagnosed with a variety of neuropsychiatric disorders (and hence presumed to be on chronic neuromodulatory medication) exhibited differential brain tumor incidence compared to the general population.

The analysis of historical cohorts has made it possible to identify strong correlations between many cancers and human behavior; however, the relative rarity of brain cancer and typical late-stage diagnosis hampers statistical analysis. Brain cancer is thus a disease with few known risk and preventative factors, including the potential association with extrinsic environmental modifiers such as use of neuromodulatory drugs in clinical settings. Fortunately, the differential incidence of more prevalent cancers (such as breast, skin, and lung) among neuropsychiatric patients has prompted investigation of the relationships of these co-morbidities.

Reports of brain tumor incidence in some of these studies allowed retrospective assessment of correlations between psychiatric diagnosis (and presumed neuromodulator consumption) on brain cancer risk. Published studies were identified from 2000 onwards that report patients with co-morbid neurologic or psychiatric conditions and cancer. From these, eight studies were found that reported brain cancer incidence rates following an initial neurologic or psychiatric diagnosis. In the analysis of these studies, it was assumed that patients included in the studies are on chronic neuromodulatory pharmacologic therapy. This is a valid assumption for Parkinson's disease, schizophrenia and major depression in the periods of time that the studies encompass.

Figure 9:
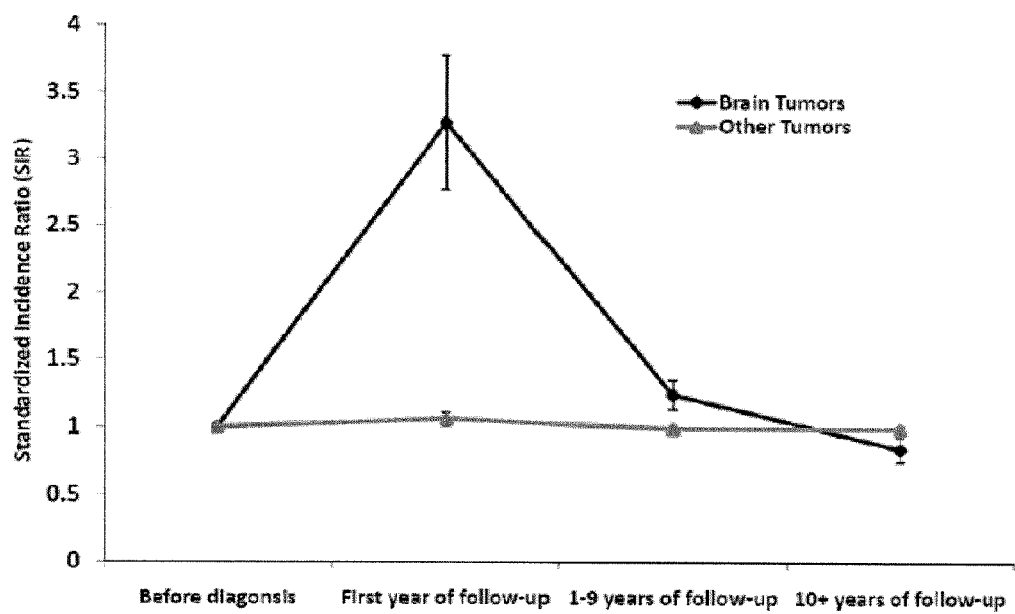
FIG. 9 shows the temporal effects of depression on the brain tumor standardized incidence ratio (SIR). Frequency of brain tumors (expressed as standard incidence ratio; SIR) in patients diagnosed with depression. Unlike other cancers, the SIR of brain tumors exhibits an initial significant rise following diagnosis of depression, which is subsequently followed by a progressive decrease in SIR with time. Data for this figure were extracted from Dalton, S. O., et al. *Am. J. Epidemiol* 155, 1088-1095 (2002).

Notably, Lalonde and Myslobodsky examined the association between breast cancer incidence, among 144,364 subjects previously diagnosed with Parkinson's disease (PD) [Lalonde, F. M. & Myslobodsky, M. Breast 12, 280-282 (2003)]. Within this study was the unremarked-upon correlation that PD patients experienced a 5-fold reduction (~0.625% vs. ~0.125%; P<0.01) in the incidence of brain tumors, as compared to a control normal population. The continuous administration of anti-Parkinsonian drugs in this cohort might have decreased NSC and/or BTSC proliferation, and thereby attenuated the cell populations that are the likely origins of cells responsible for propagating brain cancer. However, other studies that followed brain tumor incidence in patient populations presumed to be treated with psychoactive drugs revealed less conclusive correlations (See "Reported SIR" in Table 9). For example, although Lichtermann et al. [Arch. Gen. Psychiatry 58, 573-578 (2001)] also reported a reduced standardized incidence ratio (SIR) of brain tumors in schizophrenia patients (SIR=0.86), this reduction was not statistically significant. Similar non-significant reductions in brain tumor SIRs have also been noted in schizophrenic patients by others [Dalton, S. O., et al, Schizophr. Res. 75, 315-324 (2005); Goldacre, M. J., et al Br. J. Psychiatry 187, 334-338 (2005); Barak, Y., et al., Cancer 104, 2817-2821 (2005); and Grinshpoon, A., et al. 73, 333-341 (2005)]. Interestingly, other studies report an opposite and positive association between neurological diseases and brain cancer incidence [Dalton, S. O., et al. Am. J. Epidemiol. 155, 1088-1095 (2002); Olsen, J. H. et al. 92, 201-205 (2005); and Carney, C. P., et al Psychosom. Med. 66, 735-743 (2004)]. These studies, however, reveal a characteristic bimodal temporal pattern of brain tumor incidence. For example, in a study of patients with depression, although a remarkably high SIR of 3.27 for brain tumour incidence was observed within the first year following diagnosis, this value steadily decreased to 0.84 after 10 or more years from initial diagnosis (FIG. 9) [Dalton, S. O., et al. Am. J. Epidemiol. 155, 1088-1095 (2002)]. A similar bimodal phenomenon has been reported in Parkinson's disease patients: despite an initial increase in brain tumor incidence (SIR=1.32), incidence decreased substantially (SIR=0.85) five or more years after initial diagnosis [Olsen, J. H. et al. 92, 201-205 (2005)]. A third study that cited an elevated overall brain tumor incidence rate (SIR>2.00) in patients with mental illnesses similarly noted that median time to brain tumor diagnosis following psychiatric hospitalization was only 18 months [Carney, C. P., et al Psychosom. Med. 66, 735-743 (2004)]. The apparent initial increase in brain tumor incidence in these patients might in fact derive from occult pre-existing tumours associated with psychiatric manifestations. The failure to account for an initial disproportionate increase in brain tumor incidence in such patients may have obscured an important underlying relationship between psychiatric disease, its treatment, and brain tumor incidence. To account for this possible masking effect, the previous studies were re-analyzed after exclusion of brain tumors associated with the initial psychiatric or neurologic diagnosis (cancers<2 years from initial hospitalization) and indeed found a much more consistent negative correlation between psychiatric diagnosis and cancer incidence (See "Revised SIR" in Table 9). Although the low number of patients in each individual study precludes statistical significance, the pooled data sufficiently raises statistical power to reveal a significant decrease in brain tumor incidence in patients with psychiatric disorders (SIR=0.8, P=0.01, Comprehensive Meta-Analysis software). This result suggests that a wide array of neuromodulators may protect against brain cancer; such effects might derive from inhibition of the cell compartment that may give rise to brain tumors, i.e., neural stem cells, as observed in vitro [Examples 1 and 3].

Recent model system studies lend strong support to a BTSC neuromodulation hypothesis. Notably, the mGlu4 glutamate receptor agonist PHCCC has to be shown to attenuate medulloblastoma formation in vivo in mice [Iacovelli, L. et al. *J. Neurosci.* 26, 8388-8397 (2006)]. The generality of this phenomenon is suggested by the finding that a wide variety of psychoactive drugs known to act on diverse neurotransmission pathways inhibit both normal and cancerous neural precursor cell proliferation in vitro [Examples 1 and 3]. Intriguingly, the most potent anti-BTSC agents identified in these in vitro screens included the clinically prescribed dopamine agonist apomorphine [Hagell, P. & Odin, P. J. *Neurosci. Nurs.* 33, 21-28 (2001)] and the glutamate antagonist ifenprodil [Caillard, P., et al., *Angiology* 44, 552-560 (1993)]. Beyond the potential clinical implications for the long term use of neuropsychiatric agents acting on normal neural precursors, the cohort of well-tolerated neuropharmacological agents used in standard psychiatric practice offer the prospect of rapid redeployment in clinical trials for late stage brain cancers.

Example 3

To profile the signaling network of primary cultures of neural precursor cells (NPCs), 1,267 compounds were screened in the library of pharmacologically active compounds (the LOPAC™ library) for inhibitors of neurosphere proliferation, as measured by incorporation of the vital dye thiazolyl blue tetrazolium bromide (MTT) (FIG. 1a and FIG. 2a and Table 10). A Z¢ factor (16) of 0.78 and a Pearson correlation coefficient of 0.981 for replicate screens indicated that the assay was reliable. 160 compounds that significantly inhibited neurosphere proliferation (P<0.01) were clustered into groups of known pharmacologic action (Table 10 and Table 4). Known cytotoxic compounds that target essential cellular processes predictably scored as hits in the screen. Unexpectedly, however, many agents that modulate neurotransmission in the dopamine, serotonin, opioid, glutamate, vanilloid and other pathways potently inhibited growth of NPCs. Many of these agents are used in the clinical treatment of neurological disorders and are traditionally thought to act on mature central nervous system (CNS) cell populations. These compounds induced a variety of neurosphere phenotypes, including changes in sphere number, sphere size, and cell-cell or cell-surface adhesion properties, which suggests that an elaborate balance of these signaling pathways dictates NPC fate (FIG. 2b).

Figure 10:
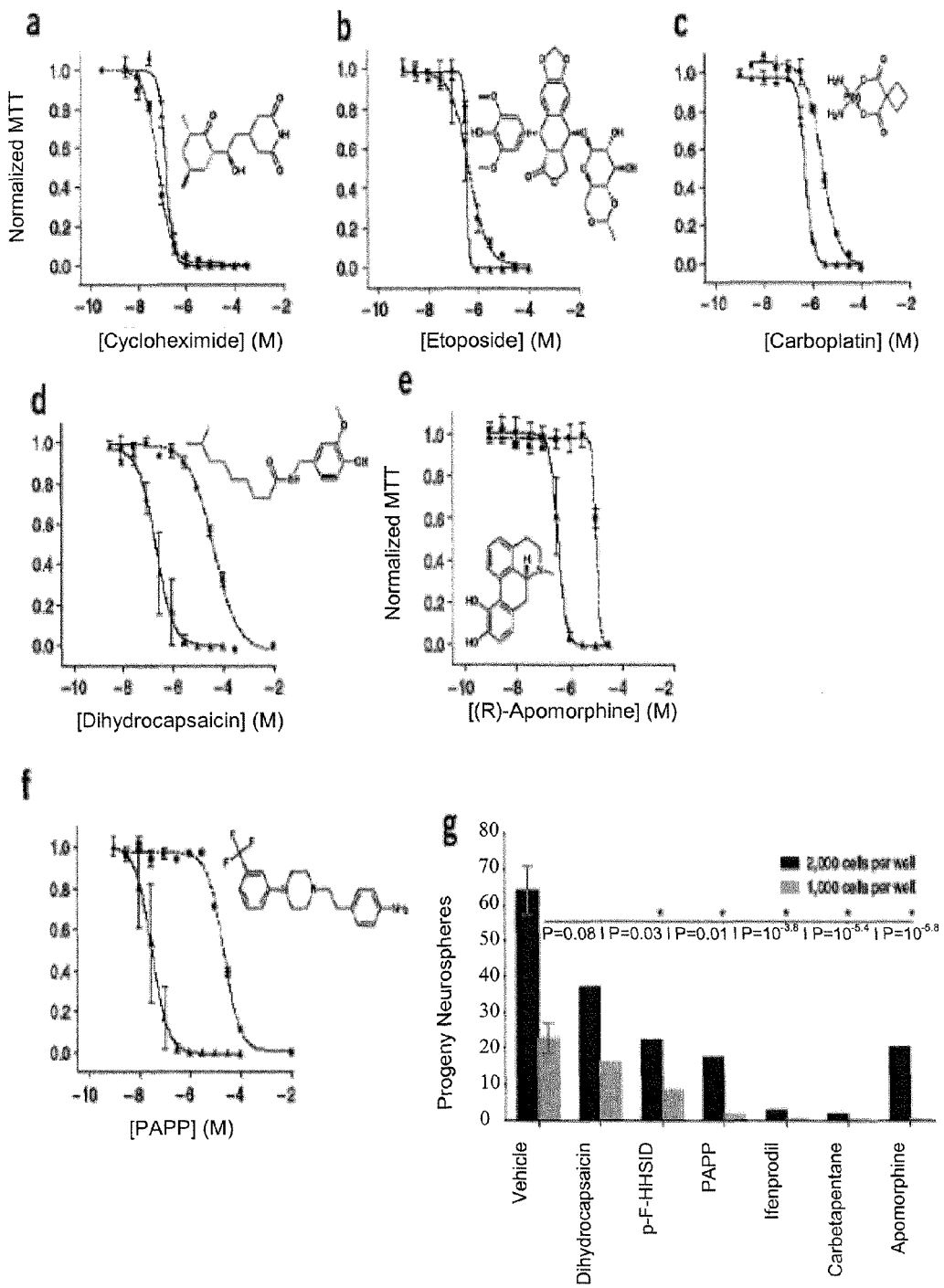
FIG. 10 shows the identification of potent NPC-specific compounds. (a-f) Dose-response curves and chemical structures of controls: cycloheximide (a), etoposide (b) and carboplatin (c), and of selected newly identified compounds: dihydrocapsaicin (d), apomorphine (e) and PAPP (f). Each plot shows the fitted sigmoidal logistic curve to MTT proliferation assay readings of both astrocytes (- -•- -) and neurosphere cultures (-▲-). Values represent the mean and s.e.m. of three independent experiments. (g) Replating colony forming efficiency of pretreated neurosphere cultures. Values represent the number of progeny neurospheres arising from 2,000 or 1,000 cells plated in fresh medium after a 7-d pretreatment of NPCs with the indicated inhibitor at the estimated $EC_{75}$ value. As the $EC_{75}$ of apomorphine did not allow the recovery of sufficient cells, an $EC_{50}$ pretreatment was used for this agent. Sphere counts for vehicle treated cells represent the mean and s.d. of six separate replicates conducted during two independent experiments. All other values represent the mean of two independent experiments. Asterisks indicate a reproduced statistically significant (P<0.05) reduction in replating efficiency when compared to vehicle control. The larger P value (of the two experiments) is reported. These differences (at both 2,000 and 1,000 cells per well) were confirmed (two-tailed paired t-test) for cultures treated with PAPP ($P_{2,000}$=0.02; $P_{1,000}$=0.008) and apomorphine ($P_{2,000}$=0.01; $P_{1,000}$=0.02) in three independent trials.

To verify hits from the primary screen, 43 representative candidates were retested at the original screen concentration of 3 mM; of these, 40 (93%) showed significant activity (P<0.05) (Table 8). Because other neural cell types express and signal through a number of neurotransmitter receptors (42), the selectivity and potency of each agent were assessed for a normal mouse astrocyte cell line versus NPCs. Dose-response curves were generated for 28 compounds in both neurosphere and astrocyte cultures and used to determine the effective concentration needed to decrease proliferation by 50% ($EC_{50}$) (FIG. 10a-f and Table 8). A neurosphere selectivity ratio, defined as $EC_{50}$ (astrocytes)/$EC_{50}$ (neurospheres), was determined for each compound and compared with that of known nonspecific inhibitors of proliferation (FIG. 10a-c). Compounds that had a neurosphere selectivity ratio greater than that observed in these control agents (45.08) were defined as NPC-specific agents (FIG. 10d-f and Table 2); 12 of the compounds tested showed high selectivity for NPCs. Notably, the serotonin agonist p-aminophenethyl-m-trifluoromethylphenyl piperazine (PAPP, 14) and the vanilloid receptor ligand dihydrocapsaicin were respectively 702- and 192-fold more selective for normal NPCs than for astrocyte cultures.

Neurospheres are comprised of a heterogeneous population of NSCs and lineage-restricted progenitor cells. To determine whether the inhibitors affected NSC self-renewal, as opposed to proliferation of more committed precursor populations, the higher order colony-forming efficiency of treated neurosphere cultures was analyzed. With the exception of dihydrocapsaicin, representative compounds from the main neurotransmission classes significantly reduced higher order neurosphere formation upon re-culture in the absence of drug (FIG. 10g). The various inhibitors therefore seem to target the neural precursor pool that is predominantly responsible for sphere formation.

Figure 11:
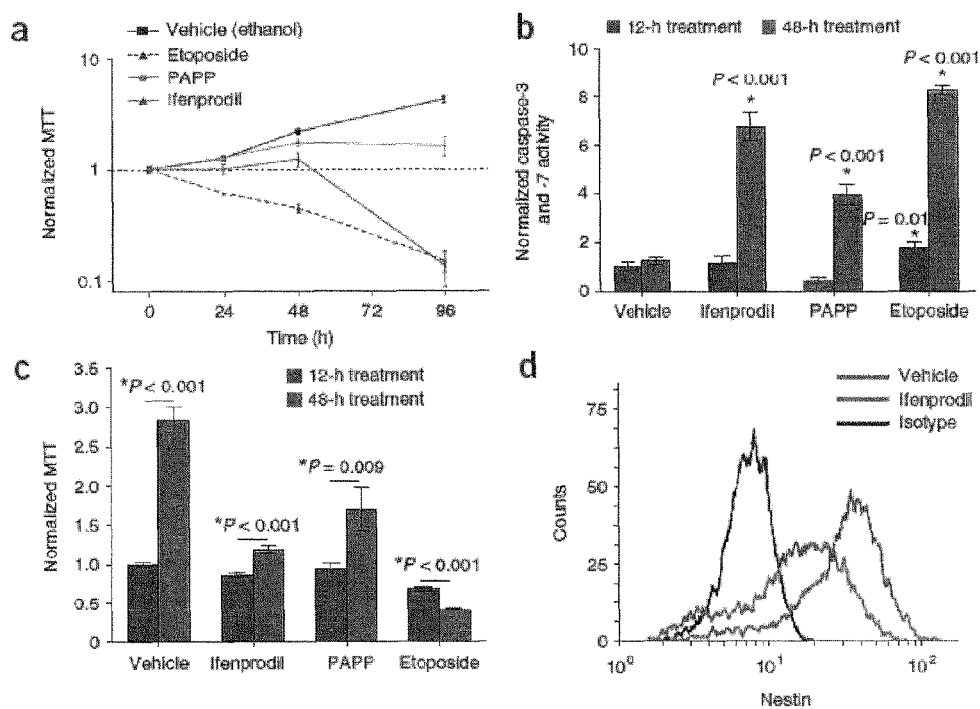
FIG. 11 shows temporal effects of neuromodulators on NPC viability and apoptotic response. (a) Proliferation dynamics of PAPP, ifenprodil and etoposide-treated NPCs. (b) Normalized caspase-3 and caspase-7 activity in NPCs after 12 h and 48 h of drug treatment. Asterisk indicates a significant change (two-tailed t-test) from the corresponding vehicle-treated data point. (c) Corresponding MTT values taken at 12 h and 2 d for the caspase-3 and caspase-7 experiments shown in b. All values represent the mean and s.d. of one representative experiment (from three independent trials) of NPCs treated with PAPP (1 μM), ifenprodil (3 μM), etoposide (3 μM) or vehicle. (d) Flow cytometric analysis of the neural precursor marker nestin in NPCs after 2 d of treatment with ifenprodil (5 μM) or vehicle. Representative histograms of vehicle treated (20% nestin negative; shown as the curve having the right-most peak on the graph) and ifenprodil treated (63% nestin negative; shown as the curve that peaks in the middle of the graph) cells compared with the isotype control (100% nestin negative; shown as the curve with the left-most peak on the graph) are shown from two independent experiments.

To further delineate the mechanism through which neuromodulatory agents impede expansion of NPCs in culture, timecourse analyses were performed for both cell viability and apoptosis. Unlike etoposide (FIG. 11a) and cycloheximide (data not shown), which have immediate effects on cell proliferation and viability, the neurotransmission modulators PAPP and ifenprodil decreased viable cell numbers only after 2 d post-treatment (FIG. 11a). Similar delayed-onset effects were observed for butaclamol, p-fluoro-hexahydrosiladifenidol (p-FHHSiD, 8) and carbetapentane (data not shown). Consistently, caspase-3 and caspase-7 concentrations were unchanged after 12 h of PAPP and ifenprodil treatment, but increased significantly (P<0.001) after 2 d of drug treatment (FIG. 1b). This increase in the apoptotic response of treated cells occurred at concentrations of drugs that did not abolish the initial proliferation or viability of these cells (FIG. 11c). Finally, expression of the immature NPC marker nestin was substantially decreased after treatment for 2 d with ifenprodil (FIG. 11d) and PAPP (data not shown). These results suggest that appropriate neurotransmission signaling is required to maintain NSC proliferation, survival and identity.

Figure 12:
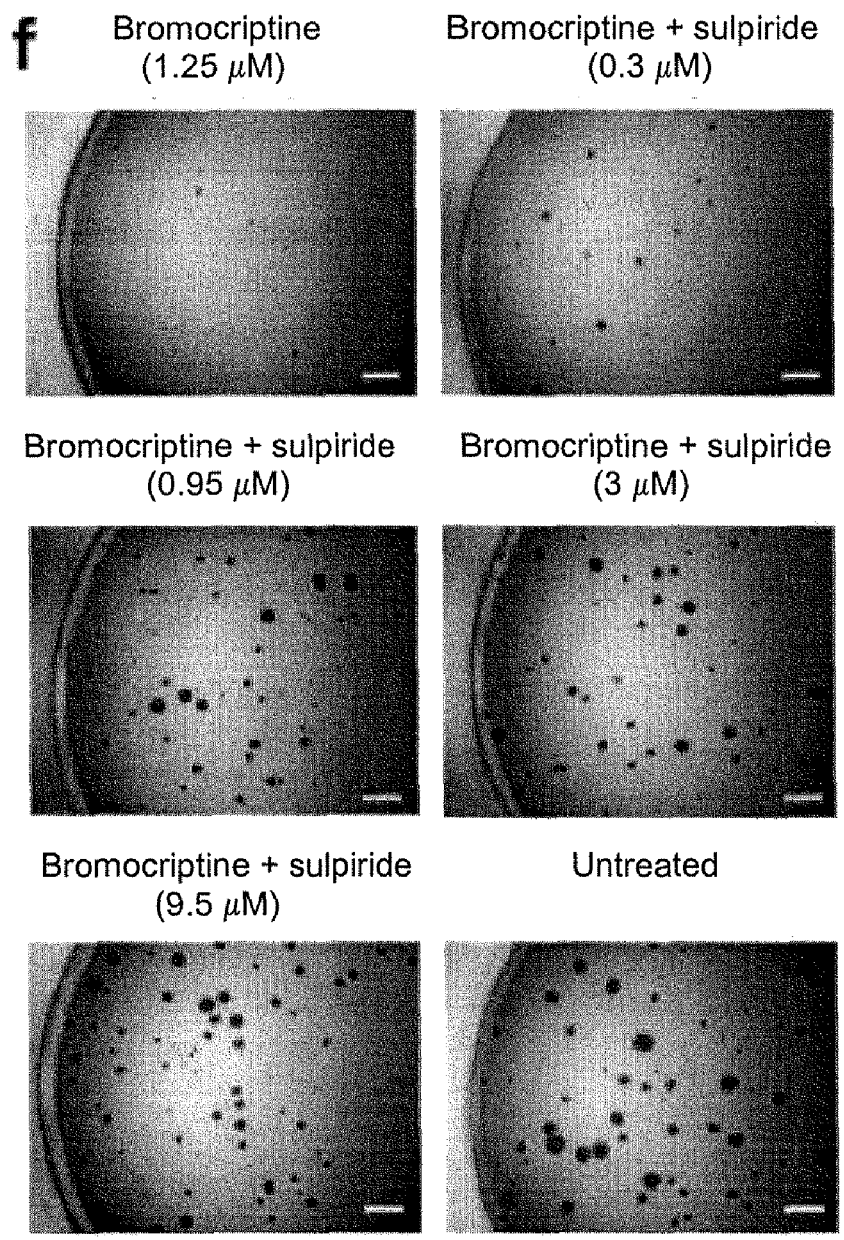
FIG. 12 shows neuromodulator drug sensitivity in normal and cancerous NPCs. (a) Ptch1+/− tumors contain cells with self-renewing neurosphere-forming potential in vitro. Scale bar, 125 mm. (b) Ptch1+/− tumor cells stain positive (M1) for the early precursor marker prominin-1 (CD133 homolog) at levels comparable to those of primary human medulloblastomas (11.6%)(4). Unstained (black curve with left-most peak on the graph) and stained (gray curve with right-most peak on the graph) specimens are shown. (c) EC50 values (mean and s.d.) for inhibition of Ptch1$^{+/-}$ Trp53$^{-/-}$ tumor sphere MTT proliferation by various neuromodulators. Compound identity indicated in Table 2. (d) RT-PCR gene expression profiles of a selection of neurotransmitter receptors in different precursor populations. mRNA from serum-differentiated neurospheres and mouse erythroid leukemia (MEL) cells were used as positive and negative controls, respectively. Vertical black line indicates noncontiguous lanes from the same experiment. (e) Inhibition of colony formation by bromocriptine in cultures with and without (±)-sulpiride supplementation. Normalized mean and s.e.m. values of three independent triplicate cultures are shown. Sulpiride challenge significantly shifted the EC$_{50}$ of bromocriptine from 1.2 µM (without sulpiride) to 2.5 µM (with sulpiride) (P<0.05), thereby indicating a rescue effect. (f) Representative micrographs of the inhibitory effects of bromocriptine on NPC expansion when challenged with a competitive antagonist. Scale bars, 500 mm.

As gene expression profiles of brain tumors resemble those of normal and embryonic NPCs (18-21), agents that inhibit normal neural precursor growth may also inhibit cultures of brain tumors that are enriched for cancer stem cells (41, 7, 18) Therefore the activity of a subset of NPC-specific inhibitors was assessed against low-passage (<4) neurosphere cultures derived from spontaneously formed medulloblastomas in heterozygous patched ($Ptch1^{+/-}$) and $Ptch1^{+/-}Trp53^{-/-}$ mice[22]. Like their normal counterparts, cancerous NPCs from these tumors grow as spheres in serum-free culture and express the neural precursor marker prominin1 (CD133) (FIG. 12a,b). The NPC-specific agents also potently suppressed the proliferation of both Ptch1+/− and Ptch1+/−Trp53−/− medulloblastoma precursor cell populations (FIG. 12c and Table 2). Notably, some of these agents were an order of magnitude more effective in the inhibition of tumor cell growth in vitro than the hedgehog signaling inhibitor cyclopamine (23). The expansion of normal human NPCs and human glioblastoma cells was also inhibited by neuromodulators (Table 9). For example, PAPP and ifenprodil had $EC_{50}$ values comparable to those of commonly used nonspecific brain tumor chemotherapeutic drugs, such as carboplatin and etoposide. Re-deployment of well-tolerated pharmacologically active agents may thus afford a new generation of chemotherapeutic agents specific for brain tumor stem cells.

As even well-characterized agents may exert biological effects through off-target pathways (34), it was verified that a number of the known receptors for various agents are indeed expressed in both normal and tumor NPCs. The dopamine (DRD2), acetylcholine (M3), NMDA (NR1) and serotonin (5HT-1A) receptors were present in primary and secondary normal mouse neurosphere cultures and Ptch1+/− tumor neurosphere cultures, as determined by RT-PCR (FIG. 12d). In addition, pharmacological inhibitors were used as a means to assess whether the growth inhibition caused by the dopamine class of neuromodulators depends on transmission through a known receptor.

Figure 13:
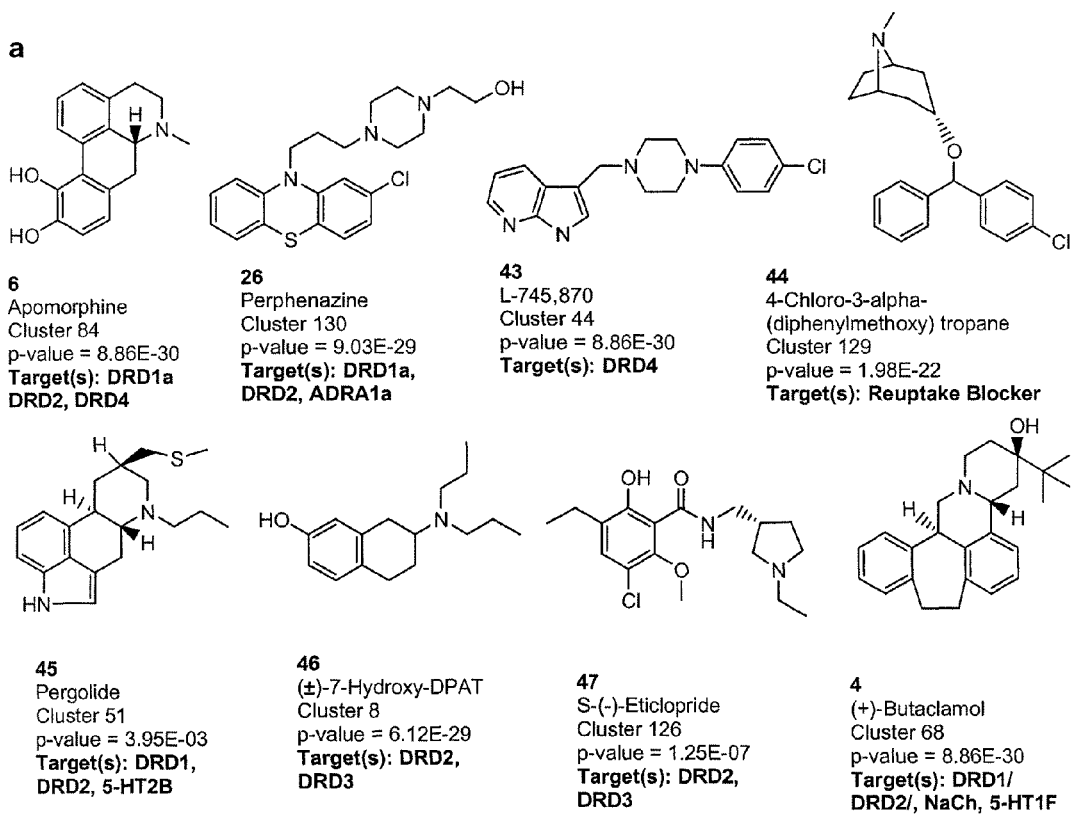
FIG. 13 shows that bioactive neuromodulators display a rich intra-class chemical diversity. (a) 8 of the 22 bioactive agents identified as dopamine signaling regulators. All 8 molecules are found in unique clusters when grouped based on 2D chemical fingerprint. A total of 10 different clusters were identified within the 22 agents known to act on the dopamine pathways. (b) 8 of the 12 bioactive agents identified as serotonin signaling regulators. All 8 molecules are found in unique clusters when grouped based on 2D chemical fingerprint. A total of 10 different clusters were identified within the 12 agents known to act on the serotonin pathway. P-value represents the original significance testing preformed from the screening data. Reported drug targets displayed in this figure represents curated data published in Wishart, D. S. et al. DrugBank: a comprehensive resource for in silico drug discovery and exploration. *Nucleic Acids Res.* 34, D668-D672 (2006) and inhouse.
Figure 13:
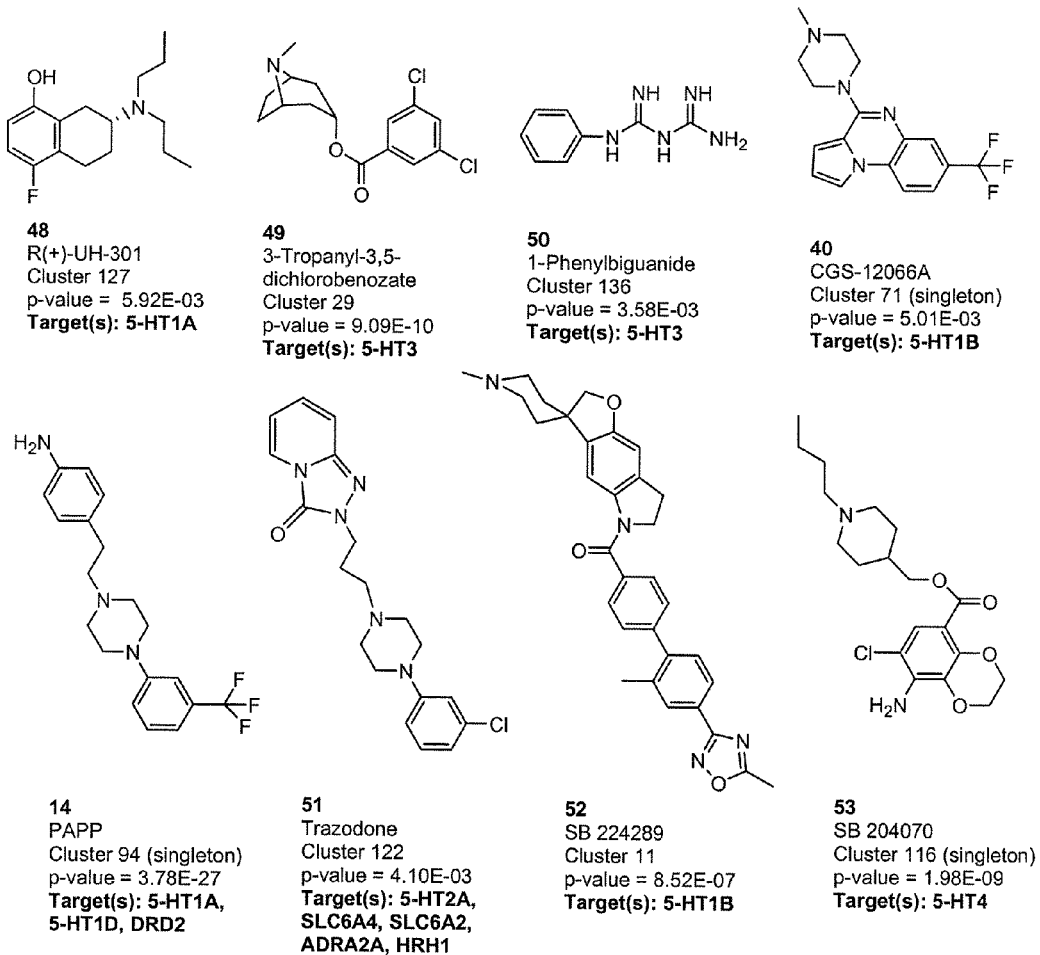

In one example, (±)-sulpride (34), a D2 dopamine receptor antagonist, was able to competitively rescue the inhibitory effects of the D2 and D3 dopamine receptor agonist bromocriptine (24), as judged by both colony formation (FIG. 12e,f) and MTT values (data not shown). To further assess the potential for off-target effects of neuromodulators in other classes, the 160 bioactive agents from the primary screen were clustered based on their chemical structures (Table 10). This analysis demonstrated substantial chemical structural diversity within each of the different neuromodulator classes. For example, the 22 bioactive dopamine agents identified in the screen spanned 10 different structural motif clusters; similarly, the 12 active serotonergic agents covered 10 different chemical clusters (FIG. 13). The observed sensitivity of NPCs to these structurally diverse agents is thus likely to arise through effects on known neurotransmission receptors, as opposed to some unknown coincident target.

The ex vivo and in situ manipulation of NSCs for treating neurological disorders, including brain cancer, will require an understanding of the global signaling network that regulates NSC behavior. Through a chemical genetic approach the existence of a complex functional 'ground state', was uncovered whereby NSC proliferation and self-renewal is regulated by numerous signaling pathways (FIG. 4d,e). Importantly, this cohort includes many neurotransmission pathways previously thought to function only in mature cells of the CNS. Therefore, NSC proliferation and self-renewal requires an appropriate local environment of neurotransmitter activities, which may be provided by a basal level of autocrine feedback from more committed cells within the neurosphere or even the NSC itself. Indeed, recent studies on individual pathways support the notion that proliferation of different progenitor subpopulations in vivo may respond to dopamine, serotonin, acetylcholine and glutamate (24). Notably, the chemical genetic profile demonstrates the simultaneous operation of these pathways in NPCs cultured under uniform experimental conditions. This sensitivity of NPC cultures to a spectrum of neuroactive compounds also supports the notion of lineage priming in the NSC compartment, similar to that seen in hematopoietic stem cells (2).

Though the precursor subpopulations targeted by each inhibitor identified in the screen have yet to be definitively identified, the strong selectivity of many agents for NPCs and primary brain tumor cells suggests that the affected pathways lie high in the hierarchical organization of the neuronal lineage. Indeed, the often complete inhibition of neurosphere proliferation and the effects on secondary replating suggest that stem cells and/or very early progenitor components of the population are affected by these agents. The finding that both inhibitors and activators of specific pathways inhibit neurosphere proliferation (for example, dopamine receptor agonists and antagonists) suggests that a complex signaling landscape dictates NSC fate (33). The pro-proliferative culture conditions used in the neurosphere assay may have biased the assay against identification of significant numbers of small molecules that stimulate proliferation. A small-molecule activator of embryonic stem cell proliferation has recently been identified (43), which suggests that analogous screens may succeed in identifying activators of NPC proliferation.

Figure 14:
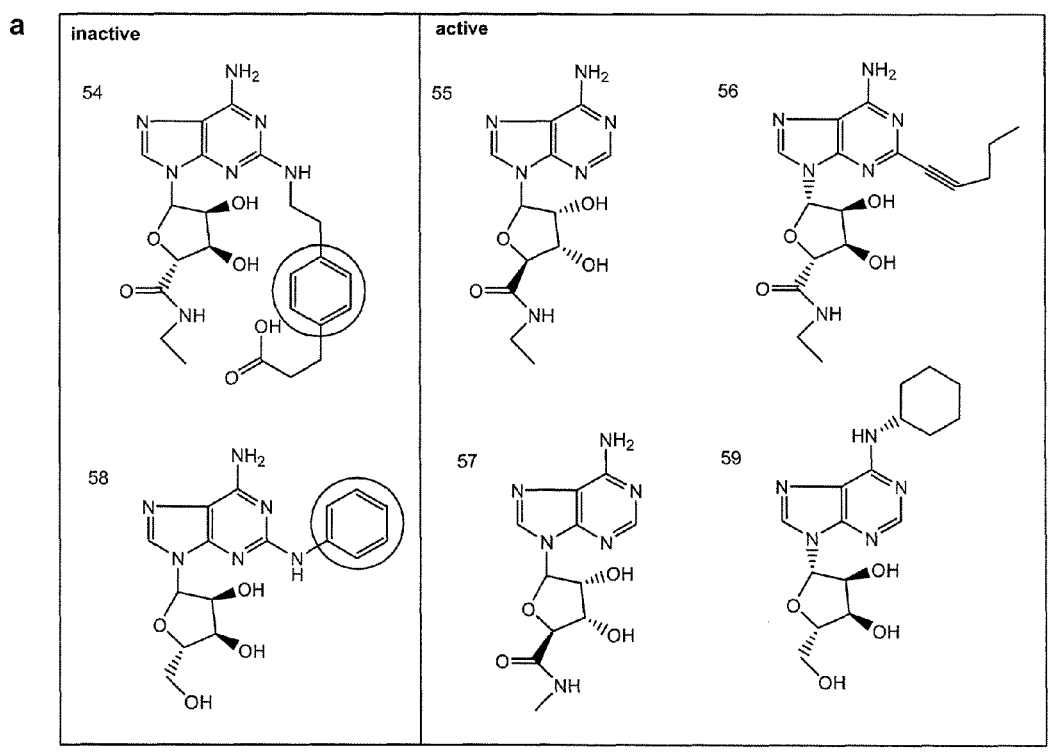
FIG. 14 shows SAR analysis of adenosine and serotonin agonists. (a) SAR analysis of an array of structurally similar adenosine agonists (cluster 132): CGSi-21680 (54), 5'-N-Ethylcarboxamidoadenosine (55), HE-NECA (56), 2-Phenylaminoadenosine (58), 5'-N-Methyl carboxamidoadenosine (57), N6-Cyclohexyladenosine (59). (b) SAR analysis of an array of structurally similar serotonin agonists (cluster 127): R(+)-UH-301 (48), S(–)-UH-301 (64), R-(+)-8-Hydroxy-DPAT (65), (±)-8-Hydroxy-DPAT (66), (±)-PPHT (67) (DRD2 agonist). "active" represents agents found to significantly suppress the number of viable cells (MTT scores) in the initial screen. "inactive" represents agents that were predicted to have activity (but did not) based on their structural similarities; suggesting important structural changes. Functional substitutions presumed to have positive (solid black in (a)) and negative (dashed black in (b)) effects on activity are circled.
Figure 14:
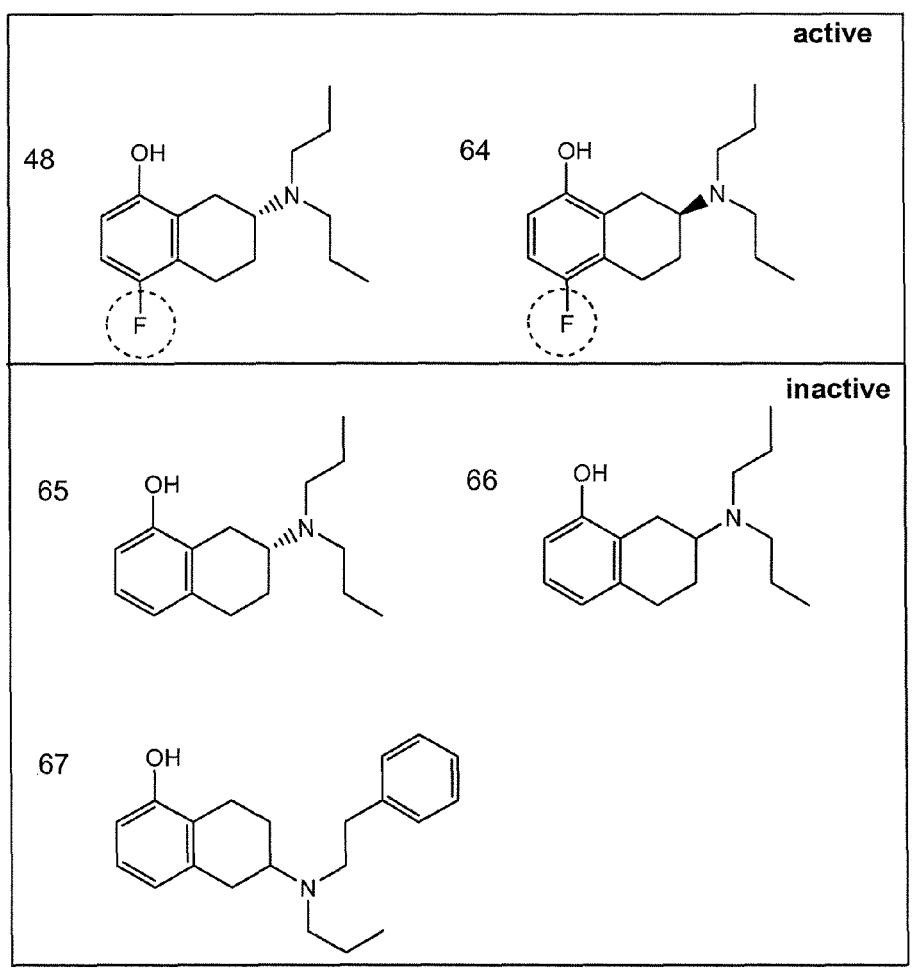
Figure 15:
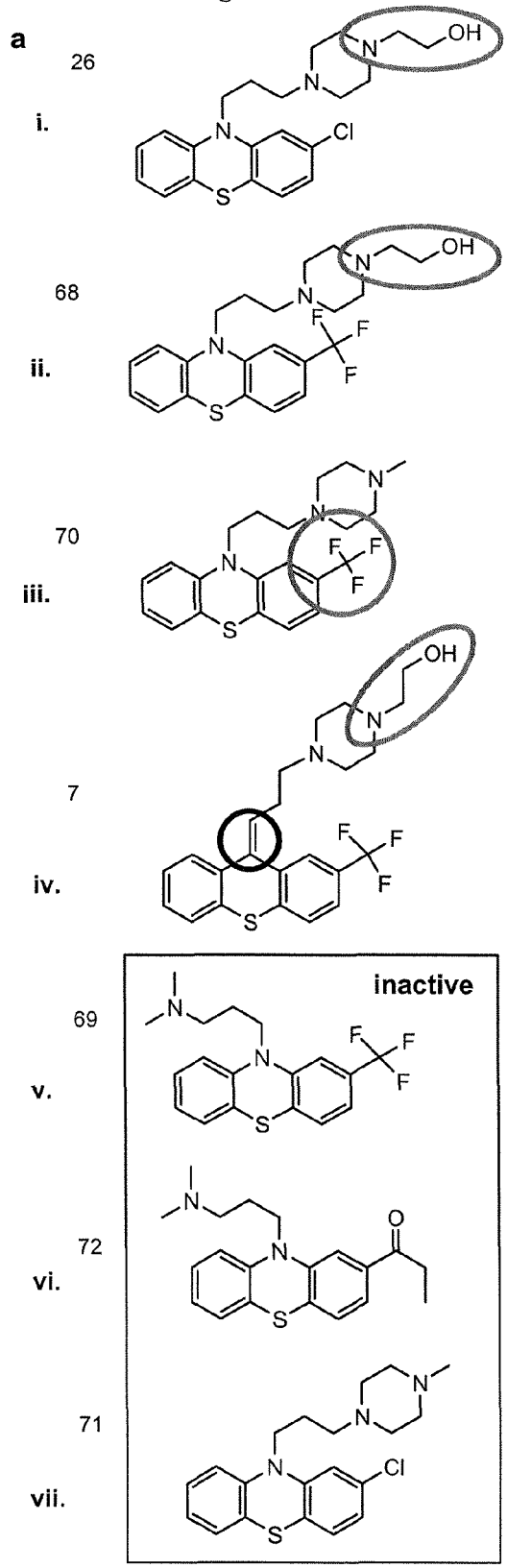
FIG. 15 shows SAR analysis of dopamine agonists and antagonist (a) SAR present in structurally related dopamine antagonists (cluster 130). i. Perphenazine (26) ii. Fluphenazine (68) iii. Trifluoperazine (70) iv. cis-(Z)-Flupenthixol (7) v. Triflupromazine (69) vi. Propionylpromazine (72) vii. Prochlorperazine (71) (b) SAR present in structurally related dopamine agonist (cluster 84). i. Apomorphine (6) ii. R(–)-Apocodeine (63) iii. R(–)-Propylnorapomorphine (5) iv. R(–)-N-Allylnorapomorphine (62) v. R(–)-2,10,11-Trihydroxyaporphine (60) vi. R(–)-2,10,11-Trihydroxy-Npropylnorapomorphine (61). All agents (unless otherwise stated) were active in the initial screen. Agents are arranged in descending order (i.=most active and vii=least active) with respect to their observed biological response. Functional substitutions presumed to have positive (light gray) and negative (dark gray) effects on activity are circled.
Figure 15:
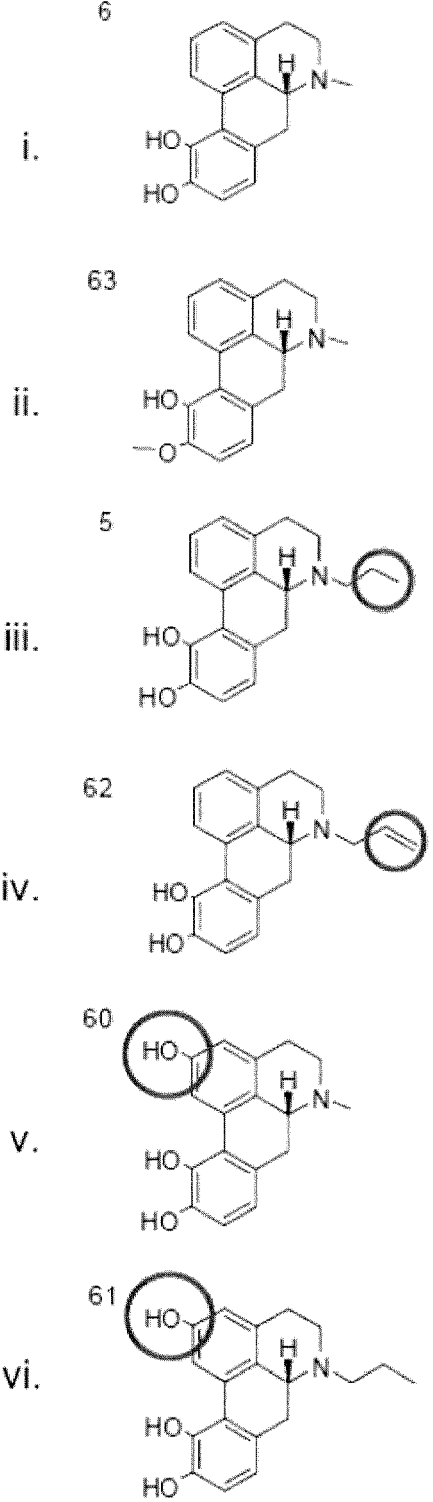

The unanticipated actions of well-characterized clinical agents on NPCs may account in whole or in part for the observed clinical benefits of these agents and/or the adverse side effects that arise after prolonged therapy. Effective in vivo concentrations of the anti-Parkinsonian drug apomorphine reach 6-7 µM (44), which is substantially higher than doses that affect NPCs in vitro. Thus the regulation of NSC proliferation by neurotransmitters may also dictate how the CNS is wired both during development and in the adult brain (45). Recent evidence suggests that appropriate GABA stimulation of NPCs is required for the proper integration of neurons in the adult hippocampus (46). Through structure-activity analysis, we also identified specific chemical substitutions that are important for the bioactivity of these agents in our in vitro system (FIGS. 14 and 15). Such modifications to the core chemical structure of many clinically used agents may afford a way to regulate the potentially therapeutic or harmful effects these drugs have on NPCs.

In light of the evidence that CNS tumors are maintained by cancer stem cells (41,5), which have similarities to normal NSCsm (18), the potent and selective antiproliferative agents identified in this study may presage a new generation of therapeutic agents in brain cancer. Notably, a retrospective analysis of cancer incidence in individuals with Parkinson disease revealed a significant reduction in the incidence of brain tumors relative to the expected incidence in the general population (35); this correlation may derive from the effect of anti-Parkinsonian drugs on the NPCs from which brain tumors are thought to arise. As the complex NSC ground state is likely to at least in part define the identity of brain tumor stem cells, re-deployment of pharmacologically approved neuroactive agents may provide an immediate and nontoxic means to treat often intractable CNS tumors.

Methods

Primary embryonic mouse NSC isolation and culture. Isolation and culture of primary embryonic (e14.5) mouse NSCs was performed as previously described in chemically defined NSC medium (37) containing 20 ng $mL^{-1}$ human recombinant epidermal growth factor (Sigma), 20 ng $mL^{-1}$ basic fibroblast growth factor (Upstate) and 2 µg $mL^{-1}$ heparin (Sigma). Cells were fed every 2-3 d (36).

Secondary mouse NSC neurosphere culture and chemical screens. Before chemical screens and other manipulations, the NSC fraction in culture was expanded by growing freshly dissected cells as primary neurospheres (8) in bulk culture ($10^6$ cells $mL^{-1}$). After 7 d, primary neurospheres were collected and enzymatically digested for 3 min at 37° C. using the ACCUTASE™ reagent (Sigma), mechanically dissociated with a 1-mL pipette and passed through a cell strainer (Falcon). Viable cells were plated at low cell densities (20 cells $\mu l^{-1}$) in 96-well plates (Falcon) in a final volume of 100 μL and screened in singlets against the LOPAC™ library (Sigma) at a concentration of 3 μM (0.03% DMSO). On day 4, each well in the screen was supplemented with an additional 50 mL of fresh mouse NSC medium and another aliquot of the LOPAC™ library (maintaining the final concentration of each compound at 3 μM). Secondary neurosphere cultures were then incubated for an additional 3 d (until day 7), at which point the effect of each compound was assessed by quantifying the total proliferation of each well using the incorporation of the vital dye MTT (Sigma) as previously described (4).

Statistical analysis for chemical screen. Background plate effects occurring from the evaporation of medium over the course of the experiment were estimated by:

$$b_i = \frac{1}{N - N_i^h} \sum_{j=1}^{N} x'_{i,j}$$

where $x'_{i,j}$ is the value at well i of plate j, $Nh_i^h$ is the number of excluded hits or outliers that were 2 s.d. below the mean, N is the total number of plates in the screen, and $b_i$ is the estimated background at each well position (39). The respective background was then subtracted from the raw MTT value measured for each point. To calculate significance (z score and P value), the theoretical probability density function N(1.0, 0.11) was fitted to the empirical normalized distribution obtained from the screen. Compounds that caused optical density readings to significantly deviate from this predicted underlying distribution function (P<0.01) were designated as bioactive (40).

Dose-response curves and $EC_{50}$ calculations. Potency of confirmed bioactive compounds was quantified by generating dose-response curves for mouse NSC under the same cell density and culture conditions described for the initial screen. Starting from initial concentrations between 300 and 30 μM, each compound was titrated across a series of ten half-log dilutions. Each agent was tested in triplicate in at least three independent experiments. $EC_{50}$ values for each agent were calculated by fitting the data points to the four-parameter logistic sigmoidal dose-response curve:

$$Y = EC_{100} + \frac{EC_0 - EC_{100}}{1 + 10^{\log(EC_{50} - X)(Hill\ Slope)}}$$

where X is the logarithm of concentration and Y is the predicted response. Curve fitting was performed with GraphPad PRISMS software (GraphPad Software, Inc.).

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the methods etc. which are reported therein which might be used in connection with the invention. Nothing herein is to be construed as an admission that the invention is not entitled to antedate such disclosure by virtue of prior invention.

TABLE 1

HTS bioactive pharmacological classes

| Class[†] | Active Agents[‡] | Total Agents | % Active in Class |
|---|---|---|---|
| Cytotoxic[§] | 38 | 114 | 33 |
| Biochemistry | 6 | 46 | 13 |
| Cannabinoid | 1 | 6 | 17 |
| Cholinergic | 8 | 77 | 10 |
| Cyclic Nucleotides | 4 | 31 | 13 |
| Dopamine | 22 | 113 | 20 |
| Glutamate | 9 | 88 | 10 |
| Intracellular $Ca^{2+}$ | 2 | 7 | 29 |
| Ion Pump | 3 | 16 | 19 |
| Lipid | 1 | 9 | 11 |
| $Na^+$ Channel | 3 | 17 | 18 |
| Nitric Oxide | 5 | 37 | 14 |
| Opioid | 6 | 27 | 22 |
| P2 Receptor | 2 | 14 | 14 |
| Phosphorylation | 9 | 93 | 10 |
| Serotonin | 12 | 83 | 14 |
| Vanilloid | 2 | 5 | 40 |
| Entire Screen | 160 | 1267 | 13[¥] |

[†]Includes all classes with a "% Active in Class" of at least 10%.
[‡]Only includes inhibitors
[§]Includes: antibiotics, apoptosis, cell cycle, cell stress, cytoskeleton, and DNA
[¥]Frequency of whole screen

TABLE 2

Highly potent and highly selective compounds identified by HTS of neurospheres

| Name | Action | Target | Selectivity | Neurosphere $EC_{50}$ (μM) | Astrocyte $EC_{50}$ (μM) | Neurosphere selectivity | Ptch1[+/−] neurosphere $EC_{50}$ (μM)[b] | Ptch1[+/−] Trp53[−/−] neurosphere $EC_{50}$ (μM)[b] |
|---|---|---|---|---|---|---|---|---|
| Controls | | | | | | | | |
| Cycloheximide (1) | Inhibitor | Protein synthesis | 60S ribosome | 0.142 | 0.071 | 0.50 | 0.042 | 0.054 |
| Etoposide (2) | Inhibitor | Topoisomerase | Topo II | 0.340 | 0.433 | 1.28 | 0.208 | n.t. |
| Carboplatin (3) | Intercalator | DNA | n.a. | 0.489 | 2.453 | 5.08 | 0.196 | n.t. |
| Selected hits[a] | | | | | | | | |
| (±) Butaclamol (4) | Antagonist | Dopamine receptor | D2 > D1 | 0.785 | 12.34 | 15.7 | 0.751 | 2.533 |
| (R)-(−)- | Agonist | Dopamine receptor | D2 | 0.351 | 8.230 | 23.4 | 0.199 | n.t. |

TABLE 2-continued

Highly potent and highly selective compounds identified by HTS of neurospheres

| Name | Action | Target | Selectivity | Neurosphere $EC_{50}$ (μM) | Astrocyte $EC_{50}$ (μM) | Neurosphere selectivity | Ptch1$^{+/-}$ neurosphere $EC_{50}$ (μM)[b] | Ptch1$^{+/-}$ Trp53$^{-/-}$ neurosphere $EC_{50}$ (μM)[b] |
|---|---|---|---|---|---|---|---|---|
| Propylnorapomorphine (5) | | | | | | | | |
| (R)-(−)-Apomorphine (6) | Agonist | Dopamine receptor | n.a. | 0.350 | 10.19 | 29.1 | 0.168 | 0.683 |
| cis-(Z)-Flupenthixol (7) | Antagonist | Dopamine receptor | n.a. | 0.199 | 1.182 | 5.93 | 0.187 | n.t. |
| p-F-HHSiD (8) | Antagonist | Acetylcholine receptor | M3 > M1 > M2 | 0.441 | 5.815 | 13.2 | 1.125 | 1.373 |
| Ifenprodil (9) | Antagonist | NMDA receptor | Polyamine site | 0.616 | 11.06 | 17.9 | 0.451 | 0.807 |
| Carbetapentane (10) | Agonist | Opioid receptor | Sigma 1 | 0.756 | 28.16 | 37.3 | 2.083 | 2.040 |
| Fenretinide (11) | Agonist | Retinoic acid receptor | n.a. | 0.334 | 2.399 | 7.18 | 0.204 | n.t. |
| WHI-P131 (12) | Antagonist | JAK3 | n.a. | 2.346 | n.d. | >10 | 1.525 | n.t. |
| SB 202190 (13) | Antagonist | p38 MAPK | n.a. | 8.063 | 64.8 | 8.04 | 3.006 | n.t. |
| PAPP (14) | Agonist | Serotonin receptor | 5-HT1A | 0.031 | 21.82 | 702 | 0.169 | 0.097 |
| Dihydrocapsaicin (15) | Agonist | Vanilloid receptor | VR1 | 0.218 | 41.83 | 192 | 0.020 | 0.651 |
| Cyclopamine (16) | Antagonist | Smoothened | | n.t. | n.t. | n.a. | 1.00 | 13.44 |

[a]Compounds listed represent confirmed hits with high selectivity for NPCs (neurosphere selectivity >5).
[b]Ptch1$^{+/-}$ and Ptch1$^{+/-}$ Trp53$^{-/-}$ neurosphere cultures were derived from mouse cerebeller tumor samples.
n.a., not applicable;
n.d., not determined at highest tested dose (30 μM);
n.t., not tested.

TABLE 3

| Product Name | Z Score | P Value | Class |
|---|---|---|---|
| L-745,870 hydrochloride | −11.273568 | 8.86E-30 | Dopamine |
| NS 521 oxalate | −11.273568 | 8.86E-30 | Glutamate |
| Pentamidine isethionate | −11.273568 | 8.86E-30 | Glutamate |
| Rotenone | −11.273568 | 8.86E-30 | Cell Stress |
| Taxol | −11.273568 | 8.86E-30 | Cytoskeleton and ECM |
| Apomorphine hydrochloride hemihydrate | −11.273568 | 8.86E-30 | Dopamine |
| Amsacrine hydrochloride | −11.273568 | 8.86E-30 | DNA Repair |
| Brefeldin A from Penicillium brefeldianum | −11.273568 | 8.86E-30 | Cytoskeleton and ECM |
| Cytosine-1-beta-D-arabinofuranoside hydrochloride | −11.273568 | 8.86E-30 | DNA Metabolism |
| Dequalinium analog, C-14 linker | −11.273568 | 8.86E-30 | Phosphorylation |
| (+)-Butaclamol hydrochloride | −11.273568 | 8.86E-30 | Dopamine |
| GBR-12935 dihydrochloride | −11.273568 | 8.86E-30 | Dopamine |
| Idarubicin | −11.273568 | 8.86E-30 | DNA Metabolism |
| ML-7 | −11.273568 | 8.86E-30 | Phosphorylation |
| Purvalanol A | −11.234146 | 1.39E-29 | Phosphorylation |
| Podophyllotoxin | −11.146914 | 3.71E-29 | Cytoskeleton and ECM |
| N,N,N-trimethyl-1-(4-trans-stilbenoxy)-2-propylammonium iodide | −11.127221 | 4.62E-29 | Cholinergic |
| (B1)-7-Hydroxy-DPAT hydrobromide | −11.102218 | 6.12E-29 | Dopamine |
| Etoposide | −11.10168 | 6.16E-29 | Apoptosis |
| Perphenazine | −11.064721 | 9.30E-29 | Dopamine |
| NG-Hydroxy-L-arginine acetate | −10.957625 | 3.05E-28 | Nitric Oxide |
| GBR-12909 dihydrochloride | −10.898733 | 5.84E-28 | Dopamine |
| Vincristine sulfate | −10.792318 | 1.87E-27 | Cytoskeleton and ECM |
| Colchicine | −10.753322 | 2.86E-27 | Cytoskeleton and ECM |
| PAPP | −10.727538 | 3.78E-27 | Serotonin |
| Chelerythrine chloride | −10.670736 | 6.98E-27 | Phosphorylation |
| MG 624 | −10.65959 | 7.86E-27 | Cholinergic |
| Tamoxifen citrate | −10.643209 | 9.38E-27 | Phosphorylation |
| Hexamethonium dichloride | −10.634291 | 1.03E-26 | Cholinergic |
| Emetine dihydrochloride hydrate | −10.632537 | 1.05E-26 | Apoptosis |
| Ro 25-6981 hydrochloride | −10.524254 | 3.34E-26 | Glutamate |
| beta-Lapachone | −10.428163 | 9.22E-26 | Apoptosis |
| 2,3-Dimethoxy-1,4-naphthoquinone | −10.39849 | 1.26E-25 | Cell Stress |
| 2-Methylthioadenosine diphosphate trisodium | −10.359444 | 1.90E-25 | P2 Receptor |
| Mitoxantrone | −10.205238 | 9.39E-25 | DNA Metabolism |
| Methotrexate | −10.20279 | 9.63E-25 | DNA Metabolism |
| Fluphenazine dihydrochloride | −10.196835 | 1.02E-24 | Dopamine |
| Naloxone hydrochloride | −10.136773 | 1.90E-24 | Opioid |
| Diphenyleneiodonium chloride | −10.067553 | 3.84E-24 | Nitric Oxide |
| Sanguinarine chloride | −10.007525 | 7.06E-24 | Ion Pump |
| Dihydrocapsaicin | −10.002879 | 7.40E-24 | Vanilloid |
| Ancitabine hydrochloride | −9.9514465 | 1.24E-23 | DNA Metabolism |
| Arecaidine propargyl ester hydrobromide | −9.931444 | 1.52E-23 | Cholinergic |
| R(−)-Apocodeine hydrochloride | −9.8651075 | 2.95E-23 | Dopamine |
| Aminopterin | −9.7829747 | 6.66E-23 | Antibiotic |

TABLE 3-continued

| | | | |
|---|---|---|---|
| Oligomycin A | −9.7309305 | 1.11E−22 | Antibiotic |
| Quinacrine dihydrochloride | −9.7123126 | 1.34E−22 | Neurotransmission |
| 4'-Chloro-3-alpha-(diphenylmethoxy)tropane hydrochloride | −9.6720309 | 1.98E−22 | Dopamine |
| (S)-(+)-Camptothecin | −9.6697698 | 2.03E−22 | Apoptosis |
| Sobuzoxane | −9.6000064 | 4.00E−22 | Gene Regulation |
| Thapsigargin | −9.5587077 | 5.96E−22 | Intracellular Calcium |
| Dequalinium dichloride | −9.5400125 | 7.14E−22 | K+ Channel |
| Vinblastine sulfate salt | −9.3963618 | 2.82E−21 | Cytoskeleton and ECM |
| XK469 | −9.3551196 | 4.18E−21 | Apoptosis |
| ML-9 | −9.3219716 | 5.71E−21 | Phosphorylation |
| Trifluoperazine dihydrochloride | −9.305347 | 6.68E−21 | Dopamine |
| 3-Tropanyl-3,5-dichlorobenzoate | −9.2724882 | 9.09E−21 | Serotonin |
| Raloxifene hydrochloride | −9.222082 | 1.46E−20 | Hormone |
| L-687,384 hydrochloride | −9.1556538 | 2.70E−20 | Opioid |
| CGP-74514A hydrochloride | −9.1170189 | 3.86E−20 | Phosphorylation |
| alpha-Guanidinoglutaric acid | −9.0407549 | 7.78E−20 | Nitric Oxide |
| N-Vanillylnonanamide | −9.0288161 | 8.68E−20 | Vanilloid |
| U-74389G maleate | −8.9415104 | 1.92E−19 | Cell Stress |
| Ganciclovir | −8.9391761 | 1.96E−19 | Cell Cycle |
| Ifenprodil tartrate | −8.9040193 | 2.69E−19 | Glutamate |
| cis-(Z)-Flupenthixol dihydrochloride | −8.8224805 | 5.60E−19 | Dopamine |
| Iodoacetamide | −8.7062214 | 1.57E−18 | Biochemistry |
| (−)Amethopterin | −8.704359 | 1.60E−18 | DNA Metabolism |
| Calmidazolium chloride | −8.5823395 | 4.65E−18 | Intracellular Calcium |
| Ellipticine | −8.3212021 | 4.35E−17 | Cell Cycle |
| R(−)-Propylnorapomorphine hydrochloride | −8.2743401 | 6.46E−17 | Dopamine |
| Metolazone | −8.1125047 | 2.48E−16 | Ion Pump |
| Carbetapentane citrate | −8.0209588 | 5.25E−16 | Opioid |
| Azathioprine | −7.9126948 | 1.26E−15 | P2 Receptor |
| R(−)-N-Allylnorapomorphine hydrobromide | −7.8390562 | 2.27E−15 | Dopamine |
| 5-Fluorouracil | −7.7492672 | 4.62E−15 | Cell Cycle |
| 3-Methoxy-morphinan hydrochloride | −7.7143362 | 6.08E−15 | Glutamate |
| Methoctramine tetrahydrochloride | −7.0117942 | 1.18E−12 | Cholinergic |
| 2-(alpha-Naphthoyl)ethyltrimethylammonium iodide | −6.7623855 | 6.79E−12 | Cholinergic |
| 3-Amino-1-propanesulfonic acid sodium | −6.6910884 | 1.11E−11 | GABA |
| Mevastatin | −6.2782013 | 1.71E−10 | Antibiotic |
| Carboplatin | −6.2035622 | 2.76E−10 | DNA |
| Retinoic acid p-hydroxyanilide | −6.013426 | 9.08E−10 | Cell Cycle |
| (B1)-Butaclamol hydrochloride | −5.9339136 | 1.48E−09 | Dopamine |
| SB 204070 hydrochloride | −5.8860023 | 1.98E−09 | Serotonin |
| S-(−)-Eticlopride hydrochloride | −5.1577465 | 1.25E−07 | Dopamine |
| 3'-Azido-3'-deoxythymidine | −5.0229615 | 2.54E−07 | Immune System |
| Chlorprothixene hydrochloride | −5.0075345 | 2.76E−07 | Dopamine |
| Metaphit methanesulfonate | −4.9672663 | 3.40E−07 | Opioid |
| SB 224289 hydrochloride | −4.7857097 | 8.52E−07 | Serotonin |
| Triamterene | −4.6424998 | 1.72E−06 | Na+ Channel |
| N-Acetylprocainamide hydrochloride | −4.5574345 | 2.59E−06 | Na+ Channel |
| Guanidinoethyl disulfide dihydrobromide | −4.5207865 | 3.08E−06 | Nitric Oxide |
| SKF 96365 | −4.4967357 | 3.45E−06 | Ca2+ Channel |
| R(−)-Denopamine | −4.4857956 | 3.63E−06 | Adrenoceptor |
| Metergoline | −4.3419185 | 7.06E−06 | Serotonin |
| Disopyramide | −4.1788419 | 1.46E−05 | Na+ Channel |
| (+)-Brompheniramine maleate | −3.9756943 | 3.51E−05 | Histamine |
| Cephalexin hydrate | −3.9664324 | 3.65E−05 | Antibiotic |
| DL-alpha-Methyl-p-tyrosine | −3.9081784 | 4.65E−05 | Neurotransmission |
| Melphalan | −3.907414 | 4.66E−05 | DNA Metabolism |
| CNS-1102 | −3.7824639 | 7.76E−05 | Glutamate |
| Benztropine mesylate | −3.7491883 | 8.87E−05 | Cholinergic |
| (B1)-Brompheniramine maleate | −3.5302827 | 0.0002076 | Histamine |
| Actinonin | −3.501397 | 0.0002314 | Biochemistry |
| Protoporphyrin IX disodium | −3.4407749 | 0.00029 | Cyclic Nucleotides |
| (+)-cis-Dioxolane iodide | −3.4020249 | 0.0003344 | Cholinergic |
| Indomethacin morpholinylamide | −3.397557 | 0.00034 | Cannabinoid |
| Ketanserin tartrate | −3.3253093 | 0.0004416 | Serotonin |
| Cephalosporin C zinc salt | −3.3091048 | 0.000468 | Antibiotic |
| R(−)-2,10,11-Trihydroxyaporphine hybrobromide | −3.3089272 | 0.0004683 | Dopamine |
| Methoxamine hydrochloride | −3.255451 | 0.0005661 | Adrenoceptor |
| Chlorothiazide | −3.1649704 | 0.0007755 | Biochemistry |
| Hydrocortisone | −3.0490238 | 0.0011479 | Hormone |
| 7,7-Dimethyl-(5Z,8Z)-eicosadienoic acid | −3.0454142 | 0.0011618 | Lipid |
| Cefaclor | −3.0087895 | 0.0013115 | Antibiotic |
| Daidzein | −2.9308316 | 0.0016903 | Cell Cycle |
| Prazosin hydrochloride | −2.9017416 | 0.0018555 | Adrenoceptor |
| Z-L-Phe chloromethyl ketone | −2.901083 | 0.0018594 | Biochemistry |
| N6-Cyclohexyladenosine | −2.8830026 | 0.0019695 | Adenosine |
| SB 415286 | −2.8700993 | 0.0020517 | Phosphorylation |
| (B1) trans-U-50488 methanesulfonate | −2.833112 | 0.0023049 | Opioid |
| Isoliquiritigenin | −2.8170739 | 0.0024232 | Cyclic Nucleotides |
| Niclosamide | −2.784072 | 0.0026841 | Antibiotic |
| BRL 52537 hydrochloride | −2.7605861 | 0.0028849 | Neurotransmission |

TABLE 3-continued

| | | | |
|---|---|---|---|
| R(−)-2,10,11-Trihydroxy-N-propylnoraporphine hydrobromide | −2.744256 | 0.0030324 | Dopamine |
| Oxymetazoline hydrochloride | −2.7197914 | 0.0032662 | Adrenoceptor |
| S(−)-UH-301 hydrochloride | −2.7057206 | 0.0034078 | Serotonin |
| 1-Phenylbiguanide | −2.6893106 | 0.00358 | Serotonin |
| NS 2028 | −2.6836419 | 0.0036413 | Cyclic Nucleotides |
| SDZ-205,557 hydrochloride | −2.6806511 | 0.003674 | Serotonin |
| Betaine hydrochloride | −2.6682884 | 0.0038119 | Biochemistry |
| 6-Methoxy-1,2,3,4-tetrahydro-9H-pyrido[3,4b] indole | −2.6610326 | 0.0038951 | Neurotransmission |
| Pergolide methanesulfonate | −2.656684 | 0.0039457 | Dopamine |
| Bepridil hydrochloride | −2.6553943 | 0.0039608 | Ca2+ Channel |
| (−)-Sulpiride | −2.6474564 | 0.004055 | Dopamine |
| Trazodone hydrochloride | −2.6437716 | 0.0040994 | Serotonin |
| R-(+)-7-Hydroxy-DPAT hydrobromide | −2.5903598 | 0.0047938 | Dopamine |
| 5'-N-Ethylcarboxamidoadenosine | −2.5867918 | 0.0048437 | Adenosine |
| 5'-N-Methyl carboxamidoadenosine | −2.5824426 | 0.0049052 | Adenosine |
| 3',4'-Dichlorobenzamil | −2.5808785 | 0.0049275 | Ion Pump |
| Cefazolin sodium | −2.5795106 | 0.004947 | Antibiotic |
| CGS-12066A maleate | −2.5753256 | 0.0050073 | Serotonin |
| m-Iodobenzylguanidine hemisulfate | −2.5641032 | 0.0051721 | Apoptosis |
| SB 216763 | −2.5420251 | 0.0055106 | Phosphorylation |
| R(+)-UH-301 hydrochloride | −2.5168671 | 0.0059202 | Serotonin |
| 1-(2-Chlorophenyl)-1-(4-chlorophenyl)-2,2-dichloroethane | −2.5077494 | 0.0060751 | Hormone |
| Zaprinast | −2.5059482 | 0.0061062 | Cyclic Nucleotides |
| HE-NECA | −2.5037672 | 0.0061439 | Adenosine |
| Noscapine hydrchloride | −2.4554145 | 0.0070361 | Opioid |
| Dubinidine | −2.4370692 | 0.0074034 | Anticonvulsant |
| Quinolinic acid | −2.4191885 | 0.0077776 | Glutamate |
| 1-Aminocyclopropanecarboxylic acid hydrochloride | −2.4013395 | 0.0081676 | Glutamate |
| Nimesulide | −2.3951538 | 0.0083067 | Prostaglandin |
| (B1)-AMT hydrochloride | −2.3661687 | 0.0089866 | Nitric Oxide |
| 2-Chloro-2-deoxy-D-glucose | −2.3643801 | 0.0090301 | Biochemistry |
| Efaroxan hydrochloride | −2.3380161 | 0.0096932 | Imidazoline |
| L-2-aminoadipic acid | −2.3335424 | 0.0098098 | Glutamate |
| Ritodrine hydrochloride | −2.3317783 | 0.0098562 | Adrenoceptor |
| 3-Aminopropylphosphonic acid | −2.3313919 | 0.0098664 | GABA |
| Tyrphostin AG 34 | −2.3191864 | 0.0101925 | Phosphorylation |
| S-(−)-Carbidopa | −2.3143606 | 0.010324 | Biochemistry |
| Quercetin dihydrate | −2.3024758 | 0.0106542 | Cyclic Nucleotides |
| SB 204741 | −2.2992889 | 0.0107443 | Serotonin |
| cis-(B1)-8-OH-PBZI hydrobromide | −2.2973336 | 0.0107999 | Dopamine |
| Praziquantel | −2.2959636 | 0.010839 | Antibiotic |
| Corticosterone | −2.2852893 | 0.0111479 | Hormone |
| Cefsulodin sodium salt hydrate | −2.2766421 | 0.0114038 | Antibiotic |
| Tyrphostin AG 494 | −2.2753482 | 0.0114425 | Phosphorylation |
| (B1)-6-Chloro-PB hydrobromide | −2.2671332 | 0.011691 | Dopamine |
| Gabaculine hydrochloride | −2.2563811 | 0.0120234 | GABA |
| (B1)-2,3-Dichloro-alpha-methylbenzylamine hydrochloride | −2.2508783 | 0.0121966 | Neurotransmission |
| cis-Azetidine-2,4-dicarboxylic acid | −2.2508387 | 0.0121979 | Glutamate |
| WB-4101 hydrochloride | −2.2469819 | 0.0123206 | Adrenoceptor |
| Acetohexamide | −2.2399587 | 0.0125468 | Hormone |
| (+)-Nicotine (+)-di-p-toluoyl tartrate | −2.232955 | 0.012776 | Cholinergic |
| Isoguvacine hydrochloride | −2.2200937 | 0.0132062 | GABA |
| Cortisone 21-acetate | −2.2178586 | 0.0132822 | Hormone |
| Morin | −2.2158114 | 0.0133522 | Cell Stress |
| R(+)3PPP hydrochloride | −2.2129185 | 0.0134516 | Dopamine |
| Serotonin hydrochloride | −2.1965835 | 0.0140251 | Serotonin |
| Ro 8-4304 | −2.1881143 | 0.0143306 | Glutamate |
| Bumetanide | −2.1822656 | 0.014545 | Ion Pump |
| Ro 16-6491 hydrochloride | −2.1810515 | 0.0145898 | Neurotransmission |
| 6-Aminohexanoic acid | −2.179453 | 0.014649 | Immune System |
| 1-Allyl-3,7-dimethyl-8-p-sulfophenylxanthine | −2.1783219 | 0.014691 | Adenosine |
| Mesulergine hydrochloride | −2.1600214 | 0.0153855 | Dopamine |
| p-MPPF dihydrochloride | −2.1595489 | 0.0154038 | Serotonin |
| TTNPB | −2.1577952 | 0.0154719 | Transcription |
| (E)-4-amino-2-butenoic acid | −2.1488314 | 0.0158239 | GABA |
| D-ribofuranosylbenzimidazole | −2.143935 | 0.016019 | Transcription |
| Alprenolol hydrochloride | −2.1429898 | 0.016057 | Adrenoceptor |
| (E)-5-(2-Bromovinyl)-2'-deoxyuridine | −2.1233283 | 0.0168632 | Immune System |
| Pinacidil | −2.116539 | 0.0171495 | K+ Channel |
| (B1)-Chlorpheniramine maleate | −2.1163839 | 0.0171561 | Histamine |
| Fenofibrate | −2.1155765 | 0.0171904 | Transcription |
| N6-Cyclopentyl-9-methyladenine | −2.111923 | 0.0173465 | Adenosine |
| Mecamylamine hydrochloride | −2.107644 | 0.0175309 | Cholinergic |
| Ranolazine dihydrochloride | −2.103503 | 0.0177109 | Lipid |
| Lorglumide sodium | −2.0918704 | 0.0182251 | Cholecystokinin |
| Rolipram | −2.0912266 | 0.0182539 | Cyclic Nucleotides |
| 4-Imidazolemethanol hydrochloride | −2.076595 | 0.0189195 | Histamine |
| PPNDS tetrasodium | −2.066969 | 0.0193685 | P2 Receptor |
| U-101958 maleate | −2.0647776 | 0.019472 | Dopamine |
| O-(Carboxymethyl)hydroxylamine hemihydrochloride | −2.0584119 | 0.0197753 | Biochemistry |

TABLE 3-continued

| | | | |
|---|---|---|---|
| Pyrocatechol | −2.0530659 | 0.0200331 | Cell Cycle |
| 3-Phenylpropargylamine hydrochloride | −2.0432437 | 0.0205142 | Dopamine |
| Clemastine fumarate | −2.0227881 | 0.0215475 | Histamine |
| R(−)-N6-(2-Phenylisopropyl)adenosine | −2.0227607 | 0.0215489 | Adenosine |
| T-1032 | −2.0203758 | 0.0216722 | Cyclic Nucleotides |
| DM 235 | −2.0192498 | 0.0217306 | Nootropic |
| TCPOBOP | −2.0077453 | 0.0223352 | Transcription |
| R(+)-Terguride | −2.0044262 | 0.0225212 | Dopamine |
| Budesonide | −1.9941208 | 0.0230694 | Hormone |
| Metoclopramide hydrochloride | −1.9921723 | 0.0231761 | Dopamine |
| SP600125 | −1.9856473 | 0.0235362 | Phosphorylation |
| Mifepristone | −1.9702729 | 0.0244035 | Hormone |
| (B1)-Vesamicol hydrochloride | −1.9674995 | 0.0245628 | Cholinergic |
| Niflumic acid | −1.957802 | 0.0251266 | Prostaglandin |
| Acetamide | −1.9401968 | 0.0261779 | Biochemistry |
| Succinylcholine chloride | −1.9304248 | 0.0267771 | Cholinergic |
| Quinidine sulfate | −1.9299053 | 0.0268093 | Na+ Channel |
| SKF-525A hydrochloride | −1.927618 | 0.0269513 | Multi-Drug Resistance |
| (B1)-PPHT hydrochloride | −1.9154974 | 0.0277145 | Dopamine |
| Proglumide | −1.9073728 | 0.0282362 | Cholecystokinin |
| IMID-4F hydrochloride | −1.9058093 | 0.0283375 | K+ Channel |
| Guanabenz acetate | −1.9057108 | 0.0283439 | Adrenoceptor |
| (B1)-Muscarine chloride | −1.9052038 | 0.0283768 | Cholinergic |
| CNQX disodium | −1.9037516 | 0.0284713 | Glutamate |
| Thiothixene hydrochloride | −1.8991787 | 0.0287705 | Dopamine |
| (B1)-3-(3,4-dihydroxyphenyl)-2-methyl-DL-alanine | −1.8936993 | 0.0291325 | Neurotransmission |
| 2',3'-didehydro-3'-deoxythymidine | −1.8781951 | 0.0301772 | Immune System |
| (−)-Tetramisole hydrochloride | −1.8662258 | 0.0310049 | Phosphorylation |
| GYKI 52466 hydrochloride | −1.863546 | 0.0311927 | Glutamate |
| Doxazosin mesylate | −1.8613755 | 0.0313456 | Adrenoceptor |
| N-Methyl-D-aspartic acid | −1.8603889 | 0.0314153 | Glutamate |
| Citalopram hydrobromide | −1.8575581 | 0.0316159 | Serotonin |
| (−)-Bicuculline methbromide, 1(S), 9(R) | −1.8420868 | 0.0327312 | GABA |
| Fenoterol hydrobromide | −1.8408571 | 0.0328213 | Adrenoceptor |
| Loratadine | −1.8228962 | 0.0341596 | Histamine |
| Triflupromazine hydrochloride | −1.8204023 | 0.0343489 | Dopamine |
| (B1)-Vanillylmandelic acid | −1.8112351 | 0.0350522 | Adrenoceptor |
| 2,3-Butanedione monoxime | −1.8102985 | 0.0351248 | K+ Channel |
| AL-8810 | −1.8055248 | 0.0354963 | Prostaglandin |
| Cyproterone acetate | −1.8034569 | 0.0356582 | Hormone |
| L-alpha-Methyl-p-tyrosine | −1.8000599 | 0.0359256 | Neurotransmission |
| (B1)-Normetanephrine hydrochloride | −1.7963521 | 0.0362193 | Adrenoceptor |
| Carisoprodol | −1.794693 | 0.0363513 | Neurotransmission |
| Dihydro-beta-erythroidine hydrobromide | −1.7884178 | 0.0368543 | Cholinergic |
| Diacylglycerol kinase inhibitor I | −1.7818091 | 0.0373902 | Phosphorylation |
| Buspirone hydrochloride | −1.7754735 | 0.0379099 | Serotonin |
| Tulobuterol hydrochloride | −1.7667466 | 0.0386353 | Adrenoceptor |
| SIB 1757 | −1.7523223 | 0.0398592 | Glutamate |
| S-Methyl-L-thiocitrulline acetate | −1.7510795 | 0.0399661 | Nitric Oxide |
| Rauwolscine hydrochloride | −1.7473494 | 0.0402884 | Adrenoceptor |
| Tyrphostin A9 | −1.7464939 | 0.0403626 | Phosphorylation |
| Clofibrate | −1.7375097 | 0.0411486 | Lipid |
| NCS-382 | −1.7333038 | 0.0415208 | GABA |
| N,N-Dipropyl-5-carboxamidotryptamine maleate | −1.730004 | 0.0418148 | Serotonin |
| BRL 37344 sodium | −1.7246038 | 0.0422994 | Adrenoceptor |
| Naphazoline hydrochloride | −1.7242327 | 0.0423329 | Adrenoceptor |
| Pempidine tartrate | −1.7188055 | 0.0428249 | Cholinergic |
| BP 897 | −1.7150002 | 0.0431726 | Dopamine |
| E-64 | −1.708761 | 0.0437476 | Biochemistry |
| 5'-(N-Cyclopropyl)carboxamidoadenosine | −1.7011833 | 0.0444543 | Adenosine |
| SB 222200 | −1.6945866 | 0.0450769 | Tachykinin |
| WB 64 | −1.6833761 | 0.0461512 | Cholinergic |
| ATPO | −1.6800087 | 0.0464775 | Glutamate |
| 3-Bromo-7-nitroindazole | −1.6799458 | 0.0464839 | Nitric Oxide |
| Salbutamol | −1.6779642 | 0.046677 | Adrenoceptor |
| NBQX disodium | −1.6747884 | 0.0469879 | Glutamate |
| 5-Aminovaleric acid hydrochloride | −1.6700597 | 0.0474538 | GABA |
| OXA-22 iodide | −1.6660744 | 0.0478493 | Cholinergic |
| 5,5-Dimethyl-1-pyrroline-N-oxide | −1.6658221 | 0.0478744 | Cell Stress |
| 6-Chloromelatonin | −1.6590916 | 0.0485487 | Melatonin |
| Yohimbine hydrochloride | −1.6564033 | 0.0488201 | Adrenoceptor |
| (B1)-Ibotenic acid | −1.649771 | 0.0494949 | Glutamate |
| S-Nitroso-N-acetylpenicillamine | −1.6450464 | 0.0499801 | Nitric Oxide |
| 2,3-Butanedione | −1.6415063 | 0.0503462 | Cytoskeleton and ECM |
| SC 19220 | −1.6402237 | 0.0504793 | Prostaglandin |
| Pentoxifylline | −1.6370526 | 0.0508097 | Cyclic Nucleotides |
| IC 261 | −1.6304637 | 0.0515018 | Phosphorylation |
| Karakoline | −1.6253205 | 0.0520471 | Cholinergic |
| 2-Hydroxysaclofen | −1.624107 | 0.0521765 | GABA |
| Trifluperidol hydrochloride | −1.6214132 | 0.0524645 | Dopamine |

TABLE 3-continued

| | | | |
|---|---|---|---|
| N-Acetyl-L-Cysteine | −1.6210885 | 0.0524993 | Glutamate |
| Pyrazinecarboxamide | −1.6171791 | 0.0529198 | Antibiotic |
| (B1)-CGP-12177A hydrochloride | −1.6114253 | 0.0535435 | Adrenoceptor |
| N-Phenylanthranilic acid | −1.6103679 | 0.0536588 | Cl− Channel |
| Nitrendipine | −1.6096413 | 0.0537381 | Ca2+ Channel |
| Tyrphostin AG 527 | −1.6074748 | 0.0539751 | Phosphorylation |
| Tyrphostin AG 879 | −1.6068612 | 0.0540424 | Phosphorylation |
| S-Ethylisothiourea hydrobromide | −1.5993298 | 0.0548737 | Nitric Oxide |
| (B1)-SKF 38393, N-allyl-, hydrobromide | −1.5895709 | 0.0559658 | Dopamine |
| Propionylpromazine hydrochloride | −1.5842258 | 0.0565712 | Dopamine |
| 1-(4-Chlorobenzyl)-5-methoxy-2-methylindole-3-acetic acid | −1.5842122 | 0.0565727 | Multi-Drug Resistance |
| H-8 dihydrochloride | −1.582792 | 0.0567344 | Phosphorylation |
| Decamethonium dibromide | −1.5718137 | 0.0579969 | Cholinergic |
| p-Benzoquinone | −1.5713686 | 0.0580485 | DNA Repair |
| Ouabain | −1.5679492 | 0.0584465 | Ion Pump |
| (B1)-Octopamine hydrochloride | −1.5674371 | 0.0585063 | Adrenoceptor |
| Quinelorane dihydroechloride | −1.5670037 | 0.0585569 | Dopamine |
| (−)-Quinpirole hydrochloride | −1.5653999 | 0.0587446 | Dopamine |
| Kenpaullone | −1.5549547 | 0.0599784 | Phosphorylation |
| MK-886 | −1.5492409 | 0.0606619 | Leukotriene |
| SR 2640 | −1.5478816 | 0.0608254 | Leukotriene |
| (+)-Pilocarpine hydrochloride | −1.547825 | 0.0608322 | Cholinergic |
| 10-(alpha-Diethylaminopropionyl)-phenothiazine hydrochloride | −1.5445928 | 0.0612224 | Biochemistry |
| Aminophylline ethylenediamine | −1.5370027 | 0.0621463 | Adenosine |
| Phenelzine sulfate | −1.5362935 | 0.0622332 | Neurotransmission |
| Propantheline bromide | −1.5337772 | 0.0625422 | Cholinergic |
| 3-Tropanyl-indole-3-carboxylate hydrochloride | −1.5275718 | 0.0633094 | Serotonin |
| Domperidone | −1.5246276 | 0.063676 | Dopamine |
| PD 168,077 maleate | −1.5158641 | 0.0647769 | Dopamine |
| 4-Aminopyridine | −1.5155783 | 0.064813 | K+ Channel |
| Phenoxybenzamine hydrochloride | −1.5122144 | 0.0652397 | Adrenoceptor |
| Flecainide acetate | −1.4984719 | 0.0670053 | Na+ Channel |
| Chlorzoxazone | −1.496158 | 0.0673062 | Nitric Oxide |
| Hexahydro-sila-difenidol hydrochloride, p-fluoro analog | −1.4916183 | 0.0678996 | Cholinergic |
| R(−)-Isoproterenol (+)-bitartrate | −1.4852187 | 0.0687429 | Adrenoceptor |
| Pirfenidone | −1.4819638 | 0.069175 | Immune System |
| Histamine dihydrochloride | −1.4762679 | 0.069936 | Histamine |
| Histamine, R(−)-alpha-methyl-, dihydrochloride | −1.4694515 | 0.0708552 | Histamine |
| 13-cis-retinoic acid | −1.4690859 | 0.0709047 | Transcription |
| L-733,060 hydrochloride | −1.4652604 | 0.0714249 | Tachykinin |
| Aminobenztropine | −1.4551121 | 0.0728191 | Cholinergic |
| Idazoxan hydrochloride | −1.4475909 | 0.0738658 | Imidazoline |
| Quipazine dimaleate | −1.4441402 | 0.0743498 | Serotonin |
| Tranylcypromine hydrochloride | −1.4406843 | 0.0748369 | Neurotransmission |
| Cortexolone maleate | −1.4340948 | 0.0757726 | Dopamine |
| L-Histidine hydrochloride | −1.4212033 | 0.0776288 | Histamine |
| SB-366791 | −1.4192379 | 0.0779148 | Vanilloid |
| L(−)-Norepinephrine bitartrate | −1.4177813 | 0.0781273 | Adrenoceptor |
| R(−)-Me5 | −1.4142867 | 0.0786389 | Na+ Channel |
| 7-Cyclopentyl-5-(4-phenoxy)phenyl-7H-pyrrolo[2,3-d]pyrimidin-4-ylamine | −1.412018 | 0.0789723 | Phosphorylation |
| NG-Nitro-L-arginine methyl ester hydrochloride | −1.4106378 | 0.0791757 | Nitric Oxide |
| (B1)-Methoxyverapamil hydrochloride | −1.4065891 | 0.0797746 | Ca2+ Channel |
| Semicarbazide hydrochloride | −1.4048769 | 0.080029 | Neurotransmission |
| Harmane | −1.4028297 | 0.0803338 | Imidazoline |
| Phosphomycin disodium | −1.4016291 | 0.080513 | Antibiotic |
| SR 57227A | −1.4000539 | 0.0807486 | Serotonin |
| 5-azacytidine | −1.3976868 | 0.0811036 | DNA Metabolism |
| Theobromine | −1.3917931 | 0.0819925 | Adenosine |
| beta-Chloro-L-alanine hydrochloride | −1.3900717 | 0.0822536 | Biochemistry |
| Diacylglycerol Kinase Inhibitor II | −1.3898874 | 0.0822815 | Phosphorylation |
| NG-Monomethyl-L-arginine acetate | −1.385845 | 0.0828971 | Nitric Oxide |
| Nylidrin hydrochloride | −1.3754281 | 0.0844994 | Adrenoceptor |
| Cinnarizine | −1.3747128 | 0.0846103 | Ca2+ Channel |
| N^G, N^G-Dimethylarginine hydrochloride | −1.3726345 | 0.084933 | Nitric Oxide |
| 2′,3′-dideoxycytidine | −1.3665696 | 0.0858801 | Immune System |
| SB 206553 hydrochloride | −1.365122 | 0.0861073 | Serotonin |
| N-Bromoacetamide | −1.3615557 | 0.0866691 | Na+ Channel |
| Sulfaphenazole | −1.3615444 | 0.0866709 | Multi-Drug Resistance |
| SKF 83959 hydrobromide | −1.3570686 | 0.0873797 | Dopamine |
| Aniracetam | −1.3545038 | 0.0877879 | Glutamate |
| 7-Nitroindazole | −1.3486346 | 0.0887272 | Nitric Oxide |
| Dipropyldopamine hydrobromide | −1.3457188 | 0.0891966 | Dopamine |
| Guvacine hydrochloride | −1.3454867 | 0.089234 | GABA |
| (B1)-DOI hydrochloride | −1.3446475 | 0.0893695 | Serotonin |
| N-Methyl-1-deoxynojirimycin | −1.3354425 | 0.0908658 | Biochemistry |
| Forskolin | −1.3305552 | 0.0916677 | Cyclic Nucleotides |
| Ciprofibrate | −1.3259385 | 0.09243 | Transcription |
| Methyl 6,7-dimethoxy-4-ethyl-beta-carboline-3-carboxylate | −1.3258027 | 0.0924525 | Benzodiazepine |
| 3-Morpholinosydnonimine hydrochloride | −1.3237029 | 0.0928009 | Nitric Oxide |

TABLE 3-continued

| Compound | Value | Value | Category |
|---|---|---|---|
| N6-2-(4-Aminophenyl)ethyladenosine | −1.322839 | 0.0929445 | Adenosine |
| Luteolin | −1.3226701 | 0.0929726 | Cell Stress |
| Altretamine | −1.3219924 | 0.0930853 | DNA Metabolism |
| (−)-Perillic acid | −1.3205658 | 0.0933231 | G protein |
| Tyrphostin AG 808 | −1.3154937 | 0.094172 | Phosphorylation |
| Fluoxetine hydrochloride | −1.3114178 | 0.0948583 | Serotonin |
| 5-Hydroxyindolacetic acid | −1.3011987 | 0.0965952 | Serotonin |
| Thiolactomycin | −1.2996027 | 0.0968686 | Antibiotic |
| S(−)-p-Bromotetramisole oxalate | −1.2954735 | 0.0975785 | Phosphorylation |
| alpha,beta-Methylene adenosine 5′-triphosphate dilithium | −1.2895624 | 0.0986013 | P2 Receptor |
| 4-Aminobenzamidine dihydrochloride | −1.2867142 | 0.099097 | Biochemistry |
| Captopril | −1.2850992 | 0.0993788 | Neurotransmission |
| B-HT 933 dihydrochloride | −1.2803089 | 0.1002183 | Adrenoceptor |
| DBO-83 | −1.2793912 | 0.1003797 | Cholinergic |
| (+)-Chlorpheniramine maleate | −1.2718073 | 0.1017208 | Histamine |
| rac-2-Ethoxy-3-hexadecanamido-1-propylphosphocholine | −1.2689544 | 0.1022287 | Phosphorylation |
| Mexiletene hydrochloride | −1.2587311 | 0.1040637 | Na+ Channel |
| GYKI 52895 | −1.2580442 | 0.1041879 | Dopamine |
| Phenylephrine hydrochloride | −1.2567788 | 0.1044169 | Adrenoceptor |
| 2-(2-Aminoethyl)isothiourea dihydrobromide | −1.251316 | 0.1054096 | Nitric Oxide |
| Norcantharidin | −1.2508813 | 0.1054889 | Phosphorylation |
| Tyrphostin AG 537 | −1.2486744 | 0.1058921 | Phosphorylation |
| MRS 2179 | −1.2460372 | 0.1063754 | P2 Receptor |
| N-(3,3-Diphenylpropyl)glycinamide | −1.2431187 | 0.106912 | Glutamate |
| D-Cycloserine | −1.2400354 | 0.1074811 | Glutamate |
| Trimethoprim | −1.2297472 | 0.1093959 | Antibiotic |
| CGS-21680 hydrochloride | −1.2250915 | 0.1102704 | Adenosine |
| SR 59230A oxalate | −1.2215096 | 0.1109466 | Adrenoceptor |
| Aminoguanidine hemisulfate | −1.2193731 | 0.1113513 | Nitric Oxide |
| N-Methyldopamine hydrochloride | −1.2189696 | 0.1114279 | Dopamine |
| LY-294,002 hydrochloride | −1.2168097 | 0.1118383 | Phosphorylation |
| Acyclovir | −1.214559 | 0.1122672 | Immune System |
| 8-(3-Chlorostyryl)caffeine | −1.2143358 | 0.1123098 | Adenosine |
| Pilocarpine nitrate | −1.213028 | 0.1125596 | Cholinergic |
| U-73122 | −1.1943557 | 0.1161694 | Lipid |
| Ribavirin | −1.1942136 | 0.1161972 | Cell Cycle |
| Minoxidil | −1.1893439 | 0.1171522 | K+ Channel |
| Adenosine 3′,5′-cyclic monophosphate | −1.1884072 | 0.1173365 | Phosphorylation |
| REV 5901 | −1.1843894 | 0.1181295 | Leukotriene |
| L-750,667 trihydrochloride | −1.1839463 | 0.1182172 | Dopamine |
| 1,4-PBIT dihydrobromide | −1.1793121 | 0.119137 | Nitric Oxide |
| O6-benzylguanine | −1.1766492 | 0.1196678 | DNA Repair |
| S(+)-PD 128,907 hydrochloride | −1.1736494 | 0.1202677 | Dopamine |
| 6-Fluoronorepinephrine hydrochloride | −1.1680109 | 0.1214012 | Adrenoceptor |
| Ketoprofen | −1.1637674 | 0.1222592 | Prostaglandin |
| Monastrol | −1.1620964 | 0.1225982 | Cell Cycle |
| TFPI hydrochloride | −1.1557919 | 0.1238831 | Nitric Oxide |
| L-allylglycine | −1.1551253 | 0.1240196 | Biochemistry |
| Endothall | −1.1434024 | 0.1264358 | Phosphorylation |
| Meloxicam sodium | −1.1395873 | 0.1272291 | Prostaglandin |
| MDL 28170 | −1.1386183 | 0.1274312 | Cell Cycle |
| SB 202190 | −1.1244198 | 0.1304175 | Phosphorylation |
| S(−)-Pindolol | −1.1219961 | 0.1309321 | Serotonin |
| 3,4-Dichloroisocoumarin | −1.119752 | 0.1314097 | Biochemistry |
| Tetraisopropyl pyrophosphoramide | −1.1141073 | 0.1326166 | Biochemistry |
| rac-2-Ethoxy-3-octadecanamido-1-propylphosphocholine | −1.1124056 | 0.1329819 | Phosphorylation |
| (B1)-threo-1-Phenyl-2-decanoylamino-3-morpholino-1-propanol hydrochloride | −1.1085022 | 0.1338225 | Sphingolipid |
| SB 269970 hydrochloride | −1.0998336 | 0.1357023 | Serotonin |
| FPL 64176 | −1.0989013 | 0.1359056 | Ca2+ Channel |
| NSC 95397 | −1.0984826 | 0.1359969 | Phosphorylation |
| Labetalol hydrochloride | −1.0972055 | 0.1362758 | Adrenoceptor |
| CGP-13501 | −1.0960408 | 0.1365305 | GABA |
| Cefotaxime sodium | −1.0959989 | 0.1365396 | Antibiotic |
| Nortriptyline hydrochloride | −1.0953265 | 0.1366868 | Adrenoceptor |
| Lamotrigine | −1.0947705 | 0.1368086 | Anticonvulsant |
| Cinoxacin | −1.0946117 | 0.1368434 | Antibiotic |
| 3-n-Propylxanthine | −1.0936716 | 0.1370495 | Adenosine |
| IB-MECA | −1.0890621 | 0.1380633 | Adenosine |
| cis-4-Aminocrotonic acid | −1.0875529 | 0.1383963 | GABA |
| CB34 | −1.0812753 | 0.1397873 | Benzodiazepine |
| GR 127935 hydrochloride | −1.0805988 | 0.1399378 | Serotonin |
| LY-278,584 maleate | −1.0738961 | 0.1414346 | Serotonin |
| 2,6-Diamino-4-pyrimidinone | −1.0718915 | 0.1418844 | Phosphorylation |
| CB 1954 | −1.0701772 | 0.1422698 | DNA |
| LE 300 | −1.0698515 | 0.1423431 | Dopamine |
| (B1)-Baclofen | −1.0691346 | 0.1425045 | GABA |
| N-Acetyl-5-hydroxytryptamine | −1.0604318 | 0.1444741 | Melatonin |
| 1,1-Dimethyl-4-phenyl-piperazinium iodide | −1.0571671 | 0.1452177 | Cholinergic |
| Benzamil hydrochloride | −1.0541202 | 0.1459139 | Ion Pump |

TABLE 3-continued

| | | | |
|---|---|---|---|
| (R,R)-cis-Diethyl tetrahydro-2,8-chrysenediol | −1.0529189 | 0.1461891 | Hormone |
| CX 546 | −1.0499852 | 0.1468625 | Glutamate |
| (B1)-2-Amino-5-phosphonopentanoic acid | −1.0451757 | 0.1479709 | Glutamate |
| Amoxapine | −1.0413683 | 0.1488523 | Adrenoceptor |
| R(+)-Lisuride hydrogen maleate | −1.0405352 | 0.1490457 | Dopamine |
| 3-aminobenzamide | −1.0343557 | 0.1504849 | Apoptosis |
| Riluzole | −1.0325771 | 0.1509009 | Glutamate |
| Reserpine | −1.0232137 | 0.1531034 | Serotonin |
| Carcinine dihydrochloride | −1.0232013 | 0.1531064 | Cell Stress |
| DL-Buthionine-[S,R]-sulfoximine | −1.0219135 | 0.1534109 | Multi-Drug Resistance |
| Metaproterenol hemisulfate | −1.0217093 | 0.1534593 | Adrenoceptor |
| 9-Amino-1,2,3,4-tetrahydroacridine hydrochloride | −1.0210782 | 0.1536087 | Cholinergic |
| (B1)-2-Amino-7-phosphonoheptanoic acid | −1.0198203 | 0.1539069 | Glutamate |
| Moxisylyte hydrochloride | −1.0177704 | 0.1543935 | Adrenoceptor |
| Doxepin hydrochloride | −1.0124523 | 0.1556609 | Adrenoceptor |
| L-741,626 | −1.0093889 | 0.1563941 | Dopamine |
| 8-Bromo-cGMP sodium | −1.004759 | 0.1575065 | Cyclic Nucleotides |
| CR 2249 | −1.0018822 | 0.1582002 | Glutamate |
| GW7647 | −0.992319 | 0.160521 | Transcription |
| Imiloxan hydrochloride | −0.9878844 | 0.1616046 | Adrenoceptor |
| 2-methoxyestradiol | −0.9832797 | 0.1627349 | Hormone |
| Daphnetin | −0.9798216 | 0.1635871 | Phosphorylation |
| Cyclophosphamide monohydrate | −0.9757597 | 0.1645918 | DNA |
| Trequinsin hydrochloride | −0.9708618 | 0.1658085 | Cyclic Nucleotides |
| Propafenone hydrochloride | −0.9673008 | 0.1666969 | K+ Channel |
| Felodipine | −0.9658091 | 0.1670699 | Ca2+ Channel |
| S(−)-Pindolol | −0.9652109 | 0.1672196 | Adrenergic |
| SR-95531 | −0.9574371 | 0.1691734 | GABA |
| 1-benzoyl-5-methoxy-2-methylindole-3-acetic acid | −0.9550434 | 0.1697779 | Multi-Drug Resistance |
| Albuterol hemisulfate | −0.9490313 | 0.1713024 | Adrenoceptor |
| Chlormezanone | −0.9465197 | 0.1719418 | Neurotransmission |
| L-N5-(1-Iminoethyl)ornithine hydrochloride | −0.9338543 | 0.1751895 | Nitric Oxide |
| Pentylenetetrazole | −0.9273972 | 0.1768602 | Neurotransmission |
| N-(4-Aminobutyl)-5-chloro-2-naphthalenesulfonamide hydrochloride | −0.922864 | 0.178039 | Intracellular Calcium |
| Imidazole-4-acetic acid hydrochloride | −0.9222582 | 0.1781969 | GABA |
| Tyrphostin 51 | −0.917695 | 0.1793893 | Phosphorylation |
| Zonisamide sodium | −0.9169252 | 0.1795909 | Anticonvulsant |
| Gallamine triethiodide | −0.9155672 | 0.179947 | Cholinergic |
| Palmitoylethanolamide | −0.913421 | 0.1805106 | Cannabinoid |
| Myricetin | −0.9113314 | 0.1810604 | Phosphorylation |
| Lithium Chloride | −0.9112667 | 0.1810774 | Neurotransmission |
| Agroclavine | −0.9109378 | 0.1811641 | Dopamine |
| Cyclothiazide | −0.9069625 | 0.1822133 | Glutamate |
| L-Canavanine sulfate | −0.9023537 | 0.1834345 | Nitric Oxide |
| L-alpha-Methyl DOPA | −0.8969902 | 0.1848621 | Biochemistry |
| D-609 potassium | −0.8963774 | 0.1850256 | Lipid |
| BWB70C | −0.893238 | 0.1858649 | Leukotriene |
| AC 915 oxalate | −0.8902927 | 0.1866544 | Opioid |
| Phosphonoacetic acid | −0.8884961 | 0.187137 | DNA |
| Promazine hydrochloride | −0.8881652 | 0.187226 | Dopamine |
| 1,10-Phenanthroline monohydrate | −0.8855339 | 0.1879344 | Biochemistry |
| loxoprofen | −0.8833347 | 0.1885277 | Prostaglandin |
| Atropine methyl bromide | −0.8715579 | 0.1917248 | Cholinergic |
| Retinoic acid | −0.8656792 | 0.1933331 | Apoptosis |
| Prochlorperazine dimaleate | −0.8601515 | 0.1948528 | Dopamine |
| Nimodipine | −0.8541979 | 0.1964977 | Ca2+ Channel |
| SIB 1893 | −0.8479837 | 0.1982235 | Glutamate |
| Chloro-IB-MECA | −0.8471487 | 0.1984561 | Adenosine |
| 1-Methylimidazole | −0.8469251 | 0.1985184 | Prostaglandin |
| (−)-Scopolamine methyl bromide | −0.8468313 | 0.1985446 | Cholinergic |
| Clomipramine hydrochloride | −0.8438525 | 0.1993759 | Serotonin |
| Tyrphostin 23 | −0.8396096 | 0.2005636 | Phosphorylation |
| Formoterol | −0.8379228 | 0.201037 | Adrenoceptor |
| (+)-Hydrastine | −0.836196 | 0.2015223 | GABA |
| L-765,314 | −0.8307837 | 0.2030479 | Adrenoceptor |
| Glipizide | −0.8295042 | 0.2034096 | K+ Channel |
| Ceramide | −0.826672 | 0.2042115 | Phosphorylation |
| Hexamethonium bromide | −0.8198763 | 0.2061433 | Cholinergic |
| (B1)-Sotalol hydrochloride | −0.8130085 | 0.2081066 | Adrenoceptor |
| S-(+)-Fluoxetine hydrochloride | −0.8087781 | 0.2093214 | Serotonin |
| 5alpha-Pregnan-3alpha-ol-11,20-dione | −0.8078192 | 0.2095973 | GABA |
| CPCCOEt | −0.8067663 | 0.2099006 | Glutamate |
| Edrophonium chloride | −0.8063734 | 0.2100138 | Cholinergic |
| Amiloride hydrochloride | −0.7992459 | 0.2120739 | Na+ Channel |
| N6-Benzyl-5′-N-ethylcarboxamidoadenosine | −0.7976302 | 0.2125426 | Adenosine |
| Dextromethorphan hydrobromide monohydrate | −0.7931617 | 0.2138418 | Glutamate |
| 4-Hydroxybenzhydrazide | −0.7887714 | 0.2151228 | Biochemistry |
| Epibestatin hydrochloride | −0.7868693 | 0.2156792 | Biochemistry |
| Methylergonovine maleate | −0.7845802 | 0.2163499 | Dopamine |
| N6-Cyclopentyladenosine | −0.7838855 | 0.2165536 | Adenosine |

TABLE 3-continued

| | | | |
|---|---|---|---|
| Urapidil, 5-Methyl- | −0.7831488 | 0.2167699 | Adrenoceptor |
| alpha-Methyl-5-hydroxytryptamine maleate | −0.7795622 | 0.2178243 | Serotonin |
| Dihydroergotamine methanesulfonate | −0.7794889 | 0.2178459 | Serotonin |
| GR-89696 fumarate | −0.7787503 | 0.2180634 | Opioid |
| Amiprilose hydrochloride | −0.7782638 | 0.2182068 | Immune System |
| 2-Methylthioadenosine triphosphate tetrasodium | −0.7763488 | 0.2187715 | P2 Receptor |
| 3-Isobutyl-1-methylxanthine | −0.7739684 | 0.2194747 | Adenosine |
| Dihydroergocristine methanesulfonate | −0.7729718 | 0.2197695 | Dopamine |
| Putrescine dihydrochloride | −0.7689496 | 0.2209616 | Glutamate |
| S(−)-Timolol maleate | −0.7674804 | 0.221398 | Adrenoceptor |
| SKF 91488 dihydrochloride | −0.7659952 | 0.2218396 | Histamine |
| erythro-9-(2-Hydroxy-3-nonyl)adenine hydrochloride | −0.7655619 | 0.2219685 | Adenosine |
| VER-3323 hemifumarate salt | −0.7613872 | 0.2232129 | Serotonin |
| Sodium Taurocholate | −0.7603721 | 0.2235161 | Multi-Drug Resistance |
| Iofetamine hydrochloride | −0.7588266 | 0.2239781 | Neurotransmission |
| Fexofenadine hydrochloride | −0.7572355 | 0.2244544 | Histamine |
| (S)-(−)-propafenone hydrochloride | −0.7523778 | 0.2259119 | Adrenoceptor |
| 1-Amino-1-cyclohexanecarboxylic acid hydrochloride | −0.7494958 | 0.2267792 | Neurotransmission |
| Loxapine succinate | −0.7476915 | 0.2273231 | Dopamine |
| (−)-Scopolamine hydrobromide | −0.7415125 | 0.2291914 | Cholinergic |
| Haloperidol | −0.7399244 | 0.2296729 | Dopamine |
| I-OMe-Tyrphostin AG 538 | −0.7369215 | 0.230585 | Phosphorylation |
| SKF 97541 hydrochloride | −0.7355176 | 0.2310122 | GABA |
| 5-Nitro-2-(3-phenylpropylamino)benzoic acid | −0.7342619 | 0.2313946 | Cl- Channel |
| S(+)-Ibuprofen | −0.7334592 | 0.2316392 | Prostaglandin |
| Choline bromide | −0.7300479 | 0.2326804 | Cholinergic |
| U-69593 | −0.727828 | 0.2333594 | Opioid |
| Dipyridamole | −0.7266604 | 0.233717 | Adenosine |
| Ketorolac tris salt | −0.7255889 | 0.2340454 | Prostaglandin |
| Parthenolide | −0.7238191 | 0.2345884 | Serotonin |
| Indatraline hydrochloride | −0.7236172 | 0.2346504 | Dopamine |
| (B1)-Nipecotic acid | −0.7215396 | 0.2352888 | GABA |
| Clotrimazole | −0.71583 | 0.2370482 | K+ Channel |
| p-Fluoro-L-phenylalanine | −0.7022606 | 0.2412583 | Neurotransmission |
| (B1)-gamma-Vinyl GABA | −0.7009701 | 0.2416608 | GABA |
| Oxotremorine methiodide | −0.7001827 | 0.2419066 | Cholinergic |
| Ritanserin | −0.6956745 | 0.2433164 | Serotonin |
| 4-Androstene-3,17-dione | −0.6917159 | 0.2445579 | Hormone |
| R-(+)-8-Hydroxy-DPAT hydrobromide | −0.6915933 | 0.2445964 | Serotonin |
| HA-100 | −0.6892375 | 0.2453369 | Phosphorylation |
| Lidocaine N-methyl hydrochloride | −0.6827508 | 0.2473822 | Na+ Channel |
| Tyrphostin AG 555 | −0.6812093 | 0.2478695 | Phosphorylation |
| (R)-(+)-WIN 55,212-2 mesylate | −0.6806866 | 0.2480349 | Cannabinnoid |
| 1,7-Dimethylxanthine | −0.6622605 | 0.2539022 | Adenosine |
| SU 5416 | −0.6621561 | 0.2539356 | Phosphorylation |
| Seglitide | −0.6620168 | 0.2539802 | Somatostatin |
| L-Hyoscyamine | −0.661048 | 0.2542908 | Cholinergic |
| BMY 7378 dihydrochloride | −0.65884590 | 0.2549974 | Serotonin |
| (B1)-Atenolol | −0.65828 | 0.2551791 | Adrenoceptor |
| Amantadine hydrochloride | −0.6531247 | 0.2568379 | Dopamine |
| Nimustine hydrochloride | −0.6523971 | 0.2570725 | DNA |
| Bethanechol chloride | −0.6493048 | 0.2580707 | Cholinergic |
| Zimelidine dihydrochloride | −0.6490088 | 0.2581663 | Serotonin |
| Tyrphostin 1 | −0.6423812 | 0.2603129 | Phosphorylation |
| N,N,N',N'-Tetramethylazodicarboxamide | −0.6392844 | 0.261319 | Cell Stress |
| Isotharine mesylate | −0.6391695 | 0.2613563 | Adrenoceptor |
| 1-(2-Methoxyphenyl)piperazine hydrochloride | −0.638803 | 0.2614756 | Serotonin |
| ET-18-OCH3 | −0.6258823 | 0.2656961 | Lipid |
| Enoximone | −0.6236691 | 0.2664225 | Cyclic Nucleotides |
| NAN-190 hydrobromide | −0.6185897 | 0.2680934 | Serotonin |
| L-655,708 | −0.6131906 | 0.2698752 | Benzodiazepine |
| Oxiracetam | −0.6130565 | 0.2699195 | Nootropic |
| Ethosuximide | −0.6123992 | 0.2701368 | Anticonvulsant |
| Cortexolone | −0.6087203 | 0.2713549 | Hormone |
| Naloxonazine dihydrochloride | −0.6060679 | 0.2722348 | Opioid |
| N-(4-Amino-2-chlorophenyl)phthalimide | −0.602074 | 0.2735624 | Anticonvulsant |
| Cysteamine hydrochloride | −0.5988785 | 0.274627 | Somatostatin |
| Vanillic acid diethylamide | −0.5948053 | 0.2759868 | Vanilloid |
| ODQ | −0.5921983 | 0.2768589 | Cyclic Nucleotides |
| L-Glutamic acid, N-phthaloyl- | −0.5891419 | 0.277883 | Glutamate |
| L-Leucinethiol, oxidized dihydrochloride | −0.5840121 | 0.2796061 | Biochemistry |
| 3,4-Dihydroxyphenylacetic acid | −0.5831905 | 0.2798825 | Dopamine |
| MK-912 | −0.582011 | 0.2802796 | Adrenoceptor |
| Cortisone | −0.5806734 | 0.2807303 | Hormone |
| 17alpha-hydroxyprogesterone | −0.5782524 | 0.2815469 | Hormone |
| Cantharidin | −0.5781481 | 0.2815821 | Phosphorylation |
| Fenspiride hydrochloride | −0.576236 | 0.2822278 | Adrenoceptor |
| 2-Cyelooctyl-2-hydroxyethylamine hydrochloride | −0.5746572 | 0.2827616 | Neurotransmission |
| (B1)-Isoproterenol hydrochloride | −0.571712 | 0.2837586 | Adrenoceptor |
| 4-Hydroxy-3-methoxyphenylacetic acid | −0.5672969 | 0.2852562 | Dopamine |

TABLE 3-continued

| | | | |
|---|---|---|---|
| 3-Nitropropionic acid | −0.5631368 | 0.2866709 | Cell Stress |
| beta-Estradiol | −0.5622806 | 0.2869624 | Hormone |
| Etodolac | −0.5581734 | 0.288363 | Prostaglandin |
| Doxycycline hydrochloride | −0.5578035 | 0.2884893 | Antibiotic |
| MHPG sulfate potassium | −0.5556352 | 0.2892301 | Adrenoceptor |
| Cantharidic Acid | −0.5529217 | 0.2901585 | Phosphorylation |
| (S)-MAP4 hydrochloride | −0.5525297 | 0.2902927 | Glutamate |
| Linopirdine | −0.5525235 | 0.2902949 | Cholinergic |
| Pireuzepine dihydrochloride | −0.5449552 | 0.2928922 | Cholinergic |
| 1-(4-Fluorobenzyl)-5-methoxy-2-methylindole-3-acetic acid | −0.5376019 | 0.2954259 | Multi-Drug Resistance |
| (S)-Propranolol hydrochloride | −0.5346361 | 0.2964508 | Adrenoceptor |
| (−)-Epinephrine bitartrate | −0.5304149 | 0.2979122 | Adrenoceptor |
| 3,5-Dinitrocatechol | −0.5293574 | 0.2982788 | Neurotransmission |
| Imipramine hydrochloride | −0.527183 | 0.2990333 | Serotonin |
| Spironolactone | −0.5258429 | 0.2994987 | Hormone |
| DL-threo-beta-hydroxyaspartic acid | −0.5215278 | 0.3009996 | Glutamate |
| Spiperone hydrochloride | −0.5167586 | 0.3026623 | Dopamine |
| GW2974 | −0.5163796 | 0.3027947 | Phosphorylation |
| (−)-Cotinine | −0.509877 | 0.3050688 | Cholinergic |
| Phosphoramidon disodium | −0.5097313 | 0.3051198 | Biochemistry |
| L-703,606 oxalate | −0.5068733 | 0.3061218 | Tachykinin |
| R-(−)-Desmethyldeprenyl hydrochloride | −0.5056059 | 0.3065667 | Neurotransmission |
| 2,6-Difluoro-4-[2-(phenylsulfonylamino)ethylthio]phenoxyacetamide | −0.4982651 | 0.3091486 | Glutamate |
| Loperamide hydrochloride | −0.4975951 | 0.3093847 | Opioid |
| WAY-100635 maleate | −0.4965254 | 0.3097619 | Serotonin |
| Salmeterol | −0.4895786 | 0.312216 | Adrenoceptor |
| Ofloxacin | −0.4888508 | 0.3124737 | Antibiotic |
| NS-1619 | −0.4877995 | 0.3128459 | K+ Channel |
| 3-Hydroxybenzylhydrazine dihydrochloride | −0.4866413 | 0.3132563 | Biochemistry |
| Flupirtine maleate | −0.4839672 | 0.3142046 | Glutamate |
| Emodin | −0.4834599 | 0.3143846 | Phosphorylation |
| Acetylsalicylic acid | −0.4811745 | 0.3151962 | Prostaglandin |
| (+)-trans-(1R,2R)-U-50488 hydrochloride | −0.4732357 | 0.3180225 | Opioid |
| L-Glutamic acid hydrochloride | −0.4726761 | 0.3182221 | Glutamate |
| Tetrahydrozoline hydrochloride | −0.4692774 | 0.3194357 | Adrenoceptor |
| Genistein | −0.4689112 | 0.3195666 | Phosphorylation |
| PK 11195 | −0.4675507 | 0.320053 | GABA |
| NO-711 hydrochloride | −0.4617631 | 0.3221256 | GABA |
| Felbamate | −0.4585863 | 0.3232656 | Glutamate |
| Diethylenetriaminepentaacetic acid | −0.4575677 | 0.3236315 | Biochemistry |
| SNC80 | −0.4574846 | 0.3236614 | Opioid |
| Isonipecotic acid | −0.4569003 | 0.3238714 | GABA |
| (B1)-Quinpirole dihydrochloride | −0.4512555 | 0.3259027 | Dopamine |
| (−)-Scopolamine methyl nitrate | −0.4508293 | 0.3260563 | Cholinergic |
| (B1)-p-Aminoglutethimide | −0.444087 | 0.3284898 | Biochemistry |
| Alloxazine | −0.4424311 | 0.3290886 | Adenosine |
| GABA | −0.4389397 | 0.3303526 | GABA |
| CV-3988 | −0.4370903 | 0.3310229 | Cytokines & Growth Factors |
| (B1)-AMPA hydrobromide | −0.4272214 | 0.334609 | Glutamate |
| S-(4-Nitrobenzyl)-6-thioinosine | −0.4271344 | 0.3346407 | Adenosine |
| DL-alpha-Difluoromethylornithine hydrochloride | −0.4243649 | 0.3356498 | Angiogenesis |
| Piperidine-4-sulphonic acid | −0.4237939 | 0.3358581 | GABA |
| S(−)-3PPP hydrochloride | −0.4205348 | 0.3370474 | Dopamine |
| Ammonium pyrrolidinedithiocarbamate | −0.4167557 | 0.3384286 | Nitric Oxide |
| Dihydrexidine hydrochloride | −0.4153013 | 0.3389607 | Dopamine |
| N-(p-Isothiocyanatophenethyl)spiperone hydrochloride | −0.4152099 | 0.3389941 | Dopamine |
| Amperozide hydrochloride | −0.4126439 | 0.3399338 | Serotonin |
| N-Oleoylethanolamine | −0.4116341 | 0.3403038 | Sphingolipid |
| CGP-7930 | −0.411034 | 0.3405238 | GABA |
| Tyrphostin AG 126 | −0.4102296 | 0.3408188 | Phosphorylation |
| LY-367,265 | −0.4069604 | 0.3420185 | Serotonin |
| Triprolidine hydrochloride | −0.4060897 | 0.3423383 | Histamine |
| BW 284c51 | −0.4016895 | 0.3439563 | Cholinergic |
| 7-Chloro-4-hydroxy-2-phenyl-1,8-naphthyridine | −0.4009727 | 0.3442201 | Adenosine |
| Indirubin-3′-oxime | −0.3965032 | 0.3458669 | Phosphorylation |
| 2-Chloroadenosine | −0.3960315 | 0.3460409 | Adenosine |
| Tyrphostin AG 538 | −0.3954838 | 0.346243 | Phosphorylation |
| 5alpha-Androstane-3alpha,17beta-diol | −0.3811247 | 0.3515553 | Hormone |
| L-N6-(1-Iminoethyl)lysine hydrochloride | −0.3808868 | 0.3516436 | Nitric Oxide |
| Piracetam | −0.375802 | 0.353532 | Glutamate |
| Flumazenil | −0.3664171 | 0.3570269 | Benzodiazepine |
| ICI 204,448 hydrochloride | −0.3635568 | 0.3580945 | Opioid |
| Maprotiline hydrochloride | −0.3614509 | 0.3588812 | Adrenoceptor |
| Naltriben methanesulfonate | −0.3605906 | 0.3592028 | Opioid |
| Glibenclamide | −0.3600391 | 0.359409 | K+ Channel |
| Ro 41-0960 | −0.3600208 | 0.3594158 | Neurotransmission |
| Indomethacin | −0.3562981 | 0.3608087 | Prostaglandin |
| S-5-Iodowillardiine | −0.3551315 | 0.3612455 | Glutamate |
| Bromoacetylcholine bromide | −0.3547425 | 0.3613913 | Cholinergic |

TABLE 3-continued

| | | | |
|---|---|---|---|
| IIK7 | −0.3544091 | 0.3615162 | Melatonin |
| trans-Azetidine-2,4-dicarboxylic acid | −0.3491146 | 0.3635016 | Glutamate |
| Levallorphan tartrate | −0.3464543 | 0.3645007 | Opioid |
| Oleic Acid | −0.3449339 | 0.365072 | Phosphorylation |
| 3-Tropanylindole-3-carboxylate methiodide | −0.3436416 | 0.3655579 | Serotonin |
| Zardaverine | −0.3412328 | 0.3664641 | Cyclic Nucleotides |
| 8-Methoxymethyl-3-isobutyl-1-methylxanthine | −0.3402529 | 0.366833 | Cyclic Nucleotides |
| LY-53,857 maleate | −0.3381844 | 0.3676121 | Serotonin |
| Acetyl-beta-methylcholine chloride | −0.3381749 | 0.3676157 | Cholinergic |
| (S)-3,5-Dihydroxyphenylglycine | −0.3364181 | 0.3682778 | Glutamate |
| Benazoline oxalate | −0.3347687 | 0.3688998 | Imidazoline |
| Adenosine amine congener | −0.3344655 | 0.3690142 | Adenosine |
| Piribedil maleate | −0.3344511 | 0.3690196 | Dopamine |
| Centrophenoxine hydrochloride | −0.3302342 | 0.3706115 | Nootropic |
| Arcaine sulfate | −0.3298798 | 0.3707454 | Glutamate |
| (B1)-Epinephrine hydrochloride | −0.3279434 | 0.3714772 | Adrenoceptor |
| Quipazine, N-methyl-, dimaleate | −0.3254481 | 0.372421 | Serotonin |
| Tetradecylthioacetic acid | −0.3237663 | 0.3730575 | Transcription |
| Phentolamine mesylate | −0.3190977 | 0.3748262 | Adrenoceptor |
| Kainic acid | −0.3168627 | 0.3756739 | Glutamate |
| Tracazolate | −0.3151455 | 0.3763256 | GABA |
| Nalidixic acid sodium | −0.3144509 | 0.3765893 | Antibiotic |
| Naltrindole hydrochloride | −0.3140306 | 0.3767489 | Opioid |
| DL-Thiorphan | −0.3115796 | 0.37768 | Neurotransmission |
| Ipratropium bromide | −0.3080062 | 0.3790388 | Cholinergic |
| Debrisoquin sulfate | −0.3034256 | 0.3807828 | Neurotransmission |
| Tolbutamide | −0.3031914 | 0.380872 | Hormone |
| U-62066 | −0.3026318 | 0.3810852 | Opioid |
| Papaverine hydrochloride | −0.2991801 | 0.3824013 | Cyclic Nucleotides |
| DL-Cycloserine | −0.2985721 | 0.3826333 | Sphingolipid |
| (−)-trans-(1S,2S)-U-50488 hydrochloride | −0.2970526 | 0.3832132 | Opioid |
| S(+)-Isoproterenol (+)-bitartrate | −0.2963012 | 0.3835 | Adrenoceptor |
| Nifedipine | −0.2937469 | 0.3844757 | Ca2+ Channel |
| 5-(N-Ethyl-N-isopropyl)amiloride | −0.2885522 | 0.386462 | Ion Pump |
| P1,P4-Di(adenosine-5')tetraphosphate triammonium | −0.2866674 | 0.3871835 | Biochemistry |
| JL-18 | −0.2861311 | 0.3873888 | Dopamine |
| (B1)-Sulpiride | −0.2841113 | 0.3881626 | Dopamine |
| Pargyline hydrochloride | −0.2793742 | 0.3899788 | Neurotransmission |
| 1400W dihydrochloride | −0.2748955 | 0.3916983 | Nitric Oxide |
| (B1)-Metoprolol (+)-tartrate | −0.2688977 | 0.3940042 | Adrenoceptor |
| Quinine sulfate | −0.2685721 | 0.3941295 | K+ Channel |
| MRS 2159 | −0.2666194 | 0.3948811 | P2 Receptor |
| Phorbol 12-myristate 13-acetate | −0.2649849 | 0.3955105 | Phosphorylation |
| 4-Imidazoleacrylic acid | −0.2635155 | 0.3960766 | Histamine |
| (B1)-Ibuprofen | −0.2623381 | 0.3965304 | Prostaglandin |
| Tyrphostin 25 | −0.2591217 | 0.3977707 | Phosphorylation |
| Ropinirole hydrochloride | −0.2551545 | 0.3993019 | Dopamine |
| Ebselen | −0.2514811 | 0.4007211 | Leukotriene |
| Iproniazid phosphate | −0.2492467 | 0.401585 | Neurotransmission |
| (B1)-p-Chlorophenylalanine | −0.2471057 | 0.4024132 | Neurotransmission |
| Etazolate hydrochloride | −0.2465468 | 0.4026295 | Adenosine |
| Imetit dihydrobromide | −0.245242 | 0.4031345 | Histamine |
| Melatonin | −0.2407208 | 0.4048858 | Melatonin |
| SKF 89976A hydrochloride | −0.2327776 | 0.4079671 | GABA |
| Pimozide | −0.2323351 | 0.4081389 | Dopamine |
| Resveratrol | −0.2295098 | 0.4092364 | Prostaglandin |
| (−)-Physostigmine | −0.2178478 | 0.4137739 | Cholinergic |
| Phenytoin sodium | −0.2165555 | 0.4142774 | Anticonvulsant |
| Metrifudil | −0.2122911 | 0.41594 | Adenosine |
| Hydrochlorothiazide | −0.2120003 | 0.4160534 | Biochemistry |
| S-Methylisothiourea hemisulfate | −0.211117 | 0.416398 | Nitric Oxide |
| UK 14,304 | −0.2102812 | 0.4167241 | Adrenoceptor |
| Adenosine | −0.2085555 | 0.4173976 | Adenosine |
| Pheniramine maleate | −0.2062238 | 0.4183081 | Histamine |
| Hydroxytacrine maleate | −0.2043258 | 0.4190494 | Cholinergic |
| Guanidinyl-naltrindole di-trifluoroacetate | −0.2037007 | 0.4192937 | Opioid |
| (+)-Bicuculline | −0.1988579 | 0.4211869 | GABA |
| GR 125487 sulfamate salt | −0.1942361 | 0.4229955 | Serotonin |
| Sulindac | −0.1941855 | 0.4230153 | Prostaglandin |
| Chlorpropamide | −0.1900506 | 0.4246347 | Hormone |
| H-9 dihydrochloride | −0.1898999 | 0.4246938 | Phosphorylation |
| Nocodazole | −0.1890617 | 0.4250222 | Cytoskeleton and ECM |
| Ciclosporin | −0.1858442 | 0.4262835 | Phosphorylation |
| Clodronic acid | −0.1841811 | 0.4269357 | Cytoskeleton and ECM |
| Triamcinolone | −0.1839952 | 0.4270086 | Hormone |
| Alaproclate hydrochloride | −0.172486 | 0.4315277 | Serotonin |
| U-75302 | −0.1722133 | 0.4316349 | Leukotriene |
| O-Methylserotonin hydrochloride | −0.1719634 | 0.4317331 | Serotonin |
| ARL 67156 trisodium salt | −0.1680119 | 0.433287 | P2 Receptor |
| GW5074 | −0.1618707 | 0.4357038 | Phosphorylation |

TABLE 3-continued

| | | | |
|---|---|---|---|
| p-Iodoclonidine hydrochloride | −0.1606282 | 0.4361931 | Adrenoceptor |
| 1-[2-(Trifluoromethyl)phenyl]imidazole | −0.1576174 | 0.4373791 | Nitric Oxide |
| L-Cycloserine | −0.1551811 | 0.4383393 | Sphingolipid |
| Thioperamide maleate | −0.1536629 | 0.4389378 | Histamine |
| (B1)-Synephrine | −0.1488224 | 0.4408469 | Adrenoceptor |
| Tyrphostin AG 528 | −0.148142 | 0.4411154 | Phosphorylation |
| Thiocitrulline | −0.1474445 | 0.4413906 | Nitric Oxide |
| S-(−)-Lisuride | −0.1473193 | 0.44144 | Dopamine |
| D-Serine | −0.142851 | 0.4432039 | Glutamate |
| SKF 75670 hydrobromide | −0.1421094 | 0.4434968 | Dopamine |
| Fusaric acid | −0.1412847 | 0.4438225 | Dopamine |
| Memantine hydrochloride | −0.1410286 | 0.4439237 | Glutamate |
| 2-Iodomelatonin | −0.1348453 | 0.4463671 | Melatonin |
| Citicoline sodium | −0.1331469 | 0.4470386 | Lipid |
| R-(−)-Fluoxetine hydrochloride | −0.1280696 | 0.449047 | Serotonin |
| Y-27632 dihydrochloride | −0.1254747 | 0.4500739 | Phosphorylation |
| 8-Cyclopentyl-1,3-dimethylxanthine | −0.1247866 | 0.4503462 | Adenosine |
| Xamoterol hemifumarate | −0.1243226 | 0.4505299 | Adrenoceptor |
| L-655,240 | −0.1210308 | 0.4518333 | Thromboxane |
| Naftopidil dihydrochloride | −0.1172241 | 0.4533412 | Adrenoceptor |
| S(−)-IBZM | −0.1165784 | 0.4535971 | Dopamine |
| Flutamide | −0.1132999 | 0.4548964 | Hormone |
| Lidocaine hydrochloride | −0.1110713 | 0.4557799 | Na+ Channel |
| (B1)-Chloro-APB hydrobromide | −0.1110031 | 0.4558069 | Dopamine |
| Arecoline hydrobromide | −0.1109986 | 0.4558087 | Cholinergic |
| S(−)-DS 121 hydrochloride | −0.0997976 | 0.4602525 | Dopamine |
| (+)-MK-801 hydrogen maleate | −0.0980507 | 0.460946 | Glutamate |
| Foliosidine | −0.0968991 | 0.4614033 | Anticonvulsant |
| Valproic acid sodium | −0.0949317 | 0.4621846 | Anticonvulsant |
| McN-A-343 | −0.0889691 | 0.4645532 | Cholinergic |
| 1,3-Dipropyl-7-methylxanthine | −0.0889564 | 0.4645583 | Adenosine |
| Pindolol | −0.0789539 | 0.4685346 | Adrenoceptor |
| DL-erythro-Dihydrosphingosine | −0.0785022 | 0.4687143 | Phosphorylation |
| Ruthenium red | −0.0738764 | 0.4705544 | Ion Pump |
| Disopyramide phosphate | −0.0718701 | 0.4713527 | K+ Channel |
| 8-Cyclopentyl-1,3-dipropylxanthine | −0.0702081 | 0.472014 | Adenosine |
| Betaine aldehyde chloride | −0.0700722 | 0.4720681 | Cholinergic |
| Demeclocycline hydrochloride | −0.0645223 | 0.4742772 | Antibiotic |
| Vancomycin hydrochloride from Streptomyces orientalis | −0.0635226 | 0.4746752 | Antibiotic |
| Terazosin hydrochloride | −0.0572176 | 0.4771859 | Adrenoceptor |
| 3-Iodo-L-tyrosine | −0.0484383 | 0.4806835 | Neurotransmission |
| p-Aminoclonidine hydrochloride | −0.0477571 | 0.4809549 | Adrenoceptor |
| gamma-D-Glutamylaminomethylsulfonic acid | −0.0464941 | 0.4814582 | Glutamate |
| SKF 89626 | −0.0436857 | 0.4825775 | Dopamine |
| Hydrocortisone 21-hemisuccinate sodium | −0.0403285 | 0.4839156 | Hormone |
| Carbachol | −0.0338084 | 0.486515 | Cholinergic |
| Lansoprazole | −0.0336022 | 0.4865972 | Ion Pump |
| 4-Chloromercuribenzoic acid | −0.031935 | 0.4872619 | Biochemistry |
| Nialamide | −0.0293668 | 0.488286 | Neurotransmission |
| N-Ethylmaleimide | −0.0281638 | 0.4887658 | Biochemistry |
| Mibefradil dihydrochloride | −0.026925 | 0.4892598 | Ca2+ Channel |
| Methysergide maleate | −0.0198344 | 0.4920877 | Serotonin |
| Tetracaine hydrochloride | −0.0195299 | 0.4922092 | Na+ Channel |
| 3-(1H-Imidazol-4-yl)propyl di(p-fluorophenyl)methyl ether hydrochloride | −0.0146618 | 0.494151 | Histamine |
| Phenylbenzene-omega-phosphono-alpha-amino acid | −0.0142281 | 0.494324 | Glycine |
| R(+)-IAA-94 | −0.0101507 | 0.4959505 | Cl− Channel |
| 1,4-Dideoxy-1,4-imino-D-arabinitol | −0.0086167 | 0.4965625 | Phosphorylation |
| 5-Fluoroindole-2-carboxylic acid | −0.0075488 | 0.4969885 | Glutamate |
| MRS 1845 | −0.0061956 | 0.4975283 | Ca2+ Channel |
| S-(p-Azidophenacyl)glutathione | −0.0027604 | 0.4988988 | Multi-Drug Resistance |
| Bretylium tosylate | −0.0017093 | 0.4993181 | Adrenoceptor |
| MRS 1523 | −0.0013116 | 0.4994768 | Adenosine |
| Aminoguanidine hydrochloride | −0.000731 | 0.4997084 | Nitric Oxide |
| Xanthine amine congener | 0.0011645 | 0.4995354 | Adenosine |
| Roscovitine | 0.0027304 | 0.4989107 | Phosphorylation |
| Acetylthiocholine chloride | 0.0042231 | 0.4983152 | Cholinergic |
| Na-p-Tosyl-L-lysine chloromethyl ketone hydrochloride | 0.0048117 | 0.4980804 | Cyclic Nucleotides |
| Benserazide hydrochloride | 0.0074665 | 0.4970213 | Biochemistry |
| 6-Nitroso-1,2-beazopyrone | 0.0113164 | 0.4954855 | Transcription |
| GW1929 | 0.0150842 | 0.4939825 | Transcription |
| Ranitidine hydrochloride | 0.0227452 | 0.4909267 | Histamine |
| 1,5-Isoquinolinediol | 0.0267361 | 0.4893351 | Apoptosis |
| (+)-Bromocriptine methanesulfonate | 0.0279151 | 0.4888649 | Dopamine |
| R(+)-Butylindazone | 0.0292353 | 0.4883385 | Ion Pump |
| 5-Hydroxy-L-tryptophan | 0.0301111 | 0.4879892 | Serotonin |
| SB 228357 | 0.0342571 | 0.4863361 | Serotonin |
| DPMA | 0.0362806 | 0.4855293 | Adenosine |
| 5-(N,N-hexamethylene)amiloride | 0.0385541 | 0.484623 | Ion Pump |
| Estrone | 0.0408124 | 0.4837227 | Hormone |

TABLE 3-continued

| | | | |
|---|---|---|---|
| YS-035 hydrochloride | 0.0431073 | 0.482808 | Ca2+ Channel |
| (−)-Nicotine hydrogen tartrate salt | 0.0449771 | 0.4820628 | Cholinergic |
| Diazoxide | 0.0451082 | 0.4820105 | K+ Channel |
| LY-310,762 hydrochloride | 0.0511143 | 0.4796172 | Serotonin |
| Fenoldopam bromide | 0.0521932 | 0.4791874 | Dopamine |
| MHPG piperazine | 0.052756 | 0.4789632 | Adrenoceptor |
| Famotidine | 0.0548884 | 0.4781137 | Histamine |
| Milrinone | 0.0550597 | 0.4780455 | Cyclic Nucleotides |
| Methyl beta-carboline-3-carboxylate | 0.0602298 | 0.4759863 | Benzodiazepine |
| Oxaprozin | 0.066155 | 0.4736272 | Prostaglandin |
| Nalbuphine hydrochloride | 0.07032 | 0.4719695 | Opioid |
| Cyclobenzaprine hydrochloride | 0.0718594 | 0.4713569 | Serotonin |
| T-0156 | 0.0770873 | 0.4692771 | Cyclic Nucleotides |
| Chlorambucil | 0.0807801 | 0.4678084 | DNA |
| L-Methionine sulfoximine | 0.0867138 | 0.4654495 | Glutamate |
| PD 404,182 | 0.0905517 | 0.4639244 | Biochemistry |
| 3-Methyl-6-(3-[trifluoromethyl]phenyl)-1,2,4-triazolo[4,3-b]pyridazine | 0.0909474 | 0.4637672 | Benzodiazepine |
| 6-Methyl-2-(phenylethynyl)pyridine hydrochloride | 0.0936604 | 0.4626895 | Glutamate |
| (B1)-Norepinephrine (+)bitartrate | 0.0990286 | 0.4605578 | Adrenoceptor |
| GR 4661 | 0.1015268 | 0.4595661 | Serotonin |
| S-(4-Nitrobenzyl)-6-thioguanosine | 0.1016687 | 0.4595098 | Adenosine |
| Azelaic acid | 0.1056824 | 0.4579172 | DNA Metabolism |
| Metrazoline oxalate | 0.107342 | 0.4572588 | Imidazoline |
| Nilutamide | 0.1188464 | 0.4526985 | Hormone |
| Spiroxatrine | 0.1219344 | 0.4514755 | Serotonin |
| Desipramine hydrochloride | 0.1226472 | 0.4511932 | Adrenoceptor |
| Tetraethylammonium chloride | 0.1229511 | 0.4510729 | Cholinergic |
| 6,7-Dichloroquinoxaline-2,3-dione | 0.1273921 | 0.449315 | Glutamate |
| DL-p-Chlorophenylalanine methyl ester hydrochloride | 0.1276252 | 0.4492228 | Neurotransmission |
| Fluvoxamine maleate | 0.1322979 | 0.4473743 | Serotonin |
| NBI 27914 | 0.134476 | 0.4465131 | Neurotransmission |
| Lomefloxacin hydrochloride | 0.1373887 | 0.4453618 | Antibiotic |
| NG-Nitro-L-arginine | 0.1385058 | 0.4449203 | Nitric Oxide |
| 1,10-Diaminodecane | 0.1393232 | 0.4445974 | Glutamate |
| Allopurinol | 0.1473025 | 0.4414466 | Cell Stress |
| AIDA | 0.1540169 | 0.4387982 | Glutamate |
| (B1)-cis-Piperidine-2,3-dicarboxylic acid | 0.1553074 | 0.4382895 | Glutamate |
| Propentofylline | 0.1562987 | 0.4378988 | Adenosine |
| Urapidil hydrochloride | 0.157212 | 0.4375389 | Adrenoceptor |
| L-Aspartic acid | 0.1631695 | 0.4351925 | Glutamate |
| Pentolinium di[L(+)-tartrate] | 0.1661577 | 0.4340164 | Cholinergic |
| Tomoxetine | 0.1672426 | 0.4335896 | Adrenoceptor |
| (−)-cis-(1S,2R)-U-50488 tartrate | 0.1710795 | 0.4320806 | Neurotransmission |
| Tranilast | 0.173632 | 0.4310773 | Leukotriene |
| Cilostamide | 0.1756328 | 0.4302912 | Cyclic Nucleotides |
| Tyrphostin 47 | 0.1775006 | 0.4295576 | Phosphorylation |
| CGS-15943 | 0.1783497 | 0.4292242 | Adenosine |
| Muscimol hydrobromide | 0.1862631 | 0.4261192 | GABA |
| 4-Androsten-4-ol-3,17-dione | 0.1944016 | 0.4229307 | Hormone |
| Palmitoyl-DL-Carnitine chloride | 0.199541 | 0.4209198 | Phosphorylation |
| Fiduxosin hydrochloride | 0.2004519 | 0.4205636 | Adrenoceptor |
| Dihydroouabain | 0.2033806 | 0.4194188 | Ion Pump |
| Quazinone | 0.2046132 | 0.4189372 | Cyclic Nucleotides |
| (S)-ENBA | 0.2078462 | 0.4176745 | Adenosine |
| Moxonidine hydrochloride | 0.2170959 | 0.4140668 | Adrenoceptor |
| L-Tryptophan | 0.2240902 | 0.4113435 | Serotonin |
| Pirenperone | 0.2278841 | 0.4098682 | Serotonin |
| 1-(1-Naphthyl)piperazine hydrochloride | 0.2300827 | 0.4090137 | Serotonin |
| Pyridostigmine bromide | 0.2310856 | 0.4086241 | Cholinergic |
| 5-hydroxydecanoic acid sodium | 0.2331661 | 0.4078162 | K+ Channel |
| Isoxanthopterin | 0.2339176 | 0.4075245 | Cell Stress |
| Thioridazine hydrochloride | 0.2356029 | 0.4068704 | Dopamine |
| (−)-Isoproterenol hydrochloride | 0.2366585 | 0.4064609 | Adrenoceptor |
| Dilazep hydrochloride | 0.2448304 | 0.4032939 | Adenosine |
| SKF 94836 | 0.245798 | 0.4029193 | Calcium Signaling |
| Bromoenol lactone | 0.2484302 | 0.4019008 | Lipid |
| RX 821002 hydrochloride | 0.2490354 | 0.4016667 | Adrenoceptor |
| Phthalamoyl-L-glutamic acid trisodium | 0.2508627 | 0.4009601 | Glutamate |
| Piroxicam | 0.2527019 | 0.4002493 | Prostaglandin |
| (B1)-Pindobind | 0.257465 | 0.3984099 | Adrenoceprors |
| Hydralazine hydrochloride | 0.2592444 | 0.3977233 | Neurotransmission |
| p-MPPI hydrochloride | 0.2605884 | 0.397205 | Serotonin |
| Benoxathian hydrochloride | 0.2652651 | 0.3954026 | Adrenoceptor |
| Lidocaine N-ethyl bromide quaternary salt | 0.265314 | 0.3953838 | Na+ Channel |
| Beclomethasone | 0.2669712 | 0.3947457 | Hormone |
| Bupropion hydrochloride | 0.267118 | 0.3946891 | Dopamine |
| SU 4312 | 0.2691773 | 0.3938966 | Phosphorylation |
| Hypotaurine | 0.2752082 | 0.3915782 | Cell Stress |
| L-3,4-Dihydroxyphenylalanine methyl ester hydrochloride | 0.2768938 | 0.3909308 | Dopamine |

TABLE 3-continued

| | | | |
|---|---|---|---|
| ATPA | 0.2831538 | 0.3885295 | Glutamate |
| L-368,899 | 0.2909288 | 0.3855529 | Neurotransmission |
| Xylometazoline hydrochloride | 0.2960167 | 0.3836087 | Adrenoceptor |
| Diclofenac sodium | 0.2987801 | 0.3825539 | Prostaglandin |
| NADPH tetrasodium | 0.3021176 | 0.3812812 | Nitric Oxide |
| Rottlerin | 0.3042416 | 0.3804719 | Phosphorylation |
| L-165,041 | 0.3061865 | 0.3797313 | Lipid Signaling |
| 1-Methylbistamine dihydrochloride | 0.3067951 | 0.3794997 | Histamine |
| BRL 15572 | 0.311685 | 0.37764 | Serotonin |
| trans-(B1)-ACPD | 0.3149054 | 0.3764167 | Glutamate |
| HA-1004 hydrochloride | 0.3161003 | 0.3759632 | Phosphorylation |
| SU 6656 | 0.3164605 | 0.3758265 | Phosphorylation |
| Dobutamine hydrochloride | 0.318514 | 0.3750475 | Adrenoceptor |
| Caffeic Acid | 0.3199066 | 0.3745196 | Cell Stress |
| (B1)-CPP | 0.3213292 | 0.3739805 | Glutamate |
| MDL 26,630 trihydrochloride | 0.3273648 | 0.371696 | Glutamate |
| 4-DAMP methiodide | 0.3311398 | 0.3702694 | Cholinergic |
| Sandoz 58-035 | 0.3324572 | 0.369772 | Lipid |
| Tyrphostin AG 112 | 0.3332617 | 0.3694684 | Phosphorylation |
| 1-(5-Isoquinolinylsulfonyl)-2-methylpiperazine dihydrochloride | 0.3351856 | 0.3687425 | Phosphorylation |
| N-p-Tosyl-L-phenylalanine chloromethyl ketone | 0.3366567 | 0.3681879 | Biochemistry |
| BRL 54443 maleate | 0.3378207 | 0.3677491 | Serotonin |
| (B1)-alpha-Lipoic Acid | 0.3418414 | 0.3662351 | Cell Stress |
| Ro 04-6790 dihydrochloride | 0.3427992 | 0.3658748 | Serotonin |
| (B1)-Propranolol hydrochloride | 0.3567231 | 0.3606496 | Adrenoceptor |
| 6,7-ADTN hydrobromide | 0.3569595 | 0.3605611 | Dopamine |
| Amifostine | 0.3591546 | 0.3597397 | Cell Stress |
| SCH-202676 hydrobromide | 0.3598564 | 0.3594773 | G protein |
| THIP hydrochloride | 0.3613052 | 0.3589356 | GABA |
| A-315456 | 0.3628354 | 0.3583639 | Adrenoceptor |
| 4-(2-Aminoethyl)benzenesulfonyl fluoride hydrochloride | 0.3634327 | 0.3581408 | Biochemistry |
| Furegrelate sodium | 0.3638005 | 0.3580035 | Phosphorylation |
| Thio-NADP sodium | 0.3660898 | 0.357149 | Intracellular Calcium |
| Theophylline | 0.3698936 | 0.3557309 | Adenosine |
| alpha-Methyl-DL-tyrosine methyl ester hydrochloride | 0.3702682 | 0.3555913 | Neurotransmission |
| Xylazine hydrochloride | 0.3754966 | 0.3536456 | Adrenoceptor |
| 6-Hydroxymelatonin | 0.376743 | 0.3531823 | Melatonin |
| Propofol | 0.3768262 | 0.3531514 | Cholinergic |
| 5-fluoro-5'-deoxyuridine | 0.3786747 | 0.3524647 | DNA Metabolism |
| Ibudilast | 0.3787299 | 0.3524442 | Cyclic Nucleotides |
| Telenzepine dihydrochloride | 0.3813181 | 0.3514836 | Cholinergic |
| N-(2-[4-(4-Chlorophenyl)piperazin-1-yl]ethyl)-3-methoxybenzamide | 0.3828304 | 0.3509228 | Dopamine |
| N-arachidonylglycine | 0.3870739 | 0.3493507 | Cannabinoid |
| nor-Binaltorphimine dihydrochloride | 0.3880758 | 0.34898 | Opioid |
| Naltrexone hydrochloride | 0.3891105 | 0.3485972 | Opioid |
| Spermine tetrahydrochloride | 0.3941956 | 0.3467183 | Glutamate |
| Flunarizine dihydrochloride | 0.3954139 | 0.3462687 | Ion Pump |
| BU224 hydrochloride | 0.404453 | 0.3429398 | Imidazoline |
| Pancuronium bromide | 0.407652 | 0.3417646 | Cholinergic |
| Ergocristine | 0.4077764 | 0.3417189 | Dopamine |
| Wortmannin from Penicillium funiculosum | 0.4078684 | 0.3416852 | Phosphorylation |
| Caffeine | 0.4113488 | 0.3404084 | Adenosine |
| Se-(methyl)selenocysteine hydrochloride | 0.4115883 | 0.3403206 | Cell Cycle |
| Cirazoline hydrochloride | 0.4239458 | 0.3358027 | Adrenoceptor |
| SKY 95282 dimaleate | 0.4240619 | 0.3357603 | Histamine |
| Progesterone | 0.4251895 | 0.3353493 | Hormone |
| Hydroquinone | 0.4279698 | 0.3343366 | Leukotriene |
| Vinpocetine | 0.4328502 | 0.3325618 | Cyclic Nucleotides |
| YC-1 | 0.4334912 | 0.332329 | Cyclic Nucleotides |
| Lonidamine | 0.4358327 | 0.331479 | Cell Stress |
| (+)-Quisqualic acid | 0.436121 | 0.3313745 | Glutamate |
| Minocycline hydrochloride | 0.4418815 | 0.3292875 | Cell Cycle |
| 3-alpha,21-Dihydroxy-5-alpha-pregnan-20-one | 0.4440753 | 0.3284941 | GABA |
| L-701,324 | 0.4512614 | 0.3259006 | Glutamate |
| Orphenadrine hydrochloride | 0.4547976 | 0.3246274 | Cholinergic |
| Imazodan | 0.4616369 | 0.3221709 | Cyclic Nucleotides |
| N-Oleoyldopamine | 0.4632861 | 0.3215796 | Neurotransmission |
| N-Acetyldopamine monohydrate | 0.4667428 | 0.320342 | Dopamine |
| Promethazine hydrochloride | 0.4745838 | 0.3175418 | Histamine |
| 1-(5-Isoquinolinylsulfonyl)-3-methylpiperazine dihydrochloride | 0.4769032 | 0.3167155 | Phosphorylation |
| Antozoline hydrochloride | 0.4853666 | 0.3137082 | Imidazoline |
| Amfonelic acid | 0.4880186 | 0.3127683 | Dopamine |
| 9-cyclopentyladenine | 0.4988192 | 0.3089534 | Cyclic Nucleotides |
| Chloroquine diphosphate | 0.4992524 | 0.3088008 | DNA |
| L-732,138 | 0.5027332 | 0.3075759 | Tachykinin |
| (+)-Catechin Hydrate | 0.5105437 | 0.3048353 | Cell Stress |
| L-Buthionine-sulfoximine | 0.5134301 | 0.3038252 | Multi-Drug Resistance |
| (B1)-Thalidomide | 0.5210337 | 0.3011717 | Cytoskeleton and ECM |
| 1-Aminobenzotriazole | 0.5235927 | 0.3002809 | Multi-Drug Resistance |
| Rilmenidine hemifumarate | 0.5264123 | 0.2993009 | Imidazoline |

TABLE 3-continued

| | | | |
|---|---|---|---|
| N6-2-Phenylethyladenosine | 0.5312319 | 0.2976291 | Adenosine |
| Taurine | 0.5327512 | 0.2971029 | Glycine |
| Diltiazem hydrochloride | 0.5395341 | 0.2947592 | Ca2+ Channel |
| CR 2945 | 0.5450668 | 0.2928538 | Cholecystokinin |
| O-Phospho-L-serine | 0.5471921 | 0.2921234 | Glutamate |
| Clozapine | 0.5473261 | 0.2920774 | Dopamine |
| Beuzamide | 0.5498247 | 0.2912198 | Apoptosis |
| alpha-Lobeline hydrochloride | 0.5498547 | 0.2912095 | Cholinergic |
| Procaine hydrochloride | 0.5501378 | 0.2911124 | Na+ Channel |
| L-Arginine | 0.5591786 | 0.2880199 | Nitric Oxide |
| SQ 22536 | 0.5615523 | 0.2872105 | Cyclic Nucleotides |
| K 185 | 0.5674427 | 0.2852067 | Melatonin |
| Trimipramine maleate | 0.5676856 | 0.2851242 | Serotonin |
| Aurintricarboxylic acid | 0.5709183 | 0.2840275 | Apoptosis |
| 2-Methyl-5-hydroxytryptamine maleate | 0.5718311 | 0.2837182 | Serotonin |
| 2-Phenylaminoadenosine | 0.5727729 | 0.2833992 | Adenosine |
| VUF 5574 | 0.5811367 | 0.2805742 | Adenosine |
| Me-3,4-dephostatin | 0.5834297 | 0.279802 | Phosphorylation |
| Ketoconazole | 0.5860476 | 0.2789218 | Multi-Drug Resistance |
| Ro 20-1724 | 0.587371 | 0.2784773 | Cyclic Nucleotides |
| Agmatine sulfate | 0.5880971 | 0.2782336 | Imidazoline |
| Sulindac sulfone | 0.5923798 | 0.2767982 | Prostaglandin |
| Oxatomide | 0.5957331 | 0.2756768 | Immune System |
| Piceatannol | 0.5957518 | 0.2756705 | Phosphorylation |
| (−)-3-Methoxynaltrexone hydrochloride | 0.5963498 | 0.2754708 | Opioid |
| (−)-Naproxen sodium | 0.6024196 | 0.2734474 | Prostaglandin |
| (+)-Cyclazocine | 0.6116099 | 0.2703979 | Opioid |
| S(−)-Atenolol | 0.6170341 | 0.2686061 | Adrenoceptor |
| Primidone | 0.6186602 | 0.2680701 | Anticonvulsant |
| Dephostatin | 0.6209485 | 0.2673167 | Phosphorylation |
| CL 316, 243 | 0.6212351 | 0.2672225 | Adrenoceptor |
| Cephapirin sodium | 0.6219276 | 0.2669947 | Antibiotic |
| JWH-015 | 0.6222735 | 0.266881 | Cannabinoid |
| Methapyrilene hydrochloride | 0.6275722 | 0.2651421 | Histamine |
| (−)-Eseroline fumarate | 0.6338836 | 0.2630784 | Cholinergic |
| DL-Stearoylcarnitine chloride | 0.6377652 | 0.2618133 | Phosphorylation |
| Terbutaline hemisulfate | 0.6409003 | 0.2607937 | Adrenoceptor |
| Bestatin hydrochloride | 0.6432311 | 0.2600371 | Biochemistry |
| Droperidol | 0.6446544 | 0.2595756 | Dopamine |
| (−)-Scopolamine,n-Butyl-, bromide | 0.6485586 | 0.2583119 | Cholinergic |
| CGP 20712A methanesulfonate | 0.6490545 | 0.2581516 | Adrenoceptor |
| Procainamide hydrochloride | 0.6535257 | 0.2567087 | Na+ Channel |
| N-omega-Methyl-5-hydroxytryptamine oxalate salt | 0.6559542 | 0.2559268 | Serotonin |
| (B1)-8-Hydroxy-DPAT hydrobromide | 0.6561179 | 0.2558741 | Serotonin |
| Nomifensine maleate | 0.6692709 | 0.2516614 | Dopamine |
| 6(5H)-Phenanthridinone | 0.6765123 | 0.2493577 | Transcription |
| H-7 dihydrochloride | 0.6812631 | 0.2478525 | Phosphorylation |
| IEM-1460 | 0.6847965 | 0.2467362 | Glutamate |
| Rutaecarpine | 0.6856989 | 0.2464515 | K+ Channel |
| Tiapride hydrochloride | 0.6889364 | 0.2454316 | Dopamine |
| S-Nitrosoglutathione | 0.6977851 | 0.2426558 | Nitric Oxide |
| N-Methyl-beta-carboline-3-carboxamide | 0.6987585 | 0.2423515 | GABA |
| Kynurenic acid | 0.7018101 | 0.2413988 | Glutamate |
| AGN 192403 hydrochloride | 0.7031502 | 0.2409811 | Imidazoline |
| Amitriptyline hydrochloride | 0.7066229 | 0.2399004 | Adrenoceptor |
| Uridine 5'-diphosphate sodium | 0.7073999 | 0.239659 | P2 Receptor |
| Oxybutynin Chloride | 0.7079682 | 0.2394825 | Cholinergic |
| U0126 | 0.7109655 | 0.2385528 | Phosphorylation |
| Cephradine | 0.7111821 | 0.2384857 | Antibiotic |
| N-Succinyl-L-proline | 0.7245654 | 0.2343593 | Neurotransmission |
| BW 723C86 | 0.7247268 | 0.2343098 | Serotonin |
| Chelidamic acid | 0.7260765 | 0.2338959 | Glutamate |
| (B1)-alpha-Methyl-4-carboxyphenylglycine | 0.726971 | 0.2336219 | Glutamate |
| N6-Phenyladenosine | 0.7283359 | 0.233204 | Adenosine |
| N6-Methyladenosine | 0.7424208 | 0.2289162 | Adenosine |
| DL-Homatropine hydrobromide | 0.7439854 | 0.2284426 | Cholinergic |
| Sodium Oxamate | 0.744881 | 0.2281718 | Biochemistry |
| ZM 39923 hydrochloride | 0.7456711 | 0.2279331 | Phosphorylation |
| Chlorpromazine hydrochloride | 0.7505935 | 0.2264487 | Dopamine |
| 1,3-Dimethyl-8-phenylxanthine | 0.7517894 | 0.2260889 | Adenosine |
| Terfenadine | 0.7552995 | 0.2250346 | Histamine |
| Protriptyline hydrochloride | 0.7602722 | 0.223546 | Adrenoceptor |
| AB-MECA | 0.7603821 | 0.2235131 | Adenosine |
| 1-(4-Hydroxybenzyl)imidazole-2-thiol | 0.7627544 | 0.2228049 | Dopamine |
| 1,3,5-tris(4-hydroxyphenyl)-4-propyl-1H-pyrazole | 0.7716697 | 0.2201551 | Hormone |
| 2,4-Dinitrophenyl 2-fluoro-2-deoxy-beta-D-glucopyranoside | 0.7720141 | 0.220053 | Biochemistry |
| Picrotoxin | 0.7771163 | 0.2185451 | GABA |
| FSCPX | 0.782467 | 0.2169701 | Adenosine |
| Hemicholinium-3 | 0.7870667 | 0.2156214 | Cholinergic |
| SKY 83565 hydrobromide | 0.7894819 | 0.2149152 | Dopamine |

TABLE 3-continued

| | | | |
|---|---|---|---|
| Phenylbutazone | 0.790229 | 0.214697 | Prostaglandin |
| L-162,313 | 0.7922885 | 0.2140962 | Neurotransmission |
| SB 205384 | 0.7968442 | 0.2127708 | GABA |
| Dantrolene sodium | 0.7984689 | 0.2122992 | Intracellular Calcium |
| DCEBIO | 0.8098904 | 0.2090016 | K+ Channel |
| Paromomycin sulfate | 0.8210123 | 0.2058196 | Antibiotic |
| Cilostazol | 0.8218663 | 0.2055765 | Cyclic Nucleotides |
| Tropicamide | 0.8227286 | 0.2053312 | Cholinergic |
| L-Glutamine | 0.8277987 | 0.2038923 | Glutamate |
| Nisoxetine hydrochloride | 0.8335605 | 0.2022643 | Adrenoceptor |
| BTCP hydrochloride | 0.8361494 | 0.2015354 | Dopamine |
| Diphenhydramine hydrochloride | 0.8449488 | 0.1990697 | Histamine |
| (B1)-Bay K 8644 | 0.8527083 | 0.1969106 | Ca2+ Channel |
| Oxotremorine sesquifumarate salt | 0.8551621 | 0.1962307 | Cholinergic |
| Chloroethylclonidine dihydrochloride | 0.8606017 | 0.1947287 | Adrenoceptor |
| 4-Diphenylacetoxy-N-(2-chloroethyl)piperidine hydrochloride | 0.86449 | 0.1936594 | Cholinergic |
| TPMPA | 0.874196 | 0.1910058 | GABA |
| Betamethasone | 0.8811058 | 0.1891303 | Hormone |
| SKF 86466 | 0.8822325 | 0.1888255 | Adrenoceptor |
| Gabapentin | 0.883778 | 0.188408 | Anticonvulsant |
| Hispidin | 0.8895833 | 0.1868448 | Phosphorylation |
| 5,7-Dichlorokynurenic acid | 0.9010634 | 0.1837773 | Glutamate |
| PD 98,059 | 0.9027126 | 0.1833392 | Phosphorylation |
| Farnesylthiosalicylic acid | 0.9061025 | 0.1824408 | G protein |
| Phloretin | 0.9164828 | 0.1797069 | Ca2+ Channel |
| Oxolinic acid | 0.9179376 | 0.1793258 | Antibiotic |
| MRS 1754 | 0.9267975 | 0.1770158 | Adenosine |
| Guanfacine hydrochloride | 0.9270566 | 0.1769486 | Adrenoceptor |
| Amiodarone hydrochloride | 0.9292209 | 0.1763873 | Adrenoceptor |
| DNQX | 0.9307443 | 0.1759929 | Glutamate |
| 4-Phenyl-3-furoxancarbonitrile | 0.9313181 | 0.1758445 | Nitric Oxide |
| 5alpha-Pregnan-3alpha-ol-20-one | 0.9335428 | 0.1752699 | GABA |
| SB 203186 | 0.9365314 | 0.1744998 | Serotonin |
| 1-(3-Chlorophenyl)piperazine dihydrochloride | 0.9515586 | 0.1706604 | Serotonin |
| U-83836 dihydrochloride | 0.9540152 | 0.170038 | Cell Stress |
| Ketotifen fumarate | 0.9572878 | 0.169211 | Histamine |
| Phaclofen | 0.9701101 | 0.1659958 | GABA |
| Mianserin hydrochloride | 0.9745504 | 0.1648917 | Serotonin |
| (6R)-5,6,7,8-Tetrahydro-L-biopterin hydrochloride | 0.9757437 | 0.1645957 | Neurotransmission |
| Quipazine, 6-nitro-, maleate | 0.9781608 | 0.1639974 | Serotonin |
| L-azetidine-2-carboxylic acid | 0.983687 | 0.1626347 | Biochemistry |
| Betaxolol hydrochloride | 0.983822 | 0.1626015 | Adrenoceptor |
| D(−)-2-Amino-7-phosphonoheptanoic acid | 0.9854635 | 0.1621982 | Glutamate |
| Pyrilamine maleate | 0.9892572 | 0.1612687 | Histamine |
| GR 113808 | 0.9919556 | 0.1606096 | Serotonin |
| (B1)-Verapamil hydrochloride | 1.008291 | 0.1566574 | Ca2+ Channel |
| N-Acetyltryptamine | 1.0201218 | 0.1538353 | Melatonin |
| Furafylline | 1.0246268 | 0.1527697 | Biochemistry |
| 4-Hydroxyphenethylamine hydrochloride | 1.029835 | 0.1515437 | Dopamine |
| BW 245C | 1.0357188 | 0.1501667 | Prostanoids |
| Clonidine hydrochloride | 1.0408277 | 0.1489778 | Adrenoceptor |
| 4-Methylpyrazole hydrochloride | 1.0424145 | 0.1486098 | Biochemistry |
| 8-(p-Sulfophenyl)theophylline | 1.0468466 | 0.1475852 | Adenosine |
| ICI 118,551 hydrochloride | 1.1005464 | 0.1355471 | Adrenoceptor |
| PPADS | 1.1058077 | 0.1344049 | P2 Receptor |
| Acetazolamide | 1.1110935 | 0.133264 | Biochemistry |
| SC-560 | 1.11293 | 0.1328693 | Prostaglandin |
| Carbamazepine | 1.1144028 | 0.1325532 | Anticonvulsant |
| NF 023 | 1.1146556 | 0.132499 | P2 Receptor |
| Hydroxyurea | 1.131284 | 0.1289678 | DNA Metabolism |
| (−)-MK-801 hydrogen maleate | 1.1329541 | 0.1286168 | Glutamate |
| 2-Chloroadenosine triphosphate tetrasodium | 1.1488299 | 0.1253131 | P2 Receptor |
| (B1)-HA-966 | 1.1567873 | 0.1236796 | Glutamate |
| (B1)-PD 128,907 hydrochloride | 1.1639888 | 0.1222143 | Dopamine |
| BU99006 | 1.1815218 | 0.1186977 | Imidazoline |
| Rp-cAMPS triethylamine | 1.185648 | 0.1178807 | Phosphorylation |
| (−)-alpha-Methylnorepinephrine | 1.1934634 | 0.116344 | Adrenoceptor |
| 6-Hydroxy-DL-DOPA | 1.2039428 | 0.1143058 | Adrenoceptor |
| 1-Phenyl-3-(2-thiazolyl)-2-thiourea | 1.2082172 | 0.1134819 | Dopamine |
| Trihexyphenidyl hydrochloride | 1.2149684 | 0.1121891 | Cholinergic |
| 8-(4-Chlorophenylthio)-cAMP sodium | 1.216597 | 0.1118796 | Cyclic Nucleotides |
| Neostigmine bromide | 1.2283216 | 0.1096631 | Cholinergic |
| Cyproheptadine hydrochloride | 1.2319756 | 0.1089791 | Serotonin |
| (2S,1'S,2'S)-2-(carboxycyclopropyl)glycine | 1.2330432 | 0.1087798 | Glutamate |
| 3-Aminopropionitrile fumarate | 1.2343921 | 0.1085284 | Multi-Drug Resistance |
| 7-Chlorokynurenic acid | 1.2408477 | 0.107331 | Glutamate |
| 1-Deoxynojirimycin hydrochloride | 1.2419225 | 0.1071326 | Biochemistry |
| Atropine sulfate | 1.2441828 | 0.1067161 | Cholinergic |
| Tryptamine hydrochloride | 1.2448961 | 0.106585 | Serotonin |
| (B1)-2-Amino-3-phosphonopropionic acid | 1.2497911 | 0.1056879 | Glutamate |

TABLE 3-continued

| | | | |
|---|---|---|---|
| S(−)-Willardiine | 1.2513159 | 0.1054096 | Glutamate |
| U-99194A maleate | 1.2553247 | 0.1046805 | Dopamine |
| Spermidine trihydrochloride | 1.2585531 | 0.1040959 | Glutamate |
| Capsazepine | 1.2598653 | 0.103859 | Vanilloid |
| (B1)-SKF-38393 hydrochloride | 1.2798286 | 0.1003027 | Dopamine |
| gamma-Acetylinic GABA | 1.2846402 | 0.099459 | GABA |
| Atropine methyl nitrate | 1.2915005 | 0.0982651 | Cholinergic |
| Caffeic acid phenethyl ester | 1.3062704 | 0.0957303 | Cell Cycle |
| PRE-084 | 1.3114125 | 0.0948592 | Opioid |
| (B1)-Taxifolin | 1.3206971 | 0.0933012 | Cell Stress |
| Ro 41-1049 hydrochloride | 1.3277095 | 0.0921371 | Neurotransmission |
| Dihydrokainic acid | 1.3286819 | 0.0919765 | Glutamate |
| Dopamine hydrochloride | 1.3517313 | 0.0882306 | Dopamine |
| SB 218795 | 1.3590835 | 0.0870601 | Neurotransmission |
| MJ33 | 1.364155 | 0.0862594 | Lipid |
| R(+)-SCH-23390 hydrochloride | 1.3752617 | 0.0845252 | Dopamine |
| 5,5-Diphenylhydantoin | 1.3825713 | 0.0833982 | Anticonvulsant |
| CP55940 | 1.3959333 | 0.0813673 | Cannabinoid |
| Sphingosine | 1.4041813 | 0.0801324 | Phosphorylation |
| Dicyclomine hydrochloride | 1.4143858 | 0.0786243 | Cholinergic |
| Tolazamide | 1.4309708 | 0.0762193 | Hormone |
| A-77636 hydrochloride | 1.4402256 | 0.0749018 | Dopamine |
| Bromoacetyl alprenolol menthane | 1.4421969 | 0.0746234 | Adrenoceptor |
| 3,7-Dimethyl-I-propargylxanthine | 1.453698 | 0.073015 | Adenosine |
| 2,2'-Bipyridyl | 1.4548052 | 0.0728616 | Biochemistry |
| L-Cysteinesulfinic Acid | 1.4577326 | 0.0724571 | Glutamate |
| (B1)-Octoclothepin maleate | 1.4730361 | 0.0703706 | Dopamine |
| GW9662 | 1.4746331 | 0.0701556 | Transcription |
| Phenamil methanesulfonate | 1.4847913 | 0.0687996 | Na+ Channel |
| Ethylene glycol-bis(2-aminoethylether)-N,N,N',N'-tetraacetic acid | 1.5069032 | 0.0659177 | Biochemistry |
| Ivermectin | 1.5073937 | 0.0658549 | Cholinergic |
| Prilocaine hydrochloride | 1.5088803 | 0.0656647 | Na+ Channel |
| Benzamidine hydrochloride | 1.509442 | 0.0655929 | Biochemistry |
| Tyrphostin AG 698 | 1.5101362 | 0.0655043 | Phosphorylation |
| AA-861 | 1.5165016 | 0.0646963 | Leukotriene |
| DSP-4 hydrochloride | 1.5180671 | 0.0644987 | Adrenoceptor |
| Clorgyline hydrochloride | 1.5204874 | 0.0641943 | Neurotransmission |
| Cisplatin | 1.522768 | 0.0639084 | DNA |
| R(+)-6-Bromo-APB hydrobromide | 1.5322395 | 0.0627317 | Dopamine |
| Olomoucine | 1.5528427 | 0.0602304 | Phosphorylation |
| Molsidomine | 1.5665706 | 0.0586075 | Nitric Oxide |
| Dextrorphan D-tartrate | 1.5687122 | 0.0583575 | Glutamate |
| Astaxanthin | 1.57146 | 0.0580379 | Cell Stress |
| Fluspirilene | 1.5892579 | 0.0560011 | Dopamine |
| R(−)-SCH-12679 maleate | 1.6092 | 0.0537863 | Dopamine |
| Hydroxylamine hydrochloride | 1.6346899 | 0.051057 | Neurotransmission |
| Mizoribine | 1.642204 | 0.0502739 | DNA Metabolism |
| Icilin | 1.6433351 | 0.0501568 | Neurotransmission |
| Cimetidine | 1.6653496 | 0.0479215 | Histamine |
| 5-Carboxamidotryptamine maleate | 1.6674691 | 0.0477106 | Serotonin |
| Risperidone | 1.6943795 | 0.0450966 | Dopamine |
| TMB-8 hydrochloride | 1.7065885 | 0.0439493 | Intracellular Calcium |
| Picotamide | 1.7355934 | 0.0413179 | Thromboxane |
| Doxylamine succinate | 1.7361393 | 0.0412696 | Histamine |
| 3-deazaadenosine | 1.7700481 | 0.0383596 | Immune System |
| 1-(m-Chlorophenyl)-biguanide hydrochloride | 1.795282 | 0.0363044 | Serotonin |
| Sepiapterin | 1.7953942 | 0.0362955 | Nitric Oxide |
| Tyrphostin AG 490 | 1.801543 | 0.0358087 | Phosphorylation |
| Apigenin | 1.8240934 | 0.034069 | Cell Cycle |
| NF449 octasodium salt | 1.8514998 | 0.0320488 | G protein |
| Methiothepin mesylate | 1.8677893 | 0.0308957 | Serotonin |
| Nicardipine hydrochloride | 1.8689406 | 0.0308155 | Ca2+ Channel |
| Tyrphostin AG 1478 | 1.8698642 | 0.0307513 | Phosphorylation |
| 5-(N-Methyl-N-isobutyl)amiloride | 1.8712718 | 0.0306537 | Ion Pump |
| 4-Amino-1,8-naphthalimide | 1.8746499 | 0.0304205 | Apoptosis |
| Furosemide | 1.8888424 | 0.0294565 | Ion Pump |
| (B1)-2-Amino-4-phosphonobutyric acid | 1.8932302 | 0.0291636 | Glutamate |
| S(+)-Raclopride L-tartrate | 1.901273 | 0.0286331 | Dopamine |
| Methylcarbamylcholine chloride | 1.9129289 | 0.0278786 | Cholinergic |
| Naloxone benzoylhydrazone | 1.9153086 | 0.0277266 | Opioid |
| N,N-Dihexyl-2-(4-fluorophenyl)indole-3-acetamide | 1.9158209 | 0.0276939 | Benzodiazepine |
| Androsterone | 1.9472383 | 0.0257531 | Hormone |
| Reactive Blue 2 | 2.0032905 | 0.0225731 | P2 Receptor |
| 1,3-Diethyl-8-phenylxanthine | 2.0054443 | 0.0224578 | Adenosine |
| Fusidic acid sodium | 2.0449995 | 0.0204275 | Cell Cycle |
| SCH-28080 | 2.1072615 | 0.0175475 | Ion Channels |
| Danazol | 2.1516479 | 0.0157125 | Hormone |
| Calcimycin | 2.1716239 | 0.014942 | Intracellular Calcium |
| Bay 11-7085 | 2.1795367 | 0.0146459 | Cell Cycle |
| Carmustine | 2.190861 | 0.0142309 | DNA |

TABLE 3-continued

| | | | |
|---|---|---|---|
| 1,3-PBIT dihydrobromide | 2.2214777 | 0.0131593 | Nitric Oxide |
| Ceftriaxone sodium | 2.2296212 | 0.0128863 | Antibiotic |
| Tyrphostin AG 835 | 2.2299784 | 0.0128744 | Phosphorylation |
| Cystamine dihydrochloride | 2.229998 | 0.0128738 | Glutamate |
| Meclofenamic acid sodium | 2.2325388 | 0.0127897 | Prostaglandin |
| Cephalothin sodium | 2.263955 | 0.0117884 | Antibiotic |
| Suramin hexasodium | 2.2844155 | 0.0111736 | P2 Receptor |
| 8-Bromo-cAMP sodium | 2.3091105 | 0.0104687 | Cyclic Nucleotides |
| Tetraethylthiuram disulfide | 2.3469984 | 0.0094627 | Biochemistry |
| WIN 62,577 | 2.3505544 | 0.0093727 | Tachykinin |
| 5-(N,N-Dimethyl)amiloride hydrochloride | 2.396012 | 0.0082873 | Ion Pump |
| Sodium nitroprusside dihydrate | 2.4043321 | 0.008101 | Nitric Oxide |
| SB 200646 hydrochloride | 2.4372612 | 0.0073995 | Serotonin |
| L-3,4-Dihydroxyphenylalanine | 2.4397458 | 0.0073488 | Dopamine |
| Cefmetazole sodium | 2.5033943 | 0.0061504 | Antibiotic |
| MDL 105,519 | 2.56506 | 0.0051579 | Glutamate |
| 5-Bromo-2$$-deoxyuridine | 2.5800017 | 0.00494 | DNA Metabolism |
| Nordihydroguaiaretic acid from Larrea divaricata (creosote bush) | 2.6297007 | 0.004273 | Leukotriene |
| Tetramisole hydrochloride | 2.6487799 | 0.0040391 | Phosphorylation |
| Pregnenolone sulfate sodium | 2.6531789 | 0.0039869 | GABA |
| Clemizole hydrochloride | 2.7881997 | 0.0026501 | Histamine |
| NCS-356 | 2.8326918 | 0.0023079 | GABA |
| (Z)-Gugglesterone | 3.204847 | 0.0006757 | Lipid Signaling |
| R(+)-Atenolol | 3.7643209 | 8.35E−05 | Adrenoceptor |
| Leflunomide | 4.1031017 | 2.04E−05 | Immune System |
| LFM-A13 | 4.4998422 | 3.40E−06 | Phosphorylation |
| 1,3-Dipropyl-8-p-sulfophenylxanthine | 4.7426719 | 1.05E−06 | Adenosine |

| Product Name | Action | Selectivity |
|---|---|---|
| L-745,870 hydrochloride | Antagonist | D4 |
| NS 521 oxalate | Modulator | Benzimidazolone |
| Pentamidine isethionate | Antagonist | NMDA |
| Rotenone | Modulator | Mitochondria |
| Taxol | Inhibitor | Tubulin |
| Apomorphine hydrochloride hemihydrate | Agonist | |
| Amsacrine hydrochloride | Inhibitor | TopoII |
| Brefeldin A from Penicillium brefeldianum | Inhibitor | Golgi apparatus |
| Cytosine-1-beta-D-arabinofuranoside hydrochloride | Inhibitor | |
| Dequalinium analog, C-14 linker | Inhibitor | PKC-alpha |
| (+)-Butaclamol hydrochloride | Antagonist | |
| GBR-12935 dihydrochloride | Inhibitor | Reuptake |
| Idarubicin | Inhibitor | |
| ML-7 | Inhibitor | MLCK |
| Purvalanol A | Inhibitor | CDK |
| Podophyllotoxin | Inhibitor | |
| N,N,N-trimethyl-1-(4-trans-stilbenoxy)-2-propylammonium iodide | Antagonist | Nicotinic |
| (B1)-7-Hydroxy-DPAT hydrobromide | Agonist | D3 |
| Etoposide | Inhibitor | Topo II |
| Perphenazine | Antagonist | DRD2 |
| NG-Hydroxy-L-arginine acetate | Metabolite | NOS |
| GBR-12909 dihydrochloride | Inhibitor | Reuptake |
| Vincristine sulfate | Inhibitor | Tubulin |
| Colchicine | Inhibitor | Tubulin |
| PAPP | Agonist | 5-HT1A |
| Chelerythrine chloride | Inhibitor | PKC |
| MG 624 | Antagonist | Nicotinic |
| Tamoxifen citrate | Inhibitor | PKC |
| Hexamethonium dichloride | Antagonist | Nicotinic |
| Emetine dihydrochloride hydrate | Activator | |
| Ro 25-6981 hydrochloride | Antagonist | NMDA-NR2B |
| beta-Lapachone | Activator | |
| 2,3-Dimethoxy-1,4-naphthoquinone | Modulator | |
| 2-Methylthioadenosine diphosphate trisodium | Agonist | P2Y |
| Mitoxantrone | Inhibitor | |
| Methotrexate | Inhibitor | |
| Fluphenazine dihydrochloride | Antagonist | D1/D2 |
| Naloxone hydrochloride | Antagonist | |
| Diphenyleneiodonium chloride | Inhibitor | eNOS |
| Sanguinarine chloride | Inhibitor | Na+/K+ ATPase |
| Dihydrocapsaicin | Agonist | |
| Ancitabine hydrochloride | Inhibitor | |
| Arecaidine propargyl ester hydrobromide | Agonist | M2 |
| R(−)-Apocodeine hydrochloride | Agonist | |
| Aminopterin | Inhibitor | Dihydrofolate reductase |
| Oligomycin A | Inhibitor | . |
| Quinacrine dihydrochloride | Inhibitor | MAO |
| 4'-Chloro-3-alpha-(diphenylmethoxy)tropane hydrochloride | Blocker | Reuptake |
| (S)-(+)-Camptothecin | Inhibitor | TopoI |
| Sobuzoxane | Inhibitor | Topo II |

TABLE 3-continued

| | | |
|---|---|---|
| Thapsigargin | Releaser | |
| Dequalinium dichloride | Blocker | |
| Vinblastine sulfate salt | Inhibitor | Tubulin |
| XK469 | Inhibitor | TopoII beta |
| ML-9 | Inhibitor | MLCK |
| Trifluoperazine dihydrochloride | Antagonist | D1/D2 |
| 3-Tropanyl-3,5-dichlorobenzoate | Antagonist | 5-HT3 |
| Raloxifene hydrochloride | Modulator | ER |
| L-687,384 hydrochloride | Agonist | sigma1 |
| CGP-74514A hydrochloride | Inhibitor | Cdk1 |
| alpha-Guanidinoglutaric acid | Inhibitor | NOS |
| N-Vanillylnonanamide | Ligand | |
| U-74389G maleate | Inhibitor | |
| Ganciclovir | Inhibitor | G2-M checkpoint |
| Ifenprodil tartrate | Blocker | Polyamine site NMDA |
| cis-(Z)-Flupenthixol dihydrochloride | Antagonist | |
| Iodoacetamide | Inhibitor | |
| (−)Amethopterin | Inhibitor | |
| Calmidazolium chloride | Inhibitor | Ca2+ATPase |
| Ellipticine | Inhibitor | CYP1A1/TopoII |
| R(−)-Propylnorapomorphine hydrochloride | Agonist | DRD2 |
| Metolazone | Inhibitor | Na+/Cl− transporter |
| Carbetapentane citrate | Ligand | sigma1 |
| Azathioprine | Inhibitor | Purine synthesis |
| R(−)-N-Allylnorapomorphine hydrobromide | Agonist | |
| 5-Fluorouracil | Inhibitor | Thymidylate synthetase |
| 3-Methoxy-morphanin hydrochloride | Antagonist | |
| Methoctramine tetrahydrochloride | Antagonist | M2 |
| 2-(alpha-Naphthoyl)ethyltrimethylammonium iodide | Inhibitor | Choline Acetyltransferase |
| 3-Amino-1-propanesulfonic acid sodium | Agonist | GABA-A |
| Mevastatin | Inhibitor | Ras, Rho |
| Carboplatin | Intercalator | |
| Retinoic acid p-hydroxyanilide | Inhibitor | |
| (B1)-Butaclamol hydrochloride | Antagonist | D2 > D1 |
| SB 204070 hydrochloride | Antagonist | 5-HT4 |
| S-(−)-Eticlopride hydrochloride | Antagonist | DRD2 |
| 3′-Azido-3′-deoxythymidine | Inhibitor | Reverse transcriptase |
| Chlorprothixene hydrochloride | Antagonist | DRD2 |
| Metaphit methanesulfonate | Antagonist | sigma |
| SB 224289 hydrochloride | Antagonist | 5-HT1B |
| Triamterene | Blocker | |
| N-Acetylprocainamide hydrochloride | Blocker | |
| Guanidinoethyl disulfide dihydrobromide | Inhibitor | iNOS |
| SKF 96365 | Inhibitor | |
| R(−)-Denopamine | Agonist | beta1 |
| Metergoline | Antagonist | 5-HT2/5-HT1D |
| Disopyramide | Blocker | |
| (+)-Brompheniramine maleate | Antagonist | HRH1 |
| Cephalexin hydrate | | Cell wall synthesis |
| DL-alpha-Methyl-p-tyrosine | Inhibitor | Tyrosine hydroxylase |
| Melphalan | Intercalator | GCC |
| CNS-1102 | Antagonist | NMDA |
| Benztropine mesylate | Antagonist | Muscarinic |
| (B1)-Brompheniramine maleate | Antagonist | HRH1 |
| Actinonin | Inhibitor | Leucine aminopeptidase |
| Protoporphyrin IX disodium | Activator | Guanylyl cyclase |
| (+)-cis-Dioxolane iodide | Agonist | Muscarinic |
| Indomethacin morpholinylamide | Ligand | CB2 |
| Ketanserin tartrate | Antagonist | 5-HT2 |
| Cephalosporin C zinc salt | | Cell wall synthesis |
| R(−)-2,10,11-Trihydroxyaporphine hybrobromide | Agonist | DRD2 |
| Methoxamine hydrochloride | Agonist | alpha1 |
| Chlorothiazide | Inhibitor | Carbonic anhydrase |
| Hydrocortisone | | Cortisol |
| 7,7-Dimethyl-(5Z,8Z)-eicosadienoic acid | Inhibitor | PLA2/Lipoxygenase |
| Cefaclor | | Cell wall synthesis |
| Daidzein | Inhibitor | Aldehyde dehydrogenase |
| Prazosin hydrochloride | Antagonist | alpha1 |
| Z-L-Phe chloromethyl ketone | Inhibitor | Chymotrypsin A-gamma |
| N6-Cyclohexyladenosine | Agonist | A1 |
| SB 415286 | Inhibitor | GSK-3 |
| (B1) trans-U-50488 methanesulfonate | Agonist | kappa |
| Isoliquiritigenin | Activator | Guanylyl cyclase |
| Niclosamide | | Protonophore |
| BRL 52537 hydrochloride | Agonist | kappa/mu opioid |
| R(−)-2,10,11-Trihydroxy-N-propylnoraporphine hydrobromide | Agonist | DRD2 |
| Oxymetazoline hydrochloride | Agonist | alpha2A |
| S(−)-UH-301 hydrochloride | Antagonist | 5-HT1A |
| 1-Phenylbiguanide | Agonist | 5-HT3 |
| NS 2028 | Inhibitor | Guanylate cyclase |

TABLE 3-continued

| | | |
|---|---|---|
| SDZ-205,557 hydrochloride | Antagonist | 5-HT4 |
| Betaine hydrochloride | Metabolite | |
| 6-Methoxy-1,2,3,4-tetrahydro-9H-pyrido[3,4b] indole | Inhibitor | MAO |
| Pergolide methanesulfonate | Agonist | D2/D1 |
| Bepridil hydrochloride | Blocker | |
| (−)-Sulpiride | Antagonist | DRD2 |
| Trazodone hydrochloride | Inhibitor | Reuptake |
| R-(+)-7-Hydroxy-DPAT hydrobromide | Agonist | D3 |
| 5'-N-Ethylcarboxamidoadenosine | Agonist | A1/A2 |
| 5'-N-Methyl carboxamidoadenosine | Agonist | A2 > A1 |
| 3',4'-Dichlorobenzamil | Inhibitor | Na+/Ca2+ exchanger |
| Cefazolin sodium | | Cell wall synthesis |
| CGS-12066A maleate | Agonist | 5-HT1B |
| m-Iodobenzylguanidine hemisulfate | Activator | |
| SB 216763 | Inhibitor | GSK-3 |
| R(+)-UH-301 hydrochloride | Agonist | 5-HT1A |
| 1-(2-Chlorophenyl)-1-(4-chlorophenyl)-2,2-dichloroethane | Inhibitor | Corticosteroid |
| Zaprinast | Inhibitor | PDE V |
| HE-NECA | Agonist | A2 |
| Noscapine hydrchloride | Ligand | |
| Dubinidine | | |
| Quinolinic acid | Antagonist | NMDA |
| 1-Aminocyclopropanecarboxylic acid hydrochloride | Agonist | NMDA-Glycine |
| Nimesulide | Inhibitor | COX-2 |
| (B1)-AMT hydrochloride | Inhibitor | iNOS |
| 2-Chloro-2-deoxy-D-glucose | Analog | Glucose |
| Efaroxan hydrochloride | Antagonist | I1 |
| L-2-aminoadipic acid | Inhibitor | Glutamine synthetase |
| Ritodrine hydrochloride | Agonist | beta2 |
| 3-Aminopropylphosphonic acid | Agonist | GABA-B |
| Tyrphostin AG 34 | Inhibitor | Tyrosine kinase |
| S-(−)-Carbidopa | Inhibitor | Aromatic amino acid decarboxylase |
| Quercetin dihydrate | Inhibitor | PDE |
| SB 204741 | Antagonist | 5-HT2B |
| cis-(B1)-8-OH-PBZI hydrobromide | Agonist | D3 |
| Praziquantel | | Ca2+ Ionophore |
| Corticosterone | | Glucocorticoid |
| Cefsulodin sodium salt hydrate | | Cell wall synthesis |
| Tyrphostin AG 494 | Inhibitor | EGFR |
| (B1)-6-Chloro-PB hydrobromide | Agonist | D1 |
| Gabaculine hydrochloride | Inhibitor | GABA transaminase |
| (B1)-2,3-Dichloro-alpha-methylbenzylamine hydrochloride | Inhibitor | PNMT |
| cis-Azetidine-2,4-dicarboxylic acid | Modulator | NMDA |
| WB-4101 hydrochloride | Antagonist | alpha1A |
| Acetohexamide | Releaser | Insulin |
| (+)-Nicotine (+)-di-p-toluoyl tartrate | Agonist | Nicotinic |
| Isoguvacine hydrochloride | Agonist | GABA-A, GABA-C |
| Cortisone 21-acetate | | Cortisol |
| Morin | Inhibitor | Antioxidant |
| R(+)-3PPP hydrochloride | Agonist | DRD2 |
| Serotonin hydrochloride | Agonist | |
| Ro 8-4304 | Antagonist | NMDA-NR2B |
| Bumetanide | Inhibitor | Na+-K+-2Cl-cotransporter |
| Ro 16-6491 hydrochloride | Inhibitor | MAO-B |
| 6-Aminohexanoic acid | Inhibitor | Blood Clotting |
| 1-Allyl-3,7-dimethyl-8-p-sulfophenylxanthine | Antagonist | A2 |
| Mesulergine hydrochloride | Agonist | |
| p-MPPF dihydrochloride | Antagonist | 5-HT1A |
| TTNPB | Ligand | RAR-alpha, beta, gamma |
| (E)-4-amino-2-butenoic acid | Agonist | GABA-C |
| D-ribofuranosylbenzimidazole | Inhibitor | |
| Alprenolol hydrochloride | Antagonist | beta |
| (E)-5-(2-Bromovinyl)-2'-deoxyuridine | Inhibitor | HSV1 |
| Pinacidil | Activator | |
| (B1)-Chlorpheniramine maleate | Antagonist | HRH1 |
| Fenofibrate | Agonist | PPAR-alpha |
| N6-Cyclopentyl-9-methyladenine | Antagonist | A1 |
| Mecamylamine hydrochloride | Antagonist | Nicotinic |
| Ranolazine dihydrochloride | Inhibitor | pFOX |
| Lorglumide sodium | Antagonist | CCK-A |
| Rolipram | Inhibitor | PDE IV |
| 4-Imidazolemethanol hydrochloride | Inhibitor | Histinol Dehydrogenase |
| PPNDS tetrasodium | Antagonist | P2X1 |
| U-101958 maleate | Antagonist | D4 |
| O-(Carboxymethyl)hydroxylamine hemihydrochloride | Inhibitor | Aminotransferase |
| Pyrocatechol | Inhibitor | |
| 3-Phenylpropargylamine hydrochloride | Inhibitor | Dopamine beta-hydroxlase |
| Clemastine fumarate | Antagonist | HRH1 |
| R(−)-N6-(2-Phenylisopropyl)adenosine | Agonist | A1 |

TABLE 3-continued

| | | |
|---|---|---|
| T-1032 | Inhibitor | PDE V |
| DM 235 | | |
| TCPOBOP | Agonist | CAR |
| R(+)-Terguride | Agonist | |
| Budesonide | | Cortisol |
| Metoclopramide hydrochloride | Antagonist | DRD2 |
| SP600125 | Inhibitor | c-JNK |
| Mifepristone | Antagonist | Progesterone |
| (B1)-Vesamicol hydrochloride | Inhibitor | ACh storage |
| Niflumic acid | Inhibitor | COX-2 |
| Acetamide | Inhibitor | Carbonic anhydrase |
| Succinylcholine chloride | Antagonist | Nicotinic |
| Quinidine sulfate | Antagonist | |
| SKF-525A hydrochloride | Inhibitor | Microsomal oxidation |
| (B1)-PPHT hydrochloride | Agonist | DRD2 |
| Proglumide | Antagonist | |
| IMID-4F hydrochloride | Blocker | |
| Guanabenz acetate | Agonist | alpha2 |
| (B1)-Muscarine chloride | Agonist | Muscarinic |
| CNQX disodium | Antagonist | AMPA/Kainate |
| Thiothixene hydrochloride | Antagonist | D1/D2 |
| (B1)-3-(3,4-dihydroxyphenyl)-2-methyl-DL-alanine | Inhibitor | L-aromatic amino acid decarboxylase |
| 2',3'-didehydro-3'-deoxythymidine | Inhibitor | Reverse Transcriptase |
| (−)-Tetramisole hydrochloride | Inhibitor | |
| GYKI 52466 hydrochloride | Antagonist | AMPA/kainate |
| Doxazosin mesylate | Blocker | alpha1 |
| N-Methyl-D-aspartic acid | Agonist | NMDA |
| Citalopram hydrobromide | Inhibitor | Reuptake |
| (−)-Bicuculline methbromide, 1(S), 9(R) | Antagonist | GABA-A |
| Fenoterol hydrobromide | Agonist | beta2 |
| Loratadine | Antagonist | HRH1 |
| Triflupromazine hydrochloride | Antagonist | DRD2 |
| (B1)-Vanillylmandelic acid | Metabolite | |
| 2,3-Butanedione monoxime | Blocker | ATP-sensitive |
| AL-8810 | Antagonist | FP Receptor |
| Cyproterone acetate | Antagonist | Androgen |
| L-alpha-Methyl-p-tyrosine | Inhibitor | Tyrosine hydroxylase |
| (B1)-Normetanephrine hydrochloride | Metabolite | Norepinephrine |
| Carisoprodol | | Skeletal muscle |
| Dihydro-beta-erythroidine hydrobromide | Antagonist | nAch |
| Diacylglycerol kinase inhibitor I | Inhibitor | Diacylglycerol kinase |
| Buspirone hydrochloride | Agonist | 5-HT1A |
| Tulobuterol hydrochloride | Agonist | beta |
| SIB 1757 | Antagonist | mGluR5 |
| S-Methyl-L-thiocitrulline acetate | Inhibitor | NOS |
| Rauwolscine hydrochloride | Antagonist | alpha2 |
| Tyrphostin A9 | Inhibitor | PDGFR |
| Clofibrate | Modulator | Lipoprotein lipase |
| NCS-382 | Antagonist | gamma-Hydroxybutyrate |
| N,N-Dipropyl-5-carboxamidotryptamine maleate | Agonist | 5-HT1A |
| BRL 37344 sodium | Agonist | beta3 |
| Naphazoline hydrochloride | Agonist | alpha |
| Pempidine tartrate | Antagonist | Nicotinic |
| BP 897 | Agonist | D3 |
| E-64 | Inhibitor | Cysteine protease |
| 5'-(N-Cyclopropyl)carboxamidoadenosine | Agonist | A2 |
| SB 222200 | Antagonist | NK3 |
| WB 64 | Ligand | M2 |
| ATPO | Antagonist | GluR1-4 |
| 3-Bromo-7-nitroindazole | Inhibitor | NOS |
| Salbutamol | Agonist | beta2 |
| NBQX disodium | Antagonist | AMPA/kainate |
| 5-Aminovaleric acid hydrochloride | Antagonist | GABA-B |
| OXA-22 iodide | Agonist | Muscarinic |
| 5,5-Dimethyl-1-pyrroline-N-oxide | Inhibitor | Antioxidant |
| 6-Chloromelatonin | Agonist | |
| Yohimbine hydrochloride | Antagonist | alpha2 |
| (B1)-Ibotenic acid | Agonist | NMDA |
| S-Nitroso-N-acetylpenicillamine | Donor | |
| 2,3-Butanedione | Inhibitor | Myosin ATPase |
| SC 19220 | Antagonist | EP1 |
| Pentoxifylline | Inhibitor | PDE |
| IC 261 | Inhibitor | CK-1delta/epsilon |
| Karakoline | Antagonist | Nicotinic |
| 2-Hydroxysaclofen | Antagonist | GABA-B |
| Trifluperidol hydrochloride | Antagonist | D1/D2 |
| N-Acetyl-L-Cysteine | Antagonist | |
| Pyrazinecarboxamide | | |
| (B1)-CGP-12177A hydrochloride | Agonist | beta |

TABLE 3-continued

| | | |
|---|---|---|
| N-Phenylanthranilic acid | Blocker | |
| Nitrendipine | Antagonist | L-type |
| Tyrphostin AG 527 | Inhibitor | EGFR |
| Tyrphostin AG 879 | Inhibitor | TrkA |
| S-Ethylisothiourea hydrobromide | Inhibitor | NOS |
| (B1)-SKF 38393, N-allyl-, hydrobromide | Agonist | D1 |
| Propionylpromazine hydrochloride | Antagonist | DRD2 |
| 1-(4-Chlorobenzyl)-5-methoxy-2-methylindole-3-acetic acid | Inhibitor | MRP1 |
| H-8 dihydrochloride | Inhibitor | PKA, PKG |
| Decamethonium dibromide | Agonist | Nicotinic |
| p-Benzoquinone | Inhibitor | G:C site |
| Ouabain | Inhibitor | Na+/K+ ATPase |
| (B1)-Octopamine hydrochloride | Agonist | alpha |
| Quinelorane dihydroechloride | Agonist | DRD2 |
| (−)-Quinpirole hydrochloride | Agonist | D2/D3 |
| Kenpaullone | Inhibitor | CDK1, CDK2, CDK5 |
| MK-886 | Inhibitor | |
| SR 2640 | Antagonist | CysLT1 |
| (+)-Pilocarpine hydrochloride | Agonist | Muscarinic |
| 10-(alpha-Diethylaminopropionyl)-phenothiazine hydrochloride | Inhibitor | Butyrylcholinesterase |
| Aminophylline ethylenediamine | Antagonist | A1/A2 |
| Phenelzine sulfate | Inhibitor | MAO-A/B |
| Propantheline bromide | Antagonist | Muscarinic |
| 3-Tropanyl-indole-3-carboxylate hydrochloride | Antagonist | 5-HT3 |
| Domperidone | Antagonist | DRD2 |
| PD 168,077 maleate | Agonist | D4 |
| 4-Aminopyridine | Blocker | A-type |
| Phenoxybenzamine hydrochloride | Blocker | alpha |
| Flecainide acetate | Blocker | |
| Chlorzoxazone | Inhibitor | iNOS |
| Hexahydro-sila-difenidol hydrochloride, p-fluoro analog | Antagonist | M3 > M1 > M2 |
| R(−)-Isoproterenol (+)-bitartrate | Agonist | beta |
| Pirfenidone | Inhibitor | |
| Histamine dihydrochloride | Agonist | |
| Histamine, R(−)-alpha-methyl-, dihydrochloride | Agonist | H3 |
| 13-cis-retinoic acid | Regulator | RAR-alpha, beta |
| L-733,060 hydrochloride | Antagonist | NK1 |
| Aminobenztropine | Ligand | Muscarinic |
| Idazoxan hydrochloride | Ligand | I1/I2 |
| Quipazine dimaleate | Agonist | |
| Tranylcypromine hydrochloride | Inhibitor | MAO |
| Cortexolone maleate | Antagonist | DRD2 |
| L-Histidine hydrochloride | Precursor | |
| SB-366791 | Antagonist | VR1 |
| L(−)-Norepinephrine bitartrate | Agonist | alpha, beta1 |
| R(−)-Me5 | Antagonist | |
| 7-Cyclopentyl-5-(4-phenoxy)phenyl-7H-pyrrolo[2,3-d]pyrimidin-4-ylamine | Inhibitor | Ick |
| NG-Nitro-L-arginine methyl ester hydrochloride | Inhibitor | NOS |
| (B1)-Methoxyverapamil hydrochloride | Antagonist | L-type |
| Semicarbazide hydrochloride | Inhibitor | MAO |
| Harmane | Agonist | I1 |
| Phosphomycin disodium | | Cell wall synthesis |
| SR 57227A | Agonist | 5-HT3 |
| 5-azacytidine | Inhibitor | DNA methyltransferase |
| Theobromine | Antagonist | A1 > A2 |
| beta-Chloro-L-alanine hydrochloride | Inhibitor | Alanine aminotransferase |
| Diacylglycerol Kinase Inhibitor II | Inhibitor | Diacylglycerol kinase |
| NG-Monomethyl-L-arginine acetate | Inhibitor | NOS |
| Nylidrin hydrochloride | Agonist | beta |
| Cinnarizine | Blocker | |
| N^G, N^G-Dimethylarginine hydrochloride | Inhibitor | NOS |
| 2',3'-dideoxycytidine | Inhibitor | Reverse Transcriptase |
| SB 206553 hydrochloride | Antagonist | 5-HT2C/5-HT2B |
| N-Bromoacetamide | Modulator | |
| Sulfaphenazole | Inhibitor | Cytochrome P4502C |
| SKF 83959 hydrobromide | Agonist | D1 |
| Aniracetam | Agonist | AMPA |
| 7-Nitroindazole | Inhibitor | nNOS |
| Dipropyldopamine hydrobromide | Agonist | |
| Guvacine hydrochloride | Inhibitor | Uptake |
| (B1)-DOI hydrochloride | Agonist | 5-HT2/5-HT1C |
| N-Methyl-1-deoxynojirimycin | Inhibitor | Glucosidase |
| Forskolin | Activator | Adenylate cyclase |
| Ciprofibrate | Ligand | PPAR-alpha |
| Methyl 6,7-dimethoxy-4-ethyl-beta-carboline-3-carboxylate | Agonist | |
| 3-Morpholinosydnonimine hydrochloride | Donor | |
| N6-2-(4-Aminophenyl)ethyladenosine | Agonist | A3 |
| Luteolin | Inhibitor | Antioxidant |
| Altretamine | Inhibitor | |

TABLE 3-continued

| | | |
|---|---|---|
| (−)-Perillic acid | Inhibitor | p21 Ras |
| Tyrphostin AG 808 | Inhibitor | Tyrosine kinase |
| Fluoxetine hydrochloride | Inhibitor | Reuptake |
| 5-Hydroxyindolacetic acid | Metabolite | |
| Thiolactomycin | Inhibitor | Myristate synthesis |
| S(−)-p-Bromotetramisole oxalate | Inhibitor | Alkaline phosphatase |
| alpha,beta-Methylene adenosine 5'-triphosphate dilithium | Agonist | P2X > P2Y |
| 4-Aminobenzamidine dihydrochloride | Inhibitor | Trypsin |
| Captopril | Inhibitor | ACE |
| B-HT 933 dihydrochloride | Agonist | alpha2 |
| DBO-83 | Agonist | Nicotinic |
| (+)-Chlorpheniramine maleate | Antagonist | HRH1 |
| rac-2-Ethoxy-3-hexadecanamido-1-propylphosphocholine | Inhibitor | PKC |
| Mexiletene hydrochloride | Blocker | |
| GYKI 52895 | Inhibitor | Reuptake |
| Phenylephrine hydrochloride | Agonist | alpha1 |
| 2-(2-Aminoethyl)isothiourea dihydrobromide | Inhibitor | NOS |
| Norcantharidin | Inhibitor | PP2A |
| Tyrphostin AG 537 | Inhibitor | EGFR |
| MRS 2179 | Antagonist | P2Y1 |
| N-(3,3-Diphenylpropyl)glycinamide | Blocker | NMDA |
| D-Cycloserine | Agonist | NMDA-Glycine |
| Trimethoprim | Inhibitor | Dihydrofolate reductase |
| CGS-21680 hydrochloride | Agonist | A2a |
| SR 59230A oxalate | Antagonist | beta3 |
| Aminoguanidine hemisulfate | Inhibitor | NOS |
| N-Methyldopamine hydrochloride | Agonist | |
| LY-294,002 hydrochloride | Inhibitor | PI3K |
| Acyclovir | Inhibitor | Viral DNA synthesis |
| 8-(3-Chlorostyryl)caffeine | Antagonist | A2A |
| Pilocarpine nitrate | Agonist | Muscarinic |
| U-73122 | Inhibitor | PLC, A2 |
| Ribavirin | Inhibitor | IMP dehydrogenase |
| Minoxidil | Activator | ATP sensitive |
| Adenosine 3',5'-cyclic monophosphate | Activator | PKA |
| REV 5901 | Antagonist | LTD4 |
| L-750,667 trihydrochloride | Antagonist | D4 |
| 1,4-PBIT dihydrobromide | Inhibitor | NOS |
| O6-benzylguanine | Inhibitor | . |
| S(+)-PD 128,907 hydrochloride | Agonist | D3 |
| 6-Fluoronorepinephrine hydrochloride | Agonist | alpha |
| Ketoprofen | Inhibitor | COX-1 |
| Monastrol | Inhibitor | EgG5 |
| TEPI hydrochloride | Inhibitor | nNOS |
| L-allylglycine | Inhibitor | . |
| Endothall | Inhibitor | PP2A |
| Meloxicam sodium | Inhibitor | COX-2 |
| MDL 28170 | Inhibitor | Calpain I/II |
| SB 202190 | Inhibitor | p38 MAPK |
| S(−)-Pindolol | Agonist | 5-HT1A |
| 3,4-Dichloroisocoumarin | Inhibitor | Serine Protease |
| Tetraisopropyl pyrophosphoramide | Inhibitor | Butyrylcholinesterase |
| rac-2-Ethoxy-3-octadecanamido-1-propylphosphocholine | Inhibitor | PKC |
| (B1)-threo-1-Phenyl-2-decanoylamino-3-morpholino-1-propanol hydrochloride | Inhibitor | Glucosylceramide synthase |
| SB 269970 hydrochloride | Antagonist | 5-HT7 |
| FPL 64176 | Activator | L-type |
| NSC 95397 | Inhibitor | Cdc25 |
| Labetalol hydrochloride | Antagonist | beta |
| CGP-13501 | Modulator | GABA-B |
| Cefotaxime sodium | | Cell wall synthesis |
| Nortriptyline hydrochloride | Inhibitor | Uptake |
| Lamotrigine | | |
| Cinoxacin | Inhibitor | |
| 3-n-Propylxanthine | Antagonist | A1 > A2 |
| IB-MECA | Agonist | A3 |
| cis-4-Aminocrotonic acid | Agonist | GABA-C |
| CB34 | Ligand | |
| GR 127935 hydrochloride | Antagonist | 5-HT1B/1D |
| LY-278,584 maleate | Antagonist | 5-HT3 |
| 2,6-Diamino-4-pyrimidinone | Inhibitor | GTP cyclohydrolase I |
| CB 1954 | Intercalator | |
| LE 300 | Antagonist | D1 |
| (B1)-Baclofen | Agonist | GABA-B |
| N-Acetyl-5-hydroxytryptamine | Precursor | |
| 1,1-Dimethyl-4-phenyl-piperazinium iodide | Agonist | |
| Benzamil hydrochloride | Blocker | Na+/H+, Na+/Ca2+ Pump |
| (R,R)-cis-Diethyl tetrahydro-2,8-chrysenediol | Antagonist | ER-beta |
| CX 546 | Modulator | AMPA |
| (B1)-2-Amino-5-phosphonopentanoic acid | Antagonist | NMDA |

TABLE 3-continued

| | | |
|---|---|---|
| Amoxapine | Inhibitor | Uptake |
| R(+)-Lisuride hydrogen maleate | Agonist | DRD2 |
| 3-aminobenzamide | Inhibitor | PARS |
| Riluzole | Antagonist | Release |
| Reserpine | Inhibitor | Uptake |
| Carcinine dihydrochloride | Inhibitor | Antioxidant |
| DL-Buthionine-[S,R]-sulfoximine | Inhibitor | |
| Metaproterenol hemisulfate | Agonist | beta2 |
| 9-Amino-1,2,3,4-tetrahydroacridine hydrochloride | Inhibitor | Cholinesterase |
| (B1)-2-Amino-7-phosphonoheptanoic acid | Antagonist | NMDA |
| Moxisylyte hydrochloride | Antagonist | alpha1 |
| Doxepin hydrochloride | Inhibitor | Uptake |
| L-741,626 | Antagonist | DRD2 |
| 8-Bromo-cGMP sodium | Activator | |
| CR 2249 | Agonist | NMDA-Glycine |
| GW7647 | Agonist | PPAR-alpha |
| Imiloxan hydrochloride | Antagonist | alpha2B |
| 2-methoxyestradiol | Metabolite | Estrogen |
| Daphnetin | Inhibitor | PK |
| Cyclophosphamide monohydrate | Intercalator | |
| Trequinsin hydrochloride | Inhibitor | PDE III |
| Propafenone hydrochloride | Blocker | hKv1.5 |
| Felodipine | Blocker | L-type |
| S(−)-Pindolol | Antagonist | beta |
| SR-95531 | Antagonist | GABA-A |
| 1-benzoyl-5-methoxy-2-methylindole-3-acetic acid | Inhibitor | MRP1 |
| Albuterol hemisulfate | Agonist | beta2 |
| Chlormezanone | Modulator | Muscle relaxant |
| L-N5-(1-Iminoethyl)ornithine hydrochloride | Inhibitor | NOS |
| Pentylenetetrazole | Modulator | CNS |
| N-(4-Aminobutyl)-5-chloro-2-naphthalenesulfonamide hydrochloride | Antagonist | Calmodulin |
| Imidazole-4-acetic acid hydrochloride | Antagonist | GABA-C |
| Tyrphostin 51 | Inhibitor | EGFR |
| Zonisamide sodium | | |
| Gallamine triethiodide | Antagonist | M2 |
| Palmitoylethanolamide | Agonist | CB2 |
| Myricetin | Inhibitor | Casein Kinase II |
| Lithium Chloride | Inhibitor | Inositol monophosphatase |
| Agroclavine | Agonist | |
| Cyclothiazide | Agonist | AMPA |
| L-Canavanine sulfate | Inhibitor | iNOS |
| L-alpha-Methyl DOPA | Inhibitor | Aromatic amino acid decarboxylase |
| D-609 potassium | Inhibitor | PIPLC |
| BWB70C | Inhibitor | 5-lipoxygenase |
| AC 915 oxalate | Ligand | sigma1 |
| Phosphonoacetic acid | Inhibitor | DNA Polymerase |
| Promazine hydrochloride | Antagonist | DRD2 |
| 1,10-Phenanthroline monohydrate | Inhibitor | Metalloprotease |
| loxoprofen | Inhibitor | COX |
| Atropine methyl bromide | Antagonist | Muscarinic |
| Retinoic acid | Activator | |
| Prochlorperazine dimaleate | Antagonist | |
| Nimodipine | Antagonist | L-type |
| SIB 1893 | Antagonist | mGluR5 |
| Chloro-IB-MECA | Agonist | A3 |
| 1-Methylimidazole | Inhibitor | COX |
| (−)-Scopolamine methyl bromide | Antagonist | Muscarinic |
| Clomipramine hydrochloride | Inhibitor | Reuptake |
| Tyrphostin 23 | Inhibitor | EGFR |
| Formoterol | Agonist | beta2 |
| (+)-Hydrastine | Antagonist | GABA-A |
| L-765,314 | Antagonist | alpha-1B |
| Glipizide | Blocker | ATP-sensitive |
| Ceramide | Inhibitor | Diacylglycerol kinase |
| Hexamethonium bromide | Antagonist | Nicotinic |
| (B1)-Sotalol hydrochloride | Antagonist | beta |
| S-(+)-Fluoxetine hydrochloride | Inhibitor | Reuptake |
| 5alpha-Pregnan-3alpha-ol-11,20-dione | Modulator | GABA-A |
| CPCCOEt | Antagonist | mGluR1 |
| Edrophonium chloride | Inhibitor | Acetylcholinesterase |
| Amiloride hydrochloride | Blocker | Epithelial |
| N6-Benzyl-5'-N-ethylcarboxamidoadenosine | Agonist | A3 |
| Dextromethorphan hydrobromide monohydrate | Antagonist | NMDA |
| 4-Hydroxybenzhydrazide | Inhibitor | |
| Epibestatin hydrochloride | Inhibitor | Metalloprotease |
| Methylergonovine maleate | Antagonist | |
| N6-Cyclopentyladenosine | Agonist | A1 |
| Urapidil, 5-Methyl- | Antagonist | alpha1A |
| alpha-Methyl-5-hydroxytryptamine maleate | Agonist | 5-HT2 |

TABLE 3-continued

| | | |
|---|---|---|
| Dihydroergotamine methanesulfonate | Antagonist | |
| GR-89696 fumarate | Agonist | kappa |
| Amiprilose hydrochloride | Modulator | |
| 2-Methylthioadenosine triphosphate tetrasodium | Agonist | P2Y |
| 3-Isobutyl-1-methylxanthine | Inhibitor | Phosphodiesterase |
| Dihydroergocristine methanesulfonate | Agonist | |
| Putrescine dihydrochloride | Agonist | NMDA-Polyamine |
| S(−)-Timolol maleate | Antagonist | beta |
| SKF 91488 dihydrochloride | Inhibitor | Histamine N-methyltransferase |
| erythro-9-(2-Hydroxy-3-nonyl)adenine hydrochloride | Inhibitor | Adenosine deaminase |
| VER-3323 hemifumarate salt | Agonist | 5-HT2C/5-HT2B |
| Sodium Taurocholate | Modulator | Conjugate Pathway |
| Iofetamine hydrochloride | Analog | |
| Fexofenadine hydrochloride | Antagonist | HRH1 |
| (S)-(−)-propafenone hydrochloride | Blocker | beta |
| 1-Amino-1-cyclohexanecarboxylic acid hydrochloride | Substrate | |
| Loxapine succinate | Antagonist | |
| (−)-Scopolamine hydrobromide | Antagonist | Muscarinic |
| Haloperidol | Antagonist | D2/D1 |
| I-OMe-Tyrphostin AG 538 | Inhibitor | IGF-1 RTK |
| SKF 97541 hydrochloride | Agonist | GABA-B |
| 5-Nitro-2-(3-phenylpropylamino)benzoic acid | Blocker | |
| S(+)-Ibuprofen | Inhibitor | COX |
| Choline bromide | Substrate | Choline acetyltransferase |
| U-69593 | Agonist | kappa |
| Dipyridamole | Inhibitor | |
| Ketorolac tris salt | Inhibitor | COX |
| Parthenolide | Inhibitor | |
| Indatraline hydrochloride | Inhibitor | Reuptake |
| (B1)-Nipecotic acid | Inhibitor | Uptake |
| Clotrimazole | Inhibitor | Ca2+-activated K+ channel |
| p-Fluoro-L-phenylalanine | Substrate | Tyrosine Hydroxylase |
| (B1)-gamma-Vinyl GABA | Inhibitor | Transaminase |
| Oxotremorine methiodide | Agonist | Muscarinic |
| Ritanserin | Antagonist | 5-HT2/5-HT1C |
| 4-Androstene-3,17-dione | Precursor | Androgen |
| R-(+)-8-Hydroxy-DPAT hydrobromide | Agonist | 5-HT1A |
| HA-100 | Inhibitor | PKA/PKC/MLCK |
| Lidocaine N-methyl hydrochloride | Blocker | |
| Tyrphostin AG 555 | Inhibitor | EGFR |
| (R)-(+)-WIN 55,212-2 mesylate | Agonist | |
| 1,7-Dimethylxanthine | Antagonist | A1 > A2 |
| SU 5416 | Inhibitor | VEGFR PTK |
| Seglitide | Agonist | sst2 |
| L-Hyoscyamine | Antagonist | |
| BMY 7378 dihydrochloride | Agonist | 5-HT1A |
| (B1)-Atenolol | Antagonist | beta1 |
| Amantadine hydrochloride | Releaser | |
| Nimustine hydrochloride | Intercalator | |
| Bethanechol chloride | Agonist | Muscarinic |
| Zimelidine dihydrochloride | Inhibitor | Reuptake |
| Tyrphostin 1 | Inhibitor | EGFR |
| N,N,N',N'-Tetramethylazodicarboxamide | Modulator | Thiols |
| Isotharine mesylate | Agonist | beta |
| 1-(2-Methoxyphenyl)piperazine hydrochloride | Agonist | 5-HT1 > 5-HT2 |
| ET-18-OCH3 | Inhibitor | PIPLC |
| Enoximone | Inhibitor | PDE III |
| NAN-190 hydrobromide | Antagonist | 5-HT1A |
| L-655,708 | Ligand | GABA-A |
| Oxiracetam | | |
| Ethosuximide | | |
| Cortexolone | Precursor | Cortisol |
| Naloxonazine dihydrochloride | Antagonist | mu1 |
| N-(4-Amino-2-chlorophenyl)phthalimide | | |
| Cysteamine hydrochloride | Depleter | |
| Vanillic acid diethylamide | Agonist | |
| ODQ | Inhibitor | NO-sensitive guanylyl cyclase |
| L-Glutamic acid, N-phthaloyl- | Agonist | NMDA |
| L-Leucinethiol, oxidized dihydrochloride | Inhibitor | Aminopeptidase |
| 3,4-Dihydroxyphenylacetic acid | Metabolite | |
| MK-912 | Agonist | alpha2A |
| Cortisone | | Corticosteroid |
| 17alpha-hydroxyprogesterone | Metabolite | Progesterone |
| Cantharidin | Inhibitor | PP2A |
| Fenspiride hydrochloride | Antagonist | alpha |
| 2-Cyelooctyl-2-hydroxyethylamine hydrochloride | Inhibitor | PNMT |
| (B1)-Isoproterenol hydrochloride | Agonist | beta |
| 4-Hydroxy-3-methoxyphenylacetic acid | Metabolite | |
| 3-Nitropropionic acid | Toxin | |
| beta-Estradiol | | Estrogen |

TABLE 3-continued

| | | |
|---|---|---|
| Etodolac | Inhibitor | COX |
| Doxycycline hydrochloride | | Protein synthesis |
| MHPG sulfate potassium | Metabolite | |
| Cantharidic Acid | Inhibitor | PP1/PP2A |
| (S)-MAP4 hydrochloride | Antagonist | mGluR4,6,7 |
| Linopirdine | Releaser | |
| Pireuzepine dihydrochloride | Antagonist | M1 |
| 1-(4-Fluorobenzyl)-5-methoxy-2-methylindole-3-acetic acid | Inhibitor | MRP1 |
| (S)-Propranolol hydrochloride | Blocker | beta |
| (−)-Epinephrine bitartrate | Agonist | |
| 3,5-Dinitrocatechol | Inhibitor | COMT |
| Imipramine hydrochloride | Blocker | Reuptake |
| Spironolactone | Antagonist | Mineralocorticoid |
| DL-threo-beta-hydroxyaspartic acid | Inhibitor | Transport |
| Spiperone hydrochloride | Antagonist | DRD2 |
| GW2974 | Inhibitor | EGFR/ErbB-2 |
| (−)-Cotinine | Metabolite | Nicotinic |
| Phosphoramidon disodium | Inhibitor | Endopeptidase |
| L-703,606 oxalate | Antagonist | NK1 |
| R-(−)-Desmethyldeprenyl hydrochloride | Inhibitor | MAO-B |
| 2,6-Difluoro-4-[2-(phenylsulfonylamino)ethylthio]phenoxyacetamide | Agonist | AMPA |
| Loperamide hydrochloride | Ligand | |
| WAY-100635 maleate | Antagonist | 5-HT1A |
| Salmeterol | Agonist | beta2 |
| Ofloxacin | | DNA Synthesis |
| NS-1619 | Activator | Ca2+ activated |
| 3-Hydroxybenzylhydrazine dihydrochloride | Inhibitor | Amino acid decarboxylase |
| Flupirtine maleate | Antagonist | NMDA |
| Emodin | Inhibitor | p56lck TK |
| Acetylsalicylic acid | Inhibitor | COX-3 > COX-1 > COX-2 |
| (+)-trans-(1R,2R)-U-50488 hydrochloride | Agonist | kappa |
| L-Glutamic acid hydrochloride | Agonist | |
| Tetrahydrozoline hydrochloride | Agonist | alpha |
| Genistein | Inhibitor | Tyrosine kinase |
| PK 11195 | Antagonist | Benzodiazepine |
| NO-711 hydrochloride | Inhibitor | Uptake |
| Felbamate | Antagonist | |
| Diethylenetriaminepentaacetic acid | Inhibitor | Zn2+-dependent protease |
| SNC80 | Agonist | delta |
| Isonipecotic acid | Agonist | GABA-A |
| (B1)-Quinpirole dihydrochloride | Agonist | D2 > D3 |
| (−)-Scopolamine methyl nitrate | Antagonist | Muscarinic |
| (B1)-p-Aminoglutethimide | Inhibitor | P450-dependendent hydroxylation |
| Alloxazine | Antagonist | A2b |
| GABA | Agonist | |
| CV-3988 | Antagonist | PAF |
| (B1)-AMPA hydrobromide | Agonist | AMPA/kainate |
| S-(4-Nitrobenzyl)-6-thioinosine | Inhibitor | Uptake |
| DL-alpha-Difluoromethylornithine hydrochloride | Inhibitor | ODC |
| Piperidine-4-sulphonic acid | Agonist | GABA-A |
| S(−)-3PPP hydrochloride | Agonist | DRD2 |
| Ammonium pyrrolidinedithiocarbamate | Modulator | NOS |
| Dihydrexidine hydrochloride | Agonist | D1 |
| N-(p-Isothiocyanatophenethyl)spiperone hydrochloride | Antagonist | DRD2 |
| Amperozide hydrochloride | Ligand | |
| N-Oleoylethanolamine | Inhibitor | Ceramidase |
| CGP-7930 | Modulator | GABA-B |
| Tyrphostin AG 126 | Inhibitor | TNFalpha |
| LY-367,265 | Antagonist | Reuptake |
| Triprolidine hydrochloride | Antagonist | HRH1 |
| BW 284c51 | Inhibitor | Acetylcholinesterase |
| 7-Chloro-4-hydroxy-2-phenyl-1,8-naphthyridine | Antagonist | A1 |
| Indirubin-3'-oxime | Inhibitor | CDK |
| 2-Chloroadenosine | Agonist | A1 > A2 |
| Tyrphostin AG 538 | Inhibitor | IGF-1 RTK |
| 5alpha-Androstane-3alpha, 17beta-diol | Metabolite | Androgen |
| L-N6-(1-Iminoethyl)lysine hydrochloride | Inhibitor | iNOS |
| Piracetam | Modulator | AMPA |
| Flumazenil | Antagonist | |
| ICI 204,448 hydrochloride | Agonist | kappa |
| Maprotiline hydrochloride | Inhibitor | Reuptake |
| Naltriben methanesulfonate | Antagonist | delta2 |
| Glibenclamide | Blocker | ATP-dependent |
| Ro 41-0960 | Inhibitor | COMT |
| Indomethacin | Inhibitor | COX |
| S-5-Iodowillardiine | Agonist | AMPA |
| Bromoacetylcholine bromide | Ligand | |
| IIK7 | Agonist | |
| trans-Azetidine-2,4-dicarboxylic acid | Agonist | mGluR1, mGluR5 |

TABLE 3-continued

| | | |
|---|---|---|
| Levallorphan tartrate | Antagonist | |
| Oleic Acid | Activator | PKC |
| 3-Tropanylindole-3-carboxylate methiodide | Antagonist | 5-HT3 |
| Zardaverine | Inhibitor | PDE III/PDE IV |
| 8-Methoxymethyl-3-isobutyl-1-methylxanthine | Inhibitor | PDE I |
| LY-53,857 maleate | Antagonist | 5-HT2/5-HT1C |
| Acetyl-beta-methylcholine chloride | Agonist | M1 |
| (S)-3,5-Dihydroxyphenylglycine | Agonist | mGluR1 |
| Benazoline oxalate | Agonist | I2 |
| Adenosine amine congener | Agonist | A1 |
| Piribedil maleate | Agonist | D3 |
| Centrophenoxine hydrochloride | | |
| Arcaine sulfate | Antagonist | NMDA-Polyamine |
| (B1)-Epinephrine hydrochloride | Agonist | |
| Quipazine, N-methyl-, dimaleate | Agonist | 5-HT3 |
| Tetradecylthioacetic acid | Agonist | PPAR-alpha |
| Phentolamine mesylate | Antagonist | alpha |
| Kainic acid | Agonist | Kainate |
| Tracazolate | Modulator | |
| Nalidixic acid sodium | Inhibitor | DNA Gyrase |
| Naltrindole hydrochloride | Antagonist | delta |
| DL-Thiorphan | Inhibitor | Enkephalinase |
| Ipratropium bromide | Antagonist | Muscarinic |
| Debrisoquin sulfate | Antihypertensive | |
| Tolbutamide | Releaser | Insulin |
| U-62066 | Agonist | kappa |
| Papaverine hydrochloride | Inhibitor | PDE |
| DL-Cycloserine | Inhibitor | Ketosphinganine synthase, Alanine aminotransferase |
| (−)-trans-(1S,2S)-U-50488 hydrochloride | Agonist | kappa |
| S(+)-Isoproterenol (+)-bitartrate | | beta |
| Nifedipine | Antagonist | L-type |
| 5-(N-Ethyl-N-isopropyl)amiloride | Blocker | Na+/H+ Antiporter |
| P1,P4-Di(adenosine-5')tetraphosphate triammonium | Inhibitor | |
| JL-18 | Antagonist | D4 > D2 |
| (B1)-Sulpiride | Antagonist | DRD2 |
| Pargyline hydrochloride | Inhibitor | MAO-B |
| 1400W dihydrochloride | Inhibitor | iNOS |
| (B1)-Metoprolol (+)-tartrate | Antagonist | beta1 |
| Quinine sulfate | Antagonist | |
| MRS 2159 | Antagonist | P2X1 |
| Phorbol 12-myristate 13-acetate | Activator | PKC |
| 4-Imidazoleacrylic acid | Inhibitor | Histidine ammonia-lyase/decarboxylase |
| (B1)-Ibuprofen | Inhibitor | COX |
| Tyrphostin 25 | Inhibitor | EGFR |
| Ropinirole hydrochloride | Agonist | DRD2 |
| Ebselen | Inhibitor | |
| Iproniazid phosphate | Inhibitor | MAO |
| (B1)-p-Chlorophenylalanine | Inhibitor | Tryptophan hydroxylase |
| Etazolate hydrochloride | Inhibitor | Phosphodiesterase |
| Imetit dihydrobromide | Agonist | H3 |
| Melatonin | Agonist | |
| SKF 89976A hydrochloride | Inhibitor | GAT-1 |
| Pimozide | Antagonist | DRD2 |
| Resveratrol | Inhibitor | COX |
| (−)-Physostigmine | Inhibitor | Cholinesterase |
| Phenytoin sodium | | |
| Metrifudil | Agonist | A2 |
| Hydrochlorothiazide | Inhibitor | Carbonic anhydrase |
| S-Methylisothiourea hemisulfate | Inhibitor | iNOS |
| UK 14,304 | Agonist | alpha2 |
| Adenosine | Agonist | |
| Pheniramine maleate | Antagonist | HRH1 |
| Hydroxytacrine maleate | Inhibitor | Cholinesterase |
| Guanidinyl-naltrindole di-trifluoroacetate | Antagonist | kappa |
| (+)-Bicuculline | Antagonist | GABA-A |
| GR 125487 sulfamate salt | Antagonist | 5-HT4 |
| Sulindac | Inhibitor | COX |
| Chlorpropamide | Releaser | Insulin |
| H-9 dihydrochloride | Inhibitor | cAMP- and cGMP-dependent PKs |
| Nocodazole | Inhibitor | beta-tubulin |
| Ciclosporin | Inhibitor | Calcineurin phosphatase |
| Clodronic acid | Inhibitor | MMP1/collagenase |
| Triamcinolone | Agonist | Glucocorticoid |
| Alaproclate hydrochloride | Inhibitor | Reuptake |
| U-75302 | Agonist | BLI1 |
| O-Methylserotonin hydrochloride | Agonist | |
| ARL 67156 trisodium salt | Inhibitor | ecto-ATPase |

TABLE 3-continued

| | | |
|---|---|---|
| GW5074 | Inhibitor | Raf1 kinase |
| p-Iodoclonidine hydrochloride | Agonist | alpha2 |
| 1-[2-(Trifluoromethyl)phenyl]imidazole | Inhibitor | NOS |
| L-Cycloserine | Inhibitor | Ketosphinganine synthetase |
| Thioperamide maleate | Antagonist | H3 |
| (B1)-Synephrine | Agonist | alpha |
| Tyrphostin AG 528 | Inhibitor | EGFR |
| Thiocitrulline | Inhibitor | nNOS, eNOS |
| S-(−)-Lisuride | Agonist | DRD2 |
| D-Serine | Agonist | NMDA-Glycine |
| SKF 75670 hydrobromide | Agonist | D1 |
| Fusaric acid | Inhibitor | Dopamine beta-hydroxylase |
| Memantine hydrochloride | Antagonist | NMDA |
| 2-Iodomelatonin | Agonist | |
| Citicoline sodium | Inhibitor | PLA2 |
| R-(−)-Fluoxetine hydrochloride | Inhibitor | Reuptake |
| Y-27632 dihydrochloride | Inhibitor | ROCK |
| 8-Cyclopentyl-1,3-dimethylxanthine | Antagonist | A1 |
| Xamoterol hemifumarate | Agonist | beta1 |
| L-655,240 | Antagonist | TXA2 |
| Naftopidil dihydrochloride | Antagonist | alpha1 |
| S(−)-IBZM | Ligand | DRD2 |
| Flutamide | Inhibitor | Androgen |
| Lidocaine hydrochloride | Modulator | |
| (B1)-Chloro-APB hydrobromide | Agonist | D1 |
| Arecoline hydrobromide | Agonist | |
| S(−)-DS 121 hydrochloride | Antagonist | Autoreceptor |
| (+)-MK-801 hydrogen maleate | Antagonist | NMDA |
| Foliosidine | | |
| Valproic acid sodium | | |
| McN-A-343 | Agonist | M1 |
| 1,3-Dipropyl-7-methylxanthine | Antagonist | A2 |
| Pindolol | Antagonist | beta |
| DL-erythro-Dihydrosphingosine | Inhibitor | PKC/PLA2/PLD |
| Ruthenium red | Inhibitor | Mitochondrial uniporter |
| Disopyramide phosphate | Modulator | |
| 8-Cyclopentyl-1,3-dipropylxanthine | Antagonist | A1 |
| Betaine aldehyde chloride | Metabolite | Choline dehydrogenase |
| Demeclocycline hydrochloride | | Protein synthesis |
| Vancomycin hydrochloride from Streptomyces orientalis | | Cell wall synthesis |
| Terazosin hydrochloride | Antagonist | alpha1 |
| 3-Iodo-L-tyrosine | Inhibitor | Tyrosine hydroxylase |
| p-Aminoclonidine hydrochloride | Agonist | alpha2 |
| gamma-D-Glutamylaminomethylsulfonic acid | Antagonist | Kainate |
| SKF 89626 | Agonist | D1 |
| Hydrocortisone 21-hemisuccinate sodium | | Cortisol |
| Carbachol | Agonist | |
| Lansoprazole | Inhibitor | H+ pump |
| 4-Chloromercuribenzoic acid | Inhibitor | |
| Nialamide | Inhibitor | MAO |
| N-Ethylmaleimide | Inhibitor | Isocitrate dehydrogenase |
| Mibefradil dihydrochloride | Blocker | T-type |
| Methysergide maleate | Antagonist | |
| Tetracaine hydrochloride | Modulator | |
| 3-(1H-Imidazol-4-yl)propyl di(p-fluorophenyl)methyl ether hydrochloride | Antagonist | H3 |
| Phenylbenzene-omega-phosphono-alpha-amino acid | Antagonist | |
| R(+)-IAA-94 | Inhibitor | |
| 1,4-Dideoxy-1,4-imino-D-arabinitol | Inhibitor | Glycogen phosphorylase |
| 5-Fluoroindole-2-carboxylic acid | Antagonist | NMDA-Glycine |
| MRS 1845 | Inhibitor | SOC |
| S-(p-Azidophenacyl)glutathione | Modulator | Glutathione S-transferase |
| Bretylium tosylate | Blocker | |
| MRS 1523 | Antagonist | A3 |
| Aminoguanidine hydrochloride | Inhibitor | NOS |
| Xanthine amine congener | Antagonist | A1 |
| Roscovitine | Inhibitor | CDK |
| Acetyithiocholine chloride | Agonist | Nicotinic |
| Na-p-Tosyl-L-lysine chloromethyl ketone hydrochloride | Inhibitor | Adenylyl cyclase |
| Benserazide hydrochloride | Inhibitor | Decarboxylase |
| 6-Nitroso-1,2-beazopyrone | Inhibitor | PARP |
| GW1929 | Agonist | PPAR-gamma |
| Ranitidine hydrochloride | Antagonist | H2 |
| 1,5-Isoquinolinediol | Inhibitor | PARS |
| (+)-Bromocriptine methanesulfonate | Agonist | DRD2 |
| R(+)-Butylindazone | Inhibitor | K+/Cl− transport |
| 5-Hydroxy-L-tryptophan | Precursor | |
| SB 228357 | Antagonist | 5-HT2B/2C |
| DPMA | Agonist | A2 |
| 5-(N,N-hexamethylene)amiloride | Inhibitor | Na+/H+ Antiporter |

TABLE 3-continued

| | | |
|---|---|---|
| Estrone | | Estrogen |
| YS-035 hydrochloride | Blocker | L-type |
| (−)-Nicotine hydrogen tartrate salt | Agonist | Nicotinic |
| Diazoxide | Activator | ATP-sensitive |
| LY-310,762 hydrochloride | Antagonist | 5-HT1D |
| Fenoldopam bromide | Agonist | D1 |
| MHPG piperazine | Metabolite | |
| Famotidine | Antagonist | H2 |
| Milrinone | Inhibitor | PDE III |
| Methyl beta-carboline-3-carboxylate | Agonist | |
| Oxaprozin | Inhibitor | |
| Nalbuphine hydrochloride | Antagonist | |
| Cyclobenzaprine hydrochloride | Antagonist | 5-HT2 |
| T-0156 | Inhibitor | PDE V |
| Chlorambucil | Intercalator | |
| L-Methionine sulfoximine | Inhibitor | Glutamine synthase |
| PD 404,182 | Inhibitor | KDO-8-P synthase |
| 3-Methyl-6-(3-[trifluoromethyl]phenyl)-1,2,4-triazolo[4,3-b]pyridazine | Agonist | BZ1 |
| 6-Methyl-2-(phenylethynyl)pyridine hydrochloride | Antagonist | mGluR5 |
| (B1)-Norepinephrine (+)bitartrate | Agonist | |
| GR 4661 | Agonist | 5-HT1D |
| S-(4-Nitrobenzyl)-6-thioguanosine | Inhibitor | |
| Azelaic acid | Inhibitor | |
| Metrazoline oxalate | Ligand | |
| Nilutamide | Inhibitor | Androgen |
| Spiroxatrine | Agonist | 5-HT1A |
| Desipramine hydrochloride | Inhibitor | Uptake |
| Tetraethylammonium chloride | Antagonist | Nicotinic |
| 6,7-Dichloroquinoxaline-2,3-dione | Antagonist | NMDA-glycine |
| DL-p-Chlorophenylalanine methyl ester hydrochloride | Inhibitor | Tryptophan hydroxylase |
| Fluvoxamine maleate | Inhibitor | Reuptake |
| NBI 27914 | Antagonist | CRF1 |
| Lomefloxacin hydrochloride | Inhibitor | DNA Gyrase |
| NG-Nitro-L-arginine | Inhibitor | NOS |
| 1,10-Diaminodecane | Agonist (inverse) | NMDA-polyamine |
| Allopurinol | Inhibitor | Xanthine oxidase |
| AIDA | Antagonist | mGluR1 |
| (B1)-cis-Piperidine-2,3-dicarboxylic acid | Agonist | NMDA |
| Propentofylline | Inhibitor | Transporter |
| Urapidil hydrochloride | Antagonist | alpha1 |
| L-Aspartic acid | Agonist | |
| Pentolinium di[L(+)-tartrate] | Antagonist | Nicotinic |
| Tomoxetine | Inhibitor | Reuptake |
| (−)-cis-(1S,2R)-U-50488 tartrate | Ligand | Sigma receptor |
| Tranilast | Inhibitor | LTC4 |
| Cilostamide | Inhibitor | PDE III |
| Tyrphostin 47 | Inhibitor | EGFR |
| CGS-15943 | Antagonist | A1 |
| Muscimol hydrobromide | Agonist | GABA-A, GABA-C |
| 4-Androsten-4-ol-3,17-dione | Inhibitor | Aromatase |
| Palmitoyl-DL-Carnitine chloride | Modulator | PKC |
| Fiduxosin hydrochloride | Antagonist | alpha1 |
| Dihydroouabain | Inhibitor | Na+/K+ Pump |
| Quazinone | Inhibitor | PDE III |
| (S)-ENBA | Agonist | A1 |
| Moxonidine hydrochloride | Agonist | alpha2A |
| L-Tryptophan | Precursor | |
| Pirenperone | Antagonist | 5-HT2 |
| 1-(1-Naphthyl)piperazine hydrochloride | Antagonist | 5-HT2 |
| Pyridostigmine bromide | Inhibitor | Cholinesterase |
| 5-hydroxydecanoic acid sodium | Blocker | |
| Isoxanthopterin | Metabolite | |
| Thioridazine hydrochloride | Antagonist | D1/D2 |
| (−)-Isoproterenol hydrochloride | Agonist | beta |
| Dilazep hydrochloride | Inhibitor | Uptake |
| SKF 94836 | Inhibitor | PDE III |
| Bromoenol lactone | Inhibitor | PLA2 |
| RX 821002 hydrochloride | Antagonist | alpha2 |
| Phthalamoyl-L-glutamic acid trisodium | Agonist | NMDA |
| Piroxicam | Inhibitor | COX |
| (B1)-Pindobind | Ligand | beta |
| Hydralazine hydrochloride | Inhibitor | MAO-A/B |
| p-MPPI hydrochloride | Antagonist | 5-HT1A |
| Benoxathian hydrochloride | Antagonist | alpha1 |
| Lidocaine N-ethyl bromide quaternary salt | Antagonist | |
| Beclomethasone | | Glucocorticoid |
| Bupropion hydrochloride | Blocker | Reuptake |
| SU 4312 | Inhibitor | KDR |

TABLE 3-continued

| | | |
|---|---|---|
| Hypotaurine | Inhibitor | Antioxidant |
| L-3,4-Dihydroxyphenylalanine methyl ester hydrochloride | Precursor | |
| ATPA | Agonist | Kainate |
| L-368,899 | Antagonist | Oxytocin receptor |
| Xylometazoline hydrochloride | Agonist | alpha |
| Diclofenac sodium | Inhibitor | COX |
| NADPH tetrasodium | Cofactor | |
| Rottlerin | Inhibitor | PKC/CaM Kinase III |
| L-165,041 | Agonist | PPAR-gamma |
| 1-Methylhistamine dihydrochloride | Metabolite | |
| BRL 15572 | Antagonist | 5-HT1D |
| trans-(B1)-ACPD | Agonist | Metabotropic |
| HA-1004 hydrochloride | Inhibitor | PK |
| SU 6656 | Inhibitor | Src family kinase |
| Dobutamine hydrochloride | Agonist | beta1 |
| Caffeic Acid | Inhibitor | Antioxidant |
| (B1)-CPP | Antagonist | NMDA |
| MDL 26,630 trihydrochloride | Agonist | NMDA-Polyamine |
| 4-DAMP methiodide | Antagonist | M3 |
| Sandoz 58-035 | Inhibitor | ACAT |
| Tyrphostin AG 112 | Inhibitor | Tyrosine kinase |
| 1-(5-Isoquinolinylsulfonyl)-2-methylpiperazine dihydrochloride | Inhibitor | PKA/PKC |
| N-p-Tosyl-L-phenylalanine chloromethyl ketone | Inhibitor | Chymotrypsin alpha |
| BRL 54443 maleate | Agonist | 5-HT1E/1F |
| (B1)-alpha-Lipoic Acid | Coenzyme | Pyruvate dehydrogenase |
| Ro 04-6790 dihydrochloride | Antagonist | 5-HT6 |
| (B1)-Propranolol hydrochloride | Antagonist | beta |
| 6,7-ADTN hydrobromide | Agonist | |
| Amifostine | Inhibitor | Cytoprotectant |
| SCH-202676 hydrobromide | Modulator | GPCR |
| THIP hydrochloride | Agonist | GABA-A |
| A-315456 | Antagonist | alpha1D |
| 4-(2-Aminoethyl)benzenesulfonyl fluoride hydrochloride | Inhibitor | Serine Protease |
| Furegrelate sodium | Inhibitor | Thromboxane synthase |
| Thio-NADP sodium | Blocker | NAADP-induced |
| Theophylline | Antagonist | A1 > A2 |
| alpha-Methyl-DL-tyrosine methyl ester hydrochloride | Inhibitor | Tyrosine hydroxylase |
| Xylazine hydrochloride | Agonist | alpha2 |
| 6-Hydroxymelatonin | Metabolite | |
| Propofol | Inhibitor | Muscarinic |
| 5-fluoro-5'-deoxyuridine | Inhibitor | |
| Ibudilast | Inhibitor | PDE IV |
| Telenzepine dihydrochloride | Antagonist | M1 |
| N-(2-[4-(4-Chlorophenyl)piperazin-1-yl]ethyl)-3-methoxybenzamide | Agonist | D4 |
| N-arachidonylglycine | Inhibitor | FAAH |
| nor-Binaltorphimine dihydrochloride | Antagonist | kappa |
| Naltrexone hydrochloride | Antagonist | |
| Spermine tetrahydrochloride | Antagonist | NMDA-Polyamine |
| Flunarizine dihydrochloride | Blocker | Na+/Ca2+ channel |
| BU224 hydrochloride | Antagonist | I2 |
| Pancuronium bromide | Antagonist | |
| Ergocristine | Agonist | |
| Wortmannin from Penicillium funiculosum | Inhibitor | PI3K |
| Caffeine | Inhibitor | Phosphodiesterase |
| Se-(methyl)selenocysteine hydrochloride | Inhibitor | |
| Cirazoline hydrochloride | Agonist | alpha1A |
| SKY 95282 dimaleate | Antagonist | H2 |
| Progesterone | | Progesterone |
| Hydroquinone | Inhibitor | . |
| Vinpocetine | Inhibitor | PDE I |
| YC-1 | Activator | Guanylyl cyclase |
| Lonidamine | Inhibitor | Mitochondrial hexokinase |
| (+)-Quisqualic acid | Agonist | AMPA |
| Minocycline hydrochloride | Inhibitor | |
| 3-alpha,21-Dihydroxy-5-alpha-pregnan-20-one | Modulator | GABA-A |
| L-701,324 | Antagonist | NMDA-Glycine |
| Orphenadrine hydrochloride | Antagonist | Muscarinic |
| Imazodan | Inhibitor | PDE II |
| N-Oleoyldopamine | Ligand | CB1 |
| N-Acetyldopamine monohydrate | Precursor | |
| Promethazine hydrochloride | Antagonist | HRH1 |
| 1-(5-Isoquinolinylsulfonyl)-3-methylpiperazine dihydrochloride | Inhibitor | PKC |
| Antozoline hydrochloride | Agonist | |
| Amfonelic acid | Modulator | |
| 9-cyclopentyladenine | Inhibitor | Adenylate cyclase |
| Chloroquine diphosphate | Intercalator | DNA |
| L-732,138 | Antagonist | NK1 > NK2, NK3 |
| (+)-Catechin Hydrate | Inhibitor | Antioxidant |
| L-Buthionine-sulfoximine | Inhibitor | |
| (B1)-Thalidomide | Inhibitor | TNFalpha |

TABLE 3-continued

| | | |
|---|---|---|
| 1-Aminobenzotriazole | Inhibitor | CYP450, chloroperoxidase |
| Rilmenidine hemifumarate | Agonist | I1 |
| N6-2-Phenylethyladenosine | Agonist | A1 |
| Taurine | Agonist | |
| Diltiazem hydrochloride | Antagonist | L-type |
| CR 2945 | Antagonist | CCK-B |
| O-Phospho-L-serine | Antagonist | NMDA |
| Clozapine | Antagonist | D4 > D2, D3 |
| Beuzamide | Inhibitor | PARS |
| alpha-Lobeline hydrochloride | Agonist | Nicotinic |
| Procaine hydrochloride | Blocker | |
| L-Arginine | Precursor | |
| SQ 22536 | Inhibitor | Adenylyl cyclase |
| K 185 | Antagonist | |
| Trimipramine maleate | Inhibitor | Reuptake |
| Aurintricarboxylic acid | Inhibitor | TopoII |
| 2-Methyl-5-hydroxytryptamine maleate | Agonist | 5-HT3 |
| 2-Phenylaminoadenosine | Agonist | A2 > A1 |
| VUF 5574 | Antagonist | A3 |
| Me-3,4-dephostatin | Inhibitor | PP1B/SHPTP-1 |
| Ketoconazole | Inhibitor | Cytochrome P450c17 |
| Ro 20-1724 | Inhibitor | cAMP phosphodiesterase |
| Agmatine sulfate | Agonist | |
| Sulindac sulfone | Inhibitor | |
| Oxatomide | Modulator | |
| Piceatannol | Inhibitor | Syk/Lck |
| (−)-3-Methoxynaltrexone hydrochloride | Antagonist | |
| (−)-Naproxen sodium | Inhibitor | COX |
| (+)-Cyclazocine | Antagonist | |
| S(−)-Atenolol | Antagonist | beta1 |
| Primidone | | |
| Dephostatin | Inhibitor | CD45 Tyrosine Kinase |
| CL 316, 243 | Agonist | beta3 |
| Cephapirin sodium | | Cell wall synthesis |
| JWH-015 | Agonist | CB2 |
| Methapyrilene hydrochloride | Antagonist | HRH1 |
| (−)-Eseroline fumarate | Inhibitor | Cholinesterase |
| DL-Stearoylcarnitine chloride | Inhibitor | PKC |
| Terbutaline hemisulfate | Agonist | beta |
| Bestatin hydrochloride | Inhibitor | Aminopeptidase |
| Droperidol | Antagonist | D1/D2 |
| (−)-Scopolamine,n-Butyl-, bromide | Antagonist | Muscarinic |
| CGP 20712A methanesulfonate | Antagonist | beta1 |
| Procainamide hydrochloride | Antagonist | |
| N-omega-Methyl-5-hydroxytryptamine oxalate salt | Ligand | |
| (B1)-8-Hydroxy-DPAT hydrobromide | Agonist | 5-HT1A |
| Nomifensine maleate | Inhibitor | Reuptake |
| 6(5H)-Phenanthridinone | Inhibitor | PARP |
| H-7 dihydrochloride | Inhibitor | PKC |
| IEM-1460 | Inhibitor | AMPA |
| Rutaecarpine | Blocker | |
| Tiapride hydrochloride | Antagonist | D2/D3 |
| S-Nitrosoglutathione | Donor | |
| N-Methyl-beta-carboline-3-carboxamide | Antagonist | GABA-A |
| Kynurenic acid | Antagonist | NMDA-Glycine |
| AGN 192403 hydrochloride | Ligand | I1 |
| Amitriptyline hydrochloride | Inhibitor | Uptake |
| Uridine 5'-diphosphate sodium | Agonist | P2Y |
| Oxybutynin Chloride | Antagonist | Muscarinic |
| U0126 | Inhibitor | MEK1/MEK2 |
| Cephradine | | Cell wall synthesis |
| N-Succinyl-L-proline | Inhibitor | ACE |
| BW 723C86 | Agonist | 5-HT2B |
| Chelidamic acid | Inhibitor | L-glutamic decarboxylase |
| (B1)-alpha-Methyl-4-carboxyphenylglycine | Antagonist | Metabotropic |
| N6-Phenyladenosine | Agonist | A1 |
| N6-Methyladenosine | Agonist | |
| DL-Homatropine hydrobromide | Antagonist | Muscarinic |
| Sodium Oxamate | Inhibitor | Lactate Dehydrogenase |
| ZM 39923 hydrochloride | Inhibitor | JNK-3 |
| Chlorpromazine hydrochloride | Antagonist | |
| 1,3-Dimethyl-8-phenylxanthine | Antagonist | A1 |
| Terfenadine | Antagonist | HRH1 |
| Protriptyline hydrochloride | Blocker | Reuptake |
| AB-MECA | Agonist | A3 |
| 1-(4-Hydroxybenzyl)imidazole-2-thiol | Inhibitor | Dopamine beta-hydroxylase |
| 1,3,5-tris(4-hydroxyphenyl)-4-propyl-1H-pyrazole | Agonist | ER-alpha |
| 2,4-Dinitrophenyl 2-fluoro-2-deoxy-beta-D-glucopyranoside | Inhibitor | exo-beta-(1,3)-Glucanase |
| Picrotoxin | Antagonist | GABA-C |
| FSCPX | Antagonist | A1 |

TABLE 3-continued

| | | |
|---|---|---|
| Hemicholinium-3 | Blocker | Uptake |
| SKY 83565 hydrobromide | Agonist | D1 |
| Phenylbutazone | Substrate | Prostaglandin peroxidase |
| L-162,313 | Agonist | AT1 |
| SB 205384 | Modulator | GABA-A |
| Dantrolene sodium | Inhibitor | Release |
| DCEBIO | Activator | hIK1 |
| Paromomycin sulfate | | Protein synthesis |
| Cilostazol | Inhibitor | PDE III |
| Tropicamide | Antagonist | M4 |
| L-Glutamine | Agonist | |
| Nisoxetine hydrochloride | Blocker | Reuptake |
| BTCP hydrochloride | Blocker | Reuptake |
| Diphenhydramine hydrochloride | Antagonist | HRH1 |
| (B1)-Bay K 8644 | Agonist | L-type |
| Oxotremorine sesquifumarate salt | Agonist | M2 |
| Chloroethylclonidine dihydrochloride | Antagonist | alpha1B |
| 4-Diphenylacetoxy-N-(2-chloroethyl)piperidine hydrochloride | Antagonist | Muscarinic |
| TPMPA | Antagonist | GABA-C |
| Betamethasone | | Glucocorticoid |
| SKF 86466 | Antagonist | alpha2 |
| Gabapentin | | |
| Hispidin | Inhibitor | PKC-beta |
| 5,7-Dichlorokynurenic acid | Antagonist | NMDA-glycine |
| PD 98,059 | Inhibitor | MEK2 |
| Farnesylthiosalicylic acid | Antagonist | Ras |
| Phloretin | Blocker | L-Type |
| Oxolinic acid | Inhibitor | DNA Gyrase |
| MRS 1754 | Antagonist | A2B |
| Guanfacine hydrochloride | Agonist | alpha2 |
| Amiodarone hydrochloride | Agonist | alpha/beta |
| DNQX | Antagonist | Kainate/quisqualate |
| 4-Phenyl-3-furoxancarbonitrile | Donor | |
| 5alpha-Pregnan-3alpha-ol-20-one | Modulator | GABA-A |
| SB 203186 | Antagonist | 5-HT4 |
| 1-(3-Chlorophenyl)piperazine dihydrochloride | Agonist | 5-HT1 |
| U-83836 dihydrochloride | Inhibitor | |
| Ketotifen fumarate | Antagonist | HRH1 |
| Phaclofen | Antagonist | GABA-B |
| Mianserin hydrochloride | Antagonist | |
| (6R)-5,6,7,8-Tetrahydro-L-biopterin hydrochloride | Cofactor | Tyrosine |
| Quipazine, 6-nitro-, maleate | Inhibitor | Reuptake |
| L-azetidine-2-carboxylic acid | Inhibitor | Collagen |
| Betaxolol hydrochloride | Antagonist | beta1 |
| D(−)-2-Amino-7-phosphonoheptanoic acid | Antagonist | NMDA |
| Pyrilamine maleate | Antagonist | HRH1 |
| GR 113808 | Antagonist | 5-HT4 |
| (B1)-Verapamil hydrochloride | Modulator | L-type |
| N-Acetyltryptamine | Agonist-Antagonist | |
| Furafylline | Inhibitor | P450IA2 |
| 4-Hydroxyphenethylamine hydrochloride | Agonist | |
| BW 245C | Agonist | DP |
| Clonidine hydrochloride | Agonist | alpha2 |
| 4-Methylpyrazole hydrochloride | Inhibitor | Alcohol dehydrogenase |
| 8-(p-Sulfophenyl)theophylline | Antagonist | A1 > A2 |
| ICI 118,551 hydrochloride | Antagonist | beta2 |
| PPADS | Antagonist | P2 |
| Acetazolamide | Inhibitor | Carbonic anhydrase |
| SC-560 | Inhibitor | COX-1 |
| Carbamazepine | | |
| NF 023 | Antagonist | P2X1 |
| Hydroxyurea | Inhibitor | Ribonucleoside reductase |
| (−)-MK-801 hydrogen maleate | Antagonist | NMDA |
| 2-Chloroadenosine triphosphate tetrasodium | Agonist | P2Y |
| (B1)-HA-966 | Antagonist | NMDA-glycine |
| (B1)-PD 128,907 hydrochloride | Agonist | D3 |
| BU99006 | Ligand | I2 |
| Rp-cAMPS triethylamine | Inhibitor | PKA |
| (−)-alpha-Methylnorepinephrine | Agonist | |
| 6-Hydroxy-DL-DOPA | Neurotoxin | |
| 1-Phenyl-3-(2-thiazolyl)-2-thiourea | Inhibitor | beta-Hydroxylase |
| Trihexyphenidyl hydrochloride | Antagonist | Muscarinic |
| 8-(4-Chlorophenylthio)-cAMP sodium | Activator | |
| Neostigmine bromide | Inhibitor | Acetylcholinesterase |
| Cyproheptadine hydrochloride | Antagonist | 5-HT2 |
| (2S,1$$S,2$$S)-2-(carboxycyclopropyl)glycine | Agonist | mGluR2 |
| 3-Aminopropionitrile fumarate | Substrate | CYP450 |
| 7-Chlorokynurenic acid | Antagonist | NMDA |
| 1-Deoxynojirimycin hydrochloride | Inhibitor | alpha-glucosidase |

TABLE 3-continued

| | | |
|---|---|---|
| Atropine sulfate | Antagonist | Muscarinic |
| Tryptamine hydrochloride | Ligand | |
| (B1)-2-Amino-3-phosphonopropionic acid | Antagonist | NMDA |
| S(−)-Willardiine | Agonist | AMPA/kainate |
| U-99194A maleate | Antagonist | D3 |
| Spermidine trihydrochloride | Ligand | NMDA-Polyamine |
| Capsazepine | Agonist | |
| (B1)-SKF-38393 hydrochloride | Antagonist | D1 |
| gamma-Acetylinic GABA | Inhibitor | GABA transaminase |
| Atropine methyl nitrate | Antagonist | Muscarinic |
| Caffeic acid phenethyl ester | Inhibitor | NFkB |
| PRE-084 | Agonist | sigma1 |
| (B1)-Taxifolin | Inhibitor | Antioxidant |
| Ro 41-1049 hydrochloride | Inhibitor | MAO-A |
| Dihydrokainic acid | Blocker | Kainate |
| Dopamine hydrochloride | Agonist | |
| SB 218795 | Antagonist | NK3 |
| MJ33 | Inhibitor | PLA2 |
| R(+)-SCH-23390 hydrochloride | Antagonist | D1 |
| 5,5-Diphenylhydantoin | | |
| CP55940 | Agonist | |
| Sphingosine | Inhibitor | PKC |
| Dicyclomine hydrochloride | Antagonist | Muscarinic |
| Tolazamide | Releaser | Insulin |
| A-77636 hydrochloride | Agonist | D1 |
| Bromoacetyl alprenolol menthane | Antagonist | beta |
| 3,7-Dimethyl-l-propargylxanthine | Antagonist | A2 |
| 2,2$$-Bipyridyl | Inhibitor | Metalloprotease |
| L-Cysteinesulfinic Acid | Ligand | |
| (B1)-Octoclothepin maleate | Antagonist | DRD2 |
| GW9662 | Inhibitor | PPAR-gamma |
| Phenamil methanesulfonate | Inhibitor | Amiloride sensitive |
| Ethylene glycol-bis(2-aminoethylether)-N,N,N$$,N$$-tetraacetic acid | Inhibitor | Carboxypeptidase B |
| Ivermectin | Modulator | alpha7 nACh |
| Prilocaine hydrochloride | Blocker | |
| Benzamidine hydrochloride | Inhibitor | Peptidase |
| Tyrphostin AG 698 | Inhibitor | EGFR |
| AA-861 | Inhibitor | 5-lipoxygenase |
| DSP-4 hydrochloride | Neurotoxin | |
| Clorgyline hydrochloride | Inhibitor | MAO-A |
| Cisplatin | Intercalator | |
| R(+)-6-Bromo-APB hydrobromide | Agonist | D1/D5 |
| Olomoucine | Inhibitor | PK |
| Molsidomine | Donor | |
| Dextrorphan D-tartrate | Antagonist | NMDA |
| Astaxanthin | Inhibitor | Antioxidant |
| Fluspirilene | Antagonist | D2/D1 |
| R(−)-SCH-12679 maleate | Antagonist | D1 |
| Hydroxylamine hydrochloride | Inhibitor | MAO |
| Mizoribine | Inhibitor | IMP dehydrogenase |
| Icilin | Agonist | CMR1 |
| Cimetidine | Antagonist | H2 |
| 5-Carboxamidotryptamine maleate | Agonist | 5-HT7 |
| Risperidone | Antagonist | DRD2 |
| TMB-8 hydrochloride | Antagonist | |
| Picotamide | Antagonist | TXA2 |
| Doxylamine succinate | Antagonist | HRH1 |
| 3-deazaadenosine | Inhibitor | |
| 1-(m-Chlorophenyl)-biguanide hydrochloride | Agonist | 5-HT3 |
| Sepiapterin | Cofactor | NOS |
| Tyrphostin AG 490 | Inhibitor | JAK2 |
| Apigenin | Inhibitor | |
| NF449 octasodium salt | Antagonist | Gs-alpha |
| Methiothepin mesylate | Antagonist | 5-HT1E, 5-HT1F, 5-HT6 |
| Nicardipine hydrochloride | Antagonist | L-type |
| Tyrphostin AG 1478 | Inhibitor | EGFR |
| 5-(N-Methyl-N-isobutyl)amiloride | Blocker | Na+/H+ Antiporter |
| 4-Amino-1,8-naphthalimide | Inhibitor | PARP |
| Furosemide | Inhibitor | Na+, K+, Cl− cotransport |
| (B1)-2-Amino-4-phosphonobutyric acid | Antagonist | NMDA |
| S(+)-Raclopride L-tartrate | Antagonist | DRD2 |
| Methylcarbamylcholine chloride | Agonist | Nicotinic |
| Naloxone benzoylhydrazone | Agonist | kappa |
| N,N-Dihexyl-2-(4-fluorophenyl)indole-3-acetamide | Ligand | Mitochondria |
| Androsterone | | Androgen |
| Reactive Blue 2 | Antagonist | P2Y |
| 1,3-Diethyl-8-phenylxanthine | Antagonist | A1 |
| Fusidic acid sodium | Inhibitor | |
| SCH-28080 | Inhibitor | H+/K+-ATPase |
| Danazol | Inhibitor | |

TABLE 3-continued

| | | |
|---|---|---|
| Calcimycin | | Ca2+ |
| Bay 11-7085 | Inhibitor | IkB-alpha |
| Carmustine | Intercalator | |
| 1,3-PBIT dihydrobromide | Inhibitor | NOS |
| Ceftriaxone sodium | | Cell wall synthesis |
| Tyrphostin AG 835 | Inhibitor | Tyrosine kinase |
| Cystamine dihydrochloride | Inhibitor | Transglutaminase |
| Meclofenamic acid sodium | Inhibitor | COX/5-Lipoxygenase |
| Cephalothin sodium | | Cell wall synthesis |
| Suramin hexasodium | Antagonist | P2X, P2Y |
| 8-Bromo-cAMP sodium | Activator | |
| Tetraethylthiuram disulfide | Inhibitor | Alcohol Dehydrogenase |
| WIN 62,577 | Antagonist | NK1 |
| 5-(N,N-Dimethyl)amiloride hydrochloride | Blocker | Na+/H+ Antiporter |
| Sodium nitroprusside dihydrate | Releaser | |
| SB 200646 hydrochloride | Antagonist | 5-HT2C/2B |
| L-3,4-Dihydroxyphenylalanine | Precursor | |
| Cefmetazole sodium | | Cell wall synthesis |
| MDL 105,519 | Antagonist | NMDA-Glycine |
| 5-Bromo-2$$-deoxyuridine | Inhibitor | |
| Nordihydroguaiaretic acid from Larrea divaricata (creosote bush) | Inhibitor | Lipoxygenase |
| Tetramisole hydrochloride | Inhibitor | Phosphatase |
| Pregnenolone sulfate sodium | Antagonist | GABA-A |
| Clemizole hydrochloride | Antagonist | HRH1 |
| NCS-356 | Agonist | gamma-Hydroxybutyrate |
| (Z)-Gugglesterone | Antagonist | FRX |
| R(+)-Atenolol | Antagonist | beta1 |
| Leflunomide | Inhibitor | |
| LFM-A13 | Inhibitor | BTK |
| 1,3-Dipropyl-8-p-sulfophenylxanthine | Antagonist | A1 > A2 |

TABLE 4

| Class | Total active in class[†] | Total in class | % Active in class |
|---|---|---|---|
| Adenosine | 4 | 56 | 7.1 |
| Adrenceptor | 5 | 103 | 4.9 |
| Antibiotics | 8 | 29 | 27.6 |
| Anticonvulsant | 1 | 12 | 8.3 |
| Apoptosis | 6 | 11 | 54.5 |
| Biochemistry | 6 | 46 | 13.0 |
| Calcium Channels | 2 | 26 | 7.7 |
| Cannabinoid | 1 | 6 | 16.7 |
| Cell Cycle | 5 | 15 | 33.3 |
| Cell Stress | 3 | 20 | 15.0 |
| Cholinergic | 8 | 77 | 10.4 |
| Cyclic Neucleotides | 4 | 31 | 12.9 |
| Cytoskeleton and ECM | 6 | 10 | 60.0 |
| DNA | 10 | 29 | 34.5 |
| Dopamine | 22 | 113 | 19.5 |
| GABA | 2 | 41 | 4.9 |
| Glutamate | 9 | 88 | 10.2 |
| Histamine | 2 | 32 | 6.3 |
| Hormone | 3 | 33 | 9.1 |
| Imidazoline | 1 | 11 | 9.1 |
| Immune System | 1 | 11 | 9.1 |
| Intracellular Calcium | 2 | 7 | 28.6 |
| Ion Pump | 3 | 16 | 18.8 |
| K+ Channel | 1 | 17 | 5.9 |
| Lipid | 1 | 9 | 11.1 |
| Na+ Channel | 3 | 17 | 17.6 |
| Neurotransmission | 4 | 45 | 8.9 |
| Nitric Oxide | 5 | 37 | 13.5 |
| Opioid | 6 | 27 | 22.2 |
| P2 Receptor | 2 | 14 | 14.3 |
| Phosphorylation | 9 | 93 | 9.7 |
| Prostaglandin | 1 | 24 | 4.2 |
| Serotonin | 12 | 83 | 14.5 |
| Vanilloid | 2 | 5 | 40.0 |
| Screen Total | 160 | 1267 | 12.6[‡] |
| Screen Total 2[§] | 122 | 1154 | 10.6 |

[†]Only includes inhibitors of MTT readings.
[‡]Frequency of whole screen
[§]Total calculated without cytotoxic compounds: antibiotics, apoptosis, cell cycle, cell stress, cytoskeleton, and DNA

TABLE 5

HTS Bioactive Pharmacological Classes

| Name | Action | Target | Selectivity | EC 50% Neurosphere (μm) | EC 50% Astrocyte (μm) | Neurosphere Specificity |
|---|---|---|---|---|---|---|
| Negative Control | | | | | | |
| Cycloheximide | Inhibitor | Protein Synthesis | 60S Ribosome | 0.142 | 0.0711 | 0.502 |
| Etoposide | Inhibitor | Topoisomerase | Topo II | 0.340 | 0.433 | 1.28 |
| Carboplatin | Intercalator | DNA | — | 0.489 | 2.453 | 5.08 |
| Dopamine | | | | | | |
| Perphenazine | Antagonist | Dopamine Receptor | D2 | 23.12 | n.d. | >4 |
| (±)-Butaclamol hydrochloride | Antagonist | Dopamine | D2 > D1 | 0.785 | 12.34 | 15.7 |

TABLE 5-continued

HTS Bioactive Pharmacological Classes

| Name | Action | Target | Selectivity | EC 50% Neurosphere (μm) | EC 50% Astrocyte (μm) | Neurosphere Specificity |
|---|---|---|---|---|---|---|
| R(−)-Propylnorapomorphine hydrochloride | Agonist | Dopamine | D2 | 0.3512 | 8.23 | 23.4 |
| Apomorphine hydrochloride hemihydrate | Agonist | Dopamine | — | 0.3499 | 10.19 | 29.1 |
| cis-(Z)-Flupenthixol dihydrochloride | Antagonist | Dopamine Receptor | — | 0.1993 | 1.182 | 5.93 |
| Ion Channels | | | | | | |
| Bepridil hydrochloride | Blocker | Ca2+ Channel | — | 2.70 | 4.724 | 1.75 |
| Dequalinium dichloride | Blocker | K+ channels | Apamin-sensitive | 1.474 | 1.418 | 0.962 |
| Muscarinic | | | | | | |
| Hexahydro-sila-difenidol hydrochloride | Antagonist | Acetylcholine Receptor | M3 > M1 > M2 | 0.441 | 5.815 | 13.2 |
| Methoctramine tetrahydrochloride | Antagonist | Acetylcholine Receptor | M2 | 1.053 | 0.0845 | 0.802 |
| NMDA | | | | | | |
| Ifenprodil tartrate | Blocker | NMDA | Polyamine site | 0.616 | 11.06 | 17.9 |
| Pentamidine isethionate | Antagonist | NMDA Receptor | — | 0.822 | 1.995 | 2.43 |
| Nitric Oxide | | | | | | |
| Diphenyleneiodonium chloride | Inhibitor | Nitric Oxide Synthase | eNOS | 0.011 | 0.0209 | 1.88 |
| 7-Nitroindazole | Inhibitor | Nitric Oxide Synthase | nNOS | 76.3 | 282.6 | 3.71 |
| Opioid | | | | | | |
| Metaphit methanesulfonate | Antagonist | Opioid | sigma | 10.0 | 3.624 | 0.361 |
| Carbetapentane citrate | Ligand | Opioid | sigma 1 | 0.756 | 28.16 | 37.3 |
| Phosphorylation | | | | | | |
| Chelerythrine chloride | Inhibitor | PKC | — | 0.396 | 1.531 | 3.87 |
| Retinoic acid p-hydroxyanilide | Vitamin A acid analog | RAR | — | 0.334 | 2.399 | 7.18 |
| WHI-P131 | Inhibitor | JAK3 | — | 2.346 | — | >10 |
| SB 202190 | Inhibitor | p38 MAPK | — | 8.063 | 64.8 | 8.04 |
| Serotonin | | | | | | |
| Methiothepin mesylate | Antagonist | Serotonin | 5-HT1E/F, 5-HT6 | 2.663 | 3.698 | 1.39 |
| Metergoline | Antagonist | Serotonin | 5-HT2/5-HT1D | 1.624 | 3.285 | 2.02 |
| PAPP | Agonist | Serotonin | 5-HT1A | 0.031 | 21.82 | 702 |
| CGS-12066A maleate | Agonist | Serotonin | 5-HT1B | 2.007 | 14.4 | 7.17 |
| Vanilloid | | | | | | |
| Dihydrocapsaicin | Agonist | Vanilloid Receptor | VR1 | 0.218 | 41.83 | 192 |

TABLE 6

Effect of Normal Neural Precursor Specific Agents on Medulloblastoma Derived Neurospheres

| Name | Action | Target | Selectivity | Medulloblastoma Neurosphere $EC_{50}$ (μM) |
|---|---|---|---|---|
| Controls | | | | |
| Cycloheximide | Inhibitor | Protein Synthesis | 60S Ribosome | 0.042 |
| Etoposide | Inhibitor | Topoisomerase | Topo II | 0.208 |
| Carboplatin | Intercalator | DNA | — | 0.196 |
| Selected Hits† | | | | |
| (±)Butaclamol | Antagonist | Dopamine Receptor | D2 > D1 | 0.751 |
| R(−) Propylnorapomorphine | Agonist | Dopamine Receptor | D2 | 0.199 |
| Apomorphine | Agonist | Dopamine Receptor | — | 0.168 |
| cis-(Z) Flupenthixol | Antagonist | Dopamine Receptor | — | 0.187 |
| Hexahydro-sila-difenidol | Antagonist | Acetylcholine Receptor | M3 > M1 > M2 | 1.125 |
| Ifenprodil tartrate | Antagonist | NMDA Receptor | Polyamine site | 0.451 |
| Carbetapentane citrate | Agonist | Opioid Receptor | sigma 1 | 2.083 |

TABLE 6-continued

Effect of Normal Neural Precursor Specific Agents on Medulloblastoma Derived Neurospheres

| Name | Action | Target | Selectivity | Medulloblastoma Neurosphere $EC_{50}$ (μM) |
|---|---|---|---|---|
| Fenretinide | Agonist | Retinoic Acid Receptor | — | 0.204 |
| WHI-P131 | Antagonist | JAK3 | — | 1.525 |
| SB 202190 | Antagonist | p38 MAPK | — | 3.006 |
| PAPP | Agonist | Serotonin Receptor | 5-HT1A | 0.169 |
| Dihydrocapsaicin | Agonist | Vanilloid Receptor | VR1 | 0.020 |

TABLE 7

Standard incidence ratios (SIR) of brain tumors in cohorts previously diagnosed with a variety of mental disorders (only studies published after 2000 were used).

| Study | Year | Disease | "Reported SIR" (95% CI) | "Revised SIR" (95% CI)[†] |
|---|---|---|---|---|
| Lichtermann et al.[11] | 2001 | Schizophrenia | 0.88 (0.62-1.20) | 0.88 (0.62-1.20) |
| Dalton et al.[16] | 2002 | Bipolar psychosis | 0.82 (0.53-1.20) | 0.64 (0.31-1.17)[†] |
| Dalton et al.[16] | 2002 | Unipolar psychosis | 1.19 (0.99-1.43) | 0.99 (0.70-1.34)[†] |
| Dalton et al.[16] | 2002 | Reactive Depression | 1.20 (0.92-1.55) | 0.73 (0.42-1.18)[†] |
| Dalton et al.[16] | 2002 | Dysthymia | 1.34 (1.05-1.68) | 0.82 (0.52-1.23)[†] |
| Lalonde et al.[10] | 2003 | Parkinson's | 0.20 (0.17-0.23) | 0.20 (0.17-0.23) |
| Carney et al.[18] | 2004 | Any mental (Male) | 2.09 (1.22-3.59) | — |
| Carney et al.[18] | 2004 | Any mental (Female) | 2.12 (1.40-3.21) | — |
| Goldacre et al.[13] | 2005 | Schizophrenia | 0.74 (0.29-1.53) | 0.74 (0.29-1.53) |
| Olsen et al.[17] | 2005 | Parkinson's | 1.32 (0.90-1.90) | 0.85 (0.31-2.34)[†] |
| Grinshpoon et al.[15] | 2005 | Schizophrenia (Male) | 0.56 (0.32-0.81) | 0.56 (0.32-0.81) |
| Grinshpoon et al.[15] | 2005 | Schizophrenia (Female) | 0.94 (0.62-1.27) | 0.94 (0.62-1.27) |
| Barak et al.[14] | 2005 | Schizophrenia | 0.20 (0.00-1.09) | 0.20 (0.00-1.09) |
| Dalton et al.[12] | 2005 | Schizophrenia (Male) | 0.74 (0.42-1.20) | 0.74 (0.42-1.20) |
| Dalton et al.[12] | 2005 | Schizophrenia (Female) | 0.78 (0.44-1.26) | 0.78 (0.44-1.26) |
| Diamandis | 2007 | Combined | 1.15[€] (1.01-1.30)* | 0.80[€,₴] (0.67-0.95)** |

[†]Qualifying brain cancer cases have been modified as noted by authors to only include cases more than 2 years after mental disorder diagnosis.

[€]Excludes data from Lalonde et al (2003). Although supportive, the large sample size in this study would significantly skew the results of the analysis.

[₴]Excludes data from Carney et al (2004) as authors did not reanalyze their data following the observed temporal discrepancy in their brain tumor SIR.

*p = 0.04;
**p = 0.01

[10]Lalonde, F. M. & Myslobodsky, M. Breast 12, 280-282 (2003).
[11]Lichtermann, D., Arch. Gen. Psychiatry 58, 573-578 (2001).
[12]Dalton, S. O., et al, Schizophr. Res. 75, 315-324 (2005).
[13]Goldacre, M. J., et al Br. J. Psychiatry 187, 334-338 (2005).
[14]Barak, Y., et al., Cancer 104, 2817-2821 (2005).
[15]Grinshpoon, A. et al. 73, 333-341 (2005).
[16]Dalton, S. O., et al. Am. J. Epidemiol. 155, 1088-1095 (2002).
[17]Olsen, J. H. et al. 92, 201-205 (2005).
[18]Carney, C. P., et al Psychosom. Med. 66, 735-743 (2004).

TABLE 8

Assessment of the potency and selectivity of a subset of the identified bioactive agents

| Name | Action | Target | Selectivity | Neurosphere $EC_{50}$ (μM) | Astrocyte $EC_{50}$ (μM) | Neurosphere Selectivity |
|---|---|---|---|---|---|---|
| Controls | | | | | | |
| Cycloheximide (1) | Inhibitor | Protein Synthesis | 60S Ribosome | 0.142 | 0.071 | 0.50 |
| Etoposide (2) | Inhibitor | Topoisomerase | Topo II | 0.340 | 0.433 | 1.28 |
| Carboplatin (3) | Intercalator | DNA | — | 0.489 | 2.453 | 5.08 |
| Sobuzaxane (19) | Inhibitor | Topoisomerase | Topo II | 10.19 | n.t. | n/a |
| Mevastatin (20) | Inhibitor | n/a | Ras, Rho | 0.142 | n.t. | n/a |
| Taxol (21) | Inhibitor | Tubulin | — | 0.010 | n.t. | n/a |
| Vinblastine (22) | Inhibitor | Tubulin | — | 0.028 | n.t. | n/a |
| Vincristine (23) | Inhibitor | Tubulin | — | >0.001 | n.t. | n/a |
| Adrenergic | | | | | | |
| R(−)-Denopamine (24) | Agonist | Adrenoceptor | Beta 1 | 39.2 | n.t. | n/a |
| Rauwolscine (25) | Antagonist | Adrenoceptor | Alpha 2 | 66.37 | n.d. | >1.43 |

TABLE 8-continued

Assessment of the potency and selectivity of a subset of the identified bioactive agents

| Name | Action | Target | Selectivity | Neurosphere $EC_{50}$ (µM) | Astrocyte $EC_{50}$ (µM) | Neurosphere Selectivity |
|---|---|---|---|---|---|---|
| Dopamine | | | | | | |
| Perphenazine (26) | Antagonist | Dopamine Receptor | D2 | 23.12 | n.d. | >4 |
| (±)-Butaclamol (4) | Antagonist | Dopamine | D2 > D1 | 0.785 | 12.34 | 15.7 |
| R(−)-Propylnorapomorphine (5) | Agonist | Dopamine | D2 | 0.3512 | 8.23 | 23.4 |
| R(−)-Apomorphine (6) | Agonist | Dopamine | — | 0.3499 | 10.19 | 29.1 |
| cis-(Z)-Flupenthixol (7) | Antagonist | Dopamine Receptor | — | 0.1993 | 1.182 | 5.93 |
| (+)-Bromocripline (18) | Agonist | Dopamine Receptor | D2 | 1.187 | n.t. | n/a |
| Cannaboid | | | | | | |
| Indomethacin (27) | Agonist | Cannabinoid receptor | CB2 | n.d. | n.t. | n/a |
| Ion Channels | | | | | | |
| Bepridil (28) | Blocker | Ca2+ Channel | — | 2.70 | 4.724 | 1.75 |
| Dequalinium (29) | Blocker | K+ channels | Apamin-sensitive | 1.474 | 1.418 | 0.962 |
| MAO | | | | | | |
| Quinacrine (30) | Inhibitor | MAO-A/B | — | 0.936 | n.t. | n/a |
| Muscarinic | | | | | | |
| p-F-HHSID (8) | Antagonist | Acetylcholine Receptor | M3 > M1 > M2 | 0.441 | 5.815 | 13.2 |
| Methoctramine (31) | Antagonist | Acetylcholine Receptor | M2 | 1.053 | 0.0845 | 0.802 |
| NMDA | | | | | | |
| Ifenprodil (9) | Blocker | NMDA | Polyamine site | 0.616 | 11.06 | 17.9 |
| Pentamidine (32) | Antagonist | NMDA Receptor | — | 0.822 | 1.995 | 2.43 |
| Nitric Oxide | | | | | | |
| Diphenyleneiodonium (33) | Inhibitor | Nitric Oxide Synthase | eNOS | 0.011 | 0.0209 | 1.88 |
| 7-Nitroindazole (34) | Inhibitor | Nitric Oxide Synthase | nNOS | 76.3 | 282.6 | 3.71 |
| Opioid | | | | | | |
| Metaphit (35) | Antagonist | Opioid | sigma | 10.04 | 3.624 | 0.361 |
| Carbetapentane (10) | Ligand | Opioid | sigma 1 | 0.756 | 28.16 | 37.3 |
| Phosphorylation | | | | | | |
| Chelerythrine (36) | Inhibitor | PKC | — | 0.396 | 1.531 | 3.87 |
| Fenretinide (11) | Vitamin A acid analog | RAR | — | 0.334 | 2.399 | 7.18 |
| WHI-P131 (12) | Inhibitor | JAK3 | — | 2.346 | — | >10 |
| SB 202190 (13) | Inhibitor | p38 MAPK | — | 8.063 | 64.8 | 8.04 |
| Tyrphoslin AG 34 (37) | inhibitor | Tyrosine Kinase | — | 9.917 | n.t. | n/a |
| Serotonin | | | | | | |
| Methiothepin (38) | Antagonist | Serotonin | 5-HT1E/F, 5-HT6 | 2.663 | 3.698 | 1.39 |
| Metergoline (39) | Antagonist | Serotonin | 5-HT2/5-HT1D | 1.624 | 3.285 | 2.02 |
| PAPP (14) | Agonist | Serotonin | 5-HT1A | 0.031 | 21.82 | 702 |
| CGS-12066A (40) | Agonist | Serotonin | 5-HT1B | 2.007 | 14.4 | 7.17 |
| Vanilloid | | | | | | |
| Dihydrocapsaicin (15) | Agonist | Vanilloid Receptor | VR1 | 0.218 | 41.83 | 192 |
| Other | | | | | | |
| 5-Bromo-2'-deoxyuridine (41) | Inhibitor | DNA | — | 2.045 | n.t. | n/a |
| 7,7-Dimethyl-(5Z,8Z)-eicosadienoic acid (42) | Inhibitor | Phospholipase $A_2$/Lipoxygenase | — | 5.170 | n.t. | n/a | n.d. = not determined at highest tested dose (30-95 µM)

n.t. = not tested

TABLE 9

Normal and cancerous human neural precursor cells show sensitivity to a myriad of neurotransmission modulators

| Name | Action | Target | Selectivity | hFetal precursors $EC_{50}$ (μM)[¶] | hGBM1 precursors $EC_{50}$ (μM)[⁑] | hGBM2 precursors $EC_{50}$ (μM)[§] |
|---|---|---|---|---|---|---|
| Controls | | | | | | |
| Etoposide | Inhibitor | Topoisomerase | Topo II | 0.16 | 0.62 | 0.27 |
| Carboplatin | Intercalator | DNA | — | 0.43 | 2.04 | 3.30 |
| Selected Hits[†] | | | | | | |
| Apomorphine | Agonist | Dopamine Receptor | — | 5.26 | 14.58 | 0.31 |
| p-F-HHSID | Antagonist | Acetylcholine Receptor | M3 > M1 > M2 | 10.58 | 12.63 | 1.23 |
| Ifenprodil | Antagonist | NMDA Receptor | Polyamine site | 0.42 | 1.99 | 0.206 |
| Carbetapentane | Agonist | Opioid Receptor | sigma 1 | 6.12 | 5.44 | 1.73 |
| PAPP | Agonist | Serotonin Receptor | 5-HT1A | 0.22 | 1.87 | 0.31 |
| Dihydrocapsaicin | Agonist | Vanilloid Receptor | VR1 | 3.28 | 88.63 | 21.46 |

[†]Only a selected array of the identified mouse neural precursor selective agents were tested in human cells. All agents tested are displayed in this table.

[¶]Values against neural precursors derived from human fetal CNS tissue.

[⁑]Pathological diagnosis of hGBM1 was WHO grade IV GMB

[§]Pathological diagnosis of hGBM2 was WHO grade IV GBM (giant cell variant).

TABLE 10

| Product Name | Z score | p value | Activity | Class | Action | Selectivity | Likelihood score | Cluster ID |
|---|---|---|---|---|---|---|---|---|
| U-62066 | −0.303 | 3.8109E−01 | no | Opioid | Agonist | kappa | 1.9970 | 32 |
| (±) trans-U-50488 methanesulfonate | −2.833 | 2.3049E−03 | yes | Opioid | Agonist | kappa | 7.8149 | 32 |
| (−)-cis-(1S,2R)-U-50488 tartrate | 0.171 | 4.3208E−01 | no | Neurotransmission | Ligand | Sigma receptor | 5.0720 | 32 |
| (−)-trans-(1S,2S)-U-50488 hydrochloride | −0.297 | 3.8321E−01 | no | Opioid | Agonist | kappa | 7.5748 | 32 |
| (+)-trans-(1R,2R)-U-50488 hydrochloride | −0.473 | 3.1802E−01 | no | Opioid | Agonist | kappa | 7.5748 | 32 |
| BRL 52537 hydrochloride | −2.761 | 2.2849E−03 | yes | Neurotransmission | Agonist | kappa/mu opioid | 8.7509 | 32 |
| GR-89696 fumarate | −0.779 | 2.1806E−01 | no | Opioid | Ligand | kappa | 0.0475 | 32 |
| AC 915 oxalate | −0.890 | 1.8665E−01 | no | Opioid | Ligand | signal | 3.3295 | 32 |
| Fluphenazine dihydrochloride | −10.197 | 1.0242E−24 | yes | Dopamine | Antagonist | D1/D2 | 20.6718 | 130 |
| Trifluoperazine dihydrochloride | −9.305 | 6.6778E−21 | yes | Dopamine | Antagonist | D1/D2 | 17.0927 | 130 |
| Triflupromazine hydrochloride | −1.820 | 3.4449E−02 | yes | Dopamine | Antagonist | DRD2 | 12.3307 | 130 |
| Perphenazine | −11.065 | 9.3020E−29 | yes | Dopamine | Antagonist | DRD2 | 18.2918 | 130 |
| Prochlorperazine dimaleate | −0.860 | 1.9485E−01 | no | Dopamine | Antagonist | DRD2 | 11.6765 | 130 |
| Propionylpromazine hydrochloride | −1.584 | 5.6571E−02 | no | Dopamine | Antagonist | DRD2 | 6.2928 | 130 |
| cis-(Z)-Flupenthixol dihydrochloride | −8.822 | 5.5976E−19 | yes | Dopamine | Antagonist | DRD1/DRD2/A2a/ADRA1A | 19.2865 | 130 |
| Pheniramine maleate | −0.206 | 4.1831E−01 | no | Histamine | Antagonist | HRH1 | 1.4913 | 109 |
| (±)-Brompheniramine maleate | −3.530 | 2.0756E−04 | yes | Histamine | Antagonist | HRH1 | 3.9173 | 109 |
| (+)-Chlorpheniramine maleate | −1.272 | 1.0172E−01 | no | Histamine | Antagonist | HRH1 | 3.9173 | 109 |
| (+)-Brompheniramine maleate | −3.976 | 3.5087E−05 | yes | Histamine | Antagonist | HRH1 | 3.9173 | 109 |
| (±)-Chlorpheniramine maleate | −2.116 | 1.7156E−02 | yes | Histamine | Antagonist | HRH1 | 3.9173 | 109 |
| Disopyramide | −4.179 | 1.4650E−05 | yes | Na+ Channel | Blocker | | 6.0562 | 109 |
| Disopyramide phosphate | −0.072 | 4.7135E−01 | no | K+ Channel | Modulator | | 5.7949 | 109 |
| CGS-21680 hydrochloride | −1.225 | 1.1027E−01 | no | Adenosine | Agonist | A2a | 4.7849 | 132 |
| 5'-N-Ethylcarboxamidoadenosine | −2.587 | 4.8437E−03 | yes | Adenosine | Agonist | A1/A2 | 1.5341 | 132 |
| HE-NECA | −2.504 | 6.1439E−03 | yes | Adenosine | Agonist | A2 | 12.7320 | 132 |
| 5'-N-Methyl carboxamidoadenosine | −2.582 | 4.9052E−03 | yes | Adenosine | Agonist | A2 > A1 | −0.1474 | 132 |
| 2-Phenylaminoadenosine | 0.573 | 2.8340E−01 | no | Adenosine | Agonist | A2 > A1 | 1.7469 | 132 |
| N6-Cyclohexyladenosine | −2.883 | 1.9695E−03 | yes | Adenosine | Agonist | A1 | −2.8521 | 132 |
| R(−)-2,10,11-Trihydroxyaporphine | −3.309 | 4.6827E−04 | yes | Dopamine | Agonist | DRD2 | 29.2738 | 84 |
| R(−)-2,10,11-Trihydroxy-N-propylnoraporphine | −2.744 | 3.0324E−03 | yes | Dopamine | Agonist | DRD2 | 30.9879 | 84 |
| Apomorphine hydrochloride hemihydrate | −11.274 | 8.8620E−30 | yes | Dopamine | Agonist | | 29.7434 | 84 |
| R(−)-N-Allylnorapomorphine hydrobromide | −7.839 | 2.2697E−15 | yes | Dopamine | Agonist | | 30.6967 | 84 |
| R(−)-Propylnorapomorphine hydrochloride | −8.274 | 6.4584E−17 | yes | Dopamine | Agonist | | 31.4575 | 84 |
| R(−)-Apocodeine hydrochloride | −9.865 | 2.9486E−23 | yes | Dopamine | Agonist | | 28.9096 | 84 |
| Metoclopramide hydrochloride | −1.992 | 2.3116E−02 | yes | Dopamine | Antagonist | DRD2 | 7.2623 | 83 |
| Tiapride hydrochloride | 0.689 | 2.4543E−01 | no | Dopamine | Antagonist | D2/D3 | 4.0505 | 83 |
| SDZ-205,557 hydrochloride | −2.681 | 3.6740E−03 | yes | Serotonin | Antagonist | 5-HT4 | 10.9325 | 83 |
| Procainamide hydrochloride | 0.654 | 2.5671E−01 | no | Na+ Channel | Antagonist | | 3.7651 | 83 |
| N-Acetylprocainamide hydrochloride | −4.557 | 2.5891E−06 | yes | Na+ Channel | Blocker | | 6.2381 | 83 |
| N-(2-[4-(4-Chlorophenyl)piperazin-1-yl]ethyl)-3-methoxybenzamide | 0.383 | 3.5092E−01 | no | Dopamine | Agonist | D4 | 6.0821 | 83 |
| Naloxone benzoylhydrazone | 1.915 | 2.7727E−01 | no | Opioid | Agonist | kappa | 2.0832 | 59 |
| Naloxone hydrochloride | −10.137 | 1.8971E−24 | yes | Opioid | Antagonist | | 6.8882 | 59 |
| Naloxonazine dihydrochloride | −0.606 | 2.7223E−01 | no | Opioid | Antagonist | | 5.4107 | 59 |
| Naltrexone hydrochloride | 0.389 | 3.4860E−01 | no | Opioid | Antagonist | | 3.5271 | 59 |
| Nalbuphine hydrochloride | 0.070 | 4.7197E−01 | no | Opioid | Antagonist | | 0.2990 | 59 |
| (−)-3-Methoxynaltrexone hydrochloride | 0.596 | 2.7547E−01 | no | Opioid | Antagonist | mu1 | 4.8978 | 59 |
| Cephapirin sodium | 0.622 | 2.6699E−01 | no | Antibiotic | | Cell wall synthesis | 1.8833 | 54 |
| Cephalothin sodium | 2.264 | 1.1788E−02 | no | Antibiotic | | Cell wall synthesis | 4.6902 | 54 |
| Cephalosporin C zinc salt | −3.309 | 4.6797E−04 | yes | Antibiotic | | Cell wall synthesis | 12.0888 | 54 |

TABLE 10-continued

| Product Name | Z score | p value | Activity | Class | Action | Selectivity | Likelihood score | Cluster ID |
|---|---|---|---|---|---|---|---|---|
| Cefotaxime sodium | −1.096 | 1.3654E−01 | no | Antibiotic | | Cell wall synthesis | 3.9918 | 54 |
| Cefazolin sodium | −2.580 | 4.9470E−03 | yes | Antibiotic | | Cell wall synthesis | 19.8926 | 54 |
| Ceftriaxone sodium | 2.230 | 1.2886E−02 | no | Antibiotic | | Cell wall synthesis | 1.1330 | 54 |
| R(+)-UH-301 hydrochloride | −2.517 | 5.9202E−03 | yes | Serotonin | Agonist | 5-HT1A | 16.3801 | 127 |
| S(−)-UH-301 hydrochloride | −2.706 | 3.4078E−03 | yes | Serotonin | Antagonist | 5-HT1A | 16.3801 | 127 |
| R-(+)-8-Hydroxy-DPAT hydrobromide | −0.692 | 2.4460E−01 | no | Serotonin | Agonist | 5-HT1A | 9.7698 | 127 |
| (±)-8-Hydroxy-DPAT hydrobromide | 0.656 | 2.5587E−01 | no | Serotonin | Agonist | 5-HT1A | 9.7698 | 127 |
| (±)-PPHT hydrochloride | −1.915 | 2.7715E−02 | yes | Dopamine | Agonist | DRD2 | 9.6773 | 127 |
| S(+)-Raclopride L-tartrate | 1.901 | 2.8633E−02 | no | Dopamine | Antagonist | DRD2 | 4.1295 | 126 |
| S(−)IBZM | −0.117 | 4.5360E−01 | no | Dopamine | Ligand | DRD2 | 5.4292 | 126 |
| (−)-Sulpiride | −2.647 | 4.0550E−03 | yes | Dopamine | Antagonist | DRD2 | 7.5872 | 126 |
| (±)-Sulpiride | −0.284 | 3.8816E−01 | no | Dopamine | Antagonist | DRD2 | 7.5872 | 126 |
| S-(−)-Eticlopride hydrochloride | −5.158 | 1.2497E−07 | yes | Dopamine | Antagonist | DRD2 | 14.6402 | 126 |
| 3-Tropanyl-3,5-dichlorobenzoate | −9.272 | 9.0927E−21 | yes | Serotonin | Antagonist | 5-HT3 | 10.0230 | 29 |
| 4-Chloro-3-alpha-(diphenylmethoxy)tropane hydrochloride | −9.672 | 1.9822E−22 | yes | Dopamine | Blocker | Reuptake | 13.5550 | 29 |
| DL-Homatropine hydrobromide | 0.744 | 2.2844E−01 | no | Cholinergic | Antagonist | Muscarinic | 3.3069 | 29 |
| Benztropine mesylate | −3.749 | 8.8704E−05 | yes | Cholinergic | Antagonist | Muscarinic | 12.5609 | 29 |
| Aminobenztropine | −1.455 | 7.2819E−02 | no | Cholinergic | Ligand | Muscarinic | 9.8555 | 29 |
| SKF-525A hydrochloride | −1.928 | 2.6951E−02 | yes | Multi-Drug Resistance | Inhibitor | Microsomal oxidation | 3.1837 | 20 |
| PRE-084 | 1.311 | 9.4859E−02 | no | Opioid | Agonist | sigma1 | 4.7579 | 20 |
| Carbetapentane citrate | −8.021 | 5.2461E−16 | yes | Opioid | Ligand | sigma1 | 12.5359 | 20 |
| Procaine hydrochloride | 0.550 | 2.9111E−01 | yes | Na+ Channel | Blocker | | 1.0800 | 20 |
| (±)-three-1-Phenyl-2-decanoylamino-3-morpholino-1-propanol hydrochloride | −1.109 | 1.3382E−01 | no | Sphingolipid | Inhibitor | Glucosylceramide synthase | 1.4587 | 20 |
| GBR-12909 dihydrochloride | −10.899 | 5.8437E−28 | yes | Dopamine | Inhibitor | Reuptake | 17.7542 | 119 |
| GBR-12935 dihydrochloride | −11.274 | 8.8620E−30 | yes | Dopamine | Inhibitor | Reuptake | 17.4032 | 119 |
| Diphenhydramine hydrochloride | 0.845 | 1.9907E−01 | no | Histamine | Antagonist | HRH1 | 6.6928 | 119 |
| Orphenadrine hydrochloride | 0.455 | 3.2463E−01 | no | Cholinergic | Antagonist | Muscarinic | 4.7871 | 119 |
| Doxepin hydrochloride | −1.012 | 1.5566E−01 | no | Adrenoceptor | Inhibitor | Uptake | 0.7541 | 67 |
| Amitriptyline hydrochloride | 0.707 | 2.3990E−01 | no | Adrenoceptor | Inhibitor | Uptake | 2.9998 | 67 |
| Chlorprothixene hydrochloride | −5.008 | 2.7566E−07 | yes | Dopamine | Antagonist | DRD2 | 12.4473 | 67 |
| Thiothixene hydrochloride | −1.899 | 2.8770E−02 | yes | Dopamine | Antagonist | D1/D2 | 12.4318 | 67 |
| (−)-Bicuculline methbromide, 1(S), 9(R) | −1.842 | 3.2731E−02 | yes | GABA | Antagonist | GABA-A | 3.4384 | 58 |
| (+)-Bicuculline | −0.199 | 4.2119E−01 | no | GABA | Antagonist | GABA-A | 15.5316 | 58 |
| (+)-Hydrastine | −0.836 | 2.0152E−01 | no | GABA | Antagonist | GABA-A | 17.7536 | 58 |
| Noscapine hydrochloride | −2.455 | 7.0361E−03 | yes | Opioid | Ligand | | 21.4022 | 58 |
| Ritodrine hydrochloride | −2.332 | 9.8562E−03 | no | Adrenoceptor | Agonist | beta2 | 1.5332 | 53 |
| R(−)-Denopamine | −4.486 | 3.6321E−06 | yes | Adrenoceptor | Agonist | beta1 | 2.2356 | 53 |
| DL-alpha-Methyl-p-tyrosine | −3.908 | 4.6497E−05 | yes | Neurotransmission | Inhibitor | Tyrosine hydroxylase | −0.1777 | 53 |
| alpha-Methyl-DL-tyrosine methyl ester hydrochloride | −0.370 | 3.5559E−01 | no | Neurotransmission | Inhibitor | Tyrosine hydroxylase | 0.5909 | 53 |
| LY-53,857 maleate | −0.338 | 3.6761E−01 | no | Serotonin | Antagonist | 5-HT2/5-HT1C | 0.3126 | 51 |
| Mesulergine hydrochloride | −2.160 | 1.5386E−02 | no | Dopamine | Agonist | DRD2 | 4.5314 | 51 |
| Metergoline | −4.342 | 7.0622E−06 | yes | Serotonin | Antagonist | 5-HT2/5-HT1D | 14.2794 | 51 |
| Pergolide methanesulfonate | −2.657 | 3.9457E−03 | yes | Dopamine | Agonist | D2/D1 | 1.4244 | 51 |
| Retinoic acid | −0.866 | 1.9333E−01 | no | Apoptosis | Activator | | 1.3311 | 22 |
| 13-cis-retinoic acid | −1.469 | 7.0905E−02 | no | Transcription | Regulator | RAR-alpha, beta | 1.3311 | 22 |
| Retinoic acid p-hydroxyanilide | −6.013 | 9.0821E−10 | yes | Cell Cycle | Inhibitor | | 9.8493 | 22 |
| Astaxanthin | 1.571 | 5.8038E−02 | no | Cell Stress | Inhibitor | Antioxidant | 1.2987 | 22 |
| Promethazine hydrochloride | 0.475 | 3.1754E−01 | no | Histamine | Antagonist | HRH1 | 3.5263 | 16 |
| Promazine hydrochloride | −0.888 | 1.8723E−01 | no | Dopamine | Antagonist | DRD2 | 6.8657 | 16 |
| 10-(alpha-Diethylaminopropionyl)-phenothiazine | −1.545 | 6.1222E−02 | no | Biochemistry | Inhibitor | Butyrylcholinesterase | 4.2861 | 16 |

TABLE 10-continued

| Product Name | Z score | p value | Activity | Class | Action | Selectivity | Likelihood score | Cluster ID |
|---|---|---|---|---|---|---|---|---|
| Thioridazine hydrochloride | 0.236 | 4.0687E-01 | no | Dopamine | Antagonist | D1/D2 | 7.4168 | 16 |
| Clomipramine hydrochloride | -0.844 | 1.9938E-01 | no | Serotonin | Inhibitor | Reuptake | 0.4609 | 108 |
| Chlorpromazine hydrochloride | 0.751 | 2.2645E-01 | no | Dopamine | Antagonist |  | 9.8883 | 108 |
| Clorgyline hydrochloride | 1.520 | 6.4194E-02 | no | Neurotransmission | Inhibitor | MAO-A | 0.3833 | 108 |
| NG-Hydroxy-L-arginine acetate | -10.958 | 3.0541E-28 | yes | Nitric Oxide | Metabolite | NOS | -0.6344 | 104 |
| L-2-aminoadipic acid | -2.334 | 9.8098E-03 | yes | Glutamate | Inhibitor | Glutamine synthetase | -1.4913 | 104 |
| alpha-Guanidinoglutaric acid | -9.041 | 7.7797E-20 | yes | Nitric Oxide | Inhibitor | NOS | 3.7998 | 104 |
| ML-9 | -9.322 | 5.7099E-21 | yes | Phosphorylation | Inhibitor | MLCK | 17.0244 | 78 |
| ML-7 | -11.274 | 8.8620E-30 | yes | Phosphorylation | Inhibitor | MLCK | 16.9036 | 78 |
| HA-100 | -0.689 | 2.4534E-01 | yes | Phosphorylation | Inhibitor | PKA/PKC/MLCK | 2.0402 | 78 |
| Decamethonium dibromide | -1.572 | 5.7997E-02 | no | Cholinergic | Agonist | Nicotinic | 1.3227 | 76 |
| Hexamethonium bromide | -0.820 | 2.0614E-01 | no | Cholinergic | Antagonist | Nicotinic | 0.8360 | 76 |
| Hexamethonium dichloride | -10.634 | 1.0320E-26 | yes | Cholinergic | Antagonist | Nicotinic | 0.4196 | 76 |
| NS 521 oxylate | -11.274 | 8.8620E-30 | yes | Glutamate | Modulator | Benzimidazolone | 2.9504 | 55 |
| Pimozide | -0.232 | 4.0814E-01 | no | Dopamine | Antagonist | DRD2 | 2.0490 | 55 |
| Domperidone | -1.525 | 6.3676E-02 | no | Dopamine | Antagonist | DRD2 | 2.2927 | 55 |
| Purvalanol A | -11.234 | 1.3858E-29 | yes | Phosphorylation | Inhibitor | CDK | 16.1452 | 50 |
| CGP-74514A hydrochloride | -9.117 | 3.8610E-20 | yes | Phosphorylation | Inhibitor | Cdk1 | 19.7353 | 50 |
| Typhostin.AG 1478 | 1.870 | 3.0751E-02 | no | Phosphorylation | Inhibitor | EGFR | 3.1243 | 50 |
| LY-310,762 hydrochloride | 0.228 | 4.0987E-01 | no | Serotonin | Antagonist | 5-HT2 | 1.7303 | 48 |
| Pirenperone | 0.051 | 4.7962E-01 | no | Serotonin | Antagonist | 5-HT1D | 3.6520 | 48 |
| Ketanserin tartrate | -3.325 | 4.4160E-04 | yes | Serotonin | Antagonist | 5-HT2 | 6.5571 | 48 |
| Methiothepin mesylate | 1.868 | 3.0896E-02 | no | Serotonin | Antagonist | 5-HT1E, 5-HT1F, 5-HT6 | 6.2477 | 33 |
| (±)-Octoclothepin maleate | 1.473 | 7.0371E-02 | no | Dopamine | Antagonist | DRD2 | 1.6480 | 33 |
| Methoxamine hydrochloride | -3.255 | 5.6606E-04 | yes | Adrenoceptor | Agonist | alpha1 | 4.8466 | 33 |
| Phenamil methanesulfonate | 1.485 | 6.8800E-02 | yes | Na+ Channel | Inhibitor | Amiloride sensitive | 3.3719 | 14 |
| Amiloride hydrochloride | -0.799 | 2.1207E-01 | no | Na+ Channel | Blocker | Epithelial | 2.6796 | 14 |
| 3,4-Dichlorobenzamil | -2.581 | 4.9275E-03 | yes | Ion Pump | Inhibitor | Na+/Ca2+ exchanger | 11.4518 | 14 |
| Methotrexate | -10.203 | 9.6328E-25 | yes | DNA Metabolism | Inhibitor |  | 31.7569 | 13 |
| (-)Amethopterin | -8.704 | 1.5969E-18 | yes | DNA Metabolism | Inhibitor |  | 31.7569 | 13 |
| Aminopterin | -9.783 | 6.6618E-23 | yes | Antibiotic | Inhibitor | Dihydrofolate reductase | 28.1012 | 13 |
| cis-(±)-8-OH-PBZI hydrobromide | -2.297 | 1.0800E-02 | no | Dopamine | Agonist | D3 | 1.3911 | 8 |
| (±)-7-Hydroxy-DPAT hydrobromide | -11.102 | 6.1185E-29 | yes | Dopamine | Agonist | D3 | 12.3042 | 8 |
| R-(+)-7-Hydroxy-DPAT hydrobromide | -2.590 | 4.7938E-03 | yes | Dopamine | Agonist | D3 | 12.3042 | 8 |
| 1-(m-Chlorophenyl)-biguanide hydrochloride | 1.795 | 3.6304E-02 | no | Serotonin | Agonist | 5-HT3 | 3.4618 | 136 |
| 1-Phenylbiguanide | -2.689 | 3.5800E-03 | yes | Serotonin | Agonist | 5-HT3 | 2.6508 | 136 |
| U-99194A meleate | 1.255 | 1.0468E-01 | no | Dopamine | Antagonist | D3 | 2.9061 | 133 |
| YS-035 hydrochloride | 0.043 | 4.8281E-01 | no | Ca2+ Channel | Blocker | L-type | 3.7365 | 133 |
| Ifenprodil tartrate | -8.904 | 2.6930E-19 | yes | Glutamate | Antagonist | Polyamine site NMDA | 11.1544 | 128 |
| Ro 25-6981 hydrochloride | -10.524 | 3.3394E-26 | yes | Glutamate | Antagonist | NMDA-NR2B | 12.4160 | 128 |
| Trazodone hydrochloride | -2.644 | 4.0994E-03 | yes | Serotonin | Inhibitor | Reuptake | 17.8168 | 122 |
| BRL 15572 | 0.312 | 3.7764E-01 | no | Serotonin | Antagonist | 5-HT1D | 1.9532 | 122 |
| 2',3'-dideoxycytidine | -1.367 | 8.5880E-02 | no | Immune System | Inhibitor | Reverse Transcriptase | 1.8676 | 115 |
| Cytosine-1-beta-D-arabinofuranoside hydrochloride | -11.274 | 8.8620E-30 | yes | DNA Metabolism | Inhibitor |  | 4.9565 | 115 |
| Efaroxan hydrochloride | -2.338 | 9.6932E-03 | yes | Imidazoline | Antagonist | I1 | 2.0987 | 113 |
| Methoctramine tetrahydrochloride | -7.012 | 1.1764E-12 | yes | Cholinergic | Antagonist | M2 | 7.2873 | 113 |
| 3-Amino-1-propanesulfonic acid sodium | -6.691 | 1.1076E-11 | yes | GABA | Agonist | GABA-A | -2.1148 | 111 |
| 3-Aminopropylphosphonic acid | -2.331 | 9.8664E-03 | yes | GABA | Agonist | GABA-B | -2.8464 | 111 |
| Indomethacin morpholinylamide | -3.398 | 3.3995E-04 | yes | Cannabinoid | Ligand | CB2 | 6.9161 | 106 |
| Indomethacin | -0.356 | 3.6081E-01 | no | Prostaglandin | Inhibitor | COX | 0.4544 | 106 |
| 2,3-Dimethoxy-1,4-naphthoquinone | -10.398 | 1.2595E-25 | yes | Cell Stress | Modulator |  | 3.2447 | 103 |

TABLE 10-continued

| Product Name | Z score | p value | Activity | Class | Action | Selectivity | Likelihood score | Cluster ID |
|---|---|---|---|---|---|---|---|---|
| NSC 95397 | −1.098 | 1.3600E−01 | no | Phosphorylation | Inhibitor | Cdc25 | 1.5944 | 103 |
| Cefaclor | −3.009 | 1.3115E−03 | yes | Antibiotic | | Cell wall synthesis | 14.9709 | 100 |
| Cephalexin hydrate | −3.966 | 3.6478E−05 | yes | Antibiotic | | Cell wall synthesis | 13.0448 | 100 |
| Ethylene glycol-bis(2-aminoethylether)-N,N,N′,N′-tetraacetic acid | 1.507 | 6.5918E−02 | no | Biochemistry | Inhibitor | Carboxypeptidase B | 2.1263 | 91 |
| Diethylenetriaminepentaacetic acid | −0.458 | 3.2363E−01 | no | Biochemistry | Inhibitor | Zn2+-dependent protease | 1.7783 | 91 |
| 7,7-Dimethyl-(5Z,8Z)-eicosadienoic acid | −3.045 | 1.1618E−03 | yes | Lipid | Inhibitor | PLA2/Lipoxygenase | 4.7938 | 86 |
| Oleic acid | −0.345 | 3.6507E−01 | no | Phosphorylation | Activator | PKC | 0.1829 | 86 |
| Daidzein | −2.931 | 1.6903E−03 | yes | Cell Cycle | Inhibitor | Aldehyde dehydrogenase | 7.0109 | 80 |
| Genistein | −0.469 | 3.1957E−01 | no | Phosphorylation | Inhibitor | Tyrosine kinase | 1.5385 | 80 |
| 3-Methoxy-morphanin hydrochloride | −7.714 | 6.0807E−15 | yes | Glutamate | Antagonist | NMDA | 8.7457 | 79 |
| Dextromethorphan hydrobromide monohydrate | −0.793 | 2.1384E−01 | no | Glutamate | Antagonist | NMDA | 2.8232 | 79 |
| Dequalinium analog, C-14 linker | −11.274 | 8.8620E−30 | yes | Phosphorylation | Inhibitor | PKC-alpha | 23.1039 | 74 |
| Dequalinium dichloride | −9.540 | 7.1408E−21 | yes | K+ Channel | Blocker | | 22.8573 | 74 |
| Chloroquine diphosphate | 0.499 | 3.0880E−01 | no | DNA | Intercalator | DNA | 5.2087 | 72 |
| Quinacrine dihydrochloride | −9.712 | 1.3360E−22 | yes | Neurotransmission | Inhibitor | MAO | 16.3953 | 72 |
| OXA-22 iodide | −3.402 | 3.3444E−04 | yes | Cholinergic | Agonist | Muscarinic | 3.6333 | 70 |
| (+)-cis-Dioxolane iodide | −1.666 | 4.7849E−02 | yes | Cholinergic | Agonist | Muscarinic | 3.6333 | 70 |
| (±)-Butaclamol hydrochloride | −5.934 | 1.4790E−09 | yes | Dopamine | Antagonist | D2 > D1 | 23.5780 | 68 |
| (−)-Butaclamol hydrochloride | −11.274 | 8.8620E−30 | yes | Dopamine | Antagonist | | 23.5780 | 68 |
| Sanguinarine chloride | −10.008 | 7.0621E−24 | yes | Ion Pump | Inhibitor | Na+/K+ ATPase | 29.6105 | 66 |
| Chelerythrine chloride | −10.671 | 6.9758E−27 | yes | Phosphorylation | Inhibitor | PKC | 29.3180 | 66 |
| Chlorambucil | 0.081 | 4.6781E−01 | no | DNA | Intercalator | | 2.6857 | 64 |
| Melphalan | −3.907 | 4.6645E−05 | yes | DNA Metabolism | Intercalator | GCC | 0.0225 | 64 |
| L-765,314 | −0.831 | 2.0305E−01 | no | Adenoceptor | Antagonist | alpha-1B | 0.7451 | 57 |
| Prazosin hydrochloride | −2.902 | 1.8551E−03 | yes | Adenoceptor | Antagonist | alpha1 | 14.2207 | 57 |
| L-745,870 hydrochloride | −11.274 | 8.8620E−30 | yes | Dopamine | Antagonist | D4 | 6.9747 | 44 |
| L-750,667 trihydrochloride | −1.184 | 1.1822E−01 | no | Dopamine | Antagonist | D4 | 6.9180 | 44 |
| N-Vanillylnonanamide | −9.029 | 8.6770E−20 | yes | Vanilloid | Ligand | | 9.1987 | 42 |
| Dihydrocapsaicin | −10.003 | 7.4015E−24 | yes | Vanilloid | Agonist | | 9.3231 | 42 |
| Acyclovir | −1.215 | 1.1227E−01 | no | Immune System | Inhibitor | Viral DNA synthesis | 1.5146 | 40 |
| Ganciclovir | −8.939 | 1.9604E−19 | yes | Cell Cycle | Inhibitor | G2-M checkpoint | 5.7853 | 40 |
| MDL 28170 | −1.139 | 1.2743E−01 | no | Cell Cycle | Inhibitor | Calpain I/II | 1.2360 | 38 |
| Z-L-Phe chloromethyl ketone | −2.901 | 1.8594E−03 | yes | Biochemistry | Inhibitor | Chymotrypsin A-gamma | 6.0322 | 38 |
| Nimesulide | −2.395 | 8.3067E−03 | yes | Prostaglandin | Inhibitor | COX-2 | 5.3913 | 36 |
| Niclosamide | −2.784 | 2.6841E−03 | yes | Antibiotic | | Protonophore | 5.6937 | 36 |
| Vincristine sulfate | −10.792 | 1.8712E−27 | yes | Cytoskeleton and ECM | Inhibitor | Tubulin | 54.7161 | 35 |
| Vinblastine sulfate salt | −9.396 | 2.8241E−21 | yes | Cytoskeleton and ECM | Inhibitor | Tubulin | 53.7145 | 35 |
| U-74389G maleate | −8.942 | 1.9194E−19 | yes | Cell Stress | | | 13.4525 | 31 |
| U-83836 dihydrochloride | 0.954 | 1.7004E−01 | no | Cell Stress | | | 3.3297 | 31 |
| Podophyllotoxin | −11.147 | 3.7067E−29 | yes | Cytoskeleton and ECM | Inhibitor | | 18.7107 | 15 |
| Etoposide | −11.102 | 6.1554E−29 | yes | Apoptosis | Inhibitor | Topo II | 32.8884 | 15 |
| GR 127935 hydrochloride | −1.081 | 1.3994E−01 | no | Serotonin | Antagonist | 5-HT1B/1D | 6.6535 | 11 |
| SB 224289 hydrochloride | −4.786 | 8.5192E−07 | yes | Serotonin | Antagonist | 5-HT1B | 22.2519 | 11 |
| MG 624 | −10.660 | 7.8645E−27 | yes | Cholinergic | Antagonist | Nicotinic | 6.1540 | 4 |
| N,N,N-trimethyl-1-(4-trans-stilbenoxy)-2-propylammonium | −11.127 | 4.6237E−29 | yes | Cholinergic | Antagonist | Nicotinic | 7.1135 | 4 |
| Arecoline hydrobromide | −0.111 | 4.5581E−01 | no | Cholinergic | Agonist | | 3.3496 | 2 |
| Arecaidine propargyl ester hydrobromide | −9.931 | 1.5191E−23 | yes | Cholinergic | Agonist | M2 | 5.4180 | 2 |
| GR 113808 | 0.992 | 1.6061E−01 | no | Serotonin | Antagonist | 5-HT4 | 5.3510 | 135 |
| DSP-4 hydrochloride | 1.518 | 6.4499E−02 | no | Adrenoceptor | Neurotoxin | | 0.6039 | 134 |
| Cephradine | 0.711 | 2.3849E−01 | no | Antibiotic | | Cell wall synthesis | 6.0389 | 131 |
| Cefsulodin sodium salt hydrate | −2.277 | 1.1404E−02 | yes | Antibiotic | | Cell wall synthesis | 0.2849 | 129 |

TABLE 10-continued

| Product Name | Z score | p value | Activity | Class | Action | Selectivity | Likelihood score | Cluster ID |
|---|---|---|---|---|---|---|---|---|
| (R,R)-cis-Diethyl tetrahydro-2,8-chrysenediol | −1.053 | 1.4619E−01 | no | Hormone | Antagonist | ER-beta | 0.7913 | 125 |
| Metaphit methanesulfonate | −4.967 | 3.3952E−07 | yes | Opioid | Antagonist | sigma | 13.5640 | 124 |
| Betaine hydrochloride | −2.668 | 3.8119E−03 | yes | Biochemistry | Metabolite | | −2.2762 | 123 |
| Pentamidine isethionate | −11.274 | 8.8620E−30 | yes | Glutamate | Antagonist | NMDA | 7.4941 | 121 |
| Iodoacetamide | −8.706 | 1.5709E−18 | yes | Biochemistry | Inhibitor | | 0.8463 | 120 |
| Piribedil maleate | −0.334 | 3.6902E−01 | no | Dopamine | Agonist | D3 | 0.4062 | 118 |
| Isoliquiritigenin | −2.817 | 2.2432E−03 | yes | Cyclic Nucleotides | Activator | Guanylyl cyclase | 0.2223 | 117 |
| SB 204070 hydrochloride | −5.886 | 1.9782E−09 | yes | Serotonin | Antagonist | 5-HT4 | 16.2381 | 116 |
| Dubinidine | −2.437 | 7.4034E−03 | yes | Anticonvulsant | | | 11.4546 | 114 |
| Tamoxifen citrate | −10.643 | 9.3778E−27 | yes | Phosphorylation | Inhibitor | PKC | 12.2426 | 112 |
| XK469 | −9.355 | 4.1753E−21 | yes | Apoptosis | Inhibitor | TopoII beta | 15.1840 | 110 |
| beta-Lapachone | −10.428 | 9.2210E−26 | yes | Apoptosis | Activator | | 8.9996 | 107 |
| m-Iodobenzylguanidine hemisulfate | −2.564 | 5.1721E−03 | yes | Apoptosis | Activator | | 6.9672 | 105 |
| L-687,384 hydrochloride | −9.156 | 2.7015E−20 | yes | Opioid | Agonist | sigma 1 | 9.5091 | 102 |
| Ropinirole hydrochloride | −0.255 | 3.9930E−01 | no | Dopamine | Agonist | DRD2 | 0.9738 | 101 |
| 1-(2-Chlorophenyl)-1-(4-chlorophenyl)-2,2-dichloroethane | −2.508 | 6.0751E−03 | yes | Hormone | Inhibitor | Corticosteroid | 6.0772 | 99 |
| Hydrocortisone | −3.049 | 1.1479E−03 | yes | Hormone | | Cortisol | −4.7854 | 98 |
| Bepridil hydrochloride | −2.655 | 3.9608E−03 | yes | Ca2+ Channel | Blocker | | 14.2861 | 97 |
| GYKI 52466 hydrochloride | −1.864 | 3.1193E−02 | no | Glutamate | Antagonist | AMPA/kainate | 1.4609 | 96 |
| Idarubicin | −11.274 | 8.8620E−30 | yes | DNA Metabolism | Inhibitor | | 17.7420 | 95 |
| PAPP | −10.728 | 3.7791E−27 | yes | Serotonin | Agonist | 5-HT1A | 9.3713 | 94 |
| Emetine dihydrochloride hydrate | −10.633 | 1.0516E−26 | yes | Apoptosis | Activator | | 22.1870 | 93 |
| 5-Fluorouracil | −7.749 | 4.6212E−15 | yes | Cell Cycle | Inhibitor | Thymidylate synthetase | 2.4326 | 92 |
| Ellipticine | −8.321 | 4.3538E−17 | yes | Cell Cycle | Inhibitor | CYP1A1/TopoII | 3.0215 | 90 |
| (S)-(+)-Camptothecin | −2.870 | 2.0519E−03 | yes | Phosphorylation | Inhibitor | GsK-3 | 13.0577 | 89 |
| SB 415286 | 1.707 | 4.3949E−02 | no | Intracellular Calcium | Antagonist | | 0.5698 | 88 |
| TMB-8 hydrochloride | −4.521 | 3.0805E−06 | yes | Nitric Oxide | Inhibitor | iNOS | 3.2504 | 87 |
| Guanidinoethyl disulfide dihydrobromide | −4.642 | 1.7211E−06 | yes | Na+ Channel | Blocker | | 13.7962 | 85 |
| Triamterene | −8.582 | 4.6481E−18 | yes | Intracellular Calcium | Inhibitor | Ca2+ATPase | 23.6956 | 82 |
| Calmidazolium chloride | −9.670 | 2.0264E−22 | yes | Apoptosis | Inhibitor | TopoI | 14.3223 | 81 |
| Brefeldin A from Penicillium brefeldianum | −11.274 | 8.8620E−30 | yes | Cytoskeleton and ECM | Inhibitor | Golgi apparatus | 14.2446 | 77 |
| Diphenyleneiodonium chloride | −10.068 | 3.8434E−24 | yes | Nitric Oxide | Inhibitor | eNOS | 7.7864 | 75 |
| 2-Chloro-2-deoxy-D-glucose | −2.364 | 7.7642E−05 | yes | Biochemistry | Analog | Glucose | 5.2008 | 73 |
| CGS-12066A maleate | −2.575 | 5.0073E−03 | yes | Serotonin | Agonist | 5-HT1B | 10.1700 | 71 |
| (±)-AMT hydrochloride | −2.366 | 2.5883E−27 | yes | Nitric Oxide | Inhibitor | iNOS | 16.7429 | 69 |
| Reserpine | −1.023 | 1.5310E−01 | no | Serotonin | Inhibitor | Uptake | 2.7281 | 65 |
| Moxisylyte hydrochloride | −1.018 | 1.5439E−01 | no | Adrenoceptor | Antagonist | alpha1 | 1.1851 | 63 |
| Chlorothiazide | −3.165 | 7.7549E−04 | yes | Biochemistry | Inhibitor | Carbonic anhydrase | 8.3425 | 62 |
| Amsacrine hydrochloride | −11.274 | 8.8620E−30 | yes | DNA Repair | Inhibitor | TopoII | 13.9612 | 61 |
| CNS-1102 | −3.782 | 7.7642E−05 | yes | Glutamate | Antagonist | NMDA | 12.3150 | 60 |
| Colchicine | −10.753 | 2.5883E−27 | yes | Cytoskeleton and ECM | Inhibitor | Tubulin | 16.7429 | 56 |
| BTCP hydrochloride | 0.836 | 2.0154E−01 | no | Dopamine | Blocker | Reuptake | 2.4581 | 52 |
| Benzamidine hydrochloride | 1.509 | 6.5593E−02 | no | Biochemistry | Inhibitor | Peptidase | 0.3080 | 49 |
| Zaprinast | −2.506 | 6.1062E−03 | yes | Cyclic Nucleotides | Inhibitor | PDE V | 11.2791 | 47 |
| Carboplatin | −6.204 | 2.7600E−10 | yes | DNA | Intercatator | | 3.9150 | 46 |
| 2-(alpha-Naphthoyl)ethyltrimethylammonium iodide | −6.762 | 6.7869E−12 | yes | Cholinergic | Inhibitor | Choline Acetyltransferase | 4.9215 | 45 |
| SKF 96365 | −4.497 | 3.4502E−06 | yes | Ca2+ Channel | Inhibitor | | 10.6091 | 43 |
| Ancitabine hydrochloride | −9.951 | 1.2427E−23 | yes | DNA Metabolism | Inhibitor | Purine synthesis | 10.7570 | 41 |
| Azathioprine | −7.913 | 1.2594E−15 | yes | P2 Receptor | Antagonist | | 8.9517 | 39 |
| 3′-Azido-3′-deoxythymidine | −5.023 | 2.5440E−07 | yes | Immune System | Inhibitor | Reverse transcriptase | 10.8585 | 37 |
| Mevastatin | −6.278 | 1.7126E−10 | yes | Antibiotic | Inhibitor | Ras, Rho | 17.6321 | 34 |

TABLE 10-continued

| Product Name | Z score | p value | Activity | Class | Action | Selectivity | Likelihood score | Cluster ID |
|---|---|---|---|---|---|---|---|---|
| Thapsigargin | −9.559 | 5.9618E−22 | yes | Intracellular Calcium | Releaser | | 22.8812 | 30 |
| Taxol | −11.274 | 8.8620E−30 | yes | Cytoskeleton and ECM | Inhibitor | Tubulin | 28.0486 | 28 |
| Oxymetazoline hydrochloride | −2.720 | 3.2662E−03 | yes | Adrenoceptor | Agonist | alpha2A | 2.7662 | 27 |
| Quinolinic acid | −2.419 | 7.7776E−03 | yes | Glutamate | Antagonist | NMDA | −1.2408 | 26 |
| Sobuzoxane | −9.600 | 3.9970E−22 | yes | Gene Regulation | Inhibitor | Topo II | 14.1486 | 25 |
| TCPOBOP | −2.008 | 2.2335E−02 | no | Transcription | Agonist | CAR | 0.2981 | 24 |
| Raloxifene hydrochloride | −9.222 | 1.4569E−20 | yes | Hormone | Modulator | ER | 17.4412 | 23 |
| Rotenone | −11.274 | 8.8620E−30 | yes | Cell Stress | Inhibitor | Mitochondria | 17.3197 | 21 |
| 6-Methoxy-1,2,3,4-tetrahydro-9H-pyrido[3,4b]indole | −2.661 | 3.8951E−03 | yes | Neurotransmission | Inhibitor | MAO | 3.6170 | 19 |
| Metolazone | −8.113 | 2.4793E−16 | yes | Ion Pump | Inhibitor | Na+/Cl− transporter | 12.9560 | 18 |
| SKF 86466 | 0.882 | 1.8883E−01 | no | Adrenoceptor | Antagonist | alpha2 | 2.7306 | 17 |
| 1-Aminocyclopropanecarboxylic acid hydrochloride | −2.401 | 8.1676E−03 | yes | Glutamate | Agonist | NMDA-Glycine | −0.7432 | 12 |
| SB 216763 | −2.542 | 5.5106E−03 | yes | Phosphorylation | Inhibitor | GSK-3 | 11.5423 | 10 |
| Actinonin | −3.501 | 2.3141E−04 | yes | Biochemistry | Inhibitor | Leucine aminopeptidase | 10.0832 | 9 |
| 2-Methylthioadenosine diphosphate trisodium | −10.359 | 1.8958E−25 | yes | P2 Receptor | Agonist | P2Y | 2.5127 | 7 |
| NS 2028 | −2.684 | 3.6413E−03 | yes | Cyclic Nucleotides | Inhibitor | Guanylate cyclase | 8.6194 | 6 |
| Protoporphyrin IX disodium | −3.441 | 2.9003E−04 | yes | Cyclic Nucleotides | Activator | Guanylyl cyclase | 24.5736 | 5 |
| Oligomycin A | −9.731 | 1.1127E−22 | yes | Antibiotic | Inhibitor | | 32.1070 | 3 |
| Mitoxantrone | −10.205 | 9.3930E−25 | yes | DNA Metabolism | Inhibitor | | 8.1117 | 1 |
| MRS 1754 | 0.927 | 1.7702E−01 | no | Adenosine | Antagonist | A2B | −18.0505 | |
| 2-methoxyestradiol | −0.983 | 1.6273E−01 | no | Hormone | Metabolite | Estrogen | −11.8404 | |
| Cysteamine hydrochloride | −0.599 | 2.7463E−01 | no | Somatostatin | Depleter | | −2.3036 | |
| alpha,beta-Methylene adenosine 5'-triphosphate dilithium | −1.290 | 9.8601E−02 | no | P2 Receptor | Agonist | P2X > P2Y | −3.6150 | |
| O-Methylserotonin hydrochloride | −0.172 | 4.3173E−01 | no | Serotonin | Agonist | 5-HT3 | −13.8908 | |
| Se-(methyl)selenocysteine hydrochloride | 0.412 | 3.4032E−01 | no | Cell cycle | Inhibitor | | −3.8644 | |
| Myricetin | −0.911 | 1.8106E−01 | no | Phosphorylation | Inhibitor | Casein Kinase II | −13.2584 | |
| NG-Monomethyl-L-arginine acetate | −1.386 | 8.2897E−02 | no | Nitric Oxide | Inhibitor | NOS | −5.3300 | |
| MK-912 | −0.582 | 2.8028E−01 | no | Adrenoceptor | Agonist | alpha2A | −2.8536 | |
| (±)-3-(3,4-dihydroxyphenyl)-2-methyl-DL-alanine | −1.894 | 2.9132E−02 | no | Neurotransmission | Inhibitor | L-aromatic amino acid dec | −6.9387 | |
| MRS 2159 | −0.267 | 3.9488E−01 | no | P2 Receptor | Antagonist | P2X1 | −14.3488 | |
| 2,6-Difluoro-4-[2-(phenylsulfonylamino)ethylthio]phenoxyacetamide | −0.498 | 3.0915E−01 | no | Glutamate | Agonist | AMPA | −7.6987 | |
| Lorglumide sodium | −2.092 | 1.8225E−02 | no | Cholecystokinin | Antagonist | CCK-A | −4.4235 | |
| LY-278,584 maleate | −1.074 | 1.4143E−01 | no | Serotonin | Antagonist | 5-HT3 | −5.9712 | |
| R(+)-Lisuride hydrogen maleate | −1.041 | 1.4905E−01 | no | Dopamine | Agonist | DRD2 | −23.9479 | |
| L-703,606 oxalate | −0.507 | 3.0612E−01 | no | Tachykinin | Antagonist | NK1 | −1.7788 | |
| Levallorphan tartrate | −0.346 | 3.6450E−01 | no | Opioid | Ligand | | −0.6160 | |
| S-(−)-Lisuride | −0.147 | 4.4144E−01 | no | Dopamine | Agonist | DRD2 | −21.7059 | |
| Linopirdine | −0.553 | 2.9029E−01 | no | Cholinergic | Releaser | | −7.9848 | |
| L-741,626 | −1.009 | 1.5639E−01 | no | Dopamine | Antagonist | DRD2 | −11.7936 | |
| L-733,060 hydrochloride | −1.465 | 7.1425E−02 | no | Tachykinin | Antagonist | NK1 | −1.2037 | |
| R(−)-Me5 | −1.414 | 7.8639E−02 | no | Na+ Channel | Antagonist | | −3.4341 | |
| (−)-Naproxen sodium | 0.602 | 2.7345E−01 | no | Prostaglandin | Inhibitor | COX | −7.5011 | |
| 4-Methylpyrazole hydrochloride | 1.042 | 1.4861E−01 | no | Biochemistry | Inhibitor | Alcohol dehydrogenase | −5.4206 | |
| Nocodazole | −0.189 | 4.2502E−01 | no | Cytoskeleton and ECM | Inhibitor | beta-tubulin | −8.4905 | |
| N-omega-Methyl-5-hydroxytryptamine oxalate salt | 0.656 | 2.5593E−01 | no | Serotonin | Agonist | | −21.3103 | |
| Moxonidine hydrochloride | 0.217 | 4.1407E−01 | no | Adrenoceptor | Agonist | alpha2A | −9.0361 | |
| MRS 1845 | −0.006 | 4.9753E−01 | no | Ca2+ Channel | Inhibitor | SOC | −8.9172 | |
| N-Methyl-1-deoxynojirimycin | −1.335 | 9.0866E−02 | no | Biochemistry | Inhibitor | Glucosidase | −4.4000 | |
| Metaproterenol hemisulfate | −0.001 | 4.9948E−01 | no | Adenosine | Agonist | A3 | −6.3328 | |
| Mianserin hydrochloride | −1.022 | 1.5346E−01 | no | Adrenoceptor | Agonist | beta2 | −10.9972 | |
| | 0.975 | 1.6489E−01 | no | Serotonin | Antagonist | | −3.8848 | |

TABLE 10-continued

| Product Name | Z score | p value | Activity | Class | Action | Selectivity | Likelihood score | Cluster ID |
|---|---|---|---|---|---|---|---|---|
| 8-Methoxymethyl-3-isobutyl-1-methylxanthine | −0.340 | 3.6683E−01 | no | Cyclic Nucleotides | Inhibitor | PDE I | −11.1680 | |
| MK-886 | −1.549 | 6.0662E−02 | no | Leukotriene | Inhibitor | | −12.4571 | |
| Mexiletene hydrochloride | −1.259 | 1.0406E−01 | no | Na+ Channel | Blocker | | −4.9652 | |
| Methylergonovine maleate | −0.785 | 2.1635E−01 | no | Dopamine | Antagonist | | −21.8872 | |
| Molsidomine | 1.567 | 5.8608E−02 | no | Nitric Oxide | Donor | | −7.5890 | |
| 3-Methyl-6-(3-[trifluoromethyl]phenyl)-1,2,4-triazolo[4,3-b]pyridazine | 0.091 | 4.6377E−01 | no | Benzodiazepine | Agonist | BZ1 | −3.2042 | |
| Mizorbine | 1.642 | 5.0274E−02 | no | DNA Metabolism | Inhibitor | IMP dehydrogenase | −5.7895 | |
| S-Methylisothiourea hemisulfate | −0.211 | 4.1640E−01 | no | Nitric Oxide | Inhibitor | iNOS | −1.3890 | |
| N-Methyl-D-aspartic acid | −1.880 | 3.1415E−02 | no | Glutamate | Agonist | NMDA | −3.3399 | |
| MJ33 | 1.364 | 8.6259E−02 | no | Lipid | Inhibitor | PLA2 | −10.8297 | |
| MRS 2179 | −1.246 | 1.0638E−01 | no | P2 Receptor | Antagonist | P2Y1 | −10.4540 | |
| Meloxicam sodium | −1.140 | 1.2723E−01 | no | Prostaglandin | Inhibitor | COX-2 | −4.9935 | |
| Morin | −2.216 | 1.3352E−02 | no | Cell Stress | Inhibitor | Antioxidant | −8.1816 | |
| Minoxidil | −1.189 | 1.1715E−01 | no | K+ Channel | Activator | ATP sensitive | −4.7999 | |
| Meclofenamic acid sodium | 2.233 | 1.2790E−02 | no | Prostaglandin | Inhibitor | COX/5-Lipoxygenase | −6.5636 | |
| Milrinone | 0.055 | 4.7805E−01 | no | Cyclic Nucleotides | Inhibitor | PDE III | −13.5090 | |
| (±)-alpha-Methyl-4-carboxyphenylglycine | 0.727 | 2.3362E−01 | no | Glutamate | Antagonist | Metabotropic | −7.9747 | |
| 1-Methylhistamine dihydrochloride | 0.307 | 3.7950E−01 | no | Histamine | Agonist | | −5.4372 | |
| S-Methyl-L-thiocitrulline acetate | −1.751 | 3.9966E−02 | no | Nitric Oxide | Inhibitor | NOS | −5.2887 | |
| Melatonin | −0.241 | 4.0489E−01 | no | Melatonin | Agonist | | −15.8002 | |
| L-Methionine sulfoximine | 0.087 | 4.6545E−01 | no | Glutamate | Inhibitor | Glutamine synthase | −4.8953 | |
| (±)-Metoprolol (+)-tartrate | −0.269 | 3.9400E−01 | no | Adrenoceptor | Antagonist | beta1 | −15.9164 | |
| 6-Methyl-2-(phenylethynyl)pyridine hydrochloride | 0.094 | 4.6269E−01 | no | Glutamate | Antagonist | mGluR5 | −4.7043 | |
| Mibefradil dihydrochloride | −0.027 | 4.8926E−01 | no | Ca2+ Channel | Blocker | T-type | −8.5973 | |
| N6-Methyladenosine | 0.742 | 2.2892E−01 | no | Adenosine | Agonist | | −6.9910 | |
| (S)-MAP4 hydrochloride | −0.553 | 2.9029E−01 | no | Glutamate | Antagonist | mGluR4,6,7 | −4.5665 | |
| (±)-Methoxyverapamil hydrochloride | −1.407 | 7.9775E−02 | no | Ca2+ Channel | Antagonist | L-type | −1.2039 | |
| Metrazoline oxalate | 0.107 | 4.5726E−01 | no | Imidazoline | Ligand | | −8.0272 | |
| GW9662 | 1.475 | 7.0156E−02 | no | Transcription | Inhibitor | PPAR-gamma | −6.3233 | |
| Sodium Taurocholate | −0.760 | 2.2352E−01 | no | Multi-Drug Resistance | Modulator | Conjugate Pathway | −13.7869 | |
| Amifostine | 0.359 | 3.5974E−01 | no | Cell Stress | Inhibitor | Cytoprotectant | −5.7141 | |
| Acetazolamide | 1.111 | 1.3326E−01 | no | Biochemistry | Inhibitor | Carbonic anhydrase | −3.7190 | |
| A-315456 | 0.363 | 3.5836E−01 | no | Adrenoceptor | Antagonist | alpha1D | −8.5278 | |
| GR 4661 | 0.102 | 4.5957E−01 | no | Serotonin | Agonist | 5-HT1D | −11.8529 | |
| 2-Hydroxysaclofen | −1.624 | 5.2176E−02 | no | GABA | Antagonist | GABA-B | −3.8336 | |
| Nicardipine hydrochloride | 1.869 | 3.0816E−02 | no | Ca2+ Channel | Antagonist | L-type | −17.3875 | |
| Nifedipine | −0.294 | 3.8448E−01 | no | Ca2+ Channel | Antagonist | L-type | −12.3093 | |
| 7-Nitroindazole | −1.349 | 8.8727E−02 | no | Nitric Oxide | Inhibitor | nNOS | −9.4168 | |
| 6-Nitroso-1,2-benzopyrone | 0.011 | 4.9549E−01 | no | Transcription | Inhibitor | PARP | −6.2052 | |
| Nilutamide | 0.119 | 4.5270E−01 | no | Hormone | Antagonist | Androgen | −5.4365 | |
| NF 023 | 1.115 | 1.3250E−01 | no | P2 Receptor | Antagonist | P2X1 | −15.4323 | |
| Nimsutine hydrochloride | −0.652 | 2.5707E−01 | no | DNA | Intercalator | | −6.1040 | |
| Norcantharidin | −1.251 | 1.0549E−01 | no | Phosphorylation | Inhibitor | PP2A | −2.1578 | |
| (+)-Nicotine (+)-di-p-toluoyl tartrate | −2.233 | 1.2776E−02 | no | Cholinergic | Agonist | Nicotinic | −5.5323 | |
| Naltrindole hydrochloride | −0.314 | 3.7675E−01 | no | Opioid | Antagonist | delta | −8.3412 | |
| N-(p-Isothiocyanatophenethyl)spiperone hydrochloride | −0.415 | 3.3899E−01 | no | Dopamine | Antagonist | DRD2 | −3.6574 | |
| NO-711 hydrochloride | −0.462 | 3.2213E−01 | no | GABA | Inhibitor | Uptake | −2.5809 | |
| Atropine methyl bromide | −0.872 | 1.9172E−01 | no | Cholinergic | Antagonist | Muscarinic | −16.1459 | |
| Amperozide hydrochloride | −0.413 | 3.3993E−01 | no | Serotonin | Antagonist | | −2.3932 | |
| Aminoguanidine hemisulfate | −1.219 | 1.1135E−01 | no | Nitric Oxide | Inhibitor | NOS | −3.7892 | |
| Agmatine sulfate | 0.588 | 2.7823E−01 | no | Imidazoline | Agonist | | −3.1654 | |

TABLE 10-continued

| Product Name | Z score | p value | Activity | Class | Action | Selectivity | Likelihood score | Cluster ID |
|---|---|---|---|---|---|---|---|---|
| 4-Aminobenzamidine dihydrochloride | -1.287 | 9.9097E-02 | no | Biochemistry | Inhibitor | Trypsin | -1.1605 | |
| Mifepristone | -1.970 | 2.4404E-02 | no | Horomone | Antagonist | Progesterone | -8.2079 | |
| L-alpha-Methyl-p-tyrosine | -1.800 | 3.5926E-02 | no | Neurotransmission | Inhibitor | Tyrosine hydroxylase | -0.1777 | |
| Monastrol | -1.162 | 1.2260E-01 | no | Cell Cycle | Inhibitor | EgG5 | -10.4422 | |
| 1-Methylimidazole | -0.847 | 1.9852E-01 | no | Prostaglandin | Inhibitor | COX | -2.1232 | |
| Mecamylamine hydrochloride | -2.108 | 1.7531E-02 | no | Cholinergic | Antagonist | Nicotinic | -6.6672 | |
| Methapyrilene hydrochloride | 0.628 | 2.6514E-01 | no | Histamine | Antagonist | HRH1 | -6.6557 | |
| Memantine hydrochloride | -0.141 | 4.4392E-01 | no | Glutamate | Antagonist | NMDA | -2.7403 | |
| Me-3,4-dephostatin | 0.583 | 2.7980E-01 | no | Phosphorylation | Inhibitor | PP1B/SHPTP-1 | -7.1731 | |
| Minocycline hydrochloride | 0.442 | 3.2929E-01 | no | Cell Cycle | Inhibitor | | -11.6737 | |
| Maprotiline hydrochloride | -0.361 | 3.5888E-01 | no | Adrenoceptor | Inhibitor | Reuptake | -5.6469 | |
| H-8 dihydrochloride | -1.583 | 5.6734E-02 | no | Phosphorylation | Inhibitor | PKA, PKG | -12.8645 | |
| Proglumide | -1.907 | 2.8236E-02 | no | Cholecystokinin | Antagonist | | -0.7173 | |
| (±)-Muscarine chloride | -1.905 | 2.8377E-02 | no | Cholinergic | Agonist | Muscarinic | -4.2822 | |
| (+)-MK-801 hydrogen maleate | -0.098 | 4.6095E-01 | no | Glutamate | Antagonist | NMDA | -7.4893 | |
| (−)-MK-801 hydrogen maleate | 1.133 | 1.2862E-01 | no | Glutamate | Antagonist | NMDA | -7.4893 | |
| 2-Methyl-5-hydroxytryptamine maleate | 0.572 | 2.8372E-01 | no | Serotonin | Agonist | 5-HT3 | -11.8280 | |
| alpha-Methyl-5-hydroxytryptamine maleate | -0.780 | 2.1782E-01 | no | Serotonin | Agonist | 5-HT2 | -20.4376 | |
| L-alpha-Methyl DOPA | -0.897 | 1.8486E-01 | no | Biochemistry | Inhibitor | Aromatic amino acid decar | -6.9387 | |
| Methysergide maleate | -0.020 | 4.9209E-01 | no | Serotonin | Antagonist | 5-HT1A | -8.8270 | |
| Methylcarbamylcholine chloride | 1.913 | 2.7879E-02 | no | Cholinergic | Agonist | Nicotinic | -8.1124 | |
| MDL 26,630 trihydrochloride | 0.327 | 3.7170E-01 | no | Glutamate | Agonist | NMDA-Polyamine | -4.5631 | |
| ZM 39923 hydrochloride | 0.746 | 2.2793E-01 | no | Phosphorylation | Inhibitor | JNK-3 | -2.6434 | |
| 3-Morpholinosydnonimine hydrochloride | -1.324 | 9.2801E-02 | no | Nitric Oxide | Donor | | -5.4749 | |
| p-MPPI hydrochloride | 0.261 | 3.9702E-01 | no | Serotonin | Antagonist | 5-HT1A | -9.5404 | |
| MDL 105,519 | 2.565 | 5.1579E-03 | no | Glutamate | Antagonist | NMDA-Glycine | -6.9319 | |
| Metrifudil | -0.212 | 4.1594E-01 | no | Adenosine | Agonist | A2 | -8.6255 | |
| p-MPPF dihydrochloride | -2.160 | 1.5404E-02 | no | Serotonin | Antagonist | 5-HT1A | -9.6044 | |
| Niflumic acid | -1.958 | 2.5127E-02 | no | Prostaglandin | Inhibitor | COX-2 | -5.2950 | |
| Nialamide | -0.029 | 4.8829E-01 | no | Neurotransmission | Inhibitor | MAO | -7.2169 | |
| Nomifensine maleate | 0.669 | 2.5166E-01 | no | Dopamine | Antagonist | Reuptake | -6.9261 | |
| nor-Binaltorphimine dihydrochloride | 0.388 | 3.4898E-01 | no | Opioid | Antagonist | kappa | -6.3339 | |
| Neostigmine bromide | 1.228 | 1.0966E-01 | no | Cholinergic | Inhibitor | Acetylcholinesterase | -5.7277 | |
| CR 2249 | -1.002 | 1.5820E-01 | no | Glutamate | Agonist | NMDA-Glycine | -6.4049 | |
| S-(4-Nitrobenzyl)-6-thioinosine | -0.427 | 3.3464E-01 | no | Adenosine | Inhibitor | Uptake | -10.0990 | |
| S-Nitroso-N-acetylpenicillamine | -1.645 | 4.9980E-02 | no | Nitric Oxide | Donor | | -5.3835 | |
| NAN-190 hydrobromide | -0.619 | 2.6809E-01 | no | Serotonin | Antagonist | 5-HT1A | -8.8603 | |
| NCS-356 | 2.833 | 2.3079E-03 | no | GABA | Agonist | gamma-Hydrocybutyrate | -5.1409 | |
| S-Nitrosoglutathione | 0.698 | 2.4266E-01 | no | Nitric Oxide | Donor | | -9.5229 | |
| NCS-382 | -1.733 | 4.1521E-02 | no | GABA | Antagonist | gamma-Hydroxybutyrate | -4.9225 | |
| Nalidixic acid sodium | -0.314 | 3.7659E-01 | no | Antibiotic | Inhibitor | DNA Gyrase | -12.6120 | |
| 5-Nitro-2-(3-phenylpropylamino)benzoic acid | -0.734 | 2.3139E-01 | no | Cl− Channel | Blocker | | -7.9444 | |
| NF449 octasodium salt | 1.851 | 3.2049E-02 | no | G protein | Antagonist | Gs-alpha | -13.0359 | |
| Nordihydroguaiaretic acid from Larrea divaricata (creosote bush) | 2.630 | 4.2730E-03 | no | Leukotriene | Inhibitor | Lipoxygenase | -6.6401 | |
| (−)-Nicotine hydrogen tartrate salt | 0.045 | 4.8206E-01 | no | Cholinergic | Agonist | Nicotinic | -3.2819 | |
| NG-Nitro-L-arginine | 0.139 | 4.4492E-01 | no | Nitric Oxide | Inhibitor | NOS | -7.8438 | |
| Naphazoline hydrochloride | -1.724 | 4.2333E-02 | no | Adrenoceptor | Agonist | alpha | -4.9453 | |
| 3-Nitropropionic acid | -0.563 | 2.8667E-01 | no | Cell Stress | Toxin | | -4.6291 | |
| NG-Nitro-L-arginine methyl ester hydrochlodride | -1.411 | 7.9176E-02 | no | Nitric Oxide | Inhibitor | NOS | -5.3340 | |
| (±)-Normetanephrine hydrochloride | -1.796 | 3.6219E-02 | no | Adrenoceptor | Metabolite | Norepinephrine | -2.4055 | |
| Nortriptyline hydrochloride | -1.095 | 1.3669E-01 | no | Adrenoceptor | Inhibitor | Uptake | -4.0728 | |

TABLE 10-continued

| Product Name | Z score | p value | Activity | Class | Action | Selectivity | Likelihood score | Cluster ID |
|---|---|---|---|---|---|---|---|---|
| NADPH tetrasodium | 0.302 | 3.8128E-01 | no | Nitric Oxide | Cofactor | | -10.4977 | |
| Valproic acid sodium | -0.095 | 4.6218E-01 | no | Anticonvulsant | | | -4.3774 | |
| Praziquantel | -2.296 | 1.0839E-02 | no | Antibiotic | | | -6.6721 | |
| Propafenone hydrochloride | -0.967 | 1.6670E-01 | no | K+ Channel | Blocker | hKv1.5 | -12.0390 | |
| 5alpha-Pregnan-3alpha-ol-11,20-dione | -0.808 | 2.0960E-01 | no | GABA | Modulator | GABA-A | -14.4850 | |
| Pempidine tartrate | -1.719 | 4.2825E-02 | no | Cholinergic | Antagonist | Nicotinic | -2.9296 | |
| Piracetam | -0.376 | 3.5353E-01 | no | Glutamate | Modulator | AMPA | -7.7089 | |
| Phosphomycin disodium | -1.402 | 8.0513E-02 | no | Antibiotic | | Cell wall synthesis | -4.3038 | |
| Pyrilamine maleate | 0.989 | 1.6127E-01 | no | Histamine | Antagonist | HRH1 | -6.9749 | |
| Piroxicam | 0.253 | 4.0025E-01 | no | Prostaglandin | Inhibitor | COX | -7.4543 | |
| 3-n-Propylxanthine | -1.094 | 1.3705E-01 | no | Adenosine | Antagonist | A1 > A2 | -11.5600 | |
| Phenylephrine hydrochloride | -1.257 | 1.0442E-01 | no | Adrenoceptor | Agonist | alpha1 | -11.1360 | |
| Pentylenetetrazole | -0.927 | 1.7686E-01 | no | Neurotransmission | Modulator | CNS | -3.7535 | |
| (+)-Pilocarpine hydrochloride | -1.548 | 6.0832E-02 | no | Cholinergic | Agonist | Muscarinic | -3.6887 | |
| Pilocarpine nitrate | -1.213 | 1.1256E-01 | no | Cholinergic | Agonist | Muscarinic | -5.4850 | |
| Nitrendipine | -1.610 | 5.3738E-02 | no | Ca2+ Channel | Antagonist | L-type | -18.7148 | |
| Nimodipine | -0.854 | 1.9650E-01 | no | Ca2+ Channel | Antagonist | L-type | -16.0786 | |
| Nisoxetine hydrochloride | 0.834 | 2.0226E-01 | no | Adrenoceptor | Blocker | Reuptake | -11.0438 | |
| Nylidrin hydrochloride | -1.375 | 8.4499E-02 | no | Adrenoceptor | Agonist | beta | -0.0022 | |
| N6-Cyclopentyl-9-methyladenine | -2.112 | 1.7347E-02 | no | Adenosine | Antagonist | A1 | -3.0271 | |
| Naltriben methanesulfonate | -0.361 | 3.5920E-01 | no | Opioid | Antagonist | delta2 | -6.1337 | |
| Naftopidil dihydrochloride | -0.117 | 4.5334E-01 | no | Adrenoceptor | Antagonist | alpha1 | -12.5115 | |
| BW 245C | 1.036 | 1.5017E-01 | no | Prostanoids | Agonist | DP | -6.6950 | |
| NS-1619 | -0.488 | 3.1285E-01 | no | K+ Channel | Activator | Ca2+ activated | -0.7044 | |
| NBQX disodium | -1.675 | 4.6988E-02 | no | Glutamate | Antagonist | AMPA/kainate | -8.4171 | |
| (±)-Octopamine hydrochloride | -1.567 | 5.8506E-02 | no | Adrenoceptor | Agonist | alpha | -2.8789 | |
| N-Oleoylethanolamine | -0.412 | 3.4030E-01 | no | Sphingolipid | Inhibitor | Ceramidase | -2.3589 | |
| Oxolinic acid | 0.918 | 1.7933E-01 | no | Antibiotic | Inhibitor | DNA Gyrase | -2.8871 | |
| Olomoucine | 1.553 | 6.0230E-02 | no | Phosphorylation | Inhibitor | PK | -3.6670 | |
| Sodium Oxamate | 0.745 | 2.2817E-01 | no | Biochemistry | Inhibitor | Lactate Dehydrogenase | -4.3313 | |
| Oxybutynin Chloride | 0.708 | 2.3948E-01 | no | Cholinergic | Antagonist | Muscarinic | -4.4857 | |
| Oxiracetam | -0.613 | 2.6992E-01 | no | Nootropic | | | -5.2602 | |
| Ouabain | -1.568 | 5.8446E-02 | no | Ion Pump | Inhibitor | Na+/K+ ATPase | -5.3647 | |
| ODQ | -0.592 | 2.7686E-01 | no | Cyclic Nucleotides | Inhibitor | NO-sensitive guanylyl cyc | -3.1837 | |
| Ofloxacin | -0.489 | 3.1247E-01 | no | Antibodies | | DNA Synthesis | -6.7858 | |
| Oxotremorine sesquifumarate salt | 0.855 | 1.9623E-01 | no | Cholinergic | Agonist | M2 | -8.1581 | |
| Oxatomide | 0.596 | 2.7568E-01 | no | Immune System | Modulator | | -1.1963 | |
| Oxaprozin | 0.066 | 4.7363E-01 | no | Prostaglandin | Inhibitor | | -4.2022 | |
| Oxotremorine methiodide | -0.700 | 2.4191E-01 | no | Cholinergic | Agonist | Muscarinic | -8.3627 | |
| Progesterone | 0.425 | 3.3535E-01 | no | Hormone | | Progesterone | -12.7869 | |
| Palmitoylethanolamide | -0.913 | 1.8051E-01 | no | Cannabinoid | Agonist | CB2 | -2.3737 | |
| Piceatannol | 0.596 | 2.7567E-01 | no | Phosphorylation | Inhibitor | Syk/Lck | -10.2033 | |
| Parthenolide | -0.724 | 2.3459E-01 | no | Serotonin | Inhibitor | | -4.0799 | |
| Pindolol | -0.079 | 4.6853E-01 | no | Adrenoceptor | Antagonist | beta | -25.5497 | |
| O-Phospho-L-serine | 0.547 | 2.9212E-01 | no | Glutamate | Antagonist | NMDA | -5.3290 | |
| (±)-Propranolol hydrochloride | 0.357 | 3.6065E-01 | no | Adrenoceptor | Antagonist | beta | -17.1649 | |
| Picrotoxin | 0.777 | 2.1855E-01 | no | GABA | Antagonist | GABA-C | -3.0384 | |
| 4-Phenyl-3-furoxancarbonitrile | 0.931 | 1.7584E-01 | no | Nitric Oxide | Donor | | -6.6936 | |
| Pentoxifylline | -1.637 | 5.0810E-02 | no | Cyclic Nucleotides | Inhibitor | PDE | -16.7236 | |
| L-Glutamic acid, N-phthaloyl- | -0.589 | 2.7788E-01 | no | Glutamate | Agonist | | -4.9887 | |
| Pancuronium bromide | 0.408 | 3.4176E-01 | no | Cholinergic | Antagonist | NMDA | -12.6977 | |

TABLE 10-continued

| Product Name | Z score | p value | Activity | Class | Action | Selectivity | Likelihood score | Cluster ID |
|---|---|---|---|---|---|---|---|---|
| 3-alpha,21-Dihydroxy-5-alpha-pregnan-20-one | 0.444 | 3.2849E-01 | no | GABA | Modulator | GABA-A | -15.4033 | |
| Pirfenidone | -1.482 | 6.9175E-02 | no | Immune System | Inhibitor | | -1.4000 | |
| 1,3-Dimethyl-8-phenylxanthine | 0.752 | 2.2609E-01 | no | Adenosine | Antagonist | A1 | -19.9006 | |
| PPNDS tetrasodium | -2.067 | 1.9369E-02 | no | P2 Receptor | Antagonist | P2X1 | -17.6537 | |
| PD 404,182 | 0.091 | 4.6392E-01 | no | Biochemistry | Inhibitor | KDO-8-P synthase | -4.8559 | |
| Papaverine hydrochloride | -0.299 | 3.8240E-01 | no | Cyclic Nucleotides | Inhibitor | PDE | -1.5223 | |
| Pentolinium di[L(+)-tartrate] | 0.166 | 4.3402E-01 | no | Cholinergic | Antagonist | Nicotinic | -4.8241 | |
| 1-Phenyl-3-(2-thiazolyl)-2-thiourea | 1.208 | 1.1348E-01 | no | Dopamine | Inhibitor | beta-Hydroxylase | -7.0804 | |
| Thiolactomycin | -1.300 | 9.6869E-02 | no | Antibiotic | Inhibitor | Myristine synthesis | -4.4790 | |
| Cisplatin | 1.523 | 6.3908E-02 | no | DNA | Intercalator | | -1.2264 | |
| Palmitoyl-DL-Carnitine chloride | 0.200 | 4.2092E-01 | no | Phosphorylation | Modulator | PKC | -2.9027 | |
| R(-)-N6-(2-Phenylisopropyl)adenosine | -2.023 | 2.1549E-02 | no | Adenosine | Agonist | A1 | -5.5885 | |
| N-Phenylanthranilic acid | -1.610 | 5.3659E-02 | no | Cl- Channel | Blocker | | -6.7826 | |
| S(-)-p-Bromotetramisole oxalate | -1.295 | 9.7578E-02 | no | Phosphorylation | Inhibitor | Alkaline phosphatase | -8.7258 | |
| 5-Aminovaleric acid hydrochloride | -1.670 | 4.7454E-02 | no | GABA | Antagonist | GABA-B | -2.9370 | |
| (±)-Nipecotic acid | -0.722 | 2.3529E-01 | no | GABA | Inhibitor | Uptake | -4.7970 | |
| Azelaic acid | 0.106 | 4.5792E-01 | no | DNA Metabolism | Inhibitor | | -1.4943 | |
| Tryptamine hydrochloride | 1.245 | 1.0658E-01 | no | Serotin | Ligand | | -15.7942 | |
| 5-Fluoroindole-2-carboxylic acid | -0.008 | 4.9699E-01 | no | Glutamate | Antagonist | NMDA-Glycine | -8.5717 | |
| PD 168,077 maleate | -1.516 | 6.4777E-02 | no | Dopamine | Agonist | D4 | -9.9614 | |
| SU 6656 | 0.316 | 3.7583E-01 | no | Phosphorylation | Inhibitor | Src family kinase | -9.8898 | |
| Quercetin dihydrate | -2.302 | 1.0654E-02 | no | Cyclic Nucleotides | Inhibitor | PDE | -14.2835 | |
| Quinidine sulfate | -1.930 | 2.6809E-02 | no | Na+ Channel | Antagonist | | -0.1268 | |
| Quipazine dimaleate | -1.444 | 7.4350E-02 | no | Serotonin | Agonist | | -10.3024 | |
| Quinine sulfate | -0.269 | 3.9413E-01 | no | Serotonin | Antagonist | | -0.1268 | |
| (+)-Quisqualic acid | 0.436 | 3.3137E-01 | no | Glutamate | Agonist | AMPA | -5.8739 | |
| Quazinone | 0.205 | 4.1894E-01 | no | Cyclic Nucleotides | Inhibitor | PDE III | -4.2156 | |
| (-)-Quinpirole hydrochloride | -1.565 | 5.8745E-02 | no | Dopamine | Agonist | D2/D3 | -8.0415 | |
| Quipazine, N-methyl-, dimaleate | -0.325 | 3.7242E-01 | no | Serotonin | Agonist | 5-HT3 | -5.2567 | |
| Quinelorane dihydrochloride | 0.978 | 1.6400E-01 | no | Serotonin | Inhibitor | Reuptake | -14.7627 | |
| (±)-Quinpirole dihydrochloride | -1.567 | 5.8557E-02 | no | Dopamine | Agonist | DRD2 | -5.7572 | |
| Cortexolone | -0.451 | 3.2590E-01 | no | Dopamine | Agonist | D2 > D3 | -6.9743 | |
| Phenelzine sulfate | -0.609 | 2.7135E-01 | no | Hormone | Precursor | Cortisol | -10.9265 | |
| Phosphonoacetic acid | -1.556 | 6.2233E-02 | no | Neurotransmission | Inhibitor | MAO-A/B | -4.6157 | |
| (-)-Perilic acid | -0.888 | 1.8714E-01 | no | DNA | Inhibitor | DNA Polymerase | -3.1115 | |
| Pyrazinecarboxamide | -1.321 | 9.3323E-02 | no | G protein | Inhibitor | p21 Ras | -5.2521 | |
| Primidone | -1.617 | 5.2920E-02 | no | Antibiotic | | | -4.8113 | |
| Pirenzepine dihydrochloride | 0.619 | 2.6807E-01 | no | Anticonvulsant | | | -4.0977 | |
| Putrescine dihydrochloride | -0.545 | 2.9289E-01 | no | Cholinergic | Antagonist | M1 | -3.8093 | |
| Phentolamine mesylate | -0.769 | 2.2096E-01 | no | Glutamate | Agonist | NMDA-Polyamine | -2.3789 | |
| Phloretin | -0.319 | 3.7483E-01 | no | Adrenoceptor | Antagonist | alpha | -7.3473 | |
| Pargyline hydrochloride | 0.916 | 1.7971E-01 | no | Ca2+ Channel | Blocker | L-Type | -2.5179 | |
| Phorbol 12-myristate 13-acetate | -0.279 | 3.8998E-01 | no | Neurotransmission | Inhibitor | MAO-B | -2.0187 | |
| 1,3-PBIT dihydrobromide | -0.265 | 3.9551E-01 | no | Phosphorylation | Activator | PKC | -2.8929 | |
| 1,4-PBIT dihydrobromide | 2.221 | 1.3159E-02 | no | Nitric Oxide | Inhibitor | NOS | -4.5252 | |
| Phenylbutazone | -1.179 | 1.1914E-01 | no | Nitric Oxide | Inhibitor | NOS | -5.7763 | |
| Picotamide | 0.790 | 2.1470E-01 | no | Prostaglandin | Substrate | Prostaglandin peroxidase | -3.3633 | |
| Tranylcypromine hydrochloride | 1.736 | 4.1318E-02 | no | Thromboxane | Antagonist | TXA2 | -1.0308 | |
| (S)-Propranolol hydrochloride | -1.441 | 7.4837E-02 | no | Neurotransmission | Inhibitor | MAO | -6.3559 | |
| Ammonium pyrrolidinedithiocarbamate | -0.535 | 2.9645E-01 | no | Adrenoceptor | Blocker | beta | -17.1649 | |
| | -0.417 | 3.3843E-01 | no | Nitric Oxide | Modulator | NOS | -5.9065 | |

TABLE 10-continued

| Product Name | Z score | p value | Activity | Class | Action | Selectivity | Likelihood score | Cluster ID |
|---|---|---|---|---|---|---|---|---|
| (±)-cis-Piperidine-2,3-dicarboxylic acid | 0.155 | 4.3829E-01 | no | Glutamate | Agonist | NMDA | -7.4174 | |
| Protriptyline hydrochloride | 0.760 | 2.2355E-01 | no | Adrenoceptor | Blocker | Reuptake | -6.9557 | |
| 6(5H)-Phenanthridinone | 0.677 | 2.4936E-01 | no | Transcription | Inhibitor | PARP | -1.7136 | |
| 5alpha-Pregnan-3alpha-ol-20-one | 0.934 | 1.7527E-01 | no | GABA | Modulator | GABA-A | -15.2536 | |
| Propantheline bromide | -1.534 | 6.2542E-02 | no | Cholinergic | Antagonist | Muscarinic | -4.4811 | |
| Piperidine-4-sulphonic acid | -0.424 | 3.3586E-01 | no | GABA | Agonist | GABA-A | -2.9963 | |
| Paramomycin sulfate | 0.821 | 2.0582E-01 | no | Antibiotic | | Protein synthesis | -4.4506 | |
| 1,10-Phenanthroline monohydrate | -0.886 | 1.8793E-01 | no | Biochemistry | Inhibitor | Metalloprotease | -3.3402 | |
| Prilocaine hydrochloride | 1.509 | 6.5665E-02 | no | Na+ Channel | Blocker | | -8.1733 | |
| Propentofylline | 0.156 | 4.3790E-01 | no | Adenosine | Inhibitor | Transporter | -15.1399 | |
| (S)-(-)-propafenone hydrochloride | -0.752 | 2.2591E-01 | no | Adrenoceptor | Blocker | beta | -12.0390 | |
| Pyridostigmine bromide | 0.231 | 4.0862E-01 | no | Cholinergic | Inhibitor | Cholinesterase | -1.7195 | |
| R(+)-3PPP hydrochloride | -2.213 | 1.3452E-02 | no | Dopamine | Agonist | DRD2 | -10.0895 | |
| S(-)-3PPP hydrochloride | -0.421 | 3.3705E-01 | no | Dopamine | Agonist | DRD2 | -10.0895 | |
| 3-Phenylpropargylamine hydrochloride | -2.043 | 2.0514E-02 | no | Dopamine | Inhibitor | Dopamine beta-hydroxylase | -3.1720 | |
| N6-2-Phenylethyladenosine | 0.531 | 2.9763E-01 | no | Adenosine | Agonist | A1 | -7.1641 | |
| N6-Phenyladenosine | 0.728 | 2.3320E-01 | no | Adenosine | Agonist | A1 | -1.7086 | |
| Phaclofen | 0.970 | 1.6600E-01 | no | GABA | Antagonist | GABA-B | -7.2387 | |
| (±)-Pindobind | 0.257 | 3.9841E-01 | no | Adrenoceptors | Ligand | beta | -24.1169 | |
| SKF 94836 | 0.246 | 4.0292E-01 | no | Calcium Signaling | Inhibitor | PDE III | -11.6790 | |
| IC 261 | -1.630 | 5.1502E-02 | no | Phosphorylation | Inhibitor | CK-1delta/epsilon | -7.3987 | |
| S(-)-Pindolol | -1.122 | 1.3093E-01 | no | Serotonin | Agonist | 5-HT1A | -25.5497 | |
| Pinacidil | -2.117 | 1.7149E-02 | no | K+ Channel | Activator | | -11.3913 | |
| Pregnenolone sulfate sodium | 2.653 | 3.9869E-03 | no | GABA | Antagonist | GABA-A | -11.1447 | |
| PPADS | 1.106 | 1.3440E-01 | no | P2 Receptor | Antagonist | P2 | -14.7027 | |
| S(+)-PD 128,907 hydrochloride | -1.174 | 1.2027E-01 | no | Dopamine | Agonist | D3 | -2.1728 | |
| Phenylbenzene-omega-phosphono-alpha-amino acid | -0.014 | 4.9432E-01 | no | Glycine | Antagonist | | -0.7417 | |
| Phthalamoyl-L-glutamic acid trisodium | 0.251 | 4.0096E-01 | no | Glutamate | Agonist | NMDA | -5.5159 | |
| PD 98,059 | 0.903 | 1.8334E-01 | no | Phosphorylation | Inhibitor | MEK2 | -3.9645 | |
| (±)-PD 128,907 hydrochloride | 1.164 | 1.2221E-01 | no | Dopamine | Agonist | D3 | -2.1728 | |
| S-(4-Nitrobenzyl)-6-thioguanosine | 0.102 | 4.5951E-01 | no | Adenosine | Inhibitor | | -7.6238 | |
| 4-Aminopyridine | -1.516 | 6.4813E-02 | no | K+ Channel | Blocker | A-type | -4.8117 | |
| Atropine sulfate | 1.244 | 1.0672E-01 | no | Cholinergic | Antagonist | Muscarinic | -4.7393 | |
| Atropine methyl nitrate | 1.292 | 9.8265E-02 | no | Cholinergic | Antagonist | Muscarinic | -17.9825 | |
| Arcaine sulfate | -0.330 | 3.7075E-01 | no | Glutamate | Antagonist | NMDA-Polyamine | -1.0159 | |
| Sphingosine | 1.404 | 8.0132E-02 | no | Phosphorylation | Inhibitor | PKC | -1.5940 | |
| SB 269970 hydrochloride | -1.100 | 1.3570E-01 | no | Serotonin | Antagonist | 5-HT7 | -1.6559 | |
| Spiperone hydrochloride | -0.517 | 3.0266E-01 | no | Dopamine | Antagonist | DRD2 | -7.9131 | |
| SR 2640 | -1.548 | 6.0825E-02 | no | Leukotriene | Antagonist | CysLT1 | -9.7171 | |
| (-)-Scopolamine, n-Butyl-, bromide | 0.649 | 2.5831E-01 | no | Cholinergic | Antagonist | Muscarinic | -16.9904 | |
| SB 205384 | 0.797 | 2.1277E-01 | no | GABA | Modulator | GABA-A | -8.6705 | |
| CV-3988 | -0.437 | 3.3102E-01 | no | Cytokines & Growth Fa | Antagonist | PAF | -6.2993 | |
| Sulindac | -0.194 | 4.2302E-01 | no | Prostaglandin | Inhibitor | COX | -8.2302 | |
| Succinylcholine chloride | -1.930 | 2.6777E-02 | no | Cholinergic | Antagonist | Nicotinic | -4.6390 | |
| Salbutamol | -1.678 | 4.6677E-02 | no | Adrenoceptor | Agonist | beta2 | -8.6603 | |
| Salmeterol | -0.490 | 3.1222E-01 | no | Adrenoceptor | Agonist | beta2 | -8.8943 | |
| SU 5416 | -0.662 | 2.5394E-01 | no | Phosphorylation | Inhibitor | VEGFR PTK | -10.8964 | |
| (-)-Scopolamine methyl bromide | -0.847 | 1.9854E-01 | no | Cholinergic | Antagonist | Muscarinic | -16.9163 | |
| Ruthenium red | -0.074 | 4.7055E-01 | no | Ion Pump | Inhibitor | Mitochondrial uniporter | -0.9840 | |
| Rutaecarpine | 0.686 | 2.4645E-01 | no | K+ Channel | Blocker | | -7.8454 | |
| Resveratrol | -0.230 | 4.0924E-01 | no | Prostaglandin | Inhibitor | COX | -3.8617 | |

TABLE 10-continued

| Product Name | Z score | p value | Activity | Class | Action | Selectivity | Likelihood score | Cluster ID |
|---|---|---|---|---|---|---|---|---|
| REV 5901 | -1.184 | 1.1813E-01 | no | Leukotriene | Antagonist | LTD4 | -7.0078 | |
| Rottlerin | 0.304 | 3.8047E-01 | no | Phosphorylation | Inhibitor | PKC/CaM Kinase III | -6.0230 | |
| Ranolazine dihydrochloride | -2.104 | 1.7711E-02 | no | Lipid | Inhibitor | pFOX | -8.2305 | |
| Rolipram | -2.091 | 1.8254E-02 | no | Cyclic Nucleotides | Inhibitor | PDE IV | -5.1219 | |
| Phosphoramidon disodium | -0.510 | 3.0512E-01 | no | Biochemistry | Inhibitor | Endopeptidase | -20.5364 | |
| Roscovitine | 0.003 | 4.9891E-01 | no | Phosphorylation | Inhibitor | CDK | -0.0626 | |
| Ro 8-4304 | -2.188 | 1.4331E-02 | no | Glutamate | Antagonist | NMDA-NR2B | -3.3769 | |
| RX 821002 hydrochloride | 0.249 | 4.0167E-01 | no | Adrenoceptor | Antagonist | alpha2 | -5.5331 | |
| Ribavirin | -1.194 | 1.1620E-01 | no | Cell Cycle | Inhibitor | IMP dehydrogenase | -5.4344 | |
| Ranitidine hydrochloride | 0.023 | 4.9093E-01 | no | Histamine | Antagonist | H2 | -8.8616 | |
| Ritanserin | -0.696 | 2.4332E-01 | no | Serotonin | Antagonist | 5-HT2/5-HT1C | -7.7433 | |
| Rauwolscine hydrochloride | -1.747 | 4.0288E-02 | no | Adrenoceptor | Antagonist | alpha2 | -2.0332 | |
| Ro 16-6491 hydrochloride | -2.181 | 1.4590E-02 | no | Neurotransmission | Inhibitor | MAO-B | -1.0523 | |
| Ro 41-1049 hydrochloride | 1.328 | 9.2137E-02 | no | Neurotransmission | Inhibitor | MAO-A | -4.7684 | |
| Ro 41-0960 | -0.360 | 3.5942E-01 | no | Neurotransmission | Inhibitor | COMT | -7.6263 | |
| Reactive Blue 2 | 2.003 | 2.2573E-02 | no | P2 Receptor | Antagonist | P2Y | -10.1270 | |
| Riluzole | -1.033 | 1.5090E-01 | no | Glutamate | Antagonist | Release | -1.7431 | |
| Risperidone | 1.694 | 4.5097E-02 | no | Dopamine | Antagonist | DRD2 | -10.2931 | |
| Rilmenidine hemifumarate | 0.526 | 2.9930E-01 | no | Imidazoline | Agonist | I1 | -5.7097 | |
| Ro 04-6790 dihydrochloride | 0.343 | 3.6587E-01 | no | Serotonin | Antagonist | 5-HT6 | -5.2757 | |
| (±)-Sotalol hydrochloride | -0.813 | 2.0811E-01 | no | Adrenoceptor | Antagonist | beta | -4.9715 | |
| SB-366791 | -1.419 | 7.7915E-02 | no | Vanilloid | Antagonist | VR1 | -3.0156 | |
| Sodium nitroprusside dihydrate | 2.404 | 8.1010E-03 | no | Nitric Oxide | Releaser | | -1.0698 | |
| (±)-Synephrine | -0.149 | 4.4085E-01 | no | Adrenoceptor | Agonist | alpha | -5.2875 | |
| Sulfaphenazole | -1.362 | 8.6671E-02 | no | Multi-Drug Resistance | Inhibitor | Cytochrome P4502C | -9.1951 | |
| Seglitide | -0.662 | 2.5398E-01 | no | Somatostatin | Agonist | sst2 | -18.2993 | |
| Sulindac sulfone | 0.592 | 2.7680E-01 | no | Prostaglandin | Inhibitor | | -7.3445 | |
| Cortexolone maleate | -1.434 | 7.5773E-02 | no | Dopamine | Antagonist | DRD2 | -14.1896 | |
| SR 57227A | -1.400 | 8.0749E-02 | no | Serotonin | Agonist | 5-HT3 | -7.7427 | |
| (-)-Scopolamine hydrobromide | -0.742 | 2.2919E-01 | no | Cholinergic | Antagonist | Muscarinic | -10.2442 | |
| SC-560 | 1.113 | 1.3287E-01 | no | Prostaglandin | Inhibitor | COX-1 | -4.6793 | |
| Semicarbazide hydrochloride | -1.405 | 8.0029E-02 | no | Neurotransmission | Inhibitor | MAO | -5.0341 | |
| (-)-Scopolamine methyl nitrate | -0.451 | 3.2606E-01 | no | Cholinergic | Antagonist | Muscarinic | -18.9174 | |
| DL-Stearoylcarnitine chloride | 0.638 | 2.6181E-01 | no | Phosphorylation | Inhibitor | PKC | -2.3326 | |
| Spermidine trihydrochloride | 1.259 | 1.0410E-01 | no | Glutamate | Ligand | NMDA-Polyamine | -4.9703 | |
| SNC80 | -0.457 | 3.2366E-01 | no | Opioid | Agonist | delta | -4.2921 | |
| SKF 83959 hydrobromide | -1.357 | 8.7380E-02 | no | Dopamine | Agonist | D1 | -10.4451 | |
| Spermine tetrahydrochloride | 0.394 | 3.4672E-01 | no | Glutamate | Antagonist | NMDA-Polyamine | -3.3021 | |
| SKF 75670 hydrobromide | -0.142 | 4.4350E-01 | no | Dopamine | Agonist | D1 | -6.1094 | |
| SC 19220 | -1.640 | 5.0479E-02 | no | Prostaglandin | Antagonist | EP1 | -1.8074 | |
| SKF 89626 | -0.044 | 4.8258E-01 | no | Dopamine | Agonist | D1 | -10.7228 | |
| SKF 83565 hydrobromide | 0.789 | 2.1492E-01 | no | Dopamine | Agonist | D1 | -7.5982 | |
| N-Oleoyldopamine | 0.463 | 3.2158E-01 | no | Neurotransmission | Ligand | CB1 | -9.5690 | |
| Spironolactone | -0.526 | 2.9950E-01 | no | Hormone | Antagonist | Mineralocorticoid | -7.4931 | |
| SCH-202676 hydrobromide | 0.360 | 3.5948E-01 | no | G protein | Modulator | GPCR | -3.7669 | |
| D-Serine | -0.143 | 4.4320E-01 | no | Glutamate | Agonist | NMDA-Glycine | -4.1465 | |
| Albuterol hemisulfate | -0.949 | 1.7130E-01 | no | Adrenoceptor | Agonist | beta2 | -7.1289 | |
| N-Succinyl-L-proline | 0.725 | 2.3436E-01 | no | Neurotransmission | Inhibitor | ACE | -5.6487 | |
| Acetamide | -1.940 | 2.6178E-02 | no | Biochemistry | Inhibitor | Carbonic anhydrase | -2.0047 | |
| N-(4-Aminobutyl)-5-chloro-2-naphthalenesulfonamide | -0.923 | 1.7804E-01 | no | Intracellular Calcium | Antagonist | Calmodulin | -1.6370 | |
| L-azetidine-2-carboxylic acid | 0.984 | 1.6263E-01 | no | Biochemistry | Inhibitor | Collagen | -3.9080 | |

TABLE 10-continued

| Product Name | Z score | p value | Activity | Class | Action | Selectivity | Likelihood score | Cluster ID |
|---|---|---|---|---|---|---|---|---|
| p-Aminoclonidine hydrochloride | −0.048 | 4.8095E−01 | no | Adrenoceptor | Agonist | alpha2 | −8.3850 | |
| 3-aminobenzamide | −1.034 | 1.5048E−01 | no | Apoptosis | Inhibitor | PARS | −4.4936 | |
| (±)-Norepinephrine (+)bitartrate | 0.099 | 4.6056E−01 | no | Adrenoceptor | Agonist | | −10.1650 | |
| 4-Amino-1,8-naphthalimide | 1.875 | 3.0420E−02 | no | Apoptosis | Inhibitor | PARP | −1.0499 | |
| (±)-alpha-Lipoic Acid | 0.342 | 3.6624E−01 | no | Cell Stress | Coenzyme | Pyruvate dehydrogenase | −1.9717 | |
| DL-Thiorphan | −0.312 | 3.7768E−01 | no | Neurotransmission | Inhibitor | Enkephalinase | −6.4858 | |
| Tulobuterol hydrochloride | −1.767 | 3.8635E−02 | no | Adrenoceptor | Agonist | beta | −5.3849 | |
| Tyrphostin AG 34 | −2.319 | 1.0192E−02 | no | Phosphorylation | Inhibitor | Tyrosine kinase | −12.9224 | |
| Triamcinolone | −0.184 | 4.2701E−01 | no | Hormone | Agonist | Glucocorticoid | −7.5110 | |
| S(−)-Timolol maleate | −0.767 | 2.2140E−01 | no | Adrenoceptor | Antagonist | beta | −14.8252 | |
| Triprolidine hydrochloride | −0.406 | 3.4234E−01 | no | Histamine | Antagonist | HRH1 | −3.7367 | |
| Tyrphostin AG 112 | 0.333 | 3.6947E−01 | no | Phosphorylation | Inhibitor | Tyrosine kinase | −9.5119 | |
| Tyrphostin 1 | −0.642 | 2.6031E−01 | no | Phosphorylation | Inhibitor | EGFR | −9.6061 | |
| Tyrphostin 23 | −0.840 | 2.0056E−01 | no | Phosphorylation | Inhibitor | EGFR | −17.6797 | |
| TFPI hydrochloride | −1.156 | 1.2388E−01 | no | Nitric Oxide | Inhibitor | nNOS | −1.7477 | |
| Na-p-Tosyl-L-lysine chloromethyl ketone hydrochloride | 0.005 | 4.9808E−01 | no | Phosphorylation | Inhibitor | Adenylyl cyclase | −9.0928 | |
| Tyrphostin 25 | −0.259 | 3.9777E−01 | no | Phosphorylation | Inhibitor | EGFR | −14.8744 | |
| 1-[2-(Trifluoromethyl)phenyl]imidazole | −0.158 | 4.3738E−01 | no | Nitric Oxide | Inhibitor | NOS | −6.3332 | |
| SU 4312 | 0.269 | 3.9390E−01 | no | Phosphorylation | Inhibitor | KDR | −8.4051 | |
| SR 59230A oxalate | −1.222 | 1.1095E−01 | no | Adrenoceptor | Antagonist | beta3 | −11.1051 | |
| SKF 89976A hydrochloride | −0.233 | 4.0791E−01 | no | GABA | Inhibitor | GAT-1 | −0.1813 | |
| SIB 1757 | −1.752 | 3.9859E−02 | no | Glutamate | Antagonist | mGluR5 | −8.2872 | |
| SIB 1893 | −0.848 | 1.9822E−01 | no | Glutamate | Antagonist | mGluR5 | −4.4486 | |
| 1-(1-Naphthyl)piperazine hydrochloride | 0.230 | 4.0901E−01 | no | Serotonin | Agonist | 5-HT2 | −7.5485 | |
| 1-(2-Methoxyphenyl)piperazine hydrochloride | −0.639 | 2.6148E−01 | no | Serotonin | Agonist | 5-HT1 > 5-HT2 | −9.6082 | |
| Spiroxatrine | 0.122 | 4.5148E−01 | no | Serotonin | Agonist | 5-HT1A | −7.0795 | |
| SR-95531 | −0.957 | 1.6917E−01 | no | GABA | Antagonist | GABA-A | −4.7649 | |
| (±)-6-Chloro-PB hydrobromide | −2.267 | 1.1691E−02 | no | Dopamine | Agonist | D1 | −10.5959 | |
| SKF 91488 dihydrochloride | −0.766 | 2.2184E−01 | no | Histamine | Inhibitor | Histamine N-methyltransfe | −4.4216 | |
| Suramin hexasodium | 2.284 | 1.1174E−02 | no | P2 Receptor | Antagonist | P2X, P2Y | −16.9942 | |
| SQ 22536 | 0.562 | 2.8721E−01 | no | Cyclic Nucleotides | Inhibitor | Adenylyl cyclase | −4.4435 | |
| Sepiapterin | 1.795 | 3.6295E−02 | no | Nitric Oxide | Cofactor | NOS | −8.8178 | |
| R(−)-SCH-12679 maleate | 1.609 | 5.3786E−02 | no | Dopamine | Antagonist | D1 | −1.3407 | |
| (±)-SKF 38393, N-allyl-, hydrobromide | −1.590 | 5.5966E−02 | no | Dopamine | Agonist | D1 | −2.9637 | |
| SB 206553 hydrochloride | −1.365 | 8.6107E−02 | no | Serotonin | Antagonist | 5-HT2C/5-HT2B | −9.5886 | |
| L-Tryptophan | 0.224 | 4.1134E−01 | no | Serotonin | Precursor | | −17.6188 | |
| Tranilast | 0.174 | 4.3108E−01 | no | Leukotriene | Inhibitor | LTC4 | −6.2394 | |
| Taurine | 0.553 | 2.9710E−01 | no | Glycine | Agonist | | −2.4249 | |
| Tolbutamide | −0.303 | 3.8087E−01 | no | Hormone | Releaser | Insulin | −13.2463 | |
| Tetraethylthiuram disulfide | 2.347 | 9.4627E−03 | no | Biochemistry | Inhibitor | Alcohol Dehydrogenase | −2.7989 | |
| Tetraisopropyl pyrophosphoramide | −1.114 | 1.3262E−01 | no | Biochemistry | Inhibitor | Butylcholinesterase | −3.4763 | |
| Tetramisole hydrochloride | 2.649 | 4.0391E−03 | no | Phosphorylation | Inhibitor | Phosphatase | −9.6745 | |
| Trihexyphenidyl hydrochloride | 1.215 | 1.1219E−01 | no | Cholinergic | Antagonist | Muscarinic | −3.5988 | |
| Theophylline | 0.370 | 3.5573E−01 | no | Adenosine | Antagonist | A1 > A2 | −11.3611 | |
| (E)-4-amino-2-butenoic acid | −2.149 | 1.5824E−02 | no | GABA | Agonist | GABA-C | −5.0086 | |
| Tetradecylthioacetic acid | −0.324 | 3.7306E−01 | no | Transcription | Agonist | PPAR-alpha | −5.5493 | |
| Trequinsin hydrochloride | −0.971 | 1.6581E−01 | no | Cyclic Nucleotides | Inhibitor | PDE III | −4.8392 | |
| Tyrphostin AG 879 | −1.607 | 5.4042E−02 | no | Phosphorylation | Inhibitor | TrkA | −11.2234 | |
| Tetraethylammonium chloride | 0.123 | 4.5107E−01 | no | Cholinergic | Antagonist | Nicotinic | −0.9450 | |
| Tolazamide | 1.431 | 7.6219E−02 | no | Hormone | Releaser | Insulin | −13.2030 | |
| Terbutaline hemisulfate | 0.641 | 2.6079E−01 | no | Adrenoceptor | Agonist | beta | −8.9158 | |

TABLE 10-continued

| Product Name | Z score | p value | Activity Class | Action | Selectivity | Likelihood score | Cluster ID |
|---|---|---|---|---|---|---|---|
| 4-Hydroxyphenethylamine hydrochloride | 1.030 | 1.5154E-01 | no | Dopamine | Agonist | Reuptake | -2.6218 | |
| Trimipramine maleate | 0.568 | 2.8512E-01 | no | Serotonin | Inhibitor | Reuptake | -5.4862 | |
| Tyrphostin AG 490 | 1.802 | 3.5809E-02 | no | Phosphorylation | Inhibitor | JAK2 | -17.3461 | |
| TTNPB | -2.158 | 1.5472E-02 | no | Transcription | Ligand | RAR-alpha, beta gamma | -6.8131 | |
| Tetrahydrozoline hydrochloride | -0.469 | 3.1944E-01 | no | Adrenoceptor | Agonist | alpha | -6.7607 | |
| Tyrphostin AG 494 | -2.275 | 1.1443E-02 | no | Phosphorylation | Inhibitor | EGFR | -18.5744 | |
| N-p-Tosyl-L-phenylalanine chloromethyl ketone | 0.337 | 3.6819E-01 | no | Biochemistry | Cofactor | Chymotryprin alpha | -6.2244 | |
| (6R)-5,6,7,8-Tetrahydro-L-biopterin hydrochloride | 0.976 | 1.6460E-01 | no | Neurotransmission | Inhibitor | Tyrosine | -10.0438 | |
| Tyrphostin AG 527 | -1.607 | 5.3975E-02 | no | Phosphorylation | Inhibitor | EGFR | -20.3163 | |
| Theobromine | -1.392 | 8.1993E-02 | no | Adenosine | Antagonist | A1 > A2 | -8.7094 | |
| (±)-Taxifolin | 1.321 | 9.3301E-02 | no | Cell Stress | Inhibitor | Antioxidant | -12.8430 | |
| Tyrphostin AG 528 | -0.148 | 4.4112E-01 | no | Phosphorylation | Inhibitor | EGFR | -13.4954 | |
| Terazosin hydrochloride | -0.057 | 4.7719E-01 | no | Adrenoceptor | Antagonist | alpha1 | -1.6037 | |
| Tyrphostin AG 537 | -1.249 | 1.0589E-01 | no | Phosphorylation | Inhibitor | EGFR | -20.6782 | |
| Tyrphostin AG 555 | -0.681 | 2.4787E-01 | no | Phosphorylation | Inhibitor | EGFR | -20.1332 | |
| Tyrphostin AG 698 | 1.510 | 6.5504E-02 | no | Phosphorylation | Inhibitor | EGFR | -21.0985 | |
| Tyrphostin AG 808 | -1.315 | 9.4172E-02 | no | Phosphorylation | Inhibitor | Tyrosine kinase | -25.9684 | |
| Thio-NADP sodium | 0.366 | 3.5715E-01 | no | Intracellular Calcium | Blocker | NAADP-induced | -12.7713 | |
| Tyrphostin AG 835 | 2.230 | 1.2874E-02 | no | Phosphorylation | Inhibitor | Tyrosine kinase | -20.3163 | |
| Amantadine hydrochloride | -0.653 | 2.5684E-01 | no | Dopamine | Releaser | | -3.1592 | |
| Aminophylline ethylenediamine | -1.537 | 6.2146E-02 | no | Adenosine | Antagonist | A1/A2 | -15.7085 | |
| S-(p-Azidophenacyl)glutathione | -0.003 | 4.9890E-01 | no | Multi-Drug Resistance | Modulator | Glutathione S-transferase | -10.4568 | |
| N-Acetyl-5-hydroxytryptamine | -1.060 | 1.4447E-01 | no | Melatonin | Precursor | | -21.5479 | |
| Aurintricarboxylic acid | 0.571 | 2.8403E-01 | no | Apoptosis | Inhibitor | TopoII | -7.1275 | |
| (±)-2-Amino-4-phosphonobutyric acid | 1.893 | 2.9164E-02 | no | Glutamate | Antagonist | NMDA | -4.4713 | |
| N-arachidonylglycine | 0.387 | 3.4935E-01 | no | Cannabinoid | Inhibitor | FAAH | -4.2508 | |
| WIN 62,577 | 2.351 | 9.3727E-03 | no | Tachykinin | Antagonist | NK1 | -17.1837 | |
| S(−)-Willardiine | 1.251 | 1.0541E-01 | no | Glutamate | Agonist | AMPA/kainate | -7.1410 | |
| WAY-100635 maleate | -0.497 | 3.0976E-01 | no | Serotonin | Antagonist | 5-HT1A | -14.1470 | |
| S-5-Iodowillardiine | -0.355 | 3.6125E-01 | no | Glutamate | Agonist | AMPA | -6.9856 | |
| Xylazine hydrochloride | 0.375 | 3.5365E-01 | no | Adrenoceptor | Agonist | alpha2 | -8.1210 | |
| Xamoterol hemifumarate | -0.124 | 4.5053E-01 | no | Adrenoceptor | Agonist | beta1 | -15.3573 | |
| Xylometazoline hydrochloride | 0.296 | 3.8361E-01 | no | Adrenoceptor | Agonist | alpha | -1.2434 | |
| Xanthine amine congener | 0.001 | 4.9954E-01 | no | Adenosine | Antagonist | A1 | -24.1320 | |
| Yohimbine hydrochloride | -1.656 | 4.8820E-02 | no | Adrenoceptor | Antagonist | alpha2 | -2.0332 | |
| YC-1 | 0.433 | 3.3233E-01 | no | Cyclic Nucleotides | Activator | Guanylyl cyclase | -10.1316 | |
| Zonisamide sodium | -0.917 | 1.7959E-01 | no | Anticonvulsant | | | -8.1550 | |
| Zardaverine | -0.341 | 3.6646E-01 | no | Cyclic Nucleotides | Inhibitor | PDE III/PDE IV | -5.7003 | |
| Zimelidine dihydrochloride | -0.649 | 2.5817E-01 | no | Serotonin | Inhibitor | Reuptake | -4.1985 | |
| Tetracaine hydrochloride | -0.020 | 4.9221E-01 | no | Na+ Channel | Modulator | | -1.2589 | |
| Tyrphostin 47 | 0.178 | 4.2956E-01 | no | Phosphorylation | Inhibitor | EGFR | -19.4361 | |
| Tyrphostin 51 | -0.918 | 1.7939E-01 | no | Phosphorylation | Inhibitor | EGFR | -10.5293 | |
| T-1032 | -2.020 | 2.1672E-02 | no | Cyclic Nucleotides | Inhibitor | PDE V | -5.7604 | |
| I-OMe-Tyrphostin AG 538 | -0.737 | 2.3059E-01 | no | Phosphorylation | Inhibitor | IGF-1 RTK | -15.0767 | |
| Tyrphostin AG 538 | -0.395 | 3.4624E-01 | no | Phosphorylation | Inhibitor | IGF-1 RTK | -19.5274 | |
| Trimethoprim | -1.230 | 1.0940E-01 | no | Antibiotic | Inhibitor | Dihydrofolate inductase | -2.7962 | |
| Tomoxetine | 0.167 | 4.3359E-01 | no | Adrenoceptor | Inhibitor | Reuptake | -10.8802 | |
| T-0156 | 0.077 | 4.6928E-01 | no | Cyclic Nucleotides | Inhibitor | PDE V | -10.0449 | |
| D-609 potassium | -0.896 | 1.8503E-01 | no | Lipid | Inhibitor | PIPLC | -6.4571 | |
| Tyrphostin AG 126 | -0.410 | 3.4082E-01 | no | Phosphorylation | Inhibitor | TNFalpha | -16.9960 | |
| Terfenadine | 0.755 | 2.2503E-01 | no | Histamine | Antagonist | HRH1 | -3.2974 | |

TABLE 10-continued

| Product Name | Z score | p value | Activity | Class | Action | Selectivity | Likelihood score | Cluster ID |
|---|---|---|---|---|---|---|---|---|
| Tropicamide | 0.823 | 2.0533E-01 | no | Cholinergic | Antagonist | M4 | -15.2981 | |
| THIP hydrochloride | 0.361 | 3.5894E-01 | no | GABA | Agonist | GABA-A | -6.8890 | |
| Trifluperidol hydrochloride | -1.621 | 5.2465E-02 | no | Dopamine | Antagonist | D1/D2 | -5.7072 | |
| 3-Tropanyl-indole-3-carboxylate hydroiodide | -1.528 | 6.3309E-02 | no | Serotonin | Antagonist | 5-HT3 | -5.4495 | |
| Tracazolate | -0.315 | 3.7633E-01 | no | GABA | Modulator | | -10.9470 | |
| 3-Tropanylindole-3-carboxylate methiodide | -0.344 | 3.6556E-01 | no | Serotonin | Antagonist | 5-HT3 | -15.8039 | |
| Telenzepine dihydrochloride | 0.381 | 3.5148E-01 | no | Cholinergic | Antagonist | M1 | -3.9471 | |
| Thioperamide maleate | -0.154 | 4.3894E-01 | no | Histamine | Antagonist | H3 | -18.2620 | |
| (±)-Thalidomide | 0.521 | 3.0117E-01 | no | Cytoskeleton and ECM | Inhibitor | TNFalpha | -5.6805 | |
| R(+)-Terguride | -2.004 | 2.2512E-02 | no | Dopamine | Agonist | | -15.7008 | |
| Thiocitrulline | -0.147 | 4.4139E-01 | no | Nitric Oxide | Inhibitor | nNOS, eNOS | -7.7510 | |
| Tyrphostin A9 | -1.746 | 4.0363E-02 | no | Phosphorylation | Inhibitor | PDGFR | -9.9304 | |
| TPMPA | 0.874 | 1.9101E-01 | no | GABA | Antagonist | GABA-C | -5.8605 | |
| U-75302 | -0.172 | 4.3163E-01 | no | Leukotriene | Agonist | BLT1 | -8.3563 | |
| Uridine 5′-diphosphate sodium | 0.707 | 2.3966E-01 | no | P2 Receptor | Agonist | P2Y | -7.6702 | |
| U-73122 | -1.194 | 1.1617E-01 | no | Lipid | Inhibitor | PLC, A2 | -15.5197 | |
| SKF 95282 dimaleate | 0.424 | 3.3576E-01 | no | Histamine | Antagonist | H2 | -2.9694 | |
| 4-Imidazoleacrylic acid | -0.264 | 3.9608E-01 | no | Histamine | Inhibitor | Histidine ammonia-lyase/ | -12.7023 | |
| Urapidil hydrochloride | 0.157 | 4.3754E-01 | no | Adrenoceptor | Antagonist | alpha1 | -8.1990 | |
| Urapidil, 5-Methyl- | -0.783 | 2.1677E-01 | no | Adrenoceptor | Antagonist | alpha1A | -7.7682 | |
| U-69593 | -0.728 | 2.3336E-01 | no | Opioid | Agonist | kappa | -1.0973 | |
| UK 14,304 | -0.210 | 4.1672E-01 | no | Adrenoceptor | Agonist | alpha2 | -7.3309 | |
| U-10958 maleate | -2.065 | 1.9472E-02 | no | Dopamine | Antagonist | D4 | -4.7843 | |
| U0126 | 0.711 | 2.3855E-01 | no | Phosphorylation | Inhibitor | MEK1/MEK2 | -7.7131 | |
| (±)-Verapamil hydrochloride | 1.008 | 1.5666E-01 | no | Ca2+ Channel | Modulator | L-type | -1.4780 | |
| VUF 5574 | 0.581 | 2.8057E-01 | no | Adenosine | Antagonist | A3 | -7.2944 | |
| Vinpocetine | 0.433 | 3.3226E-01 | no | Cyclic Nucleotides | Inhibitor | PDE 1 | -0.0438 | |
| Vancomycin hydrochloride from *Streptomyces orientalis* | -0.064 | 4.7468E-01 | no | Antibiotic | | Cell wall synthesis | -0.4820 | |
| (±)-gamma-Vinyl GABA | -0.701 | 2.4166E-01 | no | GABA | Inhibitor | Transaminase | -1.7994 | |
| (±)Vesamicol hydrochloride | -1.967 | 2.4563E-02 | no | Cholinergic | Inhibitor | ACh storage | -4.9336 | |
| Wortmannin from *Penicillium funiculosum* | 0.408 | 3.4169E-01 | no | Phosphorylation | Inhibitor | PI3K | -8.7892 | |
| 1400W dihydrochloride | -0.275 | 3.9170E-01 | no | Nitric Oxide | Inhibitor | iNOS | -2.6662 | |
| WB 64 | -1.683 | 4.6151E-02 | no | Cholinergic | Ligand | M2 | -4.4336 | |
| (R)-(+)-WIN 55,212-2 mesylate | -0.681 | 2.4803E-01 | no | Cannabinoid | Agonist | | -1.2169 | |
| GABA | -0.439 | 3.3035E-01 | no | GABA | Agonist | | -2.7784 | |
| Acetyl-beta-methylcholine chloride | -0.338 | 3.6762E-01 | no | Cholinergic | Agonist | M1 | -1.7344 | |
| 5-azacytidine | -1.398 | 8.1104E-02 | no | DNA Metabolism | Inhibitor | DNA methyltransferase | -1.7173 | |
| 5-(N-Ethyl-N-isopropyl)amiloride | -0.289 | 3.8646E-01 | no | Ion Pump | Blocker | Na+/H+ Antiporter | -11.6381 | |
| 3-Aminopropionitrile fumarate | 1.234 | 1.0853E-01 | no | Multi-Drug Resistance | Substrate | CYP450 | -9.0810 | |
| Apigenin | 1.824 | 3.4069E-02 | no | Cell Cycle | Inhibitor | | -7.0447 | |
| Gabaculine hydrochloride | -2.256 | 1.2023E-02 | no | GABA | Inhibitor | GABA transaminase | -5.5637 | |
| AA-861 | 1.517 | 6.4696E-02 | no | Leukotriene | Inhibitor | 5-lipoxygenase | -3.1329 | |
| 9-Amino-1,2,3,4-tetrahydroacridine hydrochloride | -1.021 | 1.5361E-01 | no | Cholinergic | Inhibitor | Cholinesterase | -4.2209 | |
| AL-8810 | -1.806 | 3.5496E-02 | no | Prostaglandin | Antagonist | FP Receptor | -1.0281 | |
| 1-Aminobenzotriazole | 0.524 | 3.0028E-01 | no | Multi-Drug Resistance | Inhibitor | CYP450, chloroperoxidase | -3.6565 | |
| O-(Carboxymethyl)hydroxylamine hemihydrochloride | -2.058 | 1.9775E-02 | no | Biochemistry | Inhibitor | Aminotransferase | -3.5668 | |
| 5-(N,N-Dimethyl)amiloride hydrochloride | 2.396 | 8.2873E-03 | no | Ion Pump | Blocker | Na+/H+ Antiporter | -10.8889 | |
| Amiprilose hydrochloride | -0.778 | 2.1821E-01 | no | Immune System | Modulator | | -3.5961 | |
| Sandoz 58-035 | 0.332 | 3.6977E-01 | no | Lipid | Inhibitor | ACAT | -7.3180 | |
| (±)2-Amino-3-phosphonopropionic acid | 1.250 | 1.0569E-01 | no | Glutamate | Antagonist | NMDA | -3.8618 | |
| L-Arginine | 0.559 | 2.8802E-01 | no | Nitric Oxide | Precursor | | -3.9612 | |

TABLE 10-continued

| Product Name | Z score | p value | Activity Class | | Action | Selectivity | Likelihood score | Cluster ID |
|---|---|---|---|---|---|---|---|---|
| (±)-2-Amino-7-phosphenoheptanoic acid | −1.020 | 1.5391E−01 | Glutamate | no | Antagonist | NMDA | −4.2353 | |
| (±)-2-Amino-5-phosphonopentanoic acid | −1.045 | 1.4797E−01 | Glutamate | no | Antagonist | NMDA | −4.3519 | |
| L-732,138 | 0.503 | 3.0758E−01 | Tachykinin | no | Antagonist | NK1 > NK2, NK3 | −13.3105 | |
| Acetylsalicyclic acid | −0.481 | 3.1520E−01 | Prostaglandin | no | Inhibitor | COX-3 > COX-1 > COX-2 | −4.6918 | |
| 5-(N-Methyl-N-isobutyl)amiloride | 1.871 | 3.0654E−02 | Ion Pump | no | Blocker | Na+/H+ Antiporter | −11.0245 | |
| Acetylthiocholine chloride | 0.004 | 4.9832E−01 | Cholinergic | no | Agonist | Nicotinic | −4.7778 | |
| 4-Androsten-4-ol-3,17-dione | 0.194 | 4.2293E−01 | Hormone | no | Inhibitor | Aromatase | −14.8147 | |
| 2-(2-Aminoethyl)isothiourea dihydrobromide | −1.251 | 1.0541E−01 | Nitric Oxide | no | Inhibitor | NOS | −2.9427 | |
| cis-Azetidine-2,4-dicarboxylic acid | −2.251 | 1.2198E−02 | Glutamate | no | Agonist | NMDA | −3.5649 | |
| trans-Azetidine-2,4-dicarboxylic acid | −0.349 | 3.6350E−01 | Glutamate | no | Modulator | mGluR1, mGluR5 | −3.5649 | |
| AGN 192403 hydrochloride | 0.703 | 2.4098E−01 | Imidazoline | no | Ligand | I1 | −4.7455 | |
| AIDA | 0.154 | 4.3880E−01 | Glutamate | no | Antagonist | mGluR1 | −7.5362 | |
| A-77636 hydrochloride | 1.440 | 7.4902E−02 | Dopamine | no | Agonist | D1 | −5.7649 | |
| ATPA | 0.283 | 3.8853E−01 | Glutamate | no | Agonist | | −10.2981 | |
| ARL 67156 trisodium salt | −0.168 | 4.3329E−01 | P2 Receptor | no | Inhibitor | Ecto-ATPase | −9.5979 | |
| Beclomethasone | 0.267 | 3.9475E−01 | Hormone | no | Agonist | Glucocorticoid | −9.5218 | |
| 2,3-Butanedione monoxime | −1.810 | 3.5125E−02 | K+ Channel | no | Blocker | ATP-sensitive | −3.0410 | |
| SB 222200 | −1.695 | 4.5077E−02 | Tachykinin | no | Antagonist | NK3 | −0.3519 | |
| 1-benzoyl-5-methoxy-2-methylindole-3-acetic acid | −0.955 | 1.6978E−01 | Multi-Drug Resistance | no | Inhibitor | MRP1 | −1.2294 | |
| p-Benzoquinone | −1.571 | 5.8049E−02 | DNA Repair | no | Inhibitor | G:C site | −1.6650 | |
| 8-Bromo-cGMP sodium | −1.005 | 1.5751E−01 | Cyclic Nucleotides | no | Activator | | −12.4831 | |
| Bromoenol lactone | 0.248 | 4.0190E−01 | Lipid | no | Inhibitor | PLA2 | −2.8194 | |
| Benzamide | 0.550 | 2.9122E−01 | Apoptosis | no | Inhibitor | PARS | −2.6316 | |
| N-Acetyl-L-Cysteine | −1.621 | 5.2499E−02 | Glutamate | no | Antagonist | | −4.6646 | |
| N-Acetyltryptamine | 1.020 | 1.5384E−01 | Melatonin | no | Agonist - An | | −17.6160 | |
| (±)-Atenolol | −0.658 | 2.5518E−01 | Adrenoceptor | no | Antagonist | beta1 | −14.7808 | |
| 5alpha-Androstane-3alpha,17beta-diol | −0.381 | 3.5156E−01 | Hormone | no | Metabolite | Androgen | −15.2440 | |
| L-allylglycine | 0.147 | 4.4145E−01 | Cell Stress | no | Inhibitor | Xanthine oxidase | −3.9370 | |
| Amiodarone hydrochloride | 0.929 | 1.7639E−01 | Adrenoceptor | no | Agonist | alpha/beta | −0.5073 | |
| 4-(2-Aminoethyl)benzenesulfonyl fluoride hydrochloride | 0.363 | 3.5814E−01 | Biochemistry | no | Inhibitor | Serine Protease | −6.0757 | |
| Alprenolol hydrochloride | −2.143 | 1.6057E−02 | Adrenoceptor | no | Antagonist | beta | −15.2992 | |
| Altretamine | −1.322 | 9.3085E−02 | DNA Metabolism | no | Inhibitor | | −1.0683 | |
| N-Acetyldopamine monohydrate | 0.467 | 3.2034E−01 | Dopamine | no | Precursor | | −11.2009 | |
| Aminoguanidine hydrochloride | −0.001 | 4.9971E−01 | Nitric Oxide | no | Inhibitor | NOS | −2.9994 | |
| BW 284c51 | −0.402 | 3.4396E−01 | Cholinergic | no | Inhibitor | Acetylcholinesterase | −4.8061 | |
| Adenosine | −0.209 | 4.1740E−01 | Adenosine | no | Agonist | | −2.9711 | |
| L-Aspartic acid | 0.163 | 4.3519E−01 | Glutamate | no | Agonist | | −3.3129 | |
| N-(4-Amino-2-chlorophenyl)phthalimide | −0.602 | 2.7356E−01 | Anticonvulsant | no | | | −4.4471 | |
| Adenosine 3′,5′-cyclic monophosphate | −1.188 | 1.1734E−01 | Phosphorylation | no | Activator | PKA | −7.9942 | |
| L-(−)-Norepinephrine bitartrate | −1.418 | 7.8127E−02 | Adrenoceptor | no | Agonist | alpha, beta1 | −10.1650 | |
| 5-(N,N-hexamethylene)amiloride | 0.039 | 4.8462E−01 | Ion Pump | no | Inhibitor | Na+/H+ Antiporter | −13.0169 | |
| 4-Androstene-3,17-dione | −0.692 | 2.4458E−01 | Hormone | no | Precursor | Androgen | −13.5513 | |
| (±)-p-Aminoglutethimide | −0.444 | 3.2849E−01 | Biochemistry | no | Inhibitor | P450-dependendent hydroxy | −3.6754 | |
| (±)-HA-966 | 1.157 | 1.2368E−01 | Glutamate | no | Antagonist | NMDA-glycine | −4.5024 | |
| Androsterone | 1.947 | 2.5753E−02 | Hormone | no | | Androgen | −17.5390 | |
| Antozoline hydrochloride | 0.485 | 3.1371E−01 | Imidazoline | no | Agonist | | −4.4195 | |
| Aniracetam | −1.355 | 8.7788E−02 | Glutamate | no | Agonist | AMPA | −6.1620 | |

TABLE 10-continued

| Product Name | Z score | p value | Activity Class | Action | Selectivity | Likelihood score | Cluster ID |
|---|---|---|---|---|---|---|---|
| 1,3-Diethyl-8-phenylxanthine | 2.005 | 2.2458E-02 | no | Adenosine | Antagonist | A1 | -20.0593 | |
| 8-(p-Sulfophenyl)theophylline | 1.047 | 1.4759E-01 | no | Adenosine | Antagonist | A1 > A2 | -19.8946 | |
| 1,3-Dipropyl-8-p-sulfophenylxanthine | 4.743 | 1.0546E-06 | no | Adenosine | Antagonist | A1 > A2 | -22.1456 | |
| 2-Methylthioadenosine triphosphate tetrasodium | -0.776 | 2.1877E-01 | no | P2 Receptor | Agonist | P2Y | -0.6760 | |
| Adenosine amine congener | -0.334 | 3.8901E-01 | no | Adenosine | Agonist | A1 | -4.4147 | |
| Amoxapine | -1.041 | 1.4885E-01 | no | Adrenoceptor | Inhibitor | Uptake | -6.0297 | |
| R(+)-Atenolol | 3.764 | 8.3501E-05 | no | Adrenoceptor | Antagonist | beta1 | -14.7808 | |
| S(−)-Atenolol | 0.617 | 2.6861E-01 | no | Adrenoceptor | Antagonist | beta1 | -14.7808 | |
| 1-Allyl-3,7-dimethyl-8-p-sulfophenylxanthine | -2.178 | 1.4691E-01 | no | Adenosine | Antagonist | A2 | -13.2461 | |
| trans-(±)-ACPD | 0.315 | 3.7642E-01 | no | Glutamate | Agonist | Metabotropic | -2.0313 | |
| 1-Amino-1-cyclohexanecarboxylic acid hydrochloride | -0.749 | 2.2678E-01 | no | Neurotransmission | Substrate | | -1.3026 | |
| Alaproclate hydrochloride | -0.172 | 4.3153E-01 | no | Serotonin | Inhibitor | Reuptake | -1.0468 | |
| Rp-cAMPS triethylamine | 1.186 | 1.1788E-01 | no | Phosphorylation | Inhibitor | PKA | -12.7973 | |
| SB 200646 hydrochloride | 2.437 | 7.3995E-03 | no | Serotonin | Antagonist | 5-HT2C/2B | -11.7331 | |
| D(−)-2-Amino-7-phosphonoheptanoic acid | 0.985 | 1.6220E-01 | no | Glutamate | Antagonist | NMDA | -4.2353 | |
| Acetohexamide | -2.240 | 1.2547E-02 | no | Hormone | Releaser | Insulin | -12.1480 | |
| SKF 97541 hydrochloride | -0.736 | 2.3101E-01 | no | GABA | Agonist | GABA-B | -3.2485 | |
| cis-4-Aminocrotonic acid | -1.088 | 1.3840E-01 | no | GABA | Agonist | GABA-C | -5.0086 | |
| N6-(4-Aminophenyl)ethyladenosine | -1.323 | 9.2944E-02 | no | Adenosine | Agonist | A3 | -7.3150 | |
| Agroclavine | -0.911 | 1.8116E-01 | no | Dopamine | Agonist | | -10.9663 | |
| gamma-Acetylinic GABA | 1.285 | 9.9459E-02 | no | GABA | Inhibitor | GABA transaminase | -2.0503 | |
| AB-MECA | 0.760 | 2.2351E-01 | no | Adenosine | Agonist | A3 | -6.1580 | |
| Alloxazine | -0.442 | 3.2909E-01 | no | Adenosine | Antagonist | A2b | -5.0147 | |
| CGP-7930 | -0.411 | 3.4052E-01 | no | GABA | Modulator | GABA-B | -2.6698 | |
| CGP-13501 | -1.096 | 1.3653E-01 | no | GABA | Modulator | GABA-B | -2.8414 | |
| CP55940 | 1.396 | 8.1367E-02 | no | Cannabinoid | Agonist | | -6.5601 | |
| L-Cycloserine | -0.155 | 4.4334E-01 | no | Sphingolipid | Inhibitor | Ketosphinganine synthetas | -5.7186 | |
| (+)-Catechin Hydrate | 0.511 | 3.0484E-01 | no | Cell Stress | Inhibitor | Antioxidant | -11.1574 | |
| Chlopropamide | -0.190 | 4.2463E-01 | no | Hormone | Releaser | Insulin | -9.0400 | |
| 1-(4-Chlorobenzyl)-5-methoxy-2-methylindole-3-acetic acid | -1.584 | 5.6573E-02 | no | Multi-Drug Resistance | Inhibitor | MRP1 | -9.0898 | |
| Choline bromide | -0.730 | 2.3268E-01 | no | Cholinergic | Substrate | Choline acetyltransferase | -2.6283 | |
| Ceramide | -0.827 | 2.0421E-01 | no | Phosphorylation | Inhibitor | Diacylglycerol kinase | -0.7919 | |
| CB 1954 | -1.070 | 1.4227E-01 | no | DNA | Intercalator | | -7.7981 | |
| Carcinine dihydrochloride | -1.023 | 1.5311E-01 | no | Cell Stress | Inhibitor | Antioxidant | -10.2686 | |
| Corticosterone | -2.285 | 1.1148E-02 | no | Hormone | Agonist | Glucocorticoid | -8.9885 | |
| Cortisone | -0.581 | 2.8073E-01 | no | Hormone | Agonist | Corticosteroid | -8.5526 | |
| 3-Bromo-7-nitroindazole | -1.680 | 4.6484E-02 | no | Nitric Oxide | Inhibitor | NOS | -9.6580 | |
| (+)-Bromocriptine methanesulfonate | 0.028 | 4.8886E-01 | no | Dopamine | Agonist | DRD2 | -21.8304 | |
| O6-benzylguanine | -1.177 | 1.1967E-01 | no | DNA Repair | Inhibitor | | -6.8215 | |
| N-Bromoacetamide | -1.362 | 8.6669E-02 | no | Na+ Channel | Modulator | | -1.7090 | |
| Benzamil hydrochloride | -1.054 | 1.4591E-01 | no | Ion Pump | Blocker | Na+/H+, Na+/Ca2+ Pump | -5.3837 | |
| L-Buthionine-sulfoximine | 0.513 | 3.0383E-01 | no | Multi-Drug Resistance | Inhibitor | | -5.7085 | |
| DL-Buthionine-[S,R]-sulfoximine | -1.022 | 1.5341E-01 | no | Multi-Drug Resistance | Inhibitor | | -5.7085 | |
| Bumetanide | -2.182 | 1.4545E-02 | no | Ion Pump | Inhibitor | Na+K+2Cl− cotransporter | -5.3951 | |
| Betaine aldehyde chloride | -0.070 | 4.7207E-01 | no | Cholinergic | Metabolite | Choline dehydrogenase | -2.4729 | |
| Benazoline oxalate | -0.335 | 3.6890E-01 | no | Imidazoline | Agonist | I2 | -5.9911 | |
| BWB70C | -0.893 | 1.8586E-01 | no | Leukotriene | Inhibitor | 5-lipoxygenase | -2.7024 | |
| 5-Bromo-2′-deoxyuridine | 2.580 | 4.9400E-03 | no | DNA Metabolism | Inhibitor | | -3.6110 | |
| SB 202190 | -1.069 | 1.4250E-01 | no | Phosphorylation | Inhibitor | p38 MAPK | -7.7439 | |
| (±)-Baclofen | -1.124 | 1.3042E-01 | no | GABA | Agonist | GABA-B | -8.6028 | |
| Bay 11-7085 | 2.180 | 1.4646E-02 | no | Cell Cycle | Inhibitor | IkB-alpha | -8.0406 | |

TABLE 10-continued

| Product Name | Z score | p value | Activity | Class | Action | Selectivity | Likelihood score | Cluster ID |
|---|---|---|---|---|---|---|---|---|
| Betaxolol hydrochloride | 0.984 | 1.6260E-01 | no | Adrenoceptor | Antagonist | beta1 | -14.7476 | |
| Betamethasone | 0.881 | 1.8913E-01 | no | Hormone | | Glucocorticoid | -9.5218 | |
| Buspirone hydrochloride | -1.775 | 3.7910E-02 | no | Serotonin | Agonist | 5-HT1A | -8.0068 | |
| Benserazide hydrochloride | 0.007 | 4.9702E-01 | no | Biochemistry | Inhibitor | Decarboxylase | -7.5822 | |
| Budesonide | -1.994 | 2.3069E-02 | no | Hormone | | Cortisol | -4.0628 | |
| 8-Bromo-cAMP sodium | 2.309 | 1.0469E-02 | no | Cyclic Nucleotides | Activator | cAMP phosphodiesterase | -13.0857 | |
| Ro 20-1724 | 0.587 | 2.7848E-01 | no | Cyclic Nucleotides | Inhibitor | cAMP phosphodiesterase | -4.4839 | |
| Bestatin hydrochloride | 0.643 | 2.6004E-01 | no | Biochemistry | Inhibitor | Aminopeptidase | -6.6215 | |
| Bretylium tosylate | -0.002 | 4.9932E-01 | no | Adrenoceptor | Blocker | | -8.8373 | |
| BP 897 | -1.715 | 4.3173E-02 | no | Dopamine | Agonist | D3 | -6.2599 | |
| (E)-5-(2-Bromovinyl)-2'-deoxyuridine | -2.123 | 1.6863E-02 | no | Immune System | Inhibitor | HSV1 | -2.5745 | |
| Chloroethylclonidine dihydrochloride | 0.861 | 1.9473E-01 | no | Adrenoceptor | Antagonist | alpha1B | -7.8626 | |
| 6-Fluoronorepinephrine hydrochloride | -1.168 | 1.2140E-01 | no | Adrenoceptor | Agonist | alpha | -6.6614 | |
| Bromoacetyl alprenolol menthane | 1.442 | 7.4623E-02 | no | Adrenoceptor | Antagonist | beta | -14.5755 | |
| Benoxathian hydrochloride | 0.265 | 3.9540E-01 | no | Adrenoceptor | Antagonist | alpha1 | -7.3187 | |
| Phenoxybenzamine hydrochloride | -1.512 | 6.5240E-02 | no | Adrenoceptor | Blocker | alpha | -2.5903 | |
| Bupropion hydrochloride | 0.267 | 3.9469E-01 | no | Dopamine | Blocker | Reuptake | -3.1372 | |
| (±)Bay K 8644 | 0.853 | 1.9691E-01 | no | Ca2+ Channel | Agonist | L-type | -9.8317 | |
| Bromoacetylcholine bromide | -0.355 | 3.6139E-01 | no | Cholinergic | Ligand | | -4.7430 | |
| BMY 7378 dihydrochloride | -0.659 | 2.5500E-01 | no | Serotonin | Agonist | 5-HT1A | -8.6878 | |
| R(+)-6-Bromo-APB hydrobromide | 1.532 | 6.2732E-02 | no | Dopamine | Agonist | D1/D5 | -6.4948 | |
| N6-Benzyl-5'-N-ethylcarboxamidoadenosine | -0.798 | 2.1254E-01 | no | Adenosine | Agonist | A3 | -4.0973 | |
| BU224 hydrochloride | 0.404 | 3.4294E-01 | no | Imidazoline | Antagonist | I2 | -6.6354 | |
| B-HT 933 dihydrochloride | -1.280 | 1.0022E-01 | no | Adrenoceptor | Agonist | alpha2 | -0.5572 | |
| BRL 37344 sodium | -1.725 | 4.2299E-02 | no | Adrenoceptor | Agonist | beta3 | -6.1685 | |
| BRL 54443 maleate | 0.338 | 3.6775E-01 | no | Serotonin | Agonist | 5-HT1E/1F | -17.4858 | |
| BW 723C86 | 0.725 | 2.3431E-01 | no | Serotonin | Agonist | 5-HT2B | -17.1873 | |
| Citicoline sodium | -0.133 | 4.4704E-01 | no | Lipid | Inhibitor | PLA2 | -1.5676 | |
| Ciprofibrate | -1.326 | 9.2430E-02 | no | Transcription | Ligand | PPAR-alpha | -7.0194 | |
| 6-Chloromelatonin | -1.659 | 4.8549E-02 | no | Melatonin | Agonist | | -16.1502 | |
| Carmustine | 2.191 | 1.4231E-02 | no | DNA | Intercalator | | -5.6758 | |
| PK 11195 | -0.468 | 3.2005E-01 | no | GABA | Antagonist | Benzodiazepine | -5.6993 | |
| Caffeic Acid | 0.320 | 3.7452E-01 | no | Cell Stress | Inhibitor | Antioxidant | -12.2125 | |
| Cilostazol | 0.822 | 2.0558E-01 | no | Cyclic Nucleotides | Inhibitor | PDE III | -6.1607 | |
| Caffeine | 0.411 | 3.4041E-01 | no | Adenosine | Inhibitor | Phosphodiesterase | -14.5759 | |
| Cyclophosphamide monohydrate | -0.976 | 1.6459E-01 | no | DNA | Intercalator | | -5.5771 | |
| Caffeic acid phenethyl ester | 1.306 | 9.5730E-02 | no | Cell Cycle | Inhibitor | NFkB | -11.5965 | |
| Cinoxacin | -1.095 | 1.3684E-01 | no | Antibiotic | | | -0.0911 | |
| Carisoprodol | -1.795 | 3.6351E-02 | no | Neurotransmission | | Skeletal muscle | -6.6522 | |
| Centrophenoxine hydrochloride | -0.330 | 3.7061E-01 | no | Nootropic | | | -0.6260 | |
| Clemastine fumarate | -2.023 | 2.1547E-02 | no | Histamine | Antagonist | HRH1 | -5.4913 | |
| beta-Chloro-L-alanine hydrochloride | -1.390 | 8.2254E-02 | no | Biochemistry | Inhibitor | Alanine aminotransferase | -3.1222 | |
| Pyrocatechol | -2.053 | 2.0033E-02 | no | Cell Cycle | Inhibitor | | -2.1080 | |
| CPCCOEt | -0.807 | 2.0990E-01 | no | Glutamate | Antagonist | mGluR1 | -6.4393 | |
| L-Canavanine sulfate | -0.902 | 1.8343E-01 | no | Nitric Oxide | Inhibitor | iNOS | -5.4287 | |
| Cortisone 21-acetate | -2.218 | 1.3282E-02 | no | Hormone | | Cortisol | -9.8430 | |
| Cyproterone acetate | -1.803 | 3.5658E-02 | no | Hormone | Antagonist | Androgen | -7.0698 | |
| DL-p-Chlorophenylalanine methyl ester hydrochloride | 0.128 | 4.4922E-01 | no | Neurotransmission | Inhibitor | Tryptophan hydroxylase | -3.4208 | |
| Ciclosporin | -0.186 | 4.2628E-01 | no | Phosphorylation | Inhibitor | Calcineurin phosphatase | -6.2107 | |
| D-Cycloserine | -1.240 | 1.0748E-01 | no | Glutamate | Agonist | NMDA-Glycine | -5.7186 | |
| 8-(4-Chlorophenylthio)-cAMP sodium | 1.217 | 1.1188E-01 | no | Cyclic Nucleotides | Activator | | -10.7572 | |

TABLE 10-continued

| Product Name | Z score | p value | Activity | Class | Action | Selectivity | Likelihood score | Cluster ID |
|---|---|---|---|---|---|---|---|---|
| Carbamazepine | 1.114 | 1.3255E-01 | no | Anticonvulsant | | | -5.5460 | |
| Captopril | -1.285 | 9.9379E-02 | no | Neurotransmission | Inhibitor | ACE | -6.0164 | |
| Carbachol | -0.034 | 4.8651E-01 | no | Cholinergic | Agonist | | -7.3897 | |
| Chlorzoxazone | -1.496 | 6.7306E-02 | no | Nitric Oxide | Inhibitor | iNOS | -2.0853 | |
| L-Cysteinesulfinic Acid | 1.458 | 7.2457E-02 | no | Glutamate | Ligand | | -4.0432 | |
| 9-cyclopentyladenine | 0.499 | 3.0895E-01 | no | Cyclic Nucleotides | Inhibitor | Adenylate cyclase | -1.7579 | |
| Cimetidine | 1.665 | 4.7922E-02 | no | Histamine | Antagonist | H2 | -15.6553 | |
| Cyclobenzaprine hydrochloride | 0.072 | 4.7136E-01 | no | Serotonin | Antagonist | 5-HT2 | -0.3834 | |
| Clemizole hydrochloride | 2.788 | 2.6501E-03 | no | Histamine | Antagonist | HRH1 | -4.3715 | |
| 2-Chloroadenosine | -0.396 | 3.4604E-01 | no | Adenosine | Agonist | A1 > A2 | -4.4821 | |
| Bethanechol chloride | -0.649 | 2.5807E-01 | no | Cholinergic | Agonist | Muscarinic | -3.3990 | |
| Cinnarizine | -1.375 | 8.4610E-02 | no | Ca2+ Channel | Blocker | | -2.7921 | |
| 1-(3-Chlorophenyl)piperazine dihydrochloride | 0.952 | 1.7066E-01 | no | Serotonin | Agonist | 5-HT1 | -0.9409 | |
| SB 204741 | -2.299 | 1.0744E-02 | no | Serotonin | Antagonist | 5-HT2B | -10.7182 | |
| 4-Chloromercuribenzoic acid | -0.032 | 4.8726E-01 | no | Biochemistry | Inhibitor | | -4.9331 | |
| (-)-Cotinine | -0.510 | 3.0507E-01 | no | Cholinergic | Metabolite | Nicotinic | -9.2586 | |
| CL 316,243 | 0.621 | 2.6722E-01 | no | Adrenoceptor | Agonist | beta3 | -9.7686 | |
| 7-Chloro-4-hydroxy-2-phenyl-1,8-naphthyridine | -0.401 | 3.4422E-01 | no | Adenosine | Antagonist | A1 | -6.1894 | |
| Clotrimazole | -0.716 | 2.3705E-01 | no | K+ Channel | Inhibitor | Ca2+-activated K+ channel | -1.7128 | |
| Cyproheptadine hydrochloride | 1.232 | 1.0898E-01 | no | Serotonin | Antagonist | 5-HT2 | -5.8370 | |
| 5′-(N-Cyclopropyl)carboxamidoadenosine | -1.701 | 4.4454E-02 | no | Adenosine | Agonist | A2 | -0.6480 | |
| Cefmetazole sodium | 2.503 | 6.1504E-03 | no | Antibiotic | | Cell wall synthesis | -3.7838 | |
| Clozapine | 0.547 | 2.9208E-01 | no | Dopamine | Antagonist | D4 > D2, D3 | -3.3166 | |
| DL-Cycloserine | -0.247 | 4.0241E-01 | no | Neurotransmission | Inhibitor | Tryptophan hydroxylase | -4.5617 | |
| McN-A-343 | -1.738 | 4.1149E-02 | no | Cholinergic | Modulator | Lipoprotein lipase | -4.1199 | |
| Clofibrate | -1.081 | 1.3979E-01 | no | Lipid | Ligand | | -5.9593 | |
| CB34 | -0.299 | 3.8263E-01 | no | Benzodiazepine | | | -5.7186 | |
| Cystamine dihydrochloride | -0.089 | 4.6455E-01 | no | Sphingolipid | Inhibitor | Ketosphinganine synthase, | -4.9137 | |
| Calcimycin | 2.230 | 1.2874E-02 | no | Cholinergic | Agonist | M1 | -0.9068 | |
| Cantharidin | 2.172 | 1.4942E-02 | no | Glutamate | Inhibitor | Transglutaminase | -11.3039 | |
| Citalopram hydrobromide | -0.578 | 2.8158E-01 | no | Intracellular Calcium | | Ca2+ | -3.0587 | |
| Clonidine hydrochloride | -1.858 | 3.1616E-02 | no | Phosphorylation | Inhibitor | PP2A | -4.9204 | |
| Cilostamide | 1.041 | 1.4898E-01 | no | Serotonin | Inhibitor | Reuptake | -8.6158 | |
| Chelidamic acid | 0.176 | 4.3029E-01 | no | Adrenoceptor | Agonist | alpha2 | -7.2538 | |
| Cantharidic Acid | 0.726 | 2.3390E-01 | no | Cyclic Nucleotides | Inhibitor | PDE III | -5.4374 | |
| Phenytoin sodium | -0.784 | 2.1655E-01 | no | Glutamate | Inhibitor | L-glutamic decarboxylate | -3.3957 | |
| S(-)Pindolol | -0.553 | 2.9016E-01 | no | Adenosine | Agonist | A1 | -4.0610 | |
| (-)-alpha-Methylnorepinephrine | -0.217 | 4.1428E-01 | no | Phosphorylation | Inhibitor | PP1/PP2A | -7.1884 | |
| Dilazep hydrochloride | -0.965 | 1.6722E-01 | no | Anticonvulsant | Antagonist | beta | -25.5497 | |
| 1,7-Dimethylxanthine | 1.193 | 1.1634E-01 | no | Adrenergic | Agonist | | -6.3305 | |
| Daphnetin | 0.245 | 4.0329E-01 | no | Adrenoceptor | Inhibitor | Uptake | -4.5746 | |
| DM 235 | -0.662 | 2.5390E-01 | no | Adenosine | Antagonist | A1 > A2 | -7.6830 | |
| 5,5-Dimethyl-1-pyrroline-N-oxide | -0.980 | 1.6359E-01 | no | Phosphorylation | Inhibitor | PK | -7.3553 | |
| Diacylglycerol Kinase Inhibitor II | -2.019 | 2.1731E-02 | no | Nootropic | | | -6.9226 | |
| Dihydrexidine hydrochloride | -1.666 | 4.7874E-02 | no | Cell Stress | Inhibitor | Antioxidant | -3.0181 | |
| N-Methyldopamine hydrochloride | -1.390 | 8.2282E-02 | no | Phosphorylation | Inhibitor | Diacylglycerol kinase | -3.7809 | |
| 1,1-Dimethyl-4-phenyl-piperazinium iodide | -0.415 | 3.3896E-01 | no | Dopamine | Agonist | D1 | -5.3869 | |
| Cyclothiazide | -1.219 | 1.1143E-01 | no | Cholinergic | Agonist | | -11.1570 | |
| 8-Cyclopentyl-1,3-dipropylxanthine | -1.057 | 1.4522E-01 | no | Glutamate | Agonist | AMPA | -2.2053 | |
| | -0.907 | 1.8221E-01 | no | Adenosine | Antagonist | A1 | -2.7150 | |
| | -0.070 | 4.7201E-01 | no | | | | -21.9125 | |

TABLE 10-continued

| Product Name | Z score | p value | Activity | Class | Action | Selectivity | Likelihood score | Cluster ID |
|---|---|---|---|---|---|---|---|---|
| 8-Cyclopentyl-1,3-dimethylxanthine | -0.125 | 4.5035E-01 | no | Adenosine | Antagonist | A1 | -20.3794 | |
| (±)-CPP | 0.321 | 3.7398E-01 | no | Glutamate | Antagonist | NMDA | -4.3608 | |
| 2-Cyclooctyl-2-hydromethylamine hydrochloride | -0.575 | 2.8276E-01 | no | Neurotransmission | Inhibitor | PNMT | -3.8688 | |
| 5-Carboxamidotryptamine maleate | 1.667 | 4.7711E-02 | no | Serotonin | Agonist | 5-HT7 | -19.4950 | |
| 7-Chlorokynurenic acid | 1.241 | 1.0733E-01 | no | Glutamate | Antagonist | NMDA | -4.9223 | |
| (±)CGP-12177A hydrochloride | -1.611 | 5.5344E-02 | no | Adrenoceptor | Agonist | beta | -15.3877 | |
| S-(-)-Carbidopa | -2.314 | 1.0324E-02 | no | Biochemistry | Inhibitor | Aromatic amino acid decar | -8.9751 | |
| (±)-Chloro-APB dihydrobromide | -0.111 | 4.5581E-01 | no | Dopamine | Agonist | D1 | -6.3740 | |
| Y-27632 dihydrochloride | -0.125 | 4.5007E-01 | no | Phosphorylation | Inhibitor | ROCK | -7.9142 | |
| 2-Chloroadenosine triphosphate tetrasodium | 1.149 | 1.2531E-01 | no | P2 Receptor | Agonist | P2Y | -8.8552 | |
| (+)-Cyclazocine | 0.612 | 2.7040E-01 | no | Opioid | Antagonist | | -1.0736 | |
| Capsazepine | 1.260 | 1.0386E-01 | no | Vanilloid | Agonist | | -7.7040 | |
| Chlormezanone | -0.947 | 1.7194E-01 | no | Neurotransmission | Modulator | Muscle relaxant | -6.2721 | |
| 8-(3-Chlorostyryl)caffeine | -1.214 | 1.1231E-01 | no | Adenosine | Antagonist | A2A | -12.4931 | |
| CGS-15943 | 0.178 | 4.2922E-01 | no | Adenosine | Antagonist | A1 | -6.3372 | |
| Cirazoline hydrochloride | 0.424 | 3.3580E-01 | no | Adrenoceptor | Agonist | alpha1A | -6.6318 | |
| CGP 20712A methanesulfonate | 0.649 | 2.5815E-01 | no | Adrenoceptor | Antagonist | beta1 | -13.7874 | |
| (2S,1'S,2'S)-2-(carboxycyclopropyl)glycine | 1.233 | 1.0878E-01 | no | Glutamate | Agonist | mGluR2 | -5.6999 | |
| CNQX disodium | -1.904 | 2.8471E-02 | no | Glutamate | Antagonist | AMPA/Kainate | -8.1220 | |
| CX 546 | -1.050 | 1.4686E-01 | no | Glutamate | Modulator | AMPA | -5.5188 | |
| Chloro-IB-MECA | -0.847 | 1.9846E-01 | no | Adenosine | Agonist | A3 | -5.2500 | |
| WB-4101 hydrochloride | -2.247 | 1.2321E-02 | no | Adrenoceptor | Antagonist | alpha1A | -7.3187 | |
| DNQX | 0.931 | 1.7599E-01 | no | Glutamate | Antagonist | Kainate/quisqualate | -6.4394 | |
| Dihydroouabain | 0.203 | 4.1942E-01 | no | Ion Pump | Inhibitor | Na+/K+ Pump | -5.4302 | |
| Dobutamine hydrochloride | 0.319 | 3.7505E-01 | no | Adrenoceptor | Agonist | beta 1 | -7.2941 | |
| Dihydrokainic acid | 1.329 | 9.1976E-02 | no | Glutamate | Blocker | Kainate | -5.6560 | |
| P1,P4-Di(adenosine-5')tetraphosphate triammonium | -0.287 | 3.8718E-01 | no | Biochemistry | Inhibitor | | -9.7230 | |
| Debrisoquin sulfate | -0.303 | 3.8078E-01 | no | Neurotransmission | Antihyperten | | -5.4151 | |
| 2',3'-didehydro-3'-deoxythymidine | -1.878 | 3.0177E-02 | no | Immune System | Inhibitor | Reverse Transcriptase | -1.1860 | |
| Droperidol | 0.645 | 2.5958E-01 | no | Dopamine | Antagonist | D1/D2 | -5.2369 | |
| L-3,4-Dihydroxyphenylalanine methyl ester hydrochloride | 0.277 | 3.9093E-01 | no | Dopamine | Precursor | | -9.1222 | |
| 1,4-Dideoxy-1,4-imino-D-arabinitol | -0.009 | 4.9656E-01 | no | Phosphorylation | Inhibitor | Glycogen phosphorylase | -6.9439 | |
| 2,4-Dinitrophenyl 2-fluoro-2-deoxy-beta-D-glucopyranoside | 0.772 | 2.2005E-01 | no | Biochemistry | Inhibitor | exo-beta-(1,3)-Glucanase | -4.0687 | |
| D-ribofuranosylbenzimidazole | -2.144 | 1.6019E-02 | no | Transcription | Inhibitor | | -6.9546 | |
| Diltiazem hydrochloride | 0.540 | 2.9476E-01 | no | Ca2+ Channel | Antagonist | L-type | -4.7662 | |
| SB 203186 | 0.937 | 1.7450E-01 | no | Serotonin | Antagonist | 5-HT4 | -6.9689 | |
| Dihydroergotamine methanesulfonate | -0.779 | 2.1785E-01 | no | Cytoskeleton and ECM | Inhibitor | Myosin ATPase | -17.9041 | |
| 2,3-Butanedione | -1.642 | 5.0346E-02 | no | Cell Stress | Modulator | Thiols | -1.4471 | |
| N,N,N',N'-Tetramethylazodicarboxamide | -0.639 | 2.6132E-01 | no | Glutamate | Agonist | mGluR1 | -2.7413 | |
| (S)-3,5-Dihydroxyphenylglycine | -0.336 | 3.6828E-01 | no | Histamine | Antagonist | HRH1 | -7.1241 | |
| Doxylamine succinate | 1.736 | 4.1270E-02 | no | Adrenoceptor | Inhibitor | Uptake | -3.7735 | |
| Desipramine hydrochloride | 0.123 | 4.5119E-01 | no | Anticonvulsant | | | -7.4669 | |
| 5,5-Diphenylhydantoin | 1.383 | 8.3398E-02 | no | Nitric Oxide | Inhibitor | NOS | -6.5440 | |
| N',N'-Dimethyl-arginine hydrochloride | -1.373 | 8.4933E-02 | no | Cytoskeleton and ECM | Inhibitor | MMP1/collagenase | -6.7125 | |
| Clodronic acid | -0.184 | 4.2694E-01 | no | Dopamine | Agonist | | -3.7954 | |
| Dihydroergocristine methanesulfonate | -0.773 | 2.1977E-01 | no | Phosphorylation | Inhibitor | GTP cyclohydrolase I | -18.9281 | |
| 2,6-Diamino-4-pyrimidinone | -1.072 | 1.4188E-01 | no | Angiogenesis | Inhibitor | ODC | -1.3883 | |
| DL-alpha-Difluoromethylornithine hydrochloride | -0.424 | 3.3565E-01 | no | Ion Channels | Inhibitor | H+/K+-ATPase | -2.9978 | |
| SCH-28080 | 2.107 | 1.7547E-02 | no | Dopamine | Antagonist | Autoreceptor | -8.4419 | |
| S(-)DS 121 hydrochloride | -0.100 | 4.6025E-01 | no | Vanilloid | Agonist | | -10.3580 | |
| Vanillic acid diethylamide | -0.595 | 2.7599E-01 | no | | | | -3.4750 | |

TABLE 10-continued

| Product Name | Z score | p value | Activity Class | Action | Selectivity | Likelihood score | Cluster ID |
|---|---|---|---|---|---|---|---|
| Epibestatin hydrochloride | −0.787 | 2.1568E−01 | Biochemistry | no | Inhibitor | Metalloprotease | −6.6215 |
| Etodolac | −0.558 | 2.8836E−01 | Prostaglandin | no | Inhibitor | COX | −5.9520 |
| Enoximone | −0.624 | 2.6642E−01 | Cyclic Nucleotides | no | Inhibitor | PDE III | −5.2654 |
| ET-18-OCH3 | −0.626 | 2.6570E−01 | Lipid | no | Inhibitor | PIPLC | −13.2721 |
| Etazolate hydrochloride | −0.247 | 4.0263E−01 | Adenosine | no | Inhibitor | Phosphodiesterase | −8.8336 |
| 7-Cyclopentyl-5-(4-phenoxy)phenyl-7H-pyrrolo[2,3-d]pyrimidin-4-ylamine | −1.412 | 7.8972E−02 | Phosphorylation | no | Inhibitor | lck | −3.2409 |
| E-64 | −1.709 | 4.3748E−02 | Biochemistry | no | Inhibitor | Cysteine protease | −7.4853 |
| Diacylglycerol kinase inhibitor I | −1.782 | 3.7390E−02 | Phosphorylation | no | Inhibitor | Diacylglycerol kinase | −7.8178 |
| Demeclocycline hydrochloride | −0.065 | 4.7428E−01 | Antibiotic | no | Inhibitor | Protein synthesis | −8.0592 |
| Diclofenac sodium | 0.299 | 3.8255E−01 | Prostaglandin | no | Inhibitor | COX | −3.6420 |
| DL-erythro-Dihydrosphingosine | −0.079 | 4.6871E−01 | Phosphorylation | no | Inhibitor | PKC/PLA2/PLD | −0.1690 |
| R-(−)-Desmethyldeprenyl hydrochloride | −0.506 | 3.0657E−01 | Neurotransmission | no | Inhibitor | MAO-B | −5.6089 |
| 2,2′-Bipyridyl | 1.455 | 7.2862E−02 | Biochemistry | no | Inhibitor | Metalloprotease | −3.7379 |
| Dicyclomine hydrochloride | 1.414 | 7.8624E−02 | Cholinergic | no | Antagonist | Muscarinic | −0.8242 |
| 3,4-Dichloroisocoumarin | −1.120 | 1.3141E−01 | Biochemistry | no | Inhibitor | Serine Protease | −4.9206 |
| DBO-83 | −1.279 | 1.0038E−01 | Cholinergic | no | Agonist | Nicotinic | −7.5674 |
| Dephostatin | 0.621 | 2.6732E−01 | Phosphorylation | no | Inhibitor | CD45 Tyrosine Kinase | −3.9458 |
| 3-deazaadenosine | 1.770 | 3.8360E−02 | Immune System | no | Inhibitor | | −6.0324 |
| (Z)-Guggulesterone | 3.205 | 6.7567E−04 | Lipid Signaling | no | Antagonist | FRX | −10.5383 |
| Danazol | 2.152 | 1.5713E−02 | Hormone | no | Ligand | | −15.4776 |
| N,N-Dihexyl-2-(4-fluorophenyl)indole-3-acetamide | 1.916 | 2.7694E−02 | Benzodiazepine | no | Ligand | Mitochondria | −7.3781 |
| SP600125 | −1.986 | 2.3356E−02 | Phosphorylation | no | Inhibitor | c-JNK | −8.4226 |
| Diazoxide | 0.045 | 4.8201E−01 | K+ Channel | no | Activator | ATP-sensitive | −3.3923 |
| 3,4-Dihydroxyphenylacetic acid | −0.583 | 2.7988E−01 | Dopamine | no | Metabolite | | −10.2325 |
| Dantrolene sodium | 0.798 | 2.1230E−01 | Intracellular Calcium | no | Inhibitor | Release | −8.4822 |
| DCEBIO | 0.810 | 2.0900E−01 | K+ Channel | no | Activator | hIK1 | −3.8055 |
| 1-Deoxynojirimycin hydrochloride | 1.242 | 1.0713E−01 | Biochemistry | no | Inhibitor | alpha-glucosidase | −6.6269 |
| L-3,4-Dihydroxyphenylalanine | 2.440 | 7.3488E−03 | Dopamine | no | Precursor | | −9.9117 |
| Dipyridamole | −0.727 | 2.3372E−01 | Adenosine | no | Inhibitor | | −1.9619 |
| Doxazosin mesylate | −1.861 | 3.1346E−02 | Adrenoceptor | no | Blocker | alpha1 | −2.6413 |
| Doxycycline hydrochloride | −0.558 | 2.8849E−01 | Antibiotic | no | | Protein synthesis | −14.0343 |
| 6,7-ADTN hydrobromide | 0.357 | 3.6056E−01 | Dopamine | no | Agonist | | −6.3543 |
| Dipropyldopamine hydrobromide | −1.346 | 8.9197E−02 | Dopamine | no | Agonist | | −3.0223 |
| Amfonelic acid | 0.488 | 3.1277E−01 | Dopamine | no | Modulator | | −13.3956 |
| Icilin | 1.643 | 5.0157E−02 | Neurotransmission | no | Agonist | CMR1 | −6.3622 |
| (±)-SKF-38393 hydrochloride | 1.280 | 1.0030E−01 | Dopamine | no | Antagonist | D1 | −8.8933 |
| R(+)-SCH-23390 hydrochloride | 1.375 | 8.4525E−02 | Dopamine | no | Antagonist | D1 | −2.8442 |
| (±)-DOI hydrochloride | −1.345 | 8.9370E−02 | Serotonin | no | Agonist | 5-HT2/5-HT1C | −1.8081 |
| (±)2,3-Dichloro-alpha-methylbenzylamine hydrochloride | −2.251 | 1.2197E−02 | Neurotransmission | no | Inhibitor | PNMT | −3.2749 |
| 4-DAMP methiodide | 0.331 | 3.7027E−01 | Cholinergic | no | Antagonist | M3 | −4.8290 |
| 1,3-Dipropyl-7-methylxanthine | −0.089 | 4.6456E−01 | Adenosine | no | Antagonist | A2 | −17.0207 |
| Propofol | 0.377 | 3.5315E−01 | Cholinergic | no | Inhibitor | Muscarinic | −2.8649 |
| Dextrorphan D-tartrate | 1.569 | 5.8358E−02 | Glutamate | no | Antagonist | NMDA | −3.2343 |
| R(+)-Butylindazone | 0.029 | 4.8834E−01 | Ion Pump | no | Inhibitor | K+/Cl− transport | −9.4197 |
| DPMA | 0.036 | 4.8553E−01 | Adenosine | no | Agonist | A2 | −4.6563 |
| 3,5-Dinitrocatechol | −0.529 | 2.9828E−01 | Neurotransmission | no | Inhibitor | COMT | −6.6346 |
| N,N-Dipropyl-5-carboxamidotryptamine maleate | −1.730 | 4.1815E−02 | Serotonin | no | Agonist | 5-HT1A | −13.3021 |
| 6,7-Dichloroquinoxaline-2,3-dione | 0.127 | 4.4932E−01 | Glutamate | no | Antagonist | NMDA-glycine | −3.3370 |
| 3,7-Dimethyl-1-propargylxanthine | 1.454 | 7.3015E−02 | Adenosine | no | Antagonist | A2 | −15.2349 |
| 5,7-Dichlorokynurenic acid | 0.901 | 1.8378E−01 | Glutamate | no | Antagonist | NMDA-glycine | −4.6989 |
| 4-Diphenylacetoxy-N-(2-chloroethyl)piperidine hydrochloride | 0.864 | 1.9366E−01 | Cholinergic | no | Antagonist | Muscarinic | −1.3361 |

TABLE 10-continued

| Product Name | Z score | p value | Activity | Class | Action | Selectivity | Likelihood score | Cluster ID |
|---|---|---|---|---|---|---|---|---|
| 1,10-Diaminodecane | 0.139 | 4.4460E-01 | no | Glutamate | Agonist (inv | NMDA-polyamine | -2.0129 | |
| Dihydro-beta-erythroidine hydrobromide | -1.788 | 3.6854E-02 | no | Cholinergic | Antagonist | nAch | -2.8674 | |
| N-(3,3-Diphenylpropyl)glycinamide | -1.243 | 1.0691E-01 | no | Glutamate | Blocker | NMDA | -5.7246 | |
| Glibenclamide | -0.360 | 3.5941E-01 | no | K+ Channel | Blocker | ATP-dependent | -8.7301 | |
| GW2974 | -0.516 | 3.0279E-01 | no | Phosphorylation | Inhibitor | EGFR/ErbB-2 | -12.2358 | |
| Guanfacine hydrochloride | 0.927 | 1.7695E-01 | no | Adrenoceptor | Agonist | alpha2 | -2.0297 | |
| L-Glutamic acid hydrochloride | -0.473 | 3.1822E-01 | no | Glutamate | Agonist | | -2.3031 | |
| L-Glutamine | 0.828 | 2.0389E-01 | no | Glutamate | Agonist | | -5.0432 | |
| Guanidinyl-naltrindole di-trifluoroacetate | -0.204 | 4.1929E-01 | no | Opioid | Antagonist | kappa | -9.3192 | |
| GW1929 | 0.015 | 4.9398E-01 | no | Transcription | Agonist | PPAR-gamma | -9.5700 | |
| GW5074 | -0.162 | 4.3570E-01 | no | Phosphorylation | Inhibitor | Raf1 kinase | -8.2139 | |
| GW7647 | -0.992 | 1.6052E-01 | no | Transcription | Agonist | PPAR-alpha | -12.1570 | |
| Gallamine triethiodide | -0.916 | 1.7995E-01 | no | Cholinergic | Antagonist | M2 | -4.7485 | |
| S-Ethylisothiourea hydrobromide | -1.599 | 5.4874E-02 | no | Nitric Oxide | Inhibitor | NOS | -4.2580 | |
| Edrophonium chloride | -0.806 | 2.1001E-01 | no | Cholinergic | Inhibitor | Acetylcholinesterase | -5.3039 | |
| Ebselen | -0.251 | 4.0072E-01 | no | Leukotriene | Inhibitor | | -2.2253 | |
| rac-2-Ethoxy-3-hexadecanamido-1-propylphosphocholine | -1.269 | 1.0223E-01 | no | Phosphorylation | Inhibitor | PKC | -13.3506 | |
| rac-2-Ethoxy-3-octadecanamido-1-propylphosphocholine | -1.112 | 1.3298E-01 | no | Phosphorylation | Inhibitor | PKC | -12.3289 | |
| N-Ethylmaleimide | -0.028 | 4.8877E-01 | no | Biochemistry | Inhibitor | Isocitrate dehydrogenase | -3.3843 | |
| (−)-Epinephrine bitartrate | -0.530 | 2.9791E-01 | no | Adrenoceptor | Agonist | | -13.0202 | |
| (±)-Epinephrine hydrochloride | -0.328 | 3.7148E-01 | no | Adrenoceptor | Agonist | | -12.7284 | |
| Ethosuximide | -0.612 | 2.7014E-01 | no | Anticonvulsant | | | -1.4347 | |
| Endothall | -1.143 | 1.2644E-01 | no | Phosphorylation | Inhibitor | PP2A | -4.0878 | |
| Emodin | -0.483 | 3.1438E-01 | no | Phosphorylation | Inhibitor | p56lck TK | -5.2573 | |
| (−)-Physostigmine | -0.218 | 4.1377E-01 | no | Cholinergic | Inhibitor | Cholinesterase | -3.2224 | |
| NBI 27914 | 0.134 | 4.4651E-01 | no | Neurotransmission | Antagonist | CRF1 | -3.9632 | |
| beta-Estradiol | -0.562 | 2.8696E-01 | no | Hormone | Agonist | Estrogen | -12.0545 | |
| Estrone | 0.041 | 4.8372E-01 | no | Hormone | Agonist | Estrogen | -13.0120 | |
| Methyl beta-carboline-3-carboxylate | 0.060 | 4.7599E-01 | no | Benzodiazepine | Agonist | | -9.2192 | |
| N-Methyl-beta-carboline-3-carboxamide | 0.699 | 2.4235E-01 | no | GABA | Antagonist | GABA-A | -9.5740 | |
| Methyl 6,7-dimethoxy-4-ethyl-beta-carboline-3-carboxylate | -1.326 | 9.2453E-02 | no | Benzodiazepine | Agonist | | -5.1499 | |
| (−)-Eseroline fumarate | 0.634 | 2.6308E-01 | no | Cholinergic | Inhibitor | Cholinesterase | -5.6206 | |
| (S)-ENBA | 0.208 | 4.1767E-01 | no | Adenosine | Agonist | A1 | -8.4799 | |
| erythro-9-(2-Hydroxy-3-nonyl)adenine hydrochloride | -0.766 | 2.2197E-01 | no | Adenosine | Inhibitor | Adenosine deaminase | -1.3832 | |
| Ergocristine | 0.408 | 3.4172E-01 | no | Dopamine | Agonist | | -27.2658 | |
| Felbamate | -0.459 | 3.2327E-01 | no | Glutamate | Antagonist | | -8.5534 | |
| Fusidic acid sodium | 2.045 | 2.0427E-02 | no | Cell Cycle | Inhibitor | | -9.8579 | |
| Fenoterol hydrobromide | -1.841 | 3.2821E-02 | no | Adrenoceptor | Agonist | beta2 | -10.3422 | |
| Furosemide | 1.889 | 2.9456E-02 | no | Ion Pump | Inhibitor | Na+,K+,Cl− cotransport | -5.9592 | |
| S-(+)-Fluoxetine hydrochloride | -0.809 | 2.0932E-01 | no | Serotonin | Inhibitor | Reuptake | -9.1211 | |
| R-(−)-Fluoxetine hydrochloride | -0.128 | 4.4905E-01 | no | Serotonin | Inhibitor | Reuptake | -9.1211 | |
| Fluvoxamine maleate | 0.132 | 4.4737E-01 | no | Serotonin | Inhibitor | Reuptake | -9.4524 | |
| 1-(4-Fluorobenzyl)-5-methoxy-2-methylindole-3-acetic acid | -0.538 | 2.9543E-01 | no | Multi-Drug Resistance | Inhibitor | MRP1 | -9.0898 | |
| Furegrelate sodium | 0.364 | 3.5800E-01 | no | Phosphorylation | Inhibitor | Thromboxane synthase | -12.3958 | |
| Fiduxosin hydrochloride | 0.200 | 4.2056E-01 | no | Adrenoceptor | Antagonist | alpha1 | -5.1869 | |
| Furosemide | 1.889 | 2.9456E-02 | no | Ion Pump | Inhibitor | Na+,K+,Cl− cotransport | -5.9592 | |
| p-Fluoro-L-phenylalanine | -0.702 | 2.4126E-01 | no | Neurotransmission | Substrate | Tyrosine Hydroxylase | -4.5617 | |
| Fenofibrate | -2.116 | 1.7190E-02 | no | Transcription | Agonist | PPAR-alpha | -0.2642 | |
| Fenspiride hydrochloride | -0.576 | 2.8223E-01 | no | Adrenoceptor | Antagonist | alpha | -0.7723 | |
| Flumazenil | -0.366 | 3.5703E-01 | no | Benzodiazepine | Antagonist | | -10.4543 | |
| Foliosidine | -0.097 | 4.6140E-01 | no | Anticonvulsant | | | -6.0396 | |

TABLE 10-continued

| Product Name | Z score | p value | Activity | Class | Action | Selectivity | Likelihood score | Cluster ID |
|---|---|---|---|---|---|---|---|---|
| Fusaric acid | -0.141 | 4.4382E-01 | no | Dopamine | Inhibitor | Dopamine beta-hydroxylase | -7.0076 | |
| Flecainide acetate | -1.498 | 6.7005E-02 | no | Na+ Channel | Blocker | | -5.4913 | |
| Fenoldopam bromide | 0.052 | 4.7919E-01 | no | Dopamine | Agonist | D1 | -7.5224 | |
| Forskolin | -1.331 | 9.1668E-02 | no | Cyclic Nucleotides | Activator | Adenylate cyclase | -4.1972 | |
| Famotidine | 0.055 | 4.7811E-01 | no | Histamine | Antagonist | H2 | -7.5810 | |
| FSCPX | 0.782 | 2.1697E-01 | no | Adenosine | Antagonist | A1 | -25.0121 | |
| Farnesylthiosalicylic acid | 0.906 | 1.8244E-01 | no | G protein | Antagonist | Ras | -4.1651 | |
| Flunarizine dihydrochloride | 0.395 | 3.4627E-01 | no | Ion Pump | Blocker | Na+/Ca2+ channel | -1.9671 | |
| 5-fluoro-5'-deoxyuridine | 0.379 | 3.5246E-01 | no | DNA Metabolism | Inhibitor | | -2.9280 | |
| Flupirtine maleate | -0.484 | 3.1420E-01 | no | Glutamate | Antagonist | NMDA | -9.8407 | |
| Flutamide | -0.113 | 4.5490E-01 | no | Hormone | Inhibitor | Androgen | -7.3424 | |
| Fexofenadine hydrochloride | -0.757 | 2.2445E-01 | no | Histamine | Antagonist | HRH1 | -5.6445 | |
| Formoterol | -0.838 | 2.0104E-01 | no | Adrenoceptor | Agonist | beta2 | -16.0812 | |
| Felodipine | -0.966 | 1.6707E-01 | no | Ca2+ Channel | Blocker | L-type | -10.2014 | |
| Fluspirilene | 1.589 | 5.6001E-02 | no | Dopamine | Antagonist | D2/D1 | -5.8124 | |
| Furafylline | 1.025 | 1.5277E-01 | no | Biochemistry | Inhibitor | P450IA2 | -16.0242 | |
| FPL 64176 | -1.099 | 1.3591E-01 | no | Ca2+ Channel | Activator | L-type | -6.8541 | |
| Fluoxetine hydrochloride | -1.311 | 9.4858E-02 | no | Serotonin | Inhibitor | Reuptake | -9.1211 | |
| GR 125487 sulfamate salt | -0.194 | 4.2300E-01 | no | Serotonin | Antagonist | 5-HT4 | -4.2655 | |
| IEM-1460 | 0.685 | 2.4674E-01 | no | Glutamate | Inhibitor | AMPA | -5.2560 | |
| Ibudilast | 0.379 | 3.5244E-01 | no | Cyclic Nucleotides | Inhibitor | PDE IV | -6.2032 | |
| Imidazole-4-acetic acid hydrochloride | -0.922 | 1.7820E-01 | no | GABA | Antagonist | GABA-C | -12.6089 | |
| Indirubin-3'-oxime | -0.397 | 3.4587E-01 | no | Phosphorylation | Inhibitor | CDK | -8.4387 | |
| Imazodan | 0.462 | 3.2217E-01 | no | Cyclic Nucleotides | Inhibitor | PDE II | -12.4077 | |
| Ipratropium bromide | -0.308 | 3.7904E-01 | no | Cholinergic | Antagonist | Muscarinic | -8.9698 | |
| 2-Iodomelatonin | -0.135 | 4.4637E-01 | no | Melatonin | Agonist | | -7.1283 | |
| SB 228357 | 0.034 | 4.8634E-01 | no | Serotonin | Antagonist | 5-HT2B/2C | -4.6876 | |
| IMID-4F hydrochloride | -1.906 | 2.8337E-02 | no | K+ Channel | Blocker | | -3.6024 | |
| R(−)-Isoproterenol (+)-bitartrate | -1.485 | 6.8743E-02 | no | Adrenoceptor | Agonist | beta | -13.6004 | |
| Isoguvacine hydrochloride | -2.220 | 1.3206E-02 | no | GABA | Agonist | GABA-A, GABA-C | -5.7435 | |
| Guvacine hydrochloride | -1.345 | 8.9234E-02 | no | GABA | Inhibitor | Uptake | -5.2169 | |
| (±)-AMPA hydrobromide | -0.427 | 3.3461E-01 | no | Glutamate | Agonist | AMPA/kainate | -9.1686 | |
| Muscimol hydrobromide | 0.186 | 4.2612E-01 | no | GABA | Agonist | GABA-A, GABA-C | -6.3913 | |
| Guanabenz acetate | -1.906 | 2.8344E-02 | no | Adrenoceptor | Agonist | alpha2 | -5.3611 | |
| gamma-D-Glutamylaminomethylsulfonic acid | -0.046 | 4.8146E-01 | no | Glutamate | Antagonist | Kainate | -6.9425 | |
| Glipizide | -0.830 | 2.0341E-01 | no | K+ Channel | Blocker | ATP-sensitive | -13.3300 | |
| GYKI 52895 | -1.258 | 1.0419E-01 | no | Dopamine | Inhibitor | Reuptake | -0.3735 | |
| Gabapentin | 0.884 | 1.8841E-01 | no | Anticonvulsant | | | -4.8782 | |
| (±)-Vanillylmandelic acid | -1.811 | 3.5052E-02 | no | Adrenoceptor | Metabolite | | -1.2797 | |
| 6-Hydroxymelatonin | 0.377 | 3.5318E-01 | no | Melatonin | Metabolite | | -15.2014 | |
| 4-Hydroxy-3-methoxyphenylacetic acid | -0.567 | 2.8528E-01 | no | Dopamine | Metabolite | | -2.3077 | |
| MHPG piperazine | 0.053 | 4.7896E-01 | no | Adrenoceptor | Metabolite | | -2.0185 | |
| Hypotaurine | 0.275 | 3.9158E-01 | no | Cell Stress | Inhibitor | Antioxidant | -3.4031 | |
| Haloperidol | -0.740 | 2.2967E-01 | no | Dopamine | Antagonist | D2/D1 | -7.7150 | |
| Hydralazine hydrochloride | 0.259 | 3.9772E-01 | no | Neurotransmission | Inhibitor | MAO-A/B | -6.5236 | |
| 4-Imidazolemethanol hydrochloride | -2.077 | 1.8919E-02 | no | Histamine | Inhibitor | Histinol Dehydrogenase | -9.7374 | |
| Hydrocortisone 21-hemisuccinate sodium | -0.040 | 4.8392E-01 | no | Hormone | | Cortisol | -10.6646 | |
| 6-Hydroxy-DL-DOPA | 1.204 | 1.1431E-01 | no | Adrenoceptor | Neurotoxin | | -6.8703 | |
| DL-threo-beta-hydroxyaspartic acid | -0.522 | 3.0100E-01 | no | Glutamate | Inhibitor | Transport | -2.7459 | |
| Hydroxytacrine maleate | -0.204 | 4.1905E-01 | no | Cholinergic | Inhibitor | Cholinesterase | -8.2465 | |
| Lithium Chloride | -0.911 | 1.8108E-01 | no | Neurotransmission | Inhibitor | Inositol monophosphatase | -0.4563 | |

TABLE 10-continued

| Product Name | Z score | p value | Activity Class | Action | Selectivity | Likelihood score | Cluster ID |
|---|---|---|---|---|---|---|---|
| Hydrochlorothiazide | −0.212 | 4.1605E-01 | no | Biochemistry | Inhibitor | Carbonic anhydrase | −2.9759 | |
| SB 218795 | 1.359 | 8.7060E-02 | no | Neurotransmission | Antagonist | NK3 | −2.6055 | |
| Hispidin | 0.890 | 1.8684E-01 | no | Phosphorylation | Inhibitor | PKC-beta | −12.0505 | |
| 17alpha-hydroxyprogesterone | −0.578 | 2.8155E-01 | no | Hormone | Metabolite | Progesterone | −10.7469 | |
| 1,3,5-tris(4-hydroxyphenyl)-4-propyl-1H-pyrazole | 0.772 | 2.2016E-01 | no | Hormone | Agonist | ER-alpha | −3.3302 | |
| 1-(4-Hydroxybenzyl)imidazole-2-thiol | 0.763 | 2.2280E-01 | no | Dopamine | Inhibitor | Dopamine beta-hydroxylase | −5.7482 | |
| Histamine dihydrochloride | −1.476 | 6.9936E-02 | no | Histamine | Agonist | | −12.2180 | |
| Harmane | −1.403 | 8.0334E-02 | no | Imidazoline | Agonist | I1 | −6.4705 | |
| L-Histidine hydrochloride | −1.421 | 7.7629E-02 | no | Histamine | Precursor | | −13.7537 | |
| Dopamine hydrochloride | 1.352 | 8.8231E-02 | no | Dopamine | Agonist | | −10.1142 | |
| Hydroxyurea | 1.131 | 1.2897E-01 | no | DNA Metabolism | Inhibitor | Ribonucleoside reductase | −2.1618 | |
| MHPG sulfate potassium | −0.556 | 2.8923E-01 | no | Adrenoceptor | Metabolite | | −5.0540 | |
| 5-Hydroxyindolacetic acid | −1.301 | 9.6595E-02 | no | Serotonin | Metabolite | | −19.9055 | |
| L-Hyoscyamine | −0.661 | 2.5429E-01 | no | Cholinergic | Antagonist | | −6.4660 | |
| Hydroquinone | 0.428 | 3.3434E-01 | no | Leukotriene | Inhibitor | | −0.3944 | |
| BU99006 | 1.182 | 1.1870E-01 | no | Imidazoline | Ligand | I2 | −8.1496 | |
| 3-Hydroxybenzylhydrazine dihydrochloride | −0.487 | 3.1326E-01 | no | Biochemistry | Inhibitor | Amino acid decarboxylase | −6.6452 | |
| Serotonin hydrochloride | −2.197 | 1.4025E-02 | no | Serotonin | Agonist | | −19.9324 | |
| L-165,041 | 0.306 | 3.7973E-01 | no | Lipid Signaling | Agonist | PPAR-gamma | −1.9992 | |
| 5-Hydroxy-L-tryptophan | 0.030 | 4.8799E-01 | no | Serotonin | Precursor | | −20.5215 | |
| Hydroxylamine hydrochloride | 1.635 | 5.1057E-02 | no | Neurotransmission | Inhibitor | MAO | −2.3474 | |
| 4-Hydroxybenzhydrazide | −0.789 | 2.1512E-01 | no | Biochemistry | Inhibitor | | −3.0491 | |
| Hemicholinium-3 | 0.787 | 2.1562E-01 | no | Cholinergic | Blocker | Uptake | −5.1174 | |
| HA-1004 hydrochloride | 0.316 | 3.7596E-01 | no | Phosphorylation | Inhibitor | PK | −7.3536 | |
| H-7 dihydrochloride | 0.681 | 2.4785E-01 | no | Phosphorylation | Inhibitor | PKC | −3.0203 | |
| Hexahydro-sila-difenidol hydrochloride, p-fluoro analog | −1.492 | 6.7900E-02 | no | Cholinergic | Antagonist | M3 > M1 > M2 | −1.5458 | |
| Histamine, R(−)-alpha-methyl-, dihydrochloride | −1.469 | 7.0855E-02 | no | Histamine | Agonist | H3 | −11.9901 | |
| 5-hydroxydecanoic acid sodium | 0.233 | 4.0782E-01 | no | K+ Channel | Blocker | | −5.4081 | |
| Leflunomide | 4.103 | 2.0382E-05 | no | Immune System | Inhibitor | | −5.4344 | |
| VER-3323 hemifumarate salt | −0.761 | 2.2321E-01 | no | Serotonin | Agonist | 5-HT2C/5-HT2B | −4.5451 | |
| Lidocaine hydrochloride | −0.111 | 4.5578E-01 | no | Na+ Channel | Modulator | | −5.0834 | |
| Lidocaine N-ethyl bromide quaternary salt | 0.265 | 3.9538E-01 | no | Na+ Channel | Antagonist | | −7.1021 | |
| L-Leucinethiol, oxidized dihydrochloride | −0.584 | 2.7961E-01 | no | Biochemistry | Inhibitor | Aminopeptidase | −1.6871 | |
| LE 300 | −1.070 | 1.4234E-01 | no | Dopamine | Antagonist | D1 | −1.8116 | |
| Lansoprazole | −0.034 | 4.8660E-01 | no | Ion Pump | Inhibitor | H+ pump | −11.4889 | |
| LFM-A13 | 4.500 | 3.4002E-06 | no | Phosphorylation | Inhibitor | BTK | −7.6465 | |
| Luteolin | −1.323 | 9.2973E-02 | no | Cell Stress | Inhibitor | Antioxidant | −12.5139 | |
| L-655,240 | −0.121 | 4.5183E-01 | no | Thromboxane | Antagonist | TXA2 | −9.1983 | |
| Loratadine | −1.823 | 3.4160E-02 | no | Histamine | Antagonist | HRH1 | −7.9079 | |
| (−)-Teramisole hydrochloride | −1.866 | 3.1005E-02 | no | Phosphorylation | Inhibitor | | −9.6745 | |
| L-655,708 | −0.613 | 2.6988E-01 | no | Benzodiazepine | Ligand | GABA-A | −11.3947 | |
| LY-294,002 hydrochloride | −1.217 | 1.1184E-01 | no | Phosphorylation | Inhibitor | PI3K | −3.1040 | |
| Loxapine succinate | −0.748 | 2.2732E-01 | no | Dopamine | Antagonist | | −4.0117 | |
| (±)-Ibotenic acid | −1.650 | 4.9495E-02 | no | Glutamate | Agonist | NMDA | −7.9415 | |
| Isothiarine mesylate | −0.639 | 2.6136E-01 | no | Adrenoceptor | Inhibitor | beta | −8.8817 | |
| (±)-Ibuprofen | −0.262 | 3.9653E-01 | no | Prostaglandin | Inhibitor | COX | −8.3439 | |
| IIK7 | −0.354 | 3.6152E-01 | no | Melatonin | Agonist | | −8.6271 | |
| (±)-Isoproterenol hydrochloride | −0.572 | 2.8376E-01 | no | Adrenoceptor | Agonist | beta | −14.1845 | |
| 3-Isobutyl-1-methylxanthine | −0.774 | 2.1947E-01 | no | Adenosine | Inhibitor | Phosphodiesterase | −16.0203 | |
| Idazoxan hydrochloride | −1.448 | 7.3866E-02 | no | Imidazoline | Ligand | I1/I2 | −6.8373 | |
| 1-(5-Isoquinolinylsulfonyl)-3-methylpiperazine dihydrochloride | 0.477 | 3.1672E-01 | no | Phosphorylation | Inhibitor | PKC | −2.8972 | |

TABLE 10-continued

| Product Name | Z score | p value | Activity | Class | Action | Selectivity | Likelihood score | Cluster ID |
|---|---|---|---|---|---|---|---|---|
| (−)-Isoproterenol hydrochloride | 0.237 | 4.0646E-01 | no | Adrenoceptor | Agonist | beta | -14.1845 | |
| 1-(5-Isoquinolinylsulfonyl)-2-methylpiperazine dihydrochloride | 0.335 | 3.6874E-01 | no | Phosphorylation | Inhibitor | PKA/PKC | -3.0203 | |
| Imipramine hydrochloride | -0.527 | 2.9903E-01 | no | Serotonin | Blocker | Reuptake | -1.0708 | |
| Isoxanthopterin | 0.234 | 4.0752E-01 | no | Cell Stress | Metabolite | | -7.9514 | |
| Iproniazid phosphate | -0.249 | 4.0158E-01 | no | Neurotransmission | Inhibitor | MAO | -8.4760 | |
| S(+)Isoproterenol(+)-bitartrate | -0.296 | 3.8350E-01 | no | Adrenoceptor | | beta | -13.6004 | |
| L-N6-(1-Iminoethyl)lysine hydrochloride | -0.381 | 3.5164E-01 | no | Nitric oxide | Inhibitor | iNOS | -6.5483 | |
| 3-Iodo-L-tyrosine | -0.048 | 4.8068E-01 | no | Neurotransmission | Inhibitor | Tyrosine hydroxylase | -3.7497 | |
| L-N5-(1-Iminoethyl)ornithine hydrochloride | -0.934 | 1.7519E-01 | no | Nitric Oxide | Inhibitor | NOS | -6.6284 | |
| Ivermectin | 1.507 | 6.5855E-02 | no | Cholinergic | Modulator | alpha7 nACh | -2.3255 | |
| Imiloxan hydrochloride | -0.988 | 1.6160E-01 | no | Adrenoceptor | Antagonist | alpha2B | -5.9673 | |
| CR 2945 | 0.545 | 2.9285E-01 | no | Cholecystokinin | Antagonist | CCK-B | -13.6579 | |
| S(+)Ibuprofen | -0.733 | 2.3164E-01 | no | Prostaglandin | Inhibitor | COX | -8.3439 | |
| p-Iodoclonidine hydrochloride | -0.161 | 4.3619E-01 | no | Adrenoceptor | Agonist | alpha2 | -7.1078 | |
| R(+)-IAA-94 | -0.010 | 4.9595E-01 | no | Cl− Channel | Inhibitor | | -8.5026 | |
| Indatraline hydrochloride | -0.724 | 2.3465E-01 | no | Dopamine | Inhibitor | Reuptake | -0.1381 | |
| Iofetamine hydrochloride | -0.759 | 2.2398E-01 | no | Neurotransmission | Analog | | -4.5840 | |
| ICI 204,448 hydrochloride | -0.364 | 3.5809E-01 | no | Opioid | Agonist | kappa | -2.3593 | |
| ICI 118,551 hydrochloride | 1.101 | 1.3555E-01 | no | Adrenoceptor | Antagonist | beta2 | -6.5568 | |
| Imetit dihydrobromide | -0.245 | 4.0313E-01 | no | Histamine | Agonist | H3 | -13.0801 | |
| 1,5-Isoquinolinediol | 0.027 | 4.8934E-01 | no | Apoptosis | Inhibitor | PARS | -5.7715 | |
| IB-MECA | -1.089 | 1.3806E-01 | no | Adenosine | Agonist | A3 | -3.8357 | |
| 3-(1H-Imidazol-4-yl)propyl di(p-fluorophenyl)methyl ether | -0.015 | 4.9415E-01 | no | Histamine | Antagonist | H3 | -5.6768 | |
| Isonipecotic acid | -0.457 | 3.2387E-01 | no | GABA | Agonist | GABA-A | -4.8582 | |
| JWH-015 | 0.622 | 2.6688E-01 | no | Cannabinoid | Agonist | CB2 | -4.4913 | |
| JL-18 | -0.286 | 3.8739E-01 | no | Dopamine | Antagonist | D4 > D2 | -8.5500 | |
| Kainic acid | -0.317 | 3.7567E-01 | no | Glutamate | Agonist | Kainate | -5.9803 | |
| Ketoconazole | 0.586 | 2.7892E-01 | no | Multi-Drug Resistance | Inhibitor | Cytochrome P450c17 | -0.0583 | |
| Ketorolac tris salt | -0.726 | 2.3405E-01 | no | Prostaglandin | Inhibitor | COX | -6.3587 | |
| Ketoprofen | -1.164 | 1.2226E-01 | no | Prostaglandin | Inhibitor | COX-1 | -9.3283 | |
| K 185 | 0.567 | 2.8521E-01 | no | Melatonin | Antagonist | | -5.3276 | |
| Ketotifen fumarate | 0.957 | 1.6921E-01 | no | Histamine | Antagonist | HRH1 | -10.4823 | |
| Kynurenic acid | 0.702 | 2.4140E-01 | no | Glutamate | Antagonist | NMDA-Glycine | -6.8297 | |
| Kenpaullone | -1.555 | 5.9978E-02 | no | Phosphorylation | Inhibitor | CDK1, CDK2, CDK5 | -10.0974 | |
| Karakoline | -1.625 | 5.2047E-02 | no | Cholinergic | Antagonist | Nicotinic | -3.9500 | |
| L-701,324 | 0.451 | 3.2590E-01 | no | Glutamate | Antagonist | NMDA-Glycine | -2.3937 | |
| loxoprofen | -0.883 | 1.8853E-01 | no | Prostaglandin | Inhibitor | COX | -10.0239 | |
| Labetalol hydrochloride | -1.097 | 1.3628E-01 | no | Adrenoceptor | Antagonist | beta | -7.9308 | |
| L-162,313 | 0.792 | 2.1410E-01 | no | Neurotransmission | Agonist | AT1 | -14.2550 | |
| Lidocaine N-methyl hydrochloride | -0.683 | 2.4738E-01 | no | Na+ Channel | Blocker | | -7.4131 | |
| LY-367,265 | -0.407 | 3.4202E-01 | no | Serotonin | Antagonist | Reuptake | -10.9577 | |
| L-368,899 | 0.291 | 3.8555E-01 | no | Neurotransmission | Antagonist | Oxytocin receptor | -7.6946 | |
| Lomefloxacin hydrochloride | 0.137 | 4.4536E-01 | no | Antibiotic | Inhibitor | DNA Gyrase | -12.1961 | |
| Lamotrigine | -1.095 | 1.3681E-01 | no | Anticonvulsant | | | -2.3009 | |
| alpha-Lobeline hydrochloride | 0.550 | 2.9121E-01 | no | Cholinergic | Agonist | Nicotinic | -2.4879 | |
| Loperamide hydrochloride | -0.498 | 3.0938E-01 | no | Opioid | Ligand | | -4.0032 | |
| Lonidamine | 0.436 | 3.3148E-01 | no | Cell Stress | Inhibitor | Mitochondrial hexokinase | -5.7024 | |

REFERENCES

1. Ding, S. & Schultz, P. G. A role for chemistry in stem cell biology. Nat. Biotechnol. 22, 833-840 (2004).
2. Enver, T. & Greaves, M. Loops, lineage, and leukemia. Cell 94, 9-12 (1998).
3. Weintraub, H. Assembly and propagation of repressed and depressed chromosomal states. Cell 42, 705-711 (1985).
4. Singh, S. K. et al. Identification of a cancer stem cell in human brain tumors. Cancer Res. 63, 5821-5828 (2003).
5. Singh, S. K. et al. Identification of human brain tumour initiating cells. Nature 432, 396-401 (2004).
6. Galli, R. et al. Isolation and characterization of tumorigenic, stem-like neural precursors from human glioblastoma. Cancer Res. 64, 7011-7021 (2004).
7. Hemmati, H. D. et al. Cancerous stem cells can arise from pediatric brain tumors. Proc. Natl. Acad. Sci. U.S. A 100, 15178-15183 (2003).
8. Gritti, A. et al. Epidermal and fibroblast growth factors behave as mitogenic regulators for a single multipotent stem cell-like population from the subventricular region of the adult mouse forebrain. J. Neurosci. 19, 3287-3297 (1999).
9. Reynolds, B. A. & Weiss, S. Generation of neurons and astrocytes from isolated cells of the adult mammalian central nervous system. Science 255, 1707-1710 (1992).
10. Reynolds, B. A. & Weiss, S. Clonal and population analyses demonstrate that an EGF-responsive mammalian embryonic CNS precursor is a stem cell. Dev. Biol. 175, 1-13 (1996).
11. Groszer, M. et al. PTEN negatively regulates neural stem cell self-renewal by modulating G0-G1 cell cycle entry. Proc. Natl. Acad. Sci. U.S. A 103, 111-116 (2006).
12. Hitoshi, S. et al. Notch pathway molecules are essential for the maintenance, but not the generation, of mammalian neural stem cells. Genes Dev. 16, 846-858 (2002).
13. Molofsky, A. V. et al. Bmi-1 dependence distinguishes neural stem cell self-renewal from progenitor proliferation. Nature 425, 962-967 (2003).
14. Ahn, S. & Joyner, A. L. In vivo analysis of quiescent adult neural stem cells responding to Sonic hedgehog. Nature 437, 894-897 (2005).
15. Lie, D. C. et al. Wnt signalling regulates adult hippocampal neurogenesis. Nature 437, 1370-1375 (2005).
16. Zhang, J. H., Chung, T. D. & Oldenburg, K. R. A Simple Statistical Parameter for Use in Evaluation and Validation of High Throughput Screening Assays. J. Biomol. Screen. 4, 67-73 (1999).
17. Hertz, I., Schousboe, I., Hertz, L. & Schousboe, A. Receptor expression in primary cultures of neurons or astrocytes. Prog. Neuropsychopharmacol. Biol. Psychiatry 8, 521-527 (1984).
18. Lee, J. et al. Tumor stem cells derived from glioblastomas cultured in bFGF and EGF more closely mirror the phenotype and genotype of primary tumors than do serum-cultured cell lines. Cancer Cell 9, 391-403 (2006).
19. Phillips, H. S. et al. Molecular subclasses of high-grade glioma predict prognosis, delineate a pattern of disease progression, and resemble stages in neurogenesis. Cancer Cell 9, 157-173 (2006).
20. Taylor, M. D. et al. Radial glia cells are candidate stem cells of ependymoma. Cancer Cell 8, 323-335 (2005).
21. Pomeroy, S. L. et al. Prediction of central nervous system embryonal tumour outcome based on gene expression. Nature 4-15, 436-442 (2002).
22. Corcoran, R. B. & Scott, M. P. A mouse model for medulloblastoma and basal cell nevus syndrome. J. Neurooncol. 53, 307-318 (2001).
23. Berman, D. M. et al. Medulloblastoma growth inhibition by hedgehog pathway blockade. Science 297, 1559-1561 (2002).
24. Hagg, T. Molecular regulation of adult CNS neurogenesis: an integrated view. Trends Neurosci. 28, 589-595 (2005).
25. Baker, S. A., Baker, K. A. & Hagg, T. Dopaminergic nigrostriatal projections regulate neural precursor proliferation in the adult mouse subventricular zone. Eur. J. Neurosci. 20, 575-579 (2004).
26. Encinas, J. M., Vaahtokari, A. & Enikolopov, G. Fluoxetine targets early progenitor cells in the adult brain. Proc. Natl. Acad. Sci. U.S. A 103, 8233-8238 (2006).
27. Harrist, A. et al. Alteration of hippocampal cell proliferation in mice lacking the beta 2 subunit of the neuronal nicotinic acetylcholine receptor. Synapse 54, 200-206 (2004).
28. Hoglinger, G. U. et al. Dopamine depletion impairs precursor cell proliferation in Parkinson disease. Nat. Neurosci. 7, 726-735 (2004).
29. Kippin, T. E., Kaput, S. & van der, K. D. Dopamine specifically inhibits forebrain neural stem cell proliferation, suggesting a novel effect of antipsychotic drugs. J. Neurosci. 25, 5815-5823 (2005).
30. Nacher, J., Alonso-Llosa, G., Rosell, D. R. & McEwen, B. S. NMDA receptor antagonist treatment increases the production of new neurons in the aged rat hippocampus. Neurobiol. Aging 24, 273-284 (2003).
31. Santarelli, L. et al. Requirement of hippocampal neurogenesis for the behavioral effects of antidepressants. Science 301, 805-809 (2003).
32. Ramalho-Santos, M., Yoon, S., Matsuzaki, Y., Mulligan, R. C. & Melton, D. A. "Stemness": transcriptional profiling of embryonic and adult stem cells. Science 298, 597-600 (2002).
33. Sharom, J. R., Bellows, D. S. & Tyers, M. From large networks to small molecules. Curr. Opin. Chem. Biol. 8, 81-90 (2004).
34. Macdonald, M. L. et al. Identifying off-target effects and hidden phenotypes of drugs in human cells. Nat. Chem. Biol. 2, 329-337 (2006).
35. Lalonde, F. M. & Myslobodsky, M. Are dopamine antagonists a risk factor for breast cancer? An answer from Parkinson's disease. Breast 12, 280-282 (2003).
36. Tropepe, V. et al. Distinct neural stem cells proliferate in response to EGF and FGF in the developing mouse telencephalon. Dev. Biol. 208, 166-188 (1999).
37. Uchida, N. et al. Direct isolation of human central nervous system stem cells. Proc. Natl. Acad. Sci. U.S. A 97, 14720-14725 (2000).
38. Reynolds, B. A. & Rietze, R. L. Neural stem cells and neurospheres—re-evaluating the relationship. Nat. Methods 2, 333-336 (2005).
39. Kevorkov, D. & Makarenkov, V. Statistical analysis of systematic errors in high-throughput screening. J. Biomol. Screen. 10, 557-567 (2005).
40. Chambers, J. M., Cleveland, W. S., Kleiner, B. & Tukey, P. A. Graphical Methods for Data Analysis. Chapman and Hall, New York. (1983).

41. Galli, R. et al. Isolation and characterization of tumorigenic, stem-like neural precursors from human glioblastoma. Cancer Res. 64, 7011-7021 (2004).
42. Seifert, G., Schilling, K. & Steinhauser, C. Astrocyte dysfunction in neurological disorders: a molecular perspective. Nat. Rev. Neurosci. 7, 194-206 (2006).
43. Chen, S. et al. Self-renewal of embryonic stem cells by a small molecule. Proc. Natl. Acad. Sci. USA 103, 17266-17271 (2006).
44. Butterworth, R. F. & Barbeau, A. Apomorphine: sterotyped behavior and regional distribution in rat brain. Can. J. Biochem. 53, 308-311 (1975).
45. Lledo, P. M., Alonso, M. & Grubb, M. S. Adult neurogenesis and functional plasticity in neuronal circuits. Nat. Rev. Neurosci. 7, 179-193 (2006).
46. Ge, S., Pradhan, D. A., Ming, G. L. & Song, H. GABA sets the tempo for activitydependent adult neurogenesis. Trends Neurosci. 30, 1-8 (2007).

What is claimed is:

1. A method for treating a medulloblastoma cancer involving neural precursor cells, early neural progenitor cells, neural stem cells (NSCs) or a combination thereof, said method comprising administering to a subject in need thereof a therapeutically effective amount of a composition comprising the compound ifenprodil.

2. The method according to claim 1, wherein the ifenprodil is administered in a dosage of about 0.4 μM.

3. The method according to claim 1, wherein the ifenprodil is administered in a dosage of about 0.8 μM.

4. A method for treating a glioblastoma cancer involving neural precursor cells, early neural progenitor cells, NSCs or a combination thereof, said method comprising administering to a subject in need thereof a therapeutically effective amount of a composition comprising the compound ifenprodil.

* * * * *

UNITED STATES PATENT AND TRADEMARK OFFICE
CERTIFICATE OF CORRECTION

PATENT NO.        : 8,058,243 B2
APPLICATION NO.   : 11/871562
DATED             : November 15, 2011
INVENTOR(S)       : Mike Tyers, Phedias Diamandis and Peter B. Dirks Page 1 of 1

It is certified that error appears in the above-identified patent and that said Letters Patent is hereby corrected as shown below:

ON THE TITLE PAGE:

Item (73) Assignees, replace "HSC Research and Development Limited Partnership (CA)" with -- The Hospital for Sick Children (CA) --.

Signed and Sealed this
Seventeenth Day of April, 2012

David J. Kappos
*Director of the United States Patent and Trademark Office*